(12) United States Patent
Takáts et al.

(10) Patent No.: US 11,764,048 B2
(45) Date of Patent: Sep. 19, 2023

(54) SPECTROMETRIC ANALYSIS OF MICROBES

(71) Applicant: Micromass UK Limited, Wilmslow (GB)

(72) Inventors: Zoltán Takáts, Cambridge (GB); Frances Bolt, London (GB); Tamás Karancsi, Budapest (HU); Emrys Jones, Manchester (GB); Keith Richardson, High Peak (GB); Lajos Godorhazy, Erd (HU); Daniel Szalay, Budapest (HU); Julia Balog, Solymar (HU); Steven Derek Pringle, Darwen (GB); Daniel Simon, Morichida (HU)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 18/149,468

(22) Filed: Jan. 3, 2023

(65) Prior Publication Data

US 2023/0143849 A1  May 11, 2023

Related U.S. Application Data

(63) Continuation of application No. 17/531,490, filed on Nov. 19, 2021, now Pat. No. 11,574,803, which is a (Continued)

(30) Foreign Application Priority Data

Mar. 6, 2015  (GB) ...................... 1503863
Mar. 6, 2015  (GB) ...................... 1503864

(Continued)

(51) Int. Cl.
*H01J 49/00* (2006.01)
*H01J 49/04* (2006.01)
(Continued)

(52) U.S. Cl.
CPC ........... *H01J 49/049* (2013.01); *A61B 1/041* (2013.01); *A61B 1/2736* (2013.01); (Continued)

(58) Field of Classification Search
CPC .... H01J 49/049; H01J 49/044; H01J 49/0036; H01J 49/0404; H01J 49/0459; (Continued)

(56) References Cited

U.S. PATENT DOCUMENTS 11,289,320 B2 * 3/2022 Pringle ............... H01J 49/0004
2009/0294660 A1 * 12/2009 Whitehouse ......... H01J 49/168
250/288

(Continued)

*Primary Examiner* — Michael Maskell
(74) *Attorney, Agent, or Firm* — Goodwin Procter LLP

(57) ABSTRACT

A method of analysis using mass spectrometry and/or ion mobility spectrometry is disclosed. The method comprises: using a first device to generate smoke, aerosol or vapour from a target comprising or consisting of a microbial population; mass analysing and/or ion mobility analysing said smoke, aerosol or vapour, or ions derived therefrom, in order to obtain spectrometric data; and analysing said spectrometric data in order to analyse said microbial population.

17 Claims, 45 Drawing Sheets

Related U.S. Application Data continuation of application No. 15/556,022, filed as application No. PCT/GB2016/050610 on Mar. 7, 2016, now Pat. No. 11,282,688.

(30) Foreign Application Priority Data

| | | |
|---|---|---|
| Mar. 6, 2015 | (GB) | 1503867 |
| Mar. 6, 2015 | (GB) | 1503876 |
| Mar. 6, 2015 | (GB) | 1503877 |
| Mar. 6, 2015 | (GB) | 1503878 |
| Mar. 6, 2015 | (GB) | 1503879 |
| Sep. 9, 2015 | (GB) | 1516003 |
| Oct. 16, 2015 | (GB) | 1518369 |

(51) Int. Cl.

| | |
|---|---|
| *A61B 10/02* | (2006.01) |
| *A61B 17/32* | (2006.01) |
| *A61B 18/00* | (2006.01) |
| *A61B 18/14* | (2006.01) |
| *A61B 18/20* | (2006.01) |
| *G01N 3/00* | (2006.01) |
| *G01N 9/00* | (2006.01) |
| *G01N 33/68* | (2006.01) |
| *H01J 49/06* | (2006.01) |
| *H01J 49/16* | (2006.01) |
| *G01N 27/623* | (2021.01) |
| *A61B 90/13* | (2016.01) |
| *A61B 1/04* | (2006.01) |
| *A61B 1/273* | (2006.01) |
| *A61B 5/00* | (2006.01) |
| *A61B 5/01* | (2006.01) |
| *A61B 5/0507* | (2021.01) |
| *A61B 5/055* | (2006.01) |
| *A61B 6/03* | (2006.01) |
| *A61B 8/13* | (2006.01) |
| *A61B 10/00* | (2006.01) |
| *A61B 17/00* | (2006.01) |
| *A61B 18/04* | (2006.01) |
| *A61B 18/18* | (2006.01) |
| *A61F 13/38* | (2006.01) |
| *C12Q 1/02* | (2006.01) |
| *C12Q 1/04* | (2006.01) |
| *C12Q 1/18* | (2006.01) |
| *C12Q 1/24* | (2006.01) |
| *G01N 1/22* | (2006.01) |
| *G01N 27/624* | (2021.01) |
| *G01N 30/72* | (2006.01) |
| *G01N 33/487* | (2006.01) |
| *G01N 33/92* | (2006.01) |
| *H01J 49/02* | (2006.01) |
| *H01J 49/10* | (2006.01) |
| *H01J 49/14* | (2006.01) |
| *H01J 49/24* | (2006.01) |
| *H01J 49/26* | (2006.01) |
| *G16B 20/00* | (2019.01) |
| *G16H 10/40* | (2018.01) |
| *G16H 15/00* | (2018.01) |
| *G16H 50/20* | (2018.01) |
| *A61B 1/00* | (2006.01) |
| *A61B 1/31* | (2006.01) |
| *A61B 5/145* | (2006.01) |

(52) U.S. Cl.
CPC .......... *A61B 5/0066* (2013.01); *A61B 5/0075* (2013.01); *A61B 5/015* (2013.01); *A61B 5/055* (2013.01); *A61B 5/0507* (2013.01); *A61B 6/032* (2013.01); *A61B 6/037* (2013.01); *A61B 8/13* (2013.01); *A61B 10/00* (2013.01); *A61B 10/0041* (2013.01); *A61B 10/0233* (2013.01); *A61B 10/0283* (2013.01); *A61B 17/00* (2013.01); *A61B 17/320068* (2013.01); *A61B 18/00* (2013.01); *A61B 18/04* (2013.01); *A61B 18/042* (2013.01); *A61B 18/14* (2013.01); *A61B 18/1445* (2013.01); *A61B 18/1815* (2013.01); *A61B 18/20* (2013.01); *A61B 90/13* (2016.02); *A61F 13/38* (2013.01); *C12Q 1/025* (2013.01); *C12Q 1/04* (2013.01); *C12Q 1/18* (2013.01); *C12Q 1/24* (2013.01); *G01N 1/2202* (2013.01); *G01N 3/00* (2013.01); *G01N 9/00* (2013.01); *G01N 27/623* (2021.01); *G01N 27/624* (2013.01); *G01N 30/724* (2013.01); *G01N 33/487* (2013.01); *G01N 33/6848* (2013.01); *G01N 33/6851* (2013.01); *G01N 33/92* (2013.01); *H01J 49/0004* (2013.01); *H01J 49/0027* (2013.01); *H01J 49/0031* (2013.01); *H01J 49/0036* (2013.01); *H01J 49/025* (2013.01); *H01J 49/044* (2013.01); *H01J 49/0404* (2013.01); *H01J 49/0409* (2013.01); *H01J 49/0422* (2013.01); *H01J 49/0445* (2013.01); *H01J 49/0459* (2013.01); *H01J 49/0463* (2013.01); *H01J 49/0468* (2013.01); *H01J 49/061* (2013.01); *H01J 49/068* (2013.01); *H01J 49/10* (2013.01); *H01J 49/14* (2013.01); *H01J 49/16* (2013.01); *H01J 49/164* (2013.01); *H01J 49/24* (2013.01); *H01J 49/26* (2013.01); *A61B 1/00013* (2013.01); *A61B 1/31* (2013.01); *A61B 5/14542* (2013.01); *A61B 2010/0083* (2013.01); *A61B 2017/320069* (2017.08); *A61B 2018/00577* (2013.01); *A61B 2018/00589* (2013.01); *A61B 2018/00994* (2013.01); *A61B 2218/002* (2013.01); *A61B 2218/008* (2013.01); *G01N 33/48735* (2013.01); *G01N 2001/2223* (2013.01); *G01N 2333/195* (2013.01); *G01N 2405/00* (2013.01); *G01N 2405/04* (2013.01); *G01N 2405/08* (2013.01); *G01N 2570/00* (2013.01); *G01N 2800/26* (2013.01); *G16B 20/00* (2019.02); *G16H 10/40* (2018.01); *G16H 15/00* (2018.01); *G16H 50/20* (2018.01)

(58) Field of Classification Search
CPC ...... H01J 49/068; H01J 49/16; H01J 49/0004; H01J 49/0027; H01J 49/0031; H01J 49/025; H01J 49/0409; H01J 49/0422; H01J 49/0445; H01J 49/0463; H01J 49/0468; H01J 49/061; H01J 49/10; H01J 49/14; H01J 49/164; H01J 49/24; H01J 49/26; A61B 10/0233; A61B 10/0283; A61B 17/320068; A61B 18/00; A61B 18/14; A61B 18/20; A61B 90/13; A61B 1/041; A61B 1/2736; A61B 5/0066; A61B 5/0075; A61B 5/015; A61B 5/0507; A61B 5/055; A61B 6/032; A61B 6/037; A61B 8/13; A61B 10/00; A61B 10/0041; A61B 17/00; A61B 18/04; A61B 18/042; A61B 18/1445; A61B 18/1815; A61B 2218/008; A61B 2017/320069; A61B 1/00013; A61B 1/31; A61B 5/14542; A61B 2010/0083; A61B 2018/00577; A61B 2018/00589; A61B 2018/00994; A61B 2218/002; G01N 3/00; G01N 9/00; G01N 33/6848; G01N 1/2202; G01N 27/622;
G01N 27/624; G01N 30/724; G01N
33/487; G01N 33/6851; G01N 33/92;
G01N 33/48735; G01N 2001/2223; G01N
2333/195; G01N 2405/00; G01N
2405/04; G01N 2405/08; G01N 2570/00;
G01N 2800/26; G01N 27/62; A61F
13/38; C12Q 1/025; C12Q 1/04; C12Q
1/18; C12Q 1/24; G16B 20/00; G16H
10/40; G16H 15/00; G16H 50/20; G06F
19/324; G06F 19/3481
USPC .................................................. 250/281, 282
See application file for complete search history.

(56) References Cited

U.S. PATENT DOCUMENTS

| | | | |
|---|---|---|---|
| 2011/0012016 A1* | 1/2011 | Maier | G16B 40/10 250/282 |
| 2012/0156712 A1* | 6/2012 | Takats | H01J 49/165 435/287.1 |
| 2014/0127734 A1* | 5/2014 | Charretier | G01N 33/6851 435/23 |
| 2015/0048255 A1* | 2/2015 | Jarrell | H01J 49/16 250/424 |
| 2015/0087003 A1* | 3/2015 | Charles | C07K 1/12 435/23 |
| 2018/0053644 A1* | 2/2018 | Jones | H01J 49/0404 |

* cited by examiner

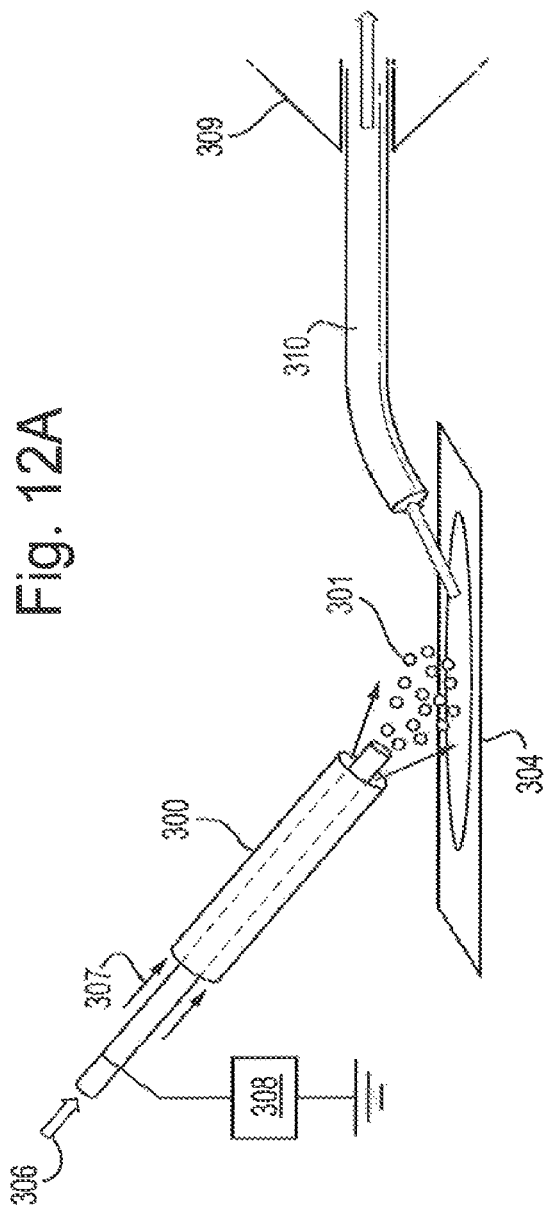
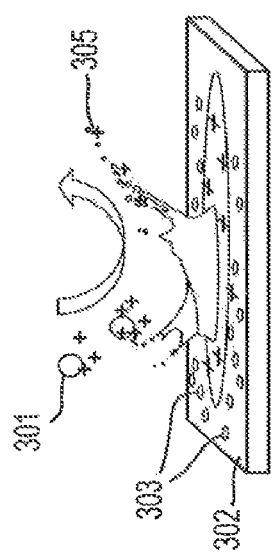

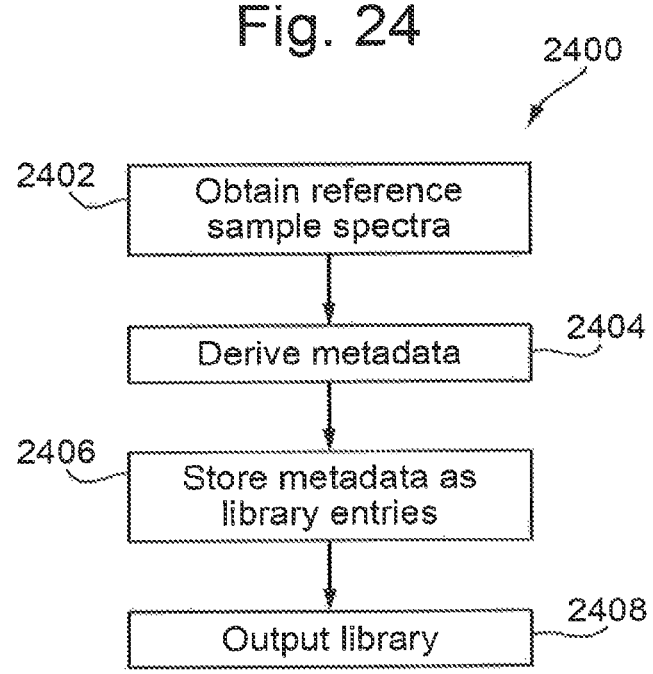
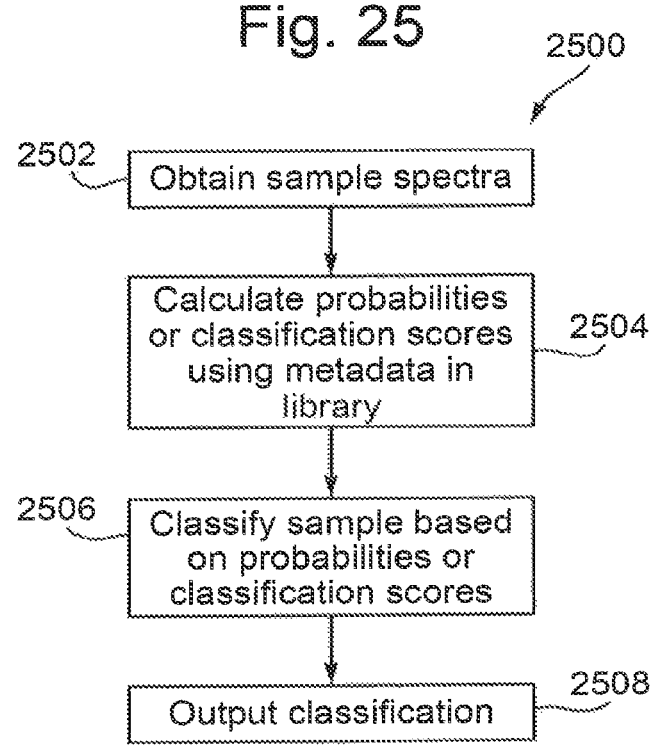

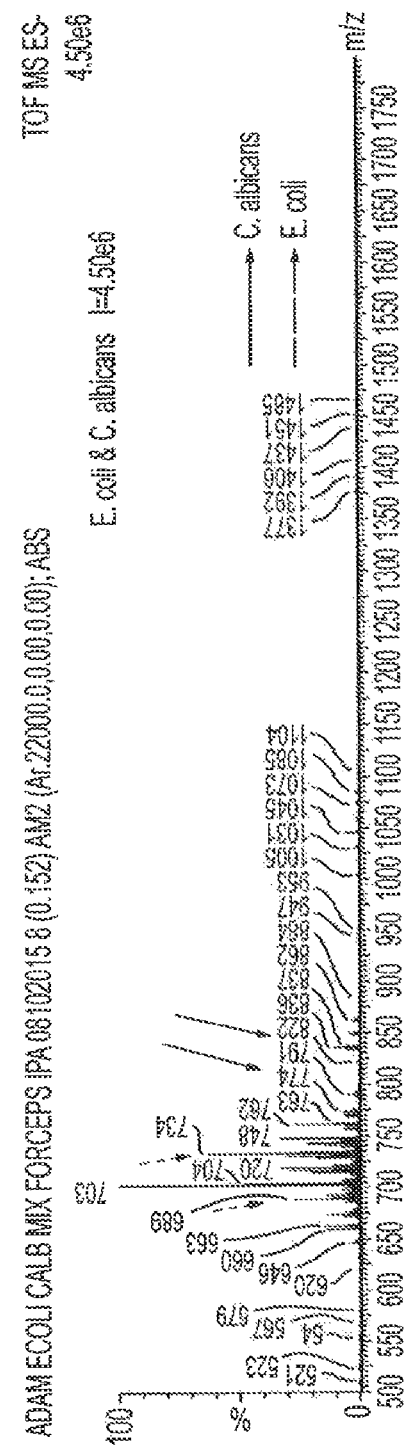

Fig. 29
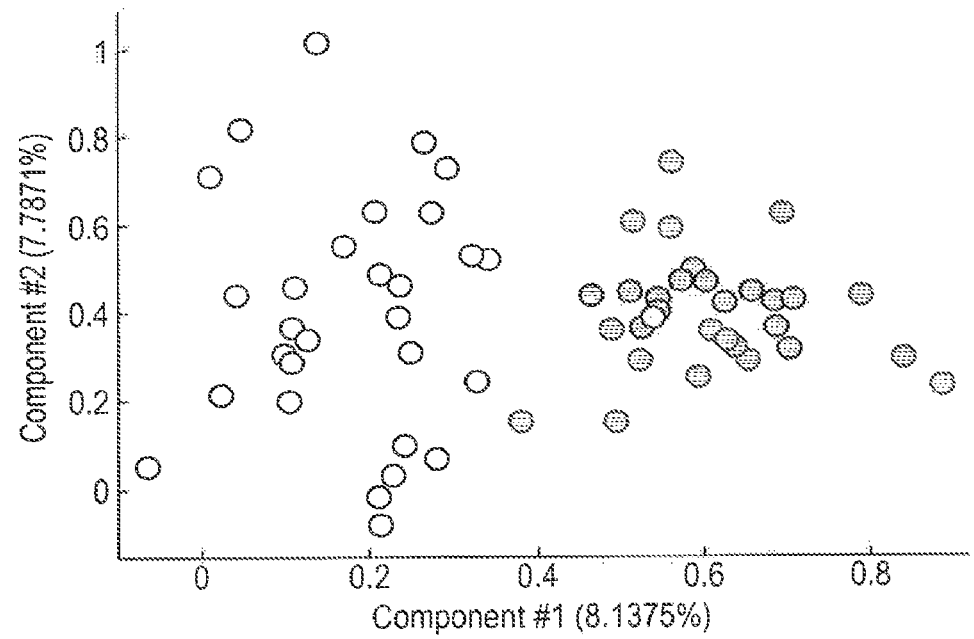
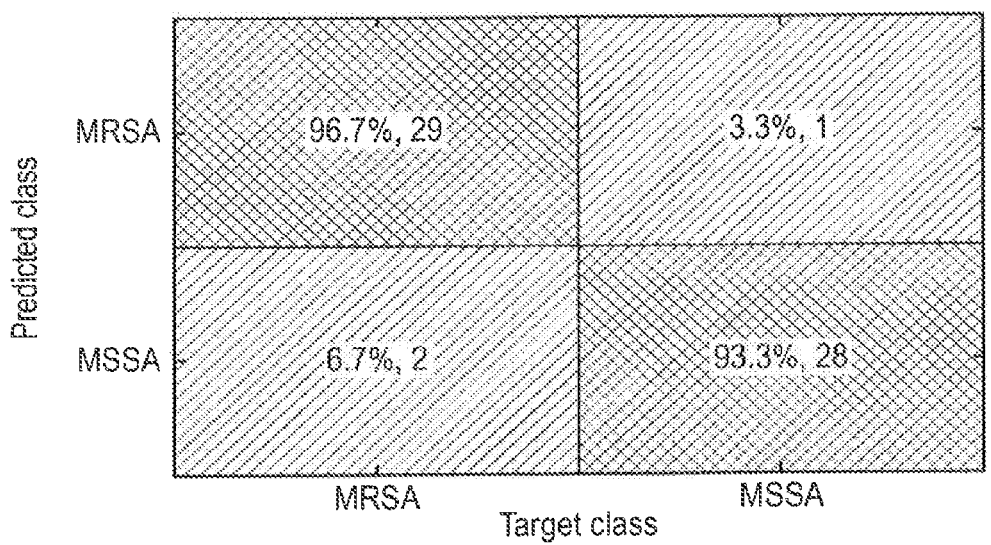

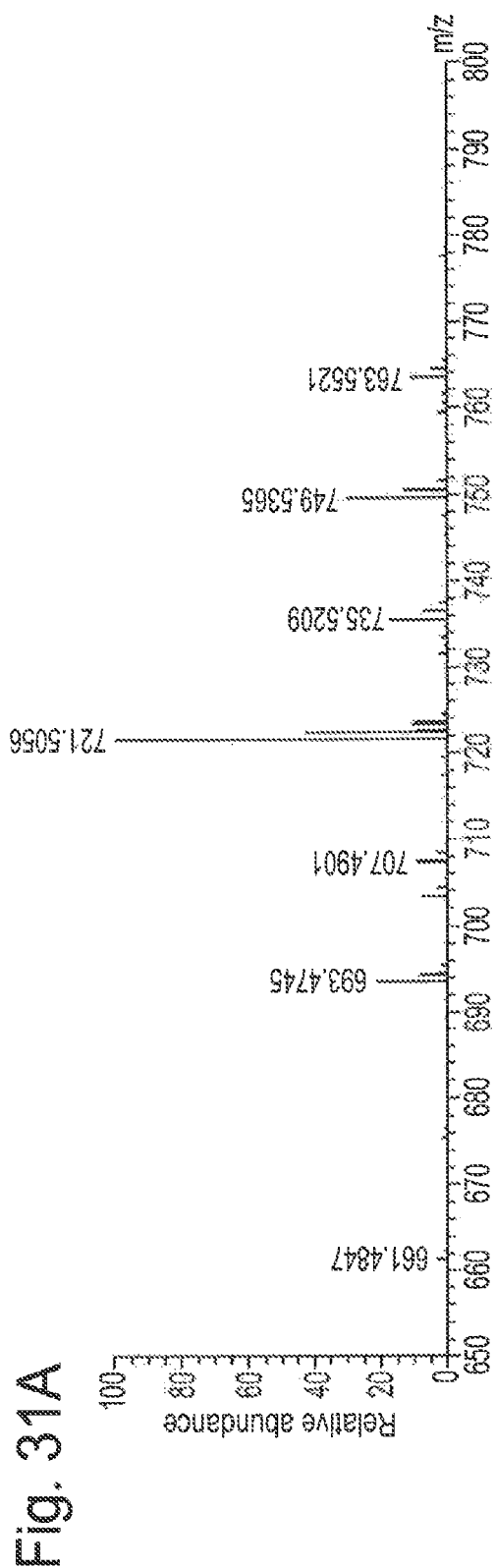
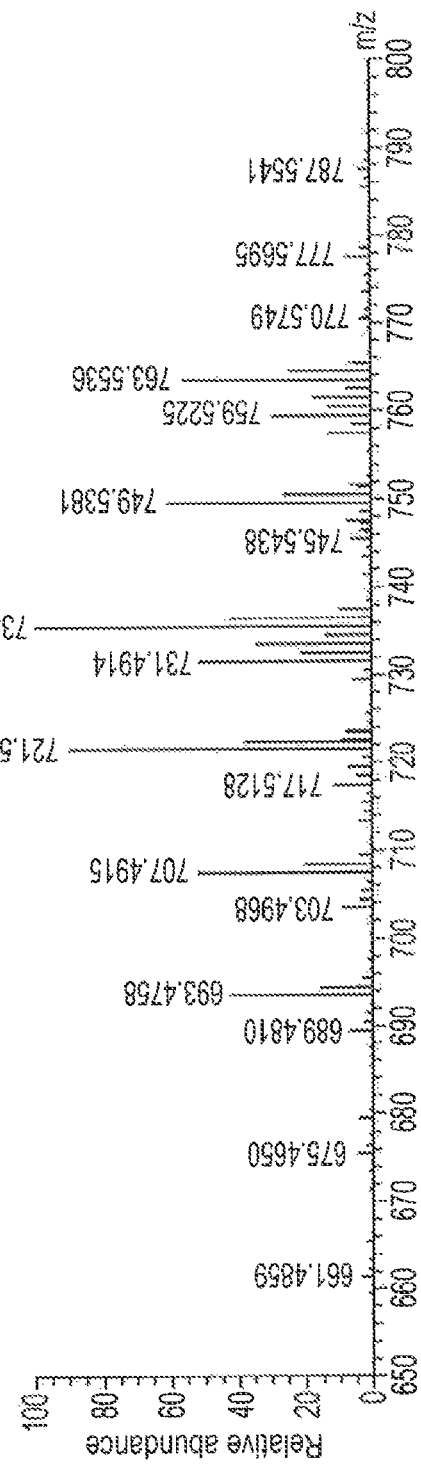
Fig. 31A
Fig. 31B

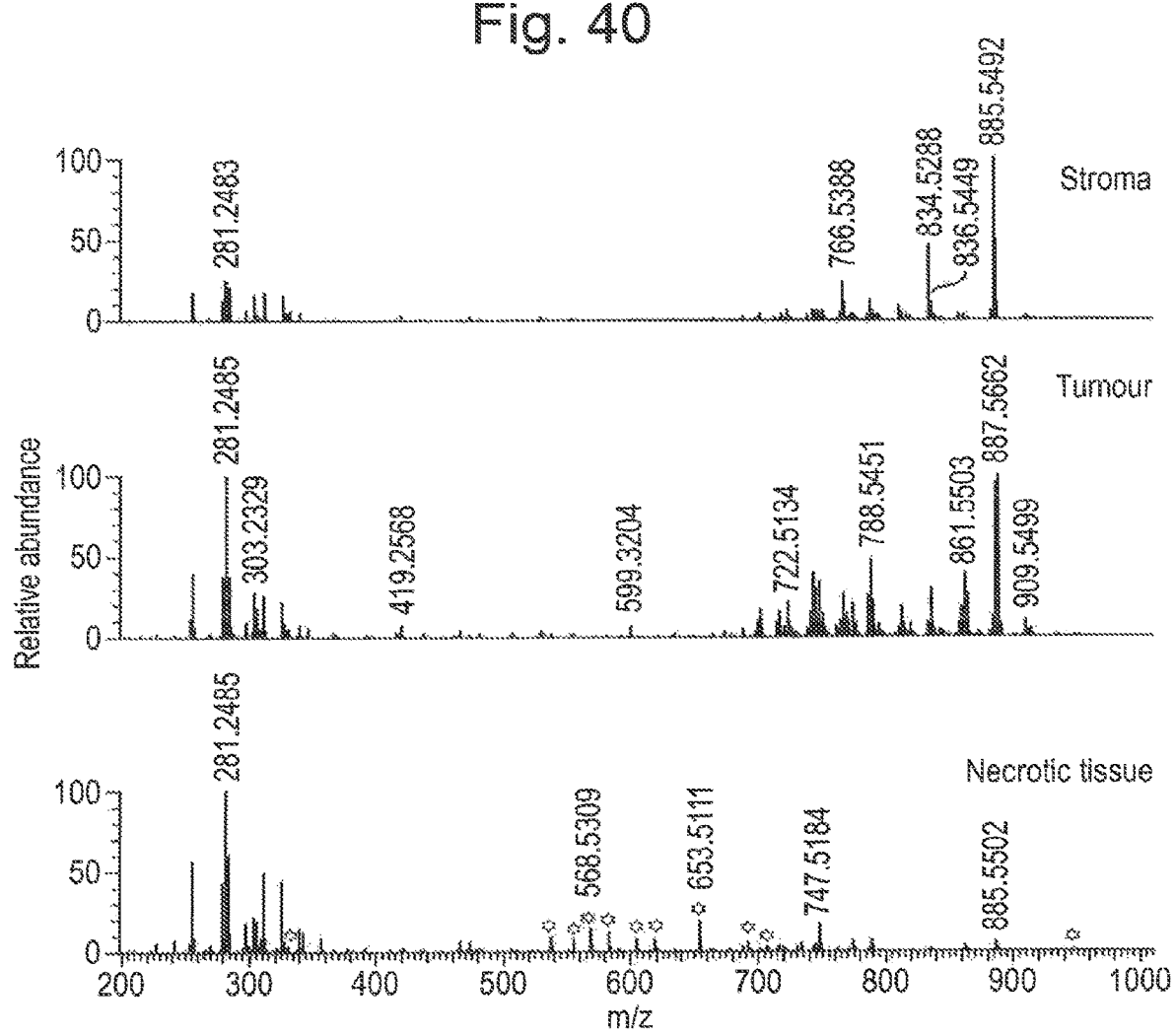

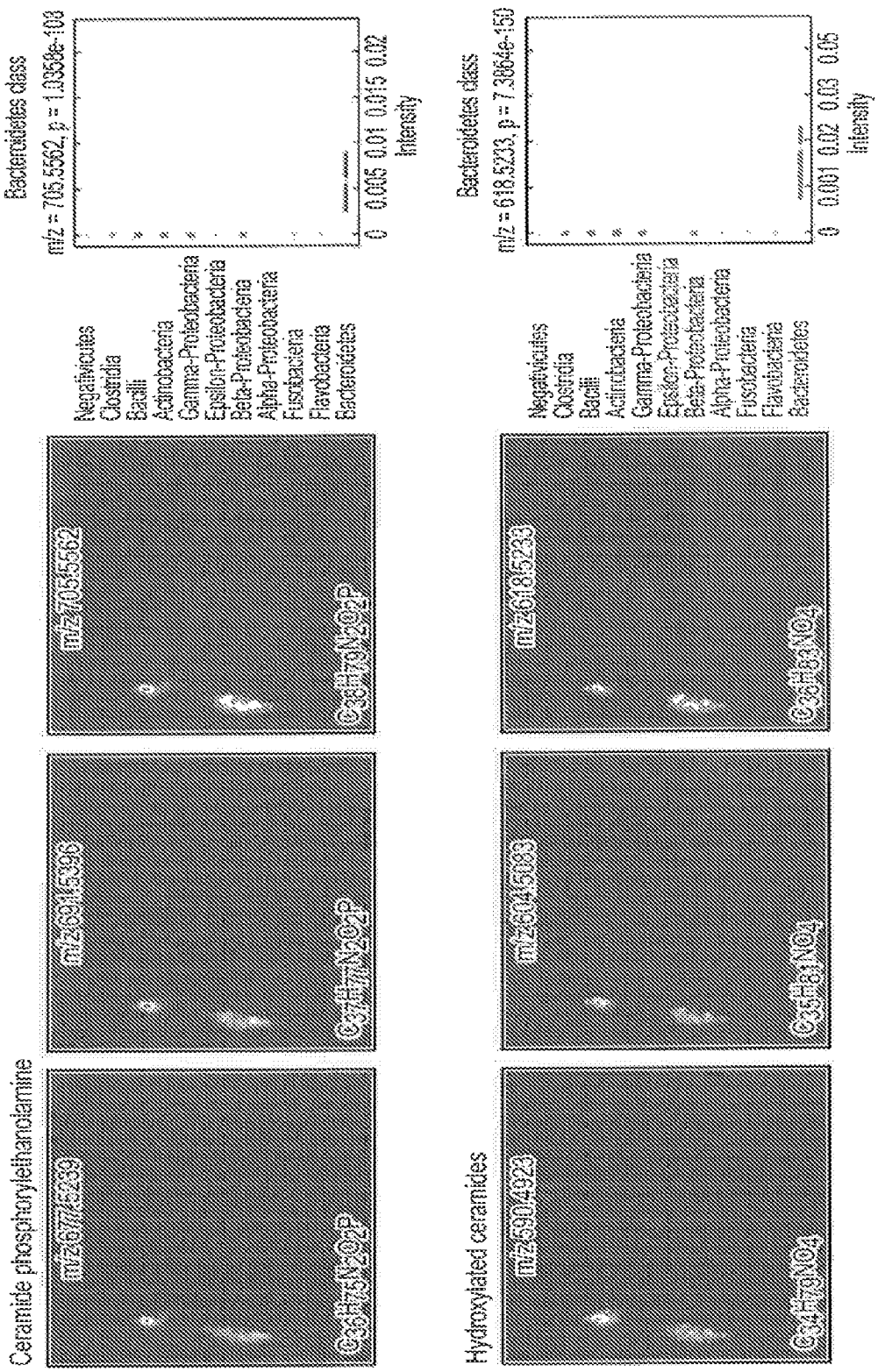

Fig. 43A
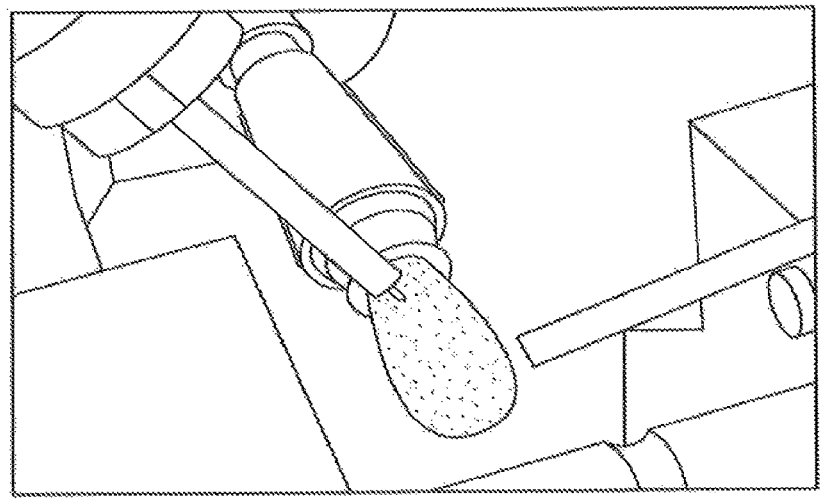
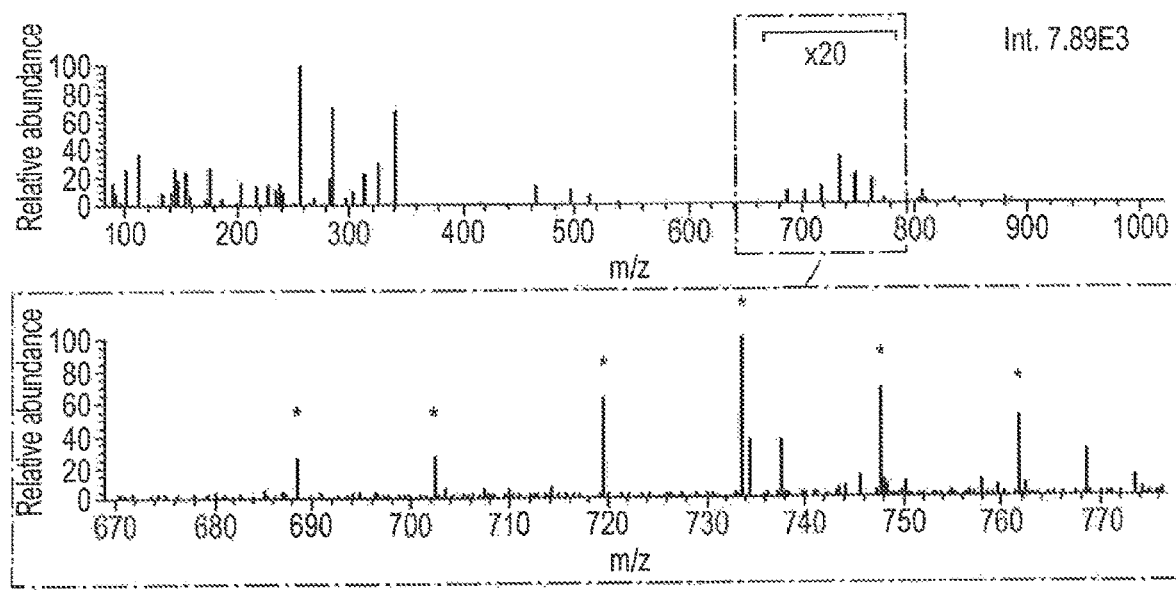

Fig. 43B
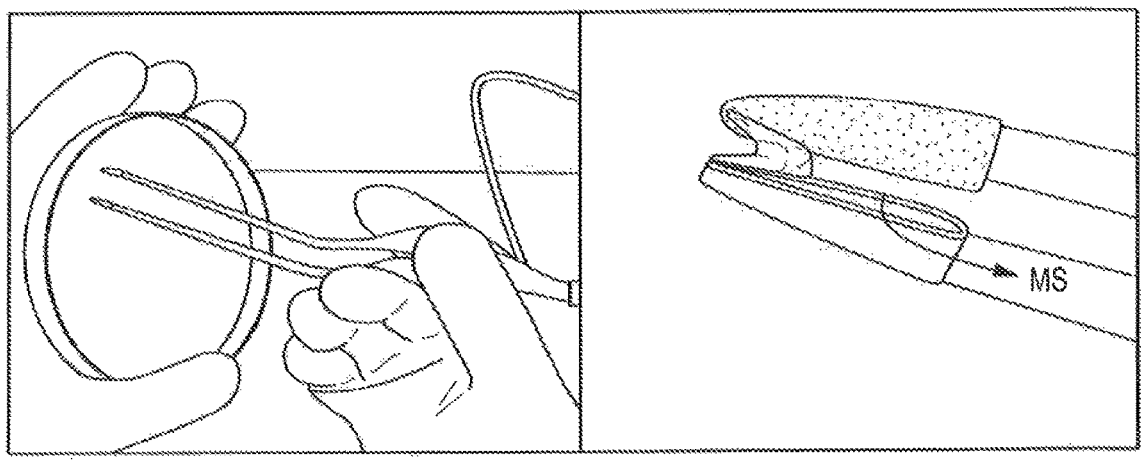
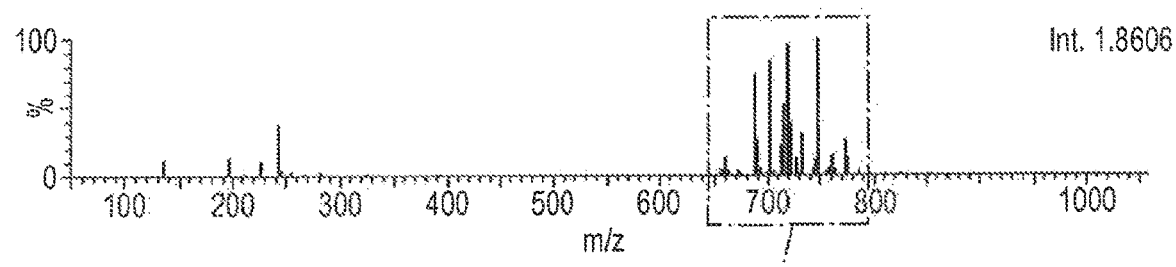
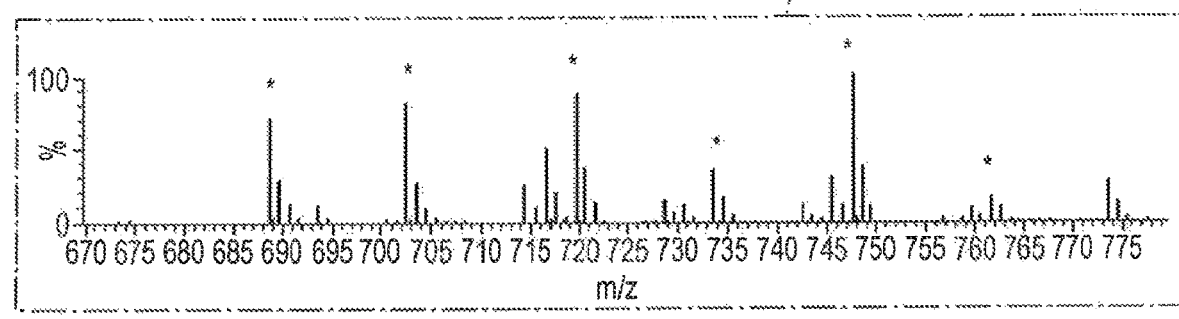

SPECTROMETRIC ANALYSIS OF MICROBES

CROSS-REFERENCE TO RELATED APPLICATIONS

This application is a continuation application of U.S. patent application Ser. No. 17/531,490, filed Nov. 19, 2021, which is a continuation of U.S. patent application Ser. No. 15/556,022, filed Sep. 6, 2017, which is the U.S. National Phase of International Application No. PCT/GB2016/050610, filed Mar. 7, 2016, which claims priority from and the benefit of United Kingdom patent application No. 1503876.3 filed on Mar. 6, 2015, United Kingdom patent application No. 1503864.9 filed on Mar. 6, 2015, United Kingdom patent application No. 1518369.2 filed on Oct. 16, 2015, United Kingdom patent application No. 1503877.1 filed on Mar. 6, 2015, United Kingdom patent application No. 1503867.2 filed on Mar. 6, 2015, United Kingdom patent application No. 1503863.1 filed on Mar. 6, 2015, United Kingdom patent application No. 1503878.9 filed on Mar. 6, 2015, United Kingdom patent application No. 1503879.7 filed on Mar. 6, 2015 and United Kingdom patent application No. 1516003.9 filed on Sep. 9, 2015. The entire contents of these applications are incorporated herein by reference.

FIELD OF THE INVENTION

The present invention relates to mass spectrometry and/or ion mobility spectrometry and in particular to methods of detecting, identifying and/or characterising microbes and/or compounds produced by microbes.

BACKGROUND

Traditional methods of microbial detection or identification rely on culture-based detection, followed by phenotypic identification of the microbe using microscopic analysis, Gram staining, culture and/or biochemical assays to detect certain biomarkers. It is estimated that only about 1% of all microorganisms can be cultured, so culture-based approaches have significant drawbacks.

Although not a taxonomical classification, the Gram strain of bacteria is a widely used classification system for bacteria, especially in clinical microbiological practice. Using Gram-staining, bacteria can generally be subdivided into two groups, Gram-positive and Gram-negative staining bacteria. The Gram-staining behaviour is determined by the capabilities of the peptidoglycan layer of the bacterial cell wall to retain the crystal violet dye. Gram-negative bacteria are encased by an inner cell membrane, a cell wall comprising peptidoglycan, and an outer cell membrane, whereas Gram-positive bacteria lack the outer cell membrane. Gram-stains are of significant importance in clinical microbiology settings because Gram-positives generally are more susceptible for antibiotics due to the lack of the outer cell membrane.

More recent methods typically involve molecular biology analysis techniques such as nucleic acid analysis using restriction enzymes, hybridisation, polymerase chain reaction (PCR) amplification and/or sequencing. These methods generally need extensive and careful sample preparation, are comparably expensive and still need at least several hours for identification. Due to these reasons, sequencing methods are rarely applied in routine clinical settings.

Bacterial species are typically defined by their 16S rRNA sequence, thus sequencing of the 16S rRNA encoding gene serves as the gold standard for bacterial identification and classification. Partial or full 16S rRNA sequencing has the advantage of being culture-independent and thus is especially valuable for fastidious microorganisms. However, the sensitivity and specificity for direct sample applications varies considerably. Moreover, in some cases bacterial species cannot be confidently identified by their 16S rRNA sequence, necessitating the application of additional techniques such as sequencing of further gene targets.

Bacteria are reliant on their cell envelope to protect them. The bacterial cell envelope is a complex structure comprising at least one phospholipid bilayer. The survival of bacteria depends especially on membrane lipid homeostasis and the ability to adjust lipid composition to adapt the bacterial cell to different environments. Most membrane phospholipids are glycerolipids that contain two fatty acid chains. These phospholipid acyl chains determine the viscosity of the membrane, which in turn influences many crucial membrane-associated functions, such as the passive permeability of hydrophobic molecules, active solute transport and protein-protein interactions.

The most commonly encountered phosphatidylglycerol lipids are phosphatidic acids (PAs), phosphatidylethanolamines (PEs), phosphatidylglycerols (PGs), phosphatidylcholines (PCs), phosphatidylinositols (PIs) and phosphatidylserines (PSs). They share a common phosphatidylglycerophosphate backbone but differ in the chemical nature of their respective headgroups. Two fatty acids are attached to the glycerol backbone in sn1- and sn2-position and usually are present in various chain lengths of between 14 and 20 carbons. Many of these fatty acids contain trans double bonds, a single cis double bond, or iso or anteiso methyl branches. The formation of cyclopropane rings by methylation of cis double bonds is another commonly occurring modification among bacteria. Bacteria have evolved a number of different mechanisms to control the de-novo formation of fatty acids and modify the structure of existing fatty acids in order to adjust membrane viscosity as required.

Another available technique is fatty acid profiling of microbes, such as bacteria, using gas-chromatography coupled to a flame ionisation detector (GC-FID).

Mass spectrometry-based identification of microorganisms has been shown to be applicable to some microorganisms. For example, matrix-assisted laser desorption ionisation time-of-flight mass spectrometry (MALDI-TOF-MS) can provide microbial identifications.

Knowledge of the identity of a pathogen causing disease facilitates adequate medical treatment, and, e.g., in clinical settings, information about certain characteristics of a microbe can be particularly useful. For example, knowledge regarding the susceptibility or resistance of a microbe to an antibiotic or other drug can help to guide treatment decisions. A quick decision on the most suitable antibiotic treatment can significantly shorten the duration of the infection and in some cases, such as meningitides or sepsis, potentially be life-saving.

Extensive research was performed using MALDI-TOF-MS to address this and other shortcomings in subspecies typing and led to solutions being developed for some of these problems such as the detection of β-lactamase activity to determine susceptibility to β-lactam antibiotics. However, these solutions require additional sample-preparation and culturing steps which are time-consuming. Moreover, only a small subset of the proteins present within a microbe can be detected with MALDI-MS measurements. It was shown that the proteins detected from whole cells by MALDI share the properties of high abundance, strong basicity, and medium hydrophobicity. In the case of *E. coli*, all of the detected proteins originated from the cell interior, with about half of those coming from the ribosome.

A major drawback of routine MALDI-TOF-MS protocols involving bacterial protein profiling is that it is not directly applicable to human samples, because the human protein background and low bacterial counts complicate bacterial detection. It is also not particularly suitable for analysing microbial mixtures, as the components of microbial mixtures typically cannot be reliably identified.

Thus, there is still an unmet need for a microbial identification method that would lead to taxonomic information, such as species-level information, while ideally simultaneously providing information on microbial phenotypes, such as information that would allow selection of an adequate antimicrobial treatment.

It is desired to provide a method of analysis, e.g., detection, identification and/or characterisation of microbes and/or compounds produced by microbes.

SUMMARY

The present invention relates generally to the application of mass spectrometry and/or ion mobility spectrometry to analyse a sample which may comprise microbes and/or compounds produced by microbes.

The invention provides a method of analysis using mass spectrometry and/or ion mobility spectrometry comprising:

(a) using a first device to generate smoke, aerosol or vapour from a target comprising or consisting of a microbial population;

(b) mass analysing and/or ion mobility analysing said smoke, aerosol or vapour, or ions derived therefrom, in order to obtain spectrometric data; and (c) analysing said spectrometric data in order to analyse said microbial population.

Various embodiments are contemplated wherein analyte ions are generated from the target, smoke, aerosol or vapour, e.g., by an ambient ionisation ion source. The analyte ions, or ions derived therefrom, may be subjected either to: (i) mass analysis by a mass analyser such as a quadrupole mass analyser or a Time of Flight mass analyser; (ii) ion mobility analysis (IMS) and/or differential ion mobility analysis (DMA) and/or Field Asymmetric Ion Mobility Spectrometry (FAIMS) analysis; and/or (iii) a combination of firstly ion mobility analysis (IMS) and/or differential ion mobility analysis (DMA) and/or Field Asymmetric Ion Mobility Spectrometry (FAIMS) analysis followed by secondly mass analysis by a mass analyser such as a quadrupole mass analyser or a Time of Flight mass analyser (or vice versa). Various embodiments also relate to an ion mobility spectrometer and/or mass analyser and a method of ion mobility spectrometry and/or method of mass analysis.

Embodiments of the methods provided herein are discussed in the detailed description.

Optional features of the methods are discussed below. Thus, unless otherwise stated, any reference to "a method" or "the method" is intended to be a reference to any of the provided methods listed herein. It is explicitly intended that any of these features may be present in any combination in any of these methods.

Also provided is a method of ion imaging comprising: automatically sampling using a rapid evaporation ionization mass spectrometry ("REIMS") device a plurality of different locations of a bacterial and/or a fungal sample which has been cultured on to a culture medium; obtaining spectrometric data corresponding to each said location; and using said obtained spectrometric data to identify one or more bacterial strains and/or one or more fungal strains at each said location.

Optionally, said culture medium comprises an agar-based medium, a carbohydrate matrix or another solid growth medium.

Optionally, said method further comprises determining the spatial distribution of one or more excreted substances emanating from one or more bacterial colonies and/or fungal colonies which have been cultured on said medium.

Optionally, said one or more excreted substances is selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; and (xx) one or more ribosomal peptides.

Optionally, the step of automatically sampling a plurality of different locations of a bacterial and/or fungal sample comprises sampling using a disposable tip.

Also provided is an ion imager comprising:

a rapid evaporation ionization mass spectrometry ("REIMS") device which is arranged to automatically sample a plurality of different locations of a bacterial and/or a fungal sample which has been cultured on to a culture medium; and a mass and/or ion mobility analyser arranged and adapted: (i) to obtain spectrometric data corresponding to each said location; and (ii) to use said obtained spectrometric data to identify one or more bacterial strains and/or one or more fungal strains at each said location.

Optionally, said culture medium comprises an agar-based medium, a carbohydrate matrix or another solid growth medium.

Optionally, said ion imager is arranged and adapted to determine the spatial distribution of one or more excreted substances emanating from one or more bacterial colonies and/or fungal colonies which have been cultured on said medium.

Optionally, said one or more excreted substances is selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; and (xx) one or more ribosomal peptides.

Optionally, said ion imager is arranged and adapted to use a disposable tip to automatically sampling a plurality of different locations of a bacterial and/or a fungal sample.

Also provided is a method of Rapid Evaporation Ionization Mass Spectrometry ("REIMS") comprising:

using a REIMS ionisation source to analyse a biological liquid for the presence or absence of bacteria in said biological liquid.

Optionally, said biological liquid is selected from the group consisting of: (i) blood; (ii) urine; (iii) saliva; (iv) sputum; or (v) serum.

Optionally, said method further comprises using a disposable sampling tip to sample said biological liquid.

Optionally, said method further comprises aspirating or passing said biological liquid through a filter media.

Optionally, said method further comprises analysing residue on said filter media which remains after said biological liquid has been aspirated or passed through said filter media.

Obtaining the spectrometric data may comprise recording the ion signal intensity of the ions derived from the smoke, aerosol or vapour as a function of one or more physicochemical property (or as a function of a property related thereto). For example, the ion signal intensity may be recorded as a function of mass to charge ratio and/or ion mobility. The location and/or size and/or pattern of peaks in this recorded ion signal may then be used to characterise or identify one or more analytes present in the smoke, aerosol or vapour.

Tandem mass spectrometry may be used to assign an analyte/compound to each of the peaks. For example, parent ions having a physicochemical property (e.g., mass to charge ratio) corresponding to that of a peak may be isolated (e.g., using a mass filter) and then fragmented or reacted so as to produce fragment or product ions. These fragment or product ions may then be analysed (e.g., by mass analysis) and their determined properties used to identify the parent ion giving rise to the peak in the ion signal. Such tandem mass spectrometry may be used, for example, to identify biomarkers in the spectrometric data.

The mass and/or ion mobility spectrometer may obtain data in negative ion mode only, positive ion mode only, or in both positive and negative ion modes. Positive ion mode spectrometric data may be combined or concatenated with negative ion mode spectrometric data. Negative ion mode can provide particularly useful spectra for classifying aerosol, smoke or vapour samples, such as aerosol, smoke or vapour samples from targets comprising lipids.

Ion mobility spectrometric data may be obtained using different ion mobility drift gases, or dopants may be added to the drift gas to induce a change in drift time of one or more species. This data may then be combined or concatenated.

Also provided is an apparatus comprising:

a Rapid Evaporation Ionization Mass Spectrometry ("REIMS") device which is arranged and adapted to analyse a biological liquid for the presence or absence of bacteria in said biological liquid.

Optionally, said biological liquid is selected from the group consisting of: (i) blood; (ii) urine; (iii) saliva; (iv) sputum; or (v) serum.

Optionally, said apparatus further comprises a disposable sampling tip to sample said biological liquid.

Optionally, said apparatus further comprises a device which is arranged and adapted to aspirate or pass said biological liquid through a filter media.

Optionally, said apparatus further comprises an analyser which is arranged and adapted to analyse residue on said filter media which remains after said biological liquid has been aspirated or passed through said filter media.

Also provided is a method comprising:

obtaining an optical image of a substrate and determining on the basis of said optical image if one or more areas of interest exist on said substrate;

wherein if one or more areas of interest are determined to exist, then said method further comprises the steps of:

(i) automatically sampling at least one location within at least one determined area of interest using a rapid evaporation ionization mass spectrometry ("REIMS") device and obtaining spectrometric data corresponding to said at least one location; and (ii) using said obtained spectrometric data to identify one or more bacterial strains and/or one or more fungal strains at said one or more locations.

Optionally, said substrate comprises a food product.

Also provided is an apparatus comprising:

a rapid evaporation ionization mass spectrometry ("REIMS") device;

a device arranged and adapted to obtain an optical image of a substrate; and a control system arranged and adapted:

(i) to determine on the basis of said optical image if one or more areas of interest exist on said substrate, wherein if one or more areas of interest are determined to exist, then said control system is further arranged and adapted to:

(ii) to automatically sample at least one location within at least one determined area of interest using said rapid evaporation ionization mass spectrometry ("REIMS") device and to obtain spectrometric data corresponding to said at least one location; and (iii) to use said obtained spectrometric data to identify one or more bacterial strains and/or one or more fungal strains at said one or more locations.

Optionally, said substrate comprises a food product.

Also provided is a method of ion imaging comprising:

dispensing a bacterial and/or fungal sample onto a culture medium, wherein one or more antibiotic and/or antifungal substances are embedded within and/or on said culture medium; automatically sampling using a rapid evaporation ionization mass spectrometry ("REIMS") device a plurality of different locations of said bacterial and/or a fungal sample which has been cultured on said culture medium; obtaining spectrometric data corresponding to each said location; and determining from said spectrometric data information concerning the resistance or otherwise of said sample to said one or more antibiotic and/or antifungal substances.

Also provided is an ion imager comprising: a rapid evaporation ionization mass spectrometry ("REIMS") device; and a control system arranged and adapted:

(i) to automatically sample using said rapid evaporation ionization mass spectrometry ("REIMS") device a plurality of different locations of a bacterial and/or a fungal sample which has been cultured on a culture medium, wherein one or more antibiotic and/or antifungal substances are embedded within and/or on said culture medium;

(ii) to obtain spectrometric data corresponding to each said location; and (iii) to determine from said spectrometric data information concerning the resistance or otherwise of said sample to said one or more antibiotic and/or antifungal substances.

Numerous different applications are contemplated and these will now be described in greater detail below.

BRIEF DESCRIPTION OF THE DRAWINGS

Various embodiments will now be described, by way of example only, and with reference to the accompanying drawings in which:

FIGS. 12A-12B show a DESI method for analyzing a target comprising or consisting of a microbial population;

FIG. 24 shows a method of analysis that comprises building a classification library according to various embodiments;

FIG. 25 shows a method of analysis that comprises using a classification library according to various embodiments;

FIG. 27C shows spectral profiles of an amalgamated sample containing an equal ratio of the two, wherein isolate specific peaks are highlighted;

FIG. 29 shows LDA and cross validation analysis of MRSA and MSSA isolates;

FIGS. 31A-31D show zoomed regions of mass spectra of *S. aureus* grown under aerobic (A and C) and anaerobic (C and D) conditions. A+B) m/z 650-800, C+D) m/z 1250-1750;

Figure 37A:
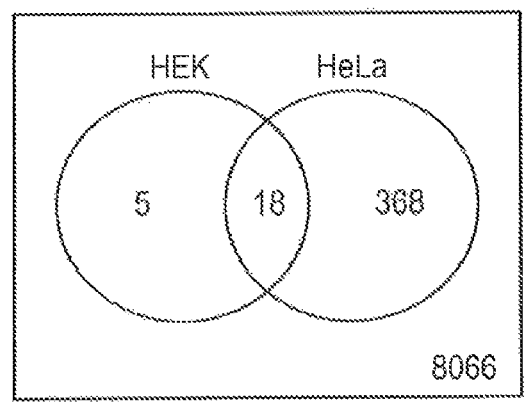
Figure 38A:
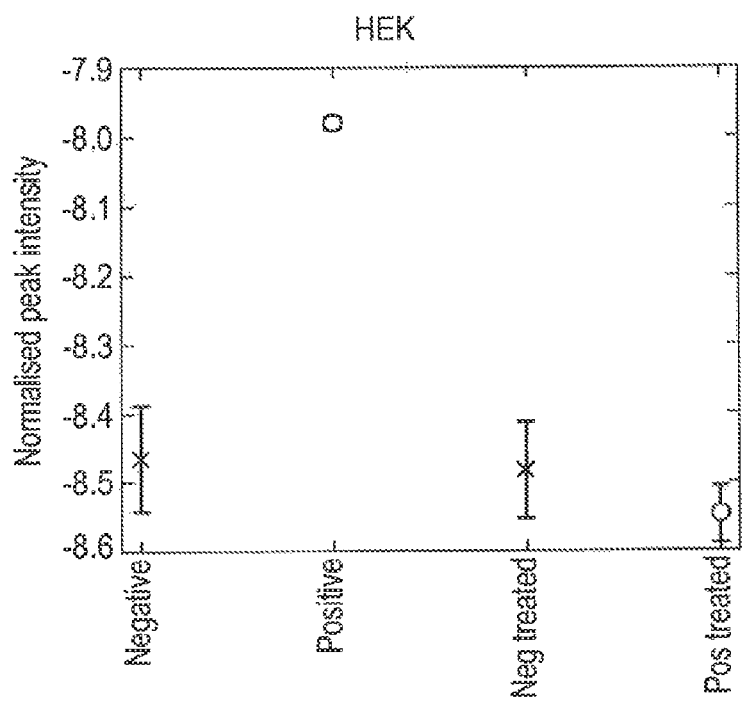
Figure 38B:
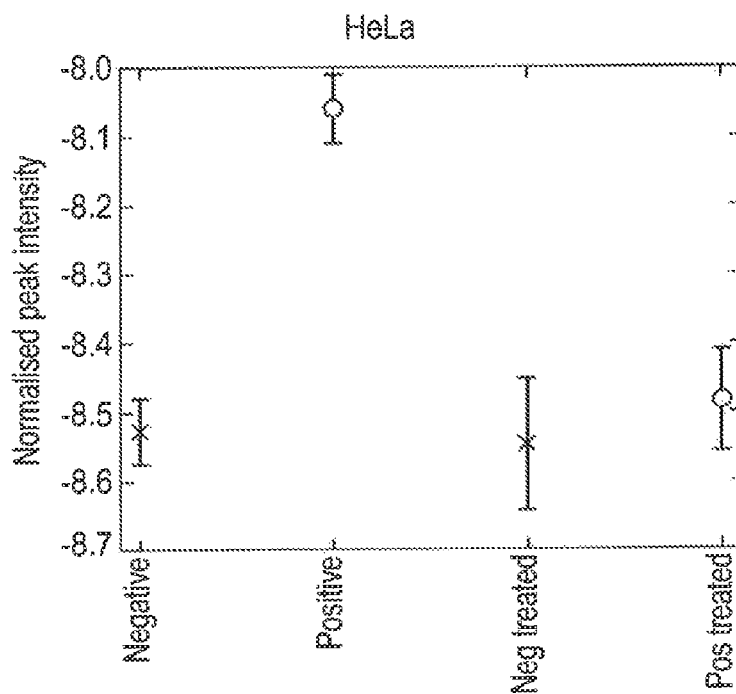
Figure 39A:
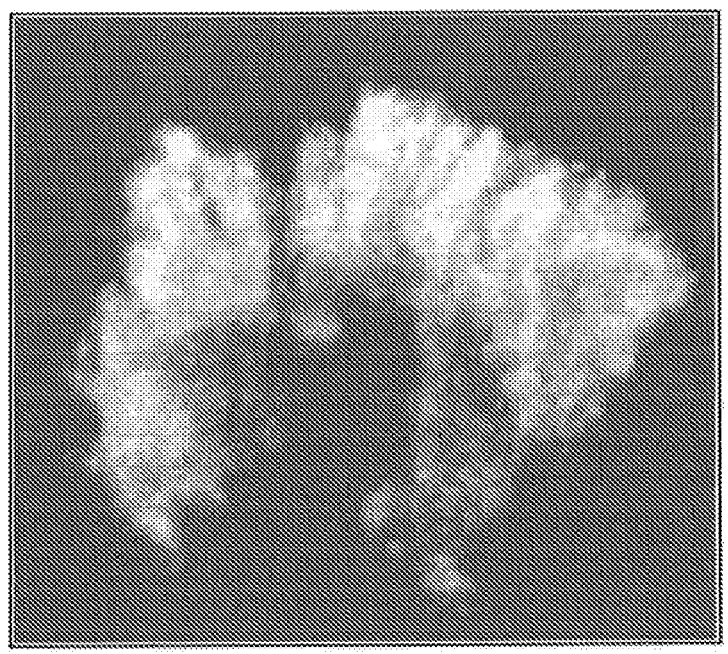
Figure 39B:
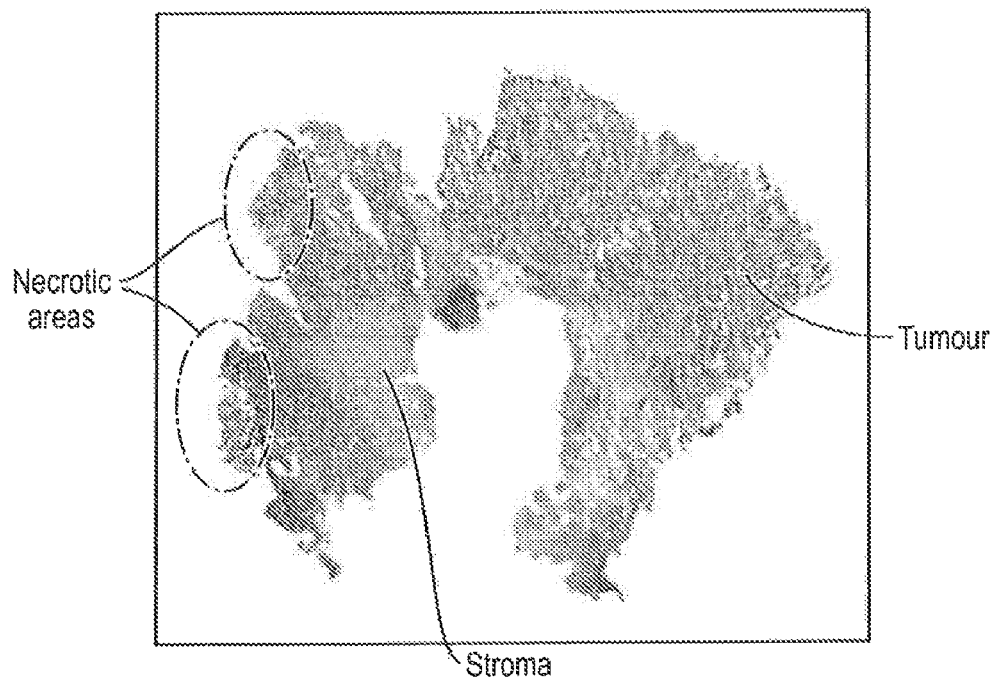
Figure 41:
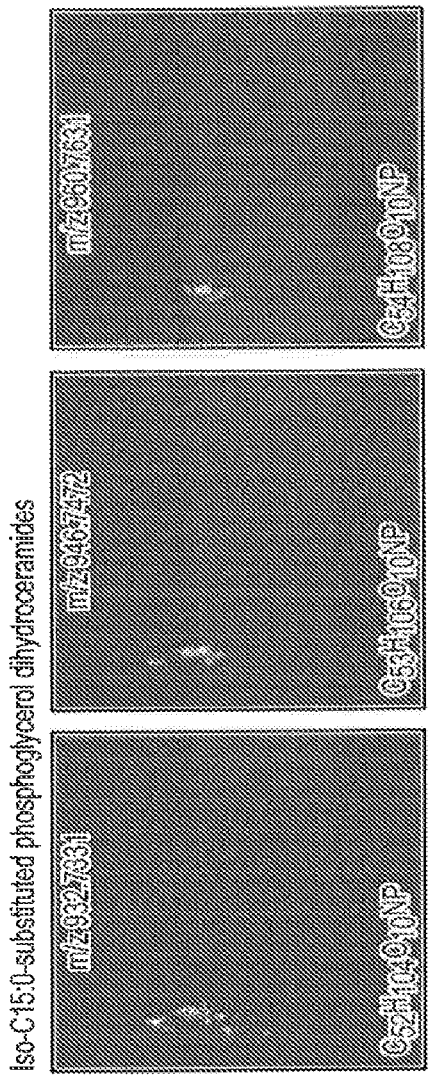
Figure 42:
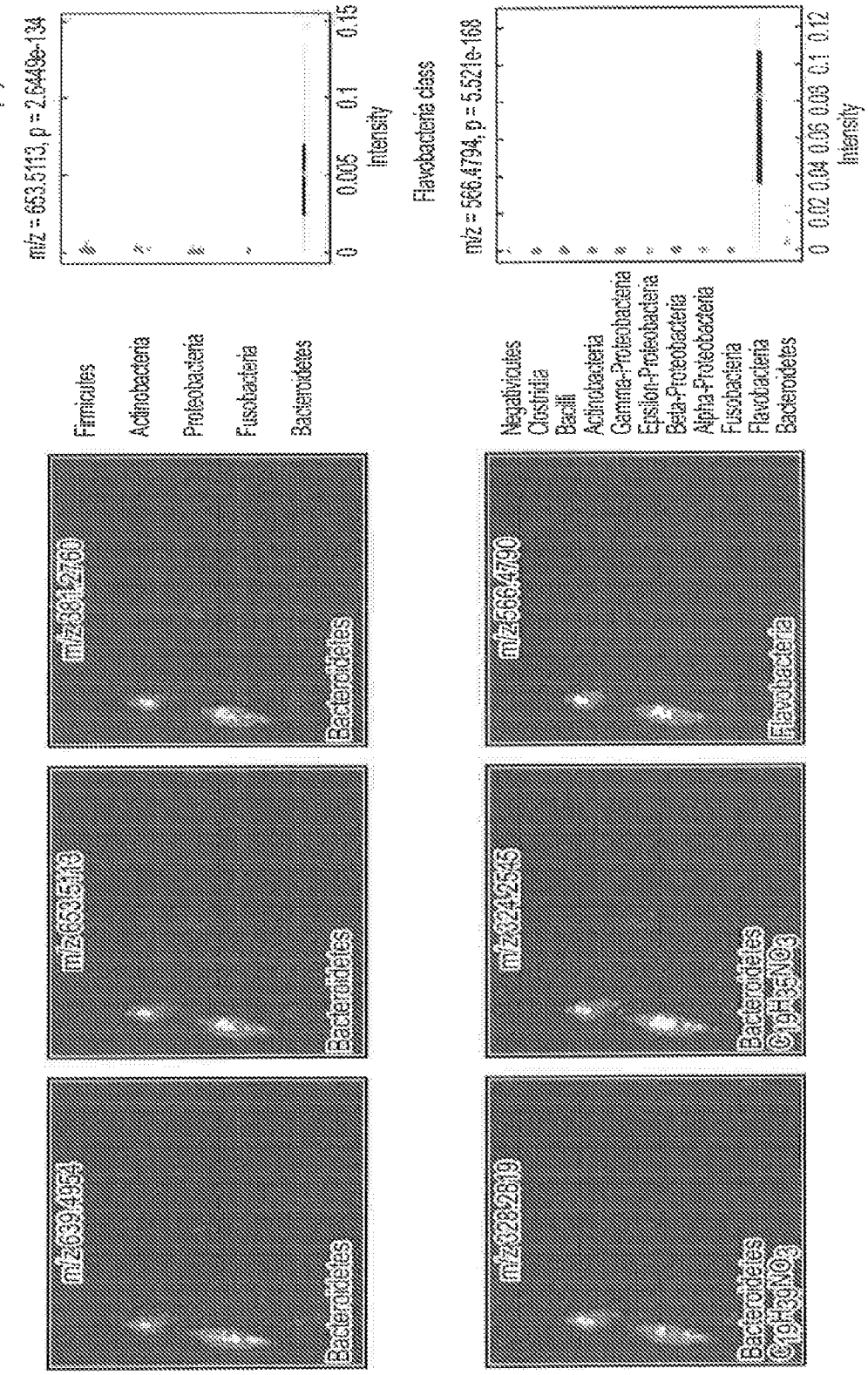
Figure 42:
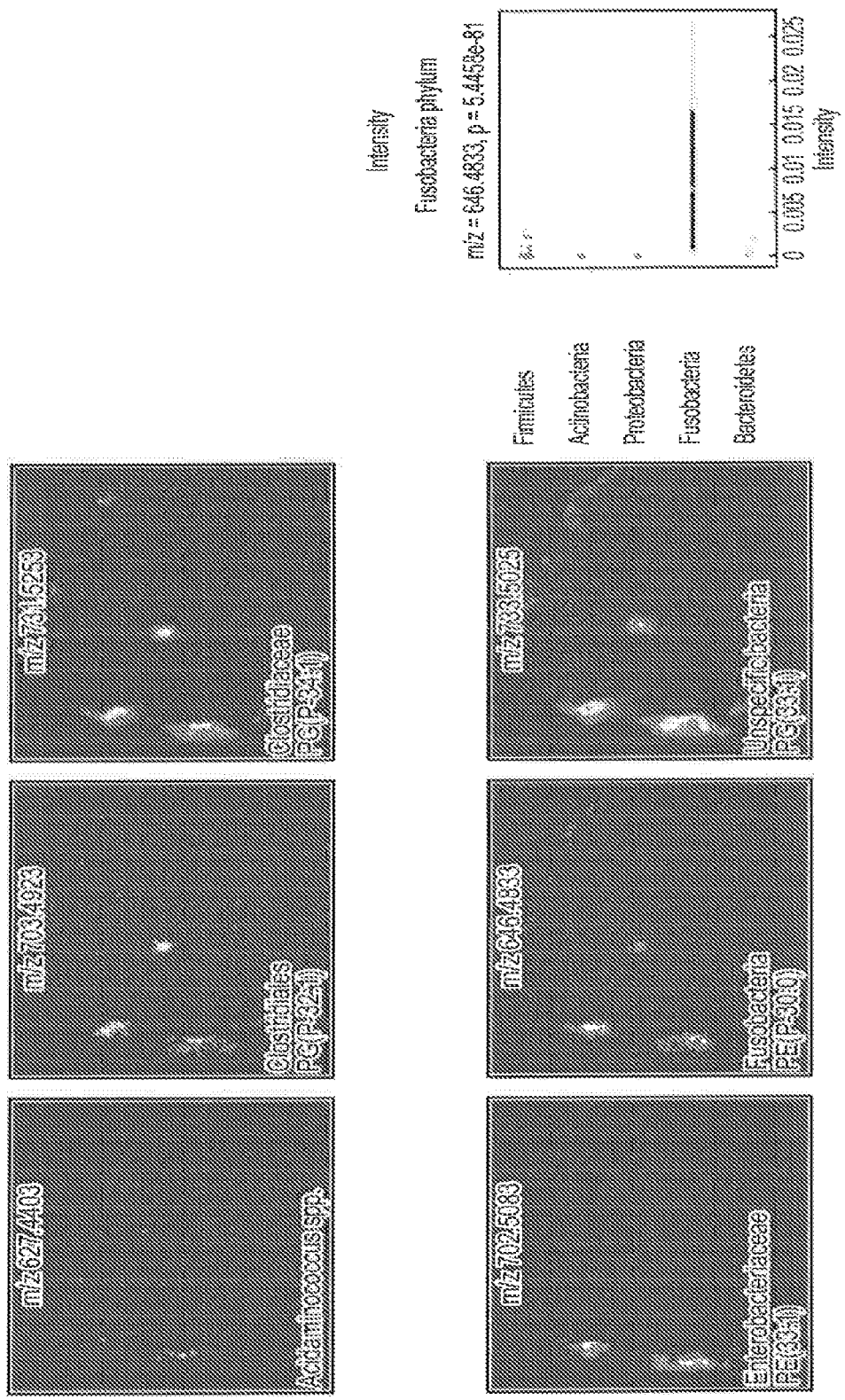
Figure 44A:
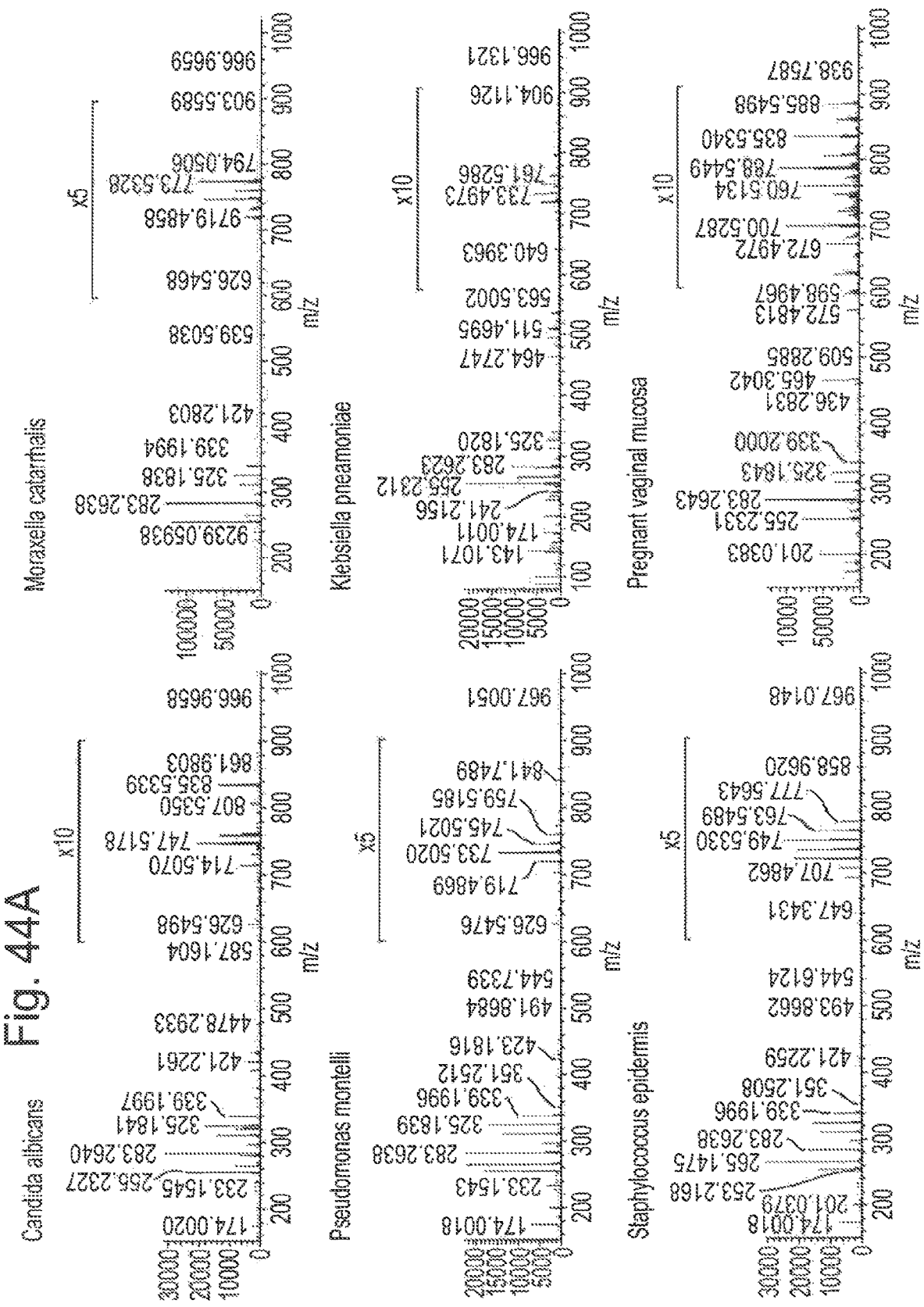
Figure 44B:
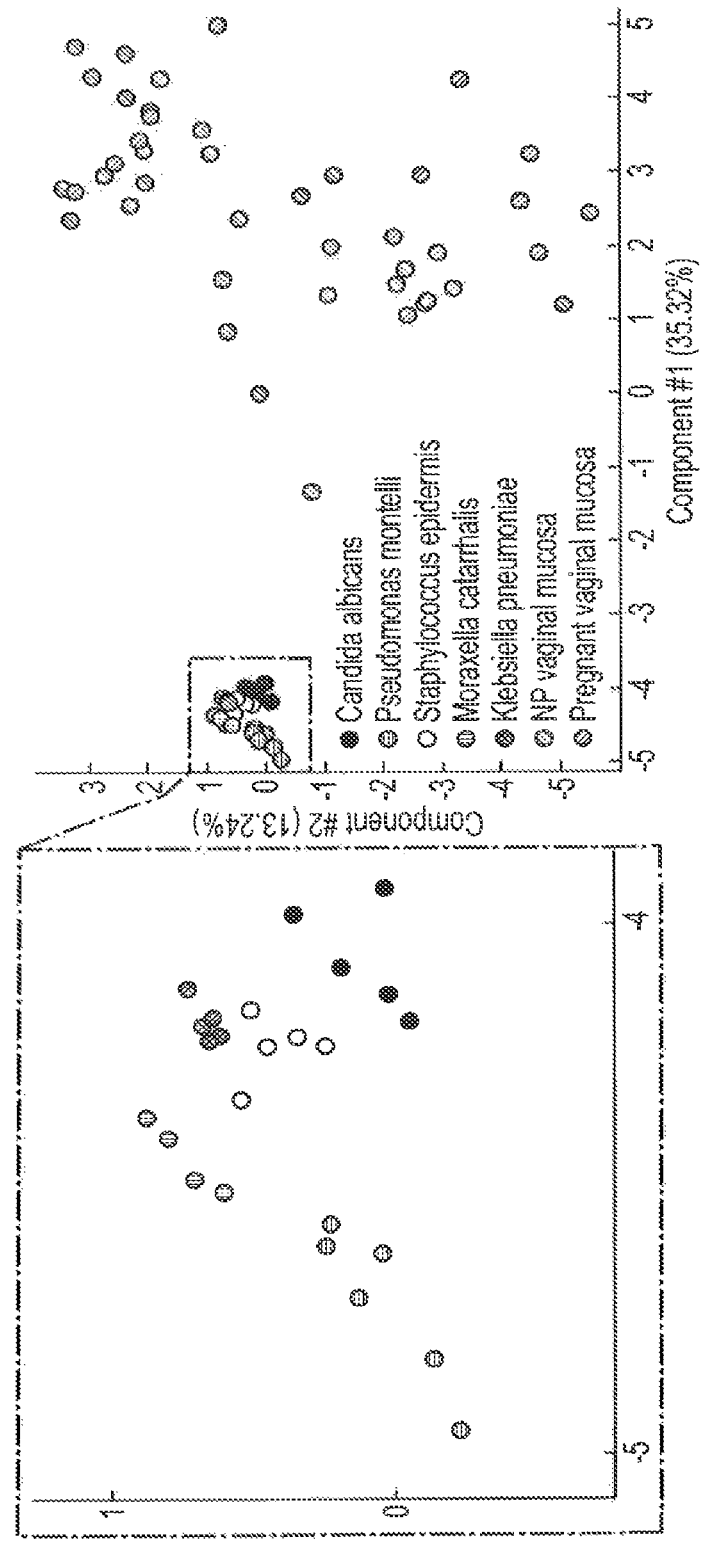
Figure 44C:
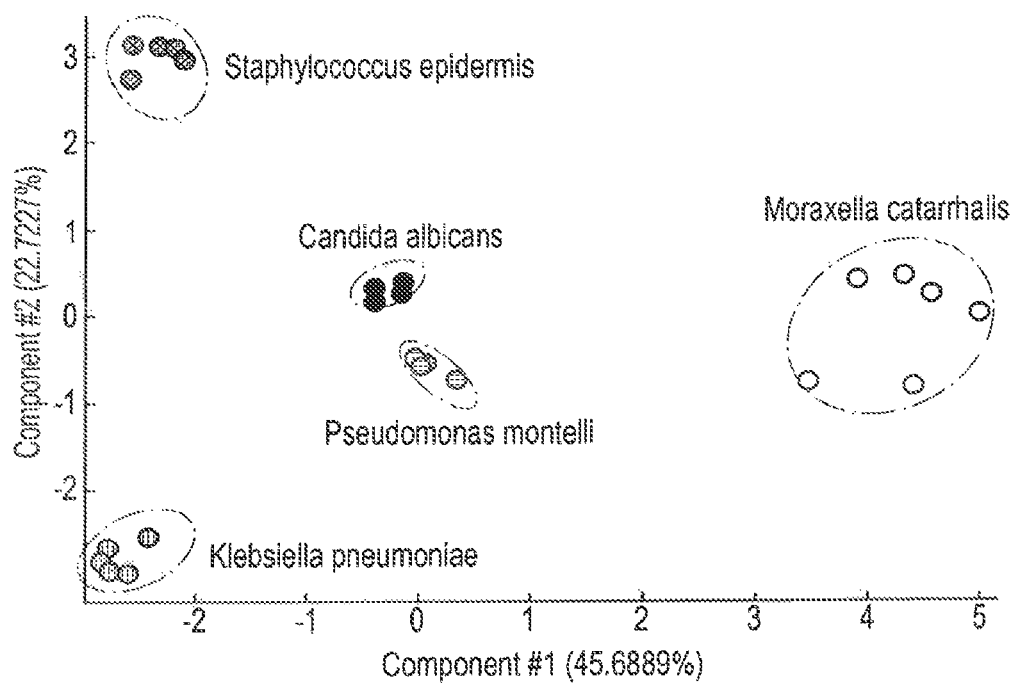

sample, day 2 corresponds with the addition of Plasmocin®, day 3 corresponds with Plasmocin® still being present, day 4 corresponds with the removal of Plasmocin® and wherein day 5 corresponds with all samples being Mycoplasma-free;

FIG. 37A shows a number of significantly higher m/z signals in Mycoplasma-infected versus Mycoplasma-free samples in HEK and HeLa cell lines. For FIG. 37B Mycoplasma-infected (+) and Mycoplasma-free (−) HEK (rectangle) and HeLa (triangle) cells were either treated (t) or untreated (u). Samples are shown as a function of PC1 and PC2 of PCA transformed samples in the space of the 18 overlapping m/z signals;

FIGS. 38A and 38B show intensities of TIC normalised and log-transformed signals at m/z=819.52 (corresponding to PG(40:7)) in mycoplasma-free, mycoplasma-infected and Plasmocin™ treated samples in HeLa (FIG. 38A) and HEK cell lines (FIG. 38B);

FIGS. 39A-B show the tissue type-distribution of a cancerous tissue specimen that originated from the centre of tumour dissected during a right hemicolectomy. FIG. 39A is a DESI-MS image displaying tissue type distribution in a colorectal tissue specimen; the original image showed tumour tissue in green and stroma tissue in red. On the black and white Figure, tumour tissue is light grey and stroma tissue is darker grey. FIG. 39B is a H&E stained and histopathologically annotated section post-DESI;

FIG. 40 shows full scan mass spectra for colorectal adenocarcinoma, tumour surrounding stroma and necrotic tissue of same tissue section shown in FIG. 39. Stars indicate major taxonomic markers;

FIG. 41 shows single ion images and representative intensity distribution plots for known and confirmed homologous sphingolipid species that showed specificity as taxonomic markers; a signal corresponding to m/z=705.5562 indicates the presence of a ceramide phosphorylethanolamine, which in turn indicates a member of the bacteriodetes class, as shown on the right; a signal corresponding to m/z=618.5233 indicates a hydroxylated ceramide, which in turn indicates a member of the bacteriodetes class, as shown on the right; a signal corresponding to m/z=946.7472 indicates an Iso-C15:0-substituted phosphoglycerol dihydroceramide, which in turn is indicative of a member of the Porphyromonadacae family;

FIG. 42 shows single ion images and intensity selected distribution plots for other taxonomical markers a signal corresponding to m/z=653.5113 is indicative of a member of the Bacteriodetes phylum, as shown on the right; a signal corresponding to m/z=566.4794 is indicative of a member of the Flavobacteria class, as shown on the right; a signal corresponding to m/z=731.5253 is indicative of a member of the Clostridiaceae family; and a signal corresponding to m/z=646.4833 is indicative of a member of the Fusobacteria phylum, as shown on the right;

FIG. 43A shows desorption electrospray ionisation ("DESI") spectrometric analysis of a microbial sample on a swab in accordance with various embodiments and shows that microbial samples can be detected using DESI, and FIG. 43B shows a comparison with rapid evaporative ionisation mass spectrometry ("REIMS") analysis in conjunction with a Time of Flight mass analysis of a microbial sample directly from an agar plate;

FIG. 44A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp as well as pregnant vaginal mucosa, and FIGS. 44B and 44C show PCA plots showing a separation between the vaginal mucosa (pregnant and non-pregnant group) from the microorganism species within the first two components, and a separation between the different bacteria and fungi species.

DETAILED DESCRIPTION

Although the methods provided herein have been described with reference to preferred embodiments, it will be understood by those skilled in the art that various changes in form and detail may be made without departing from the scope of the invention as set forth in the accompanying claims.

Mass spectrometry ("MS") based identification techniques such as ambient ionization mass spectrometry are known. Direct ambient ionization mass spectrometry, such as REIMS, has emerged as a technology allowing real-time analysis of targets.

The method provided herein may, for example, be used in or with a real-time, robust characterisation tool which utilises ambient ionisation technologies, such as REIMS.

Various embodiments are described in more detail below which in general relate to generating smoke, aerosol or vapour from a target (details of which are provided elsewhere herein) using an ambient ionization ion source. The aerosol, smoke or vapour may then be mixed with a matrix and aspirated into a vacuum chamber of a mass and/or ion mobility spectrometer. The mixture may be caused to impact upon a collision surface causing the aerosol, smoke or vapour to be ionized by impact ionization which results in the generation of analyte ions. The resulting analyte ions (or fragment or product ions derived from the analyte ions) may then be mass and/or ion mobility analysed and the resulting mass and/or ion mobility spectrometric data may be subjected to multivariate analysis or other mathematical treatment in order to determine one or more properties of the target in real time.

Ambient Ionization Ion Sources

In any of the methods provided herein a device may be used to generate an aerosol, smoke or vapour from one or more regions of a target (details of which are provided elsewhere herein). The device may comprise an ambient ionization ion source which is characterised by the ability to generate analyte aerosol, smoke or vapour from target, optionally with little or no preparation of the target for analysis. By contrast, other types of ionization ion sources such as Matrix Assisted Laser Desorption Ionisation ("MALDI") ion sources require a matrix or reagent to be added to the sample prior to ionization.

It will be apparent that the requirement to add a matrix or a reagent directly to a sample may prevent the ability to perform in vivo analysis of tissue and also, more generally, prevents the ability to provide a rapid simple analysis of target material.

Ambient ionization techniques are particularly useful since they enable a rapid simple analysis of target material to be performed. Whilst there is no requirement to add a matrix or reagent to a sample in order to perform ambient ionization techniques, the method may optionally include a step of adding a matrix or reagent to the target (e.g., directly to the target) prior to analysis. The matrix or reagent may be added to the target, e.g., to lyse the cells of the target or to enhance the signal therefrom during the analysis.

A number of different ambient ionization techniques are known and are intended to fall within the scope of the present invention. As a matter of historical record, Desorption Electrospray Ionisation ("DESI") was the first ambient ionization technique to be developed and was disclosed in 2004. Since 2004, a number of other ambient ionization techniques have been developed. These ambient ionization techniques differ in their precise ionization method but they share the same general capability of generating gas-phase ions directly from samples (e.g., without preparation of the sample for analysis). The various ambient ionization techniques which are intended to fall within the scope of the present invention may not require any sample preparation for the analysis. As a result, the various ambient ionization techniques enable targets to be analysed without the time, expense and problems associated with adding a matrix or reagent to the target material.

A list of ambient ionization techniques which are intended to fall within the scope of the present invention are given in the following table:

| Acronym | Ionisation technique |
| --- | --- |
| DESI | Desorption electrospray ionisation |
| DeSSI | Desorption sonic spray ionisation |
| DAPPI | Desorption atmospheric pressure photoionisation |
| EASI | Easy ambient sonic-spray ionisation |
| JeDI | Jet desorption electrospray ionisation |
| TM-DESI | Transmission mode desorption electrospray ionisation |
| LMJ-SSP | Liquid microjunction-surface sampling probe |
| DICE | Desorption ionisation by charge exchange |
| Nano-DESI | Nanospray desorption electrospray ionisation |
| EADESI | Electrode-assisted desorption electrospray ionisation |
| APTDCI | Atmospheric pressure thermal desorption chemical ionisation |
| V-EASI | Venturi easy ambient sonic-spray ionisation |
| AFAI | Air flow-assisted ionisation |
| LESA | Liquid extraction surface analysis |
| PTC-ESI | Pipette tip column electrospray ionisation |
| AFADESI | Air flow-assisted desorption electrospray ionisation |
| DEFFI | Desorption electro-flow focusing ionisation |
| ESTASI | Electrostatic spray ionisation |
| PASIT | Plasma-based ambient sampling ionisation transmission |
| DAPCI | Desorption atmospheric pressure chemical ionisation |
| DART | Direct analysis in real time |
| ASAP | Atmospheric pressure solid analysis probe |
| APTDI | Atmospheric pressure thermal desorption ionisation |
| PADI | Plasma assisted desorption ionisation |
| DBDI | Dielectric barrier discharge ionisation |
| FAPA | Flowing atmospheric pressure afterglow |
| HAPGDI | Helium atmospheric pressure glow discharge ionisation |
| APGDDI | Atmospheric pressure glow discharge desorption ionisation |
| LTP | Low temperature plasma |
| LS-APGD | Liquid sampling-atmospheric pressure glow discharge |
| MIPDI | Microwave induced plasma desorption ionisation |
| MFGDP | Microfabricated glow discharge plasma |
| RoPPI | Robotic plasma probe ionisation |
| PLASI | Plasma spray ionisation |
| MALDESI | Matrix assisted laser desorption electrospray ionisation |
| ELDI | Electrospray laser desorption ionisation |
| LDTD | Laser diode thermal desorption |
| LAESI | Laser ablation electrospray ionisation |
| CALDI | Charge assisted laser desorption ionisation |
| LA-FAPA | Laser ablation flowing atmospheric pressure afterglow |
| LADESI | Laser assisted desorption electrospray ionisation |
| LDESI | Laser desorption electrospray ionisation |
| LEMS | Laser electrospray mass spectrometry |
| LSI | Laser spray ionisation |
| IR-LAMICI | Infrared laser ablation metastable induced chemical ionisation |
| LDSPI | Laser desorption spray post-ionisation |
| PAMLDI | Plasma assisted multiwavelength laser desorption ionisation |
| HALDI | High voltage-assisted laser desorption ionisation |
| PALDI | Plasma assisted laser desorption ionisation |
| ESSI | Extractive electrospray ionisation |
| PESI | Probe electrospray ionisation |
| ND-ESSI | Neutral desorption extractive electrospray ionisation |
| PS | Paper spray |
| DIP-APCI | Direct inlet probe-atmospheric pressure chemical ionisation |
| TS | Touch spray |
| Wooden-tip | Wooden-tip electrospray |
| CBS-SPME | Coated blade spray solid phase microextraction |
| TSI | Tissue spray ionisation |
| RADIO | Radiofrequency acoustic desorption ionisation |
| LIAD-ESI | Laser induced acoustic desorption electrospray ionisation |
| SAWN | Surface acoustic wave nebulization |
| UASI | Ultrasonication-assisted spray ionisation |
| SPA-nanoESI | Solid probe assisted nanoelectrospray ionisation |
| PAUSI | Paper assisted ultrasonic spray ionisation |
| DPESI | Direct probe electrospray ionisation |
| ESA-Py | Electrospray assisted pyrolysis ionisation |
| APPIS | Ambient pressure pyroelectric ion source |
| RASTIR | Remote analyte sampling transport and ionisation relay |
| SACI | Surface activated chemical ionisation |
| DEMI | Desorption electrospray metastable-induced ionisation |
| REIMS | Rapid evaporative ionisation mass spectrometry |
| SPAM | Single particle aerosol mass spectrometry |
| TDAMS | Thermal desorption-based ambient mass spectrometry |
| MAII | Matrix assisted inlet ionisation |
| SAII | Solvent assisted inlet ionisation |
| SwiFERR | Switched ferroelectric plasma ioniser |
| LPTD | Leidenfrost phenomenon assisted thermal desorption |

According to an embodiment the ambient ionization ion source may comprise a rapid evaporative ionization mass spectrometry ("REIMS") ion source wherein a RF voltage is applied to one or more electrodes in order to generate smoke, aerosol or vapour by Joule heating.

However, it will be appreciated that other ambient ion sources including those referred to above may also be utilised. For example, according to another embodiment the ambient ionization ion source may comprise a laser ionization ion source. According to an embodiment the laser ionisation ion source may comprise a mid-IR laser ablation ion source. For example, there are several lasers which emit radiation close to or at 2.94 µm which corresponds with the peak in the water absorption spectrum. According to various embodiments the ambient ionization ion source may comprise a laser ablation ion source having a wavelength close to 2.94 µm on the basis of the high absorption coefficient of water at 2.94 µm. According to an embodiment the laser ablation ion source may comprise a Er:YAG laser which emits radiation at 2.94 µm.

Other embodiments are contemplated wherein a mid-infrared optical parametric oscillator ("OPO") may be used to produce a laser ablation ion source having a longer wavelength than 2.94 µm. For example, an Er:YAG pumped ZGP-OPO may be used to produce laser radiation having a wavelength of, e.g., 6.1 µm, 6.45 µm or 6.73 µm. In some situations it may be advantageous to use a laser ablation ion source having a shorter or longer wavelength than 2.94 µm since only the surface layers will be ablated and less thermal damage may result. According to an embodiment a Co:MgF$_2$ laser may be used as a laser ablation ion source wherein the laser may be tuned from 1.75-2.5 µm. According to another embodiment an optical parametric oscillator ("OPO") system pumped by a Nd:YAG laser may be used to produce a laser ablation ion source having a wavelength between 2.9-3.1 µm. According to another embodiment a CO$_2$ laser having a wavelength of 10.6 µm may be used to generate the aerosol, smoke or vapour.

According to other embodiments the ambient ionization ion source may comprise an ultrasonic ablation ion source, or a hybrid electrosurgical-ultrasonic ablation source, that generates a liquid sample which is then aspirated as an aerosol. The ultrasonic ablation ion source may comprise a focused or unfocussed ultrasound.

According to an embodiment the first device for generating aerosol, smoke or vapour from the target may comprise a tool which utilises an RF voltage, such as a continuous RF waveform. According to other embodiments a radiofrequency system may be used which is arranged to supply pulsed plasma RF energy to a tool. The tool may comprise, for example, a PlasmaBlade®. Pulsed plasma RF tools operate at lower temperatures than conventional electrosurgical tools (e.g., 40-170° C. c.f. 200-350° C.) thereby reducing thermal damage depth. Pulsed waveforms and duty cycles may be used for both cut and coagulation modes of operation by inducing electrical plasma along the cutting edge(s) of a thin insulated electrode.

According to an embodiment the first device comprises a surgical water/saline jet device such as a resection device, a hybrid of such device with any of the other devices herein, an electrosurgery argon plasma coagulation device, a hybrid argon plasma coagulation and water/saline jet device.

Other embodiments are contemplated wherein the first device for generating aerosol, smoke or vapour from the target may comprise an argon plasma coagulation ("APC") device. An argon plasma coagulation device involves the use of a jet of ionised argon gas (plasma) that is directed through a probe. The probe may be passed through an endoscope. Argon plasma coagulation is essentially a non-contact process as the probe is placed at some distance from the target. Argon gas is emitted from the probe and is then ionized by a high voltage discharge (e.g., 6 kV). High-frequency electric current is then conducted through the jet of gas, resulting in coagulation of the target on the other end of the jet. The depth of coagulation is usually only a few millimetres.

The first device, surgical or electrosurgical tool, device or probe or other sampling device or probe disclosed in any of the aspects or embodiments herein may comprise a non-contact surgical device, such as one or more of a hydrosurgical device, a surgical water jet device, an argon plasma coagulation device, a hybrid argon plasma coagulation device, a water jet device and a laser device.

A non-contact surgical device may be defined as a surgical device arranged and adapted to dissect, fragment, liquefy, aspirate, fulgurate or otherwise disrupt biologic tissue without physically contacting the tissue. Examples include laser devices, hydrosurgical devices, argon plasma coagulation devices and hybrid argon plasma coagulation devices.

As the non-contact device may not make physical contact with the tissue, the procedure may be seen as relatively safe and can be used to treat delicate tissue having low intracellular bonds, such as skin or fat.

According to the various embodiments of the invention, the first device comprises or forms part of an ambient ion or ionisation source; or said first device generates said aerosol, smoke or vapour from the target and contains ions and/or is subsequently ionised by an ambient ion or ionisation source, or other ionisation source.

Optionally, the first device comprises or forms part of a device, or an ion source selected from the group consisting of: (i) a rapid evaporative ionisation mass spectrometry ("REIMS") ion source; (ii) a desorption electrospray ionisation ("DESI") ion source; (iii) a laser desorption ionisation ("LDI") ion source; (iv) a thermal desorption ion source; (v) a laser diode thermal desorption ("LDTD") ion source; (vi) a desorption electro-flow focusing ("DEFFI") ion source; (vii) a dielectric barrier discharge ("DBD") plasma ion source; (viii) an Atmospheric Solids Analysis Probe ("ASAP") ion source; (ix) an ultrasonic assisted spray ionisation ion source; (x) an easy ambient sonic-spray ionisation ("EAST") ion source; (xi) a desorption atmospheric pressure photoionisation ("DAPPI") ion source; (xii) a paperspray ("PS") ion source; (xiii) a jet desorption ionisation ("JeDI") ion source; (xiv) a touch spray ("TS") ion source; (xv) a nano-DESI ion source; (xvi) a laser ablation electrospray ("LAESI") ion source; (xvii) a direct analysis in real time ("DART") ion source; (xviii) a probe electrospray ionisation ("PESI") ion source; (xix) a solid-probe assisted electrospray ionisation ("SPA-ESI") ion source; (xx) a cavitron ultrasonic surgical aspirator ("CUSA") device; (xxi) a hybrid CUSA-diathermy device; (xxii) a focussed or unfocussed ultrasonic ablation device; (xxiii) a hybrid focussed or unfocussed ultrasonic ablation and diathermy device; (xxiv) a microwave resonance device; (xxv) a pulsed plasma RF dissection device; (xxvi) an argon plasma coagulation device; (xxvi) a hybrid pulsed plasma RF dissection and argon plasma coagulation device; (xxvii) a hybrid pulsed plasma RF dissection and JeDI device; (xxviii) a surgical water/saline jet device; (xxix) a hybrid electrosurgery and argon plasma coagulation device; and (xxx) a hybrid argon plasma coagulation and water/saline jet device.

Optionally, the step of using said first device to generate aerosol, smoke or vapour comprises contacting said target with one or more electrodes.

Optionally, said one or more electrodes comprise either: (i) a monopolar device, wherein there is optionally provided a separate return electrode; (ii) a bipolar device; or (iii) a multi-phase RF device, wherein there is optionally provided at least one separate return electrode.

Optionally, said one or more electrodes comprise or forms part of a rapid evaporation ionization mass spectrometry ("REIMS") device.

Optionally, said method further comprises applying an AC or RF voltage to said one or more electrodes in order to generate said aerosol, smoke or vapour.

Optionally, the step of applying said AC or RF voltage to said one or more electrodes further comprises applying one or more pulses of said AC or RF voltage to said one or more electrodes.

Optionally, said step of applying said AC or RF voltage to said one or more electrodes causes heat to be dissipated into said target.

Optionally, said step of using said first device to generate aerosol, smoke or vapour from one or more regions of the target further comprises irradiating the target with a laser.

Optionally, said first device generates aerosol from one or more regions of the target by direct evaporation or vaporisation of target material from said target by Joule heating or diathermy.

Optionally, said step of using said first device to generate aerosol, smoke or vapour from one or more regions of the target further comprises directing ultrasonic energy into said target.

Optionally, said aerosol comprises uncharged aqueous droplets. The droplets may comprise cellular material.

Optionally, at least 50%, 55%, 60%, 65%, 70%, 75%, 80%, 85%, 90% or 95% of the mass or matter generated by said first device and which forms said aerosol may be in the form of droplets.

The first device may be arranged and adapted to generate aerosol wherein the Sauter mean diameter ("SMD", d32) of said aerosol is in a range: (i) <5 μm; (ii) 5-10 μm; (iii) 10-15 μm; (iv) 15-20 μm; (v) 20-25 μm; or (vi) >25 μm.

The aerosol may traverse a flow region with a Reynolds number (Re) in the range: (i) <2000; (ii) 2000-2500; (iii) 2500-3000; (iv) 3000-3500; (v) 3500-4000; or (vi) >4000.

Substantially at the point of generating the aerosol, the aerosol may comprise droplets having a Weber number (We) selected from the group consisting of: (i) <50; (ii) 50-100; (iii) 100-150; (iv) 150-200; (v) 200-250; (vi) 250-300; (vii) 300-350; (viii) 350-400; (ix) 400-450; (x) 450-500; (xi) 500-550; (xii) 550-600; (xiii) 600-650; (xiv) 650-700; (xv) 700-750; (xvi) 750-800; (xvii) 800-850; (xviii) 850-900; (xix) 900-950; (xx) 950-1000; and (xxi) >1000.

Substantially at the point of generating the aerosol, the aerosol may comprise droplets having a Stokes number (Sk) in the range: (i) 1-5; (ii) 5-10; (iii) 10-15; (iv) 15-20; (v) 20-25; (vi) 25-30; (vii) 30-35; (viii) 35-40; (ix) 40-45; (x) 45-50; and (xi) >50.

Substantially at the point of generating the aerosol, the aerosol may comprise droplets having a mean axial velocity selected from the group consisting of: (i) <20 m/s; (ii) 20-30 m/s; (iii) 30-40 m/s; (iv) 40-50 m/s; (v) 50-60 m/s; (vi) 60-70 m/s; (vii) 70-80 m/s; (viii) 80-90 m/s; (ix) 90-100 m/s; (x) 100-110 m/s; (xi) 110-120 m/s; (xii) 120-130 m/s; (xiii) 130-140 m/s; (xiv) 140-150 m/s; and (xv) >150 m/s.

Optionally, said aerosol comprises uncharged aqueous droplets. The droplets may comprise cellular material.

Optionally, the method comprises ionising at least some of said aerosol, smoke or vapour, or analyte therein, so as to generate analyte ions; wherein said analyte ions are analysed to obtain said spectrometric data.

Optionally, the method comprises directing or aspirating at least some of said aerosol, smoke or vapour into a vacuum chamber of a mass and/or ion mobility spectrometer; and/or ionising at least some said aerosol, smoke or vapour, or the analyte therein, within a, or said, vacuum chamber of said spectrometer so as to generate a plurality of analyte ions.

Optionally, the method comprises causing said aerosol, smoke or vapour, or analyte therein, to impact upon a collision surface, optionally located within a, or the, vacuum chamber of said spectrometer, so as to generate the plurality of analyte ions.

Optionally, the collision surface may be heated. The collision surface may be heated to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

Optionally, the method comprises adding a matrix to said aerosol, smoke or vapour;

optionally wherein said matrix is selected from the group consisting of: (i) a solvent for said aerosol, smoke or vapour or analyte therein; (ii) an organic solvent; (iii) a volatile compound; (iv) polar molecules; (v) water; (vi) one or more alcohols; (vii) methanol; (viii) ethanol; (ix) isopropanol; (x) acetone; (xi) acetonitrile; (xii) 1-butanol; (xiii) tetrahydrofuran; (xiv) ethyl acetate; (xv) ethylene glycol; (xvi) dimethyl sulfoxide; an aldehyde; (xviii) a ketone; (xiv) non-polar molecules; (xx) hexane; (xxi) chloroform; (xxii) butanol; and (xxiii) propanol.

Optionally, the method may be carried out using negative ion mode, so optionally, the method comprises analysing spectrometric data obtained using negative ion mode. Optionally, the method may be carried out using positive ion mode, so optionally, the method comprises analysing spectrometric data obtained using positive ion mode. Optionally, the method comprises analysing spectrometric data obtained using negative ion mode and analysing spectrometric data obtained using positive ion mode.

The matrix and/or aerosol, smoke or vapour may be doped with one or more additives to, for example, enhance the solvation or dilution of analyte with the matrix, or for enhancing the ionisation of the analyte within the aerosol, smoke or vapour.

The doping compound may be an acidic or basic additive such as, for example, formic acid or diethylamine.

The matrix and/or doping compound may cause derivatisation of the analyte in the aerosol, smoke or vapour. For example, the matrix and/or doping compound may cause the derivatisation of cholesterol or steroids in the analyte. This may render the analyte more easily ionised.

Rapid Evaporative Ionisation Mass Spectrometry ("REIMS")

Although various different ambient ionization ion sources may be used in the invention to analyse a variety of targets, a method of REIMS analysis on a microbial population will now be described in order to assist in understanding the embodiments.

Figure 10A:
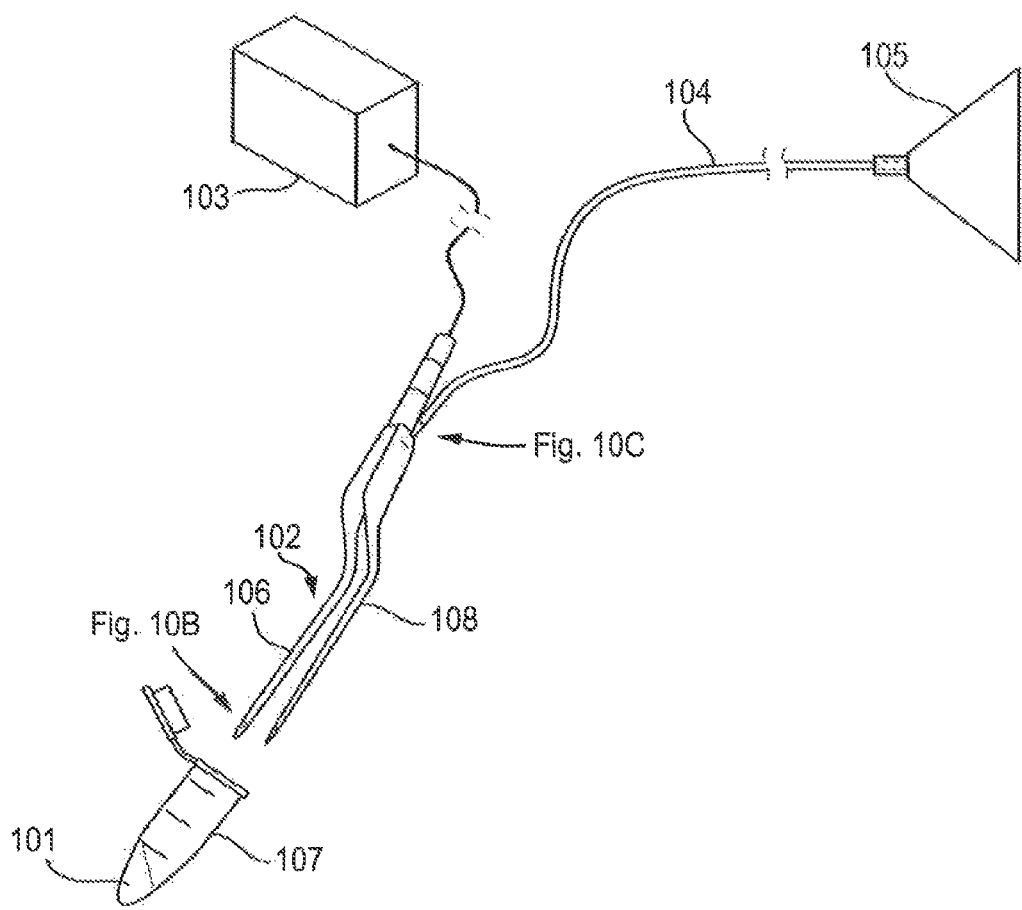
FIGS. 10A-10C show an experimental setup used for REIMS analysis of a target comprising or consisting of a microbial population which may be used in a method provided herein provided herein.
Figure 10B:
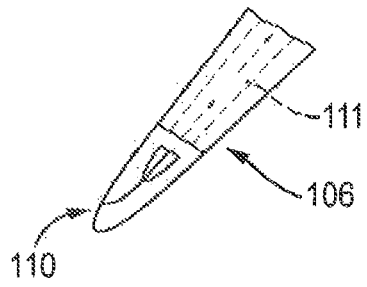
Figure 10C:
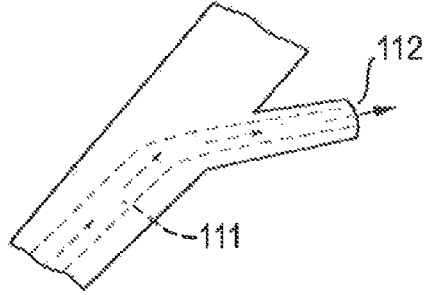

FIG. 10A shows apparatus that may be used to analyse a target, such as a microbial culture. The apparatus comprises a pair of handheld electrodes 106, 108 in the form of a forceps 102 (i.e. the first device); an RF power supply 103 for supplying an RF voltage to the electrodes 106, 108; an inlet to a mass spectrometer 105; and tubing 104 connecting a port 112 at the rear end of the forceps 102 to the inlet of the spectrometer 105. The forceps 102 and RF power supply 103 may be configured such that the forceps 102 are bipolar forceps. As shown in FIG. 10B, an open entrance port 110 is provided in the tip of one of the electrodes 106 at the front of the forceps 102. This entrance port 110 opens up into a conduit 111 within the electrode 106. The conduit 111 extends through the electrode 106 to an exit port 112 in the rear of the forceps 102, as shown in FIG. 10C.

As shown in FIG. 10A, the sample/target to be analysed may, e.g., be provided in the form of a microbial pellet 101. The microbial pellet may be provided in a container 107 such as an Eppendorf tube. The forceps 102 may be inserted into contact with the microbial pellet 101 so as to obtain biomass from the microbial pellet 101 on the tips of the electrodes 106, 108. The two electrodes 106, 108 may be subsequently brought into close proximity with each other, e.g., by pinching the biomass between the tips of the forceps 102. The RF power supply 103 may be triggered, e.g., using a foot switch, so as to energise the electrodes 106, 108. This causes the microbial biomass to be rapidly heated (e.g., by Joule or diathermy heating), due to its non-zero impedance, and smoke, aerosol or vapour to be emitted from the biomass. The smoke, aerosol or vapour may contain charged molecular species of analytes in the biomass.

Whilst a container 107 such as an Eppendorf tube is shown in FIG. 10A, the target may alternatively be, e.g., microbial biomass such as a microbial colony, e.g., on a petri dish.

The smoke, aerosol or vapour may then be captured or otherwise aspirated through the entrance port 110 and into the conduit 111 in the forceps 102. The smoke, aerosol or vapour is then drawn through the conduit 111, out of the exit port 112, along the tubing 104 and into the inlet of the mass spectrometer 105. The inherent vacuum system of the mass spectrometer may be used to draw the smoke, aerosol or vapour from the entrance port 110 to the inlet of the spectrometer 105.

Figure 11:
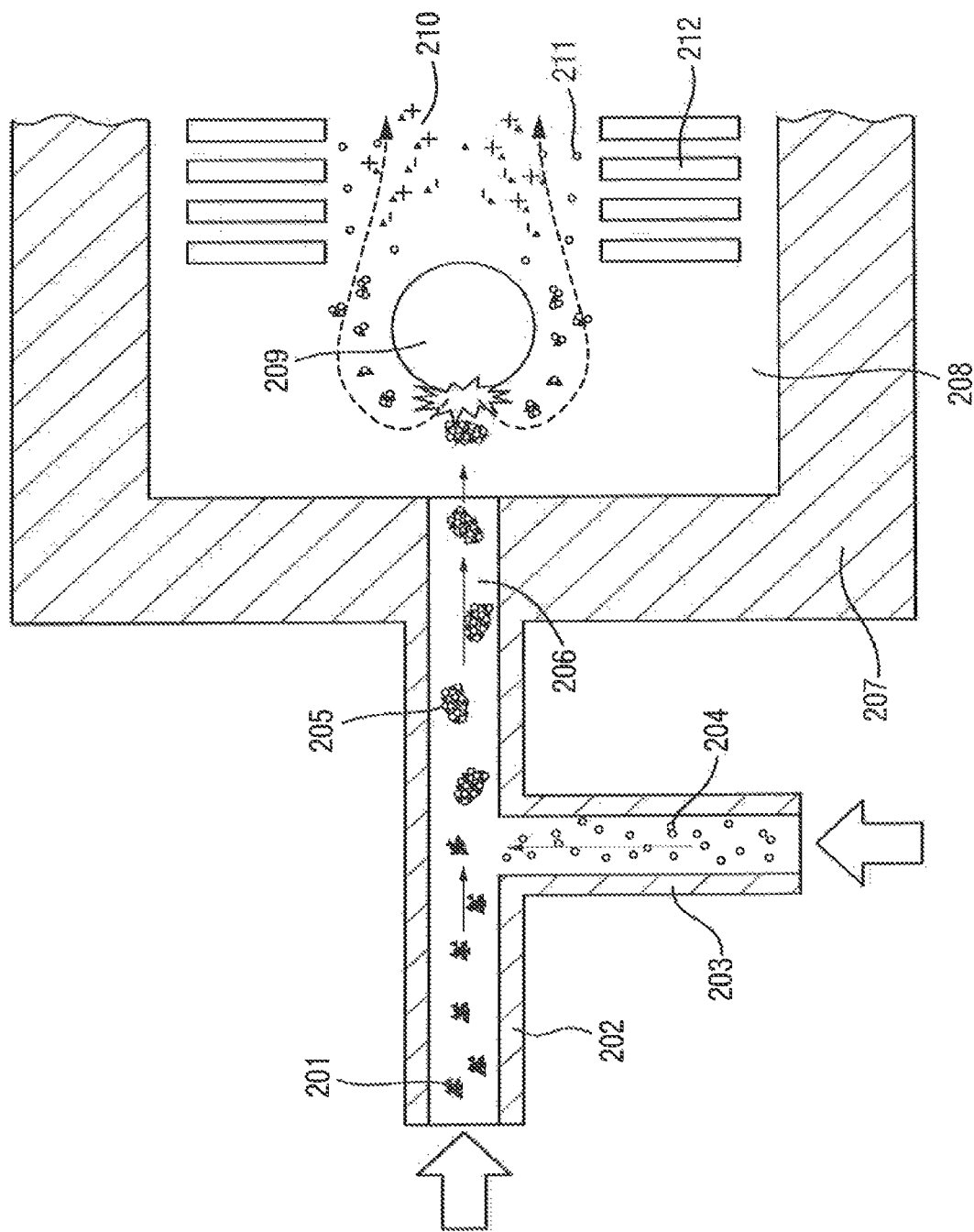
FIG. 11 shows an interface for ionizing aerosol from the target comprising or consisting of a microbial population.

FIG. 11 shows a schematic of an embodiment of an interface between the first device (e.g., forceps 102) and the mass spectrometer. The instrument may comprise an ion analyser 207 having an inlet 206 (which may correspond to inlet 5 in FIG. 10A), a vacuum region 208, a collision surface 209 and ion optics 212 (such as a Stepwave® ion guide) arranged within the vacuum region 208. The instrument also comprises a sample transfer tube 202 (corresponding to tubing 4 in FIG. 10) and a matrix introduction conduit 203. The sample transfer tube 202 has an inlet for receiving the smoke, aerosol or vapour sample 201 (which may correspond to that described in relation to FIG. 10) from a sample/target being investigated and an outlet that is connected to the inlet 206 of the ion analyser 207. The matrix introduction conduit 203 has an inlet for receiving a matrix compound and an outlet that intersects with the sample transfer tube 202 so as to allow the matrix 204 to be intermixed with the aerosol sample 201 in the sample transfer tube 202. A T-junction component may be provided at the junction between tubes 202, 203 and 206. The tubes 202, 203 and 206 may be removably inserted into the T-junction.

A method of operating the instrument shown in FIG. 11 will now be described. A sample/target, such as microbial population material, may be subjected to the REIMS technique. For example, a first device (e.g., forceps 102) may be used to generate an aerosol, e.g., as described above in relation to FIGS. 10A-10C. The aerosol particles 201 are then introduced into the inlet of the sample transfer tube 202. A matrix compound 204 is introduced into the inlet of the matrix introduction conduit 203. The aerosol particles 201 and matrix compound 204 are drawn towards the inlet 206 of the ion analyser 207 by a pressure differential caused by the vacuum chamber 208 being at a lower pressure than the inlets to the tubes 202, 203. The aerosol particles 201 may encounter the molecules of matrix compound 204 in, and downstream of, the region that the sample transfer tube 202 intersects with the matrix introduction conduit 203. The aerosol particles 201 intermix with the matrix 204 so as to form aerosol particles containing matrix molecules 205, in which both the molecular constituents of the aerosol sample 201 and the matrix compound 204 are present. The matrix molecules 204 may be in excess compared to the molecular constituents of aerosol sample 201.

The particles 205 may exit the sample transfer tube 202 and pass into the inlet 206 of the ion analyser 207. The particles 205 then enter into the decreased pressure region 208 and gain substantial linear velocity due to the adiabatic expansion of gas entering the vacuum region 208 from the sample transfer tube 202 and due to the associated free jet formation. The accelerated particles 205 may impact on the collision surface 209, where the impact event fragments the particles 205, leading to the eventual formation of gas phase ions 210 of the molecular constituents of the aerosol sample 201 and the formation of matrix molecules 211. The collision surface 209 may be controlled and maintained at a temperature that is substantially higher than the ambient temperature.

The matrix 204 includes a solvent for the analyte 201, such that the analyte 201 dissolves by the matrix 204, thereby eliminating intermolecular bonding between the analyte molecules 201. As such, when the dissolved analyte 205 is then collided with the collision surface 209, the dissolved analyte 205 will fragment into droplets and any given droplet is likely to contain fewer analyte molecules than it would if the matrix were not present. This in turn leads to a more efficient generation of analyte ions 210 when the matrix in each droplet is evaporated. The matrix may include a solvent for said aerosol, smoke or vapour or analyte therein; an organic solvent; a volatile compound; polar molecules; water; one or more alcohols; methanol; ethanol; isopropanol; acetone; acetonitrile; 1-butanol; tetrahydrofuran; ethyl acetate; ethylene glycol; dimethyl sulfoxide; an aldehyde; a ketone; non-polar molecules; hexane; chloroform; or propanol. Isopropanol is of particular interest.

The matrix molecules 211 may freely diffuse into the vacuum. In contrast, the gas phase ions 210 of the molecular constituents of the aerosol sample 201 may be transferred by the ion optics 212 to an analysis region (not shown) of the ion analyser 207. The ions 210 may be guided to the analysis region by applying voltages to the ion optics 212.

The ion optics 212 may be a StepWave® ion guide. The collision surface may be positioned along and adjacent to the central axis of the large opening of a StepWave® ion guide. As will be understood by those skilled in the art, a StepWave® ion guide comprises two conjoined ion tunnel ion guides. Each ion guide comprises a plurality of ring or other electrodes wherein ions pass through the central aperture provided by the ring or other electrodes. Ions enter a first of the ion guides, along with any neutrals that may be present, and travel through the first ion guide. Ions are then directed orthogonally into a second of the ion guides and are transmitted therethrough. Transient DC voltages or potentials are applied to the electrodes to drive the ions through them. The StepWave® ion guide is based on stacked ring ion guide technology and is designed to maximise ion transmission from the source to the mass and/or ion mobility analyser. The device allows for the active removal of neutral contaminants, since the neutrals are not directed orthogonally into the second ion guide, thereby providing an enhancement to overall signal to noise. The design enables the efficient capture of the diffuse ion cloud entering a first lower stage which is then may focused into an upper ion guide for transfer to the ion analyser. The ions are then analysed by the ion analyser, which may comprise a mass spectrometer and/or an ion mobility spectrometer, or a combination of the two. As a result of the analysis, chemical information about the sample 201 may be obtained.

A liquid trap or separator may be provided between the first device (e.g., forceps 2) and the analyser, which captures or discards undesired liquids that are aspirated by the probe whilst may allowing the smoke, aerosol or vapour itself to pass relatively uninhibited to the mass and/or ion mobility spectrometer. This prevents undesired liquid from reaching the analyser without affecting the measurement of the smoke, aerosol or vapour. The liquid trap or separator may be arranged to capture the liquid for later disposal.

As described above, although embodiments have been described in which REIMS is used to generate the smoke, aerosol or vapour for analysis, other ambient ionisation techniques may be used such as, for example, Desorption Electrospray Ionisation ("DESI").

Desorption Electrospray Ionisation ("DESI")

Desorption Electrospray Ionisation ("DESI") has also been found to be a particularly useful and convenient method for the real time rapid and direct analysis of microbes and/or compounds. DESI techniques allow direct and fast analysis of surfaces without the need for prior sample preparation. The technique will now be described in more detail with reference to FIGS. 12A-12B.

As shown in FIGS. 12A-12B, the DESI technique is an ambient ionisation method that involves directing a spray of (primary) electrically charged droplets 301 onto a target 304. The electrospray mist is pneumatically directed at the target 304 by a sprayer 300 where subsequent splashed (secondary) droplets 305 carry desorbed ionised analytes (e.g., desorbed lipid ions). The sprayer 300 may be supplied with a solvent 306, a gas 307 (such as nitrogen) and a voltage from a high voltage source 308. After ionisation, the ions travel through air into an atmospheric pressure interface 309 of a mass and/or ion mobility spectrometer and/or mass and/or ion mobility analyser (not shown), e.g., via a transfer capillary 310. The ions may be analysed by the method described in relation to FIG. 11, or by other methods. For example, the transfer capillary 310 of FIG. 12A may correspond to the sample transfer tube 202 in FIG. 11. The transfer capillary 310 may be heated, e.g., to a temperature up to 500° C.

The DESI technique allows, for example, direct analysis of targets, such as a microbial population, e.g., without requiring any advance sample preparation for the analysis.

General Methods

Provided is a method of analysis using mass spectrometry and/or ion mobility spectrometry comprising:

(a) using a first device to generate smoke, aerosol or vapour from a target comprising or consisting of a microbial population;

(b) mass analysing and/or ion mobility analysing said smoke, aerosol or vapour, or ions derived therefrom, in order to obtain spectrometric data; and (c) analysing said spectrometric data in order to analyse said microbial population.

Suitable targets are defined elsewhere herein.

The method may optionally be a method of analysing a microbe and/or a compound. Thus, optionally, the method may comprise a step of analysing a microbe and/or compound present in said target on the basis of said spectrometric data.

It should be understood that any reference herein to "analysing" a target is intended to mean that the target is analysed on the basis of the spectrometric data. Thus, for example, by an expression such as "analysing a microbe" is meant that a microbe is detected, identified and/or characterised based upon the spectrometric data. By an expression such as "identifying a microbe" or "analysing spectrometric data in order to identify a microbe" is meant that the identity of a microbe is determined based upon the spectrometric data.

A number of optional features will be described in greater detail below.

The method may optionally be a method of detecting a microbial infection, such as a vaginal infection; a method of identifying a microbe, such as a pathogenic microbe, which may optionally include a step of identifying a microbe, such as a pathogenic microbe; a method of confirming the presence of a microbe in a sample, which may optionally include a step of confirming the presence of a microbe in a sample; a method of automatically identifying a microbe, which may optionally include a step of automatically identifying a microbe; a method of identifying a cell type in a sample which may optionally include a step of identifying a cell type in a sample, wherein the cell is optionally a microbial cell; a method of detecting, identifying and/or characterising a microbe in a liquid medium, such as a body fluid, which may optionally include a step of detecting, identifying and/or characterising a microbe in a liquid medium, such as a body fluid; a method of detecting, identifying and/or characterising a microbe in a food product, which may optionally include a step of detecting, identifying and/or characterising a microbe in a food product; a method of detecting, identifying and/or characterising a virus, which may optionally include a step of detecting, identifying and/or characterising a virus; a method of characterising a microbe as being susceptible or resistant to an antimicrobial, such as a bacterium as being susceptible or resistant to an antibiotic, which may optionally include a step of characterising a microbe as being susceptible or resistant to an antimicrobial, such as a bacterium as being susceptible or resistant to an antibiotic; a method of identifying an infection as being caused by a microbe resistant to or susceptible to an antimicrobial, such as a bacterium susceptible or resistant to an antibiotic, which may optionally include a step of identifying an infection as being caused by a microbe resistant to or susceptible to an antimicrobial, such as a bacterium susceptible or resistant to an antibiotic; a method of tracking the spread of an infectious disease, which may optionally include a step of tracking the spread of an infectious disease; a method of detecting, identifying or characterising a microbe in a clinical specimen, which may optionally include a step of detecting, identifying or characterising a microbe in a clinical specimen; a method of detecting, identifying or characterising a microbe in a microbial mixture, such as a complex microbial mixture, which may optionally include a step of detecting, identifying or characterising a microbe in a microbial mixture, such as a complex microbial mixture; a method of detecting, identifying or characterising microbial lipids, which may optionally include a step of detecting, identifying or characterising microbial lipids; a metabolic profiling method for identifying a metabolic state of a subject biological sample, which may optionally include a step of metabolic profiling and identifying a metabolic state of a subject biological sample; a method for detecting, identifying and/or characterising proteins and/or metabolites secreted from a microbe, such as an intracellular bacteria, which may optionally include a step of detecting, identifying and/or characterising proteins and/or metabolites secreted from a microbe, such as an intracellular bacteria; and/or a method of analysing a wound, optionally a method of analysing fluid and/or tissue from a wound optionally comprising using one or more protein or other identification databases, which may optionally include a step of analysing a wound, optionally analysing fluid and/or tissue from a wound, optionally comprising using one or more protein or other identification databases.

The subject of analysis in the method may conveniently be referred to as the "target entity". Thus, optionally, the target entity may be a microbe and/or a compound.

In one aspect, the method may be a method of analysing a microbe, a microbial interaction, a microbial biomarker, and/or a microbiome. Thus, the method may optionally comprise a step of analysing a microbe, a microbial interaction, a microbial biomarker, and/or a microbiome.

In one aspect, the method may be a method of analysing the genotype and/or phenotype of a microbe. Thus, the method may optionally comprise a step of analysing the genotype and/or phenotype of a microbe.

In one aspect, the method may be a method of analysing a faecal and/or body fluid specimen, e.g., to analyse a microbe and/or compound. Thus, the method may optionally comprise a step of analysing a faecal and/or body fluid specimen, e.g., to analyse a microbe and/or compound In one aspect, the method may be a method of analysing a compound. Thus, the method may optionally comprise a step of analysing a compound and/or a biomarker for a compound.

Optionally, the method may include 2 or more of the aspects disclosed herein, e.g., 3 or more, 4 or more 5, or more etc. For example, the method may optionally comprise a step of analysing a faecal and/or body fluid specimen, wherein a microbial biomarker and/or a compound biomarker is analysed.

Optional features of any of these methods are discussed below. Thus, unless otherwise stated, any reference to "a method" or "the method" is intended to be a reference to any of the methods provided herein. It is explicitly intended that any of these features may be present in any combination in any of these methods.

The method may optionally be a method of screening, e.g., for the purpose of drug development. Thus, optionally, the method may comprise a step of analysing the response of a microbial population to a test agent or condition.

Optionally, the identity of a microbe may be analysed. Optionally, the infection of a target may be analysed. Optionally, the homogeneity and/or heterogeneity of a microbial population may be analysed. Optionally, the genotype and/or phenotype of a microbial population or one or more microbial types present therein may be analysed. Optionally, the state of a microbial population or one or more microbial types present therein may be analysed. Optionally, a process involving a microbial population or one or more microbial types present therein may be analysed. Optionally, the effect of manipulating the genotype and/or phenotype of a microbial population or one or more microbial types present therein may be analysed. Optionally, the effect of manipulating the environmental conditions of a microbial population may be analysed. Optionally, the method may be used to distinguish between 2 or more different microbial types within a microbial population. Optionally, the effect of a substance on a microbial population may be analysed. Optionally, the utilisation, production and/or breakdown of a substance by a microbial population may be analysed. Optionally, a plurality of microbial populations may be analysed to analyse their ability to utilise, produce and/or break down a substance. Thus, optionally, a plurality of microbial populations may be screened to analyse their productivity or efficiency with respect to the production, breakdown and/or utilisation of a substance. Optionally, the viability of a microbial population may be analysed.

The method may be a method of, or of obtaining information relevant to, predicting the viability of a microbial population in terms of its long term viability, robustness and/or efficiency.

In one aspect, the method may be a method of analysing a disease and/or a biomarker of a disease. Thus, the method may optionally comprise a step of analysing a disease and/or a biomarker of a disease.

The method may be a method of, or of obtaining information relevant to:

(i) diagnosing a disease; (ii) monitoring the progression or development of a disease;

(iii) disease prognosis; (iv) predicting the likelihood of a disease responding to treatment; (v) monitoring the response of a disease to treatment; and/or (vi) stratifying subjects.

Thus, the method may optionally comprise a step of analysing spectrometric data and on the basis of that spectrometric data: (i) diagnosing a disease; (ii) monitoring the progression or development of a disease; (iii) making disease prognosis; (iv) predicting the likelihood of a disease responding to treatment; (v) monitoring the response of a disease to treatment; and/or (vi) stratifying subjects.

Details of suitable diseases are provided elsewhere herein.

In one aspect, the method may be a method of analysing a microbe, a microbial interaction, and/or a microbial biomarker. Thus, the method may optionally comprise a step of analysing a microbe, a microbial interaction, and/or a microbial biomarker.

In one aspect, the method may be a method of analysing the genotype and/or phenotype of a cell. Thus, the method may optionally comprise a step of analysing the genotype and/or phenotype of a cell.

In one aspect, the method may be a method of treatment. Thus, the method may optionally comprise a step of administering a therapeutically effective amount of a therapeutic agent to a subject in need thereof.

In one aspect, the method may be a method of analysing a compound. Thus, the method may optionally comprise a step of analysing a compound and/or a biomarker for a compound.

Optional features of any of these methods are discussed below. Thus, unless otherwise stated, any reference to "a method" or "the method" is intended to be a reference to any of the methods provided herein. It is explicitly intended that any of these features may be present in any combination in any of these methods.

The skilled person will appreciate that any of the methods provided herein may optionally be combined with one or more of the other methods provided herein and/or with one or more further methods.

For example, provided is a method which is a combination of two or more, e.g., three or more, four or more or five or more of the methods disclosed herein.

Targets and Analysis Thereof

The method may be carried out on a "target", which may comprise or consist of a microbial population.

The term "target entity" is used herein to refer to the entity which it is desired to analyse within the target. Thus, any reference to a "target" should be understood to mean a target comprising one or more different target entities. Thus, the target entity may be a microbe and/or compound. For example, the target may be tissue and the target entity may be bacteria.

The terms "analysis", "analysing" and derivatives of these terms are used herein to encompass any of the following: detection of a target entity; identification of a target entity; characterisation of a target entity; determination of the location of target entity; determination of a status, e.g., a disease status; and/or determination of the spatial distribution of target entities.

Any reference to analysing a "microbe" should be understood to mean that a microbial population is analysed, given that single microbes are below the detection limit of the method. However, it will be apparent from the context that the term "microbe" is sometimes used to indicate that a particular microbe type within the overall microbial population may be analysed. Thus, the term "microbe" can be shorthand for a microbial subpopulation.

The analysis may be qualitative and/or quantitative. Thus, optionally, any type of analysis may involve determining the concentration, percentage, relative abundance or the like of the target entity. For example, the relative abundance of microbes in a target, and/or the concentration of a compound may be analysed. Optionally, an increase or decrease in a target entity may be analysed.

The terms "detection", "detecting" and derivations of these terms are used interchangeably herein to mean that the presence or absence of a target entity or biomarker therefor is determined.

By "identifying" a compound is meant that at least some information about the structure and/or function of the compound is obtained, e.g., the information may optionally allow a compound to be identified as comprising or consisting of a compound selected from any of the types disclosed herein, and/or as being characterised by one or more of the functional groups disclosed herein.

The target may optionally consist of a microbial population, e.g., be a microbial culture. In this context, it should be understood that culture medium, produced and/or excreted compounds and the like may be present, and that the term "consist of a microbial population" is used to indicate that no non-microbial cellular matter is present. Thus, optionally, the target does not comprise any intact non-microbial cells and/or no lysed non-microbial cells. Optionally, any reference herein to a target that "consists" of a microbial population is used interchangeably with a reference to a target that "consists of a microbial population and one or more extracellular compounds".

Alternatively, the target may comprise a microbial population and non-microbial cellular matter. For example, it may comprise tissue, intact cells and/or lysed cells, e.g., it may be a tissue or tissue specimen, a faecal specimen, and/or body fluid specimen.

The target may, e.g., be anything on or in which a microbial population may be present. Thus, the target may, e.g., a specimen derived from a subject, a clinical specimen, an environmental specimen, a food, a beverage, a plant, a plant specimen, an animal specimen, a subject, and/or an object comprising a microbe.

The microbial population may comprise or consist of one or more different microbial types. Details of microbes are provided elsewhere herein. Optionally, the microbial population may comprise or consist of microbes having the identity of any one of the microbes listed elsewhere herein.

Unless stated otherwise, any reference herein to a "cell" should be understood to be a reference to a microbial cell, or to a microbe, in the case of a unicellular microbe.

Optionally, the microbe population may be mutant and/or transgenic.

Optionally, the microbial population may have, or be/have been genetically manipulated to have, one or more properties selected from auxotrophy, production of a desired compound, and/or secretion of a desired compound. Optionally, the microbial population may be, or have been, genetically manipulated, e.g., be transgenic and/or have a knock-out genotype and/or phenotype.

Details of genetic manipulation and microbial properties are provided elsewhere herein.

Optionally, the method may comprise the analysis of one or more isogenic microbial populations.

Any reference herein to the analysis of a "microbial population" should be understood to mean that the entire microbial population, or a sample thereof, may be analysed.

The method may optionally be carried out on an entire microbial population, or on a sample thereof, or on region of the target, particularly if the target is a subject or a specimen, such as a tissue.

The "subject" may be a human or a non-human animal. The subject may be alive or dead. If the method is carried out on a living subject, then it may be referred to as an in vivo method. If the method is carried out on a specimen, then it may be referred to as an in vitro or ex vivo method. Thus, the specimen may be from a human or non-human animal.

Optionally, the animal may be a mammal, optionally selected, for example, from any livestock, domestic or laboratory animal, such as, mice, guinea pigs, hamsters, rats, goats, pigs, cats, dogs, sheep, rabbits, cows, horses and/or monkeys. Optionally, it may be an insect, bird or fish, e.g., a fly or a worm. Thus, veterinary applications are contemplated.

The method may optionally be carried out on an in vivo target, i.e. on a living subject. For example, it may be carried out by using a thermal ablation method.

Alternatively or in addition, it may optionally be carried out on a dead subject, for example as part of an autopsy or a necropathy.

Alternatively or in addition, it may optionally be carried out on an ex vivo or in vitro target, e.g., on a specimen, which may be a clinical specimen. The specimen may optionally be a provided specimen, i.e. a specimen that was previously obtained or removed from a subject. Optionally, the method may include a step of obtaining a specimen from a subject.

Thus, it may optionally be carried out on a specimen, which may optionally be selected, for example, from a tissue specimen, a body fluid specimen and/or a faecal specimen. For example, it may be a surgical resection specimen, a biopsy specimen, a swab, and/or a smear.

A tissue specimen may comprise or consist of human tissue, non-human animal tissue, and/or plant tissue.

Resection is the surgical removal of part or all of a tissue.

A biopsy specimen may optionally be obtained, e.g., by using a needle to withdraw tissue and/or fluid comprising cells; by using an endoscope; and/or during surgery. A biopsy may optionally be incisional, excisional, or be retrieved from a surgical resection. A biopsy specimen comprises cells and may optionally be a tissue specimen, for example, comprising or consisting of diseased and/or non-diseased tissue.

A "swab" is intended to be understood as comprising a "standard medical swab" i.e. a swab that is designed for sampling biological samples such as mucosal membranes. For example, the term "standard medical swab" should be understood as covering a "cotton bud" (British) or a "cotton swab" (American) i.e. a small wad of cotton wrapped around one or both ends of a tube. The tube may be made from plastic, rolled paper or wood.

A swab may optionally, for example, comprise a tissue or other cellular material, e.g., a mucosal sample.

A smear may, for example, optionally be a specimen that has been smeared onto a solid support, e.g., between two slides.

A body fluid may, for example, optionally be selected from blood, plasma, serum, sputum, lavage fluid, pus, urine, saliva, phlegm, vomit, faeces, amniotic fluid, cerebrospinal fluid, pleural fluid, semen, vaginal secretion, interstitial fluid, and/or lymph. Optionally, it may be dried, collected with a swab, and/or dispensed onto an absorbent carrier, e.g., a filter or paper. Optionally, it may be a pellet. A pellet may be prepared, e.g., as described below.

The analysis of a target tissue, faecal and/or body fluid specimen may provide information about a microbe, microbe-associated disease and/or microbiome, optionally a mucosal microbiome and/or the microbiome of the GI lumen. Thus, optionally, the method may involve the analysis of a faecal and/or body fluid specimen. For example, a faecal and/or body fluid specimen may be analysed for the presence of a compound, and/or a microbe.

The method may optionally allow an analysis of metabolic differences between various microbial populations. By identifying taxonomic specific biomarkers the method may optionally allow the analysis, e.g., diagnosis, of microbial infections and/or mixed microbial communities.

Optionally, a faecal and/or body fluid specimen may be analysed for the presence of a microbe, to analyse a microbial population, to analyse a compound and/or to analyse a microbiome.

By "microbial culture" is meant a microbial population that was cultured to maintain and/or propagate the microbe. A microbial culture may, e.g., be a liquid, semi-solid or solid culture. A microbial culture may, e.g., be a culture from a culture collection, a culture derived from an environmental sample, a culture derived from a clinical specimen, a culture derived from a subject or object, and the like. A culture may be "derived" from a subject, specimen and the like by taking a sample, e.g., via a swab, inoculating said sample in on or a suitable culture medium, and incubating the culture medium under suitable conditions for a suitable length of time to allow any microbes present therein to grow. Details of suitable culture media, which may be solid, soft or liquid, and culture conditions, are well known and also provided elsewhere herein.

The microbial culture may, e.g., be in the form of a suspension culture, a colony, a bacterial or fungal lawn, a viral plaque, or a biofilm. Optionally, it may be dried, collected with a swab, and/or dispensed onto an absorbent carrier, e.g., a filter or paper. Optionally, it may be a pellet. A pellet may be prepared, e.g., as described below.

An object comprising a microbial population may be any object, which may optionally be known or suspected to comprise a microbe, e.g., to be infected, contaminated, or colonised, by a microbe. The object may, e.g., be a household object, a tool, a surgical tool or instrument, a piece of furniture, a worktop, an item of clothing, a fabric, or the like.

A food may, e.g., be meat, fish, vegetable, fruit, and/or nut. It may optionally be a processed food, such as a sausage or pasty, or an unprocessed food, such as a steak.

The method may optionally involve the analysis of one or more different targets. Optionally, 2 or more targets from different subjects or objects, and/or from different locations within a subject or object, may be analysed. Optionally, the targets may be at or from 2 or more different locations, e.g., specimens may be at or from 2 or more locations in/of a subject or object.

Optionally, a target may be at or from one or more locations known or suspected to be healthy, non-infected, or sterile; and one or more locations known or suspected to be diseased, infected, or non-sterile.

Optionally, the method may involve the analysis of 2 or more locations of a target. Optionally, distinct locations of a target may be analysed, e.g., a series of points may be sampled, optionally with or without spatial encoding information for imaging purposes.

The analysis may optionally be made intra-operatively, i.e. whilst a surgical procedure is under way. Thus, the analysis may optionally be used to provide real-time analysis of a target. The analysis may optionally be used to identify disease margins. A disease margin may optionally be analysed, e.g., by analysing the concentration of a particular microbe type in a target region. The analysis may optionally be made in vivo, e.g., during a surgical procedure. This may optionally involve using, e.g., a thermal ablation surgical method, e.g., REIMS technology, such as the iKnife technology. For example, a tissue on which surgery is being performed, e.g., an infected tissue, may be analysed in vivo and the results of the analysis may be used to inform, influence or determine a further surgical step.

The surgery may optionally be surgery in relation to any of the diseases mentioned herein, such as cancer surgery and the like. The surgery may optionally be laparoscopic, and/or endoscopic.

The analysis may optionally be made in vitro or ex vivo. This may optionally be, e.g., in parallel to a surgical procedure. For example, a specimen, such as, a biopsy, may be obtained during a surgical procedure. Such a provided specimen may then be analysed ex vivo and the results of the analysis may be used to inform, influence or determine a further surgical step.

The method may optionally be carried out on a target that is native. By "native" is meant that the target has not been modified prior to performing the method provided herein. In particular, the target may be native in that the microbes are not subjected to a step of lysis or extraction, e.g., lipid extraction, prior to performance of the method provided herein. Thus, a target may be native in that all or substantially all of the microbes in the microbial population are intact. Thus, a target may be native in that it has not been chemically or physically modified and is thus chemically and physically native. Optionally, the target may be chemically native, i.e. it may be chemically unmodified, meaning that it has not been contacted with a chemical agent so as to change its chemistry. Contacting a target with a matrix is an example of a chemical modification.

Optionally, the target may be physically native, i.e. it may be physically unmodified, meaning that it has not been modified physically. Freezing, thawing, and/or sectioning are examples of physical modifications. The skilled person will appreciate that although physical actions, such as, freezing, may affect a specimen's chemistry, for the purpose of the methods provided herein such an action is not considered to be a chemical modification.

Thus, optionally the target may be chemically native, but not physically native, e.g., because it has been frozen and/or sectioned.

Optionally, the target may be frozen, previously frozen and then thawed, fixed, sectioned, and/or otherwise prepared, as discussed with regard to specimen preparation. Optionally, the method may be carried out on a target that has not undergone a step of preparation specifically for the purpose of mass spectrometry and/or ion mobility analysis.

The target may optionally not be/have been contacted with a solvent, or a solvent other than water, prior to generating the smoke, aerosol or vapour from the target.

Additionally, or alternatively, the target may optionally not be/have been contacted with a matrix prior to generating the smoke, aerosol or vapour from the target. For example, the target may not be/not have been contacted with a MALDI matrix or other matrix for assisting ionisation of material in the target. A MALDI matrix may, e.g., comprise or consist of small organic acids such as α-cyano-4-hydroxycinnamic acid (CHCA) and/or 2,5-dihydroxybenzoic acid (DHB).

The method may optionally be carried out on a target that has been prepared for a particular mass spectrometry and/or ion mobility analysis; and/or that has been prepared for any of the analytical methods mentioned elsewhere herein.

Specimen preparation (for any of the methods provided herein and/or any of the analytical methods disclosed herein) may optionally involve one or more of the following.

The specimen or part thereof may optionally be deposited on a solid surface, such as, a glass or plastic slide.

The specimen may optionally be fixed chemically, or via a frozen section procedure, e.g., to preserve tissue and/or microbes from degradation, and to maintain the structure of the cells and of sub-cellular components such as cell organelles, e.g., nucleus, endoplasmic reticulum, and/or mitochondria. The fixative may, for example, be 10% neutral buffered formalin. The specimen may optionally be processed with e.g., epoxy resins or acrylic resins to allow or facilitate sections to be cut. The sample may optionally be embedded, for example, in paraffin. The specimen may optionally be cut into sections of, for example, 1 μm to 200 nm. For example, the specimen may optionally be about 5 μm thick for light microscopy, or about 80-100 nm thick for electron microscopy. Optionally, the specimen may be cut into sections of at least 1, 3, 5, 7, 9, 10, 12, 14, 16, 18, 20, 22, 24 or 25 μm and no more than 100, 90, 80, 70, 60, 50, 40, 35, 30, 28, or 26 μm, for example, 5-25 μm.

Frozen sections may optionally be prepared, e.g., by freezing and slicing the specimen. Prior to freezing, the specimen may optionally be embedded, e.g., as described above. Embedding medium helps conduct heat away from the specimen during freezing, helps protect the tissue from drying during storage, and supports the tissue during sectioning.

Freezing may optionally be performed, e.g., by contacting the specimen with a suitable cooling medium, such as, dry ice, liquid nitrogen, or an agent that has been cooled in dry ice or liquid nitrogen, e.g., isopentane (2-methyl butane). Frozen specimens may optionally be stored at, e.g., between about −80 and −4 degrees Celsius, e.g., at −70 or −20 degrees Celcius and may optionally be thawed prior to performance of the method described herein.

The specimen or sections thereof may be stained, for example, with Hematoxylin and eosin (H&E stain). Hematoxylin, a basic dye, stains nuclei blue due to an affinity to nucleic acids in the cell nucleus; eosin, an acidic dye, stains the cytoplasm pink.

Optionally, a lesion, optionally of a tissue, may be analysed. A lesion is region in a tissue which is abnormal as a consequence of, e.g., injury or disease. The lesion may, for example, be selected from a wound, an ulcer, an abscess, and/or a tumour. The lesion may, for example, be a diabetic lesion, such as, a diabetic limb or digit, or a diabetic ulcer.

Optionally, tissue may be analysed, e.g., tissue affected by, or in the vicinity of, cancer or necrosis.

The tissue may optionally be selected from adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue and/or urethra tissue, soft and connective tissue, peritoneal tissue, blood vessel tissue and/or fat tissue; grade I, grade II, grade III or grade IV cancerous tissue; metastatic cancerous tissue; mixed grade cancerous tissue; a sub-grade cancerous tissue; healthy or normal tissue; or cancerous or abnormal tissue.

Optionally, the method may involve the analysis of a mucosal target, which may be in vivo, or a specimen comprising or consisting of mucosa. Optionally, the method may involve the analysis of a mucosal target to analyse a mucosal microbe; to analyse a microbial interaction with the mucosa, and/or to analyse the mucosal microbiome.

The mucosa lines several passages and cavities of the body, particularly those with openings exposed to the external environment, including the oral-pharyngeal cavity, gastrointestinal (GI) tract, respiratory tract, urogenital tract, and exocrine glands.

Thus, the mucosa may optionally be selected from Bronchial mucosa, Endometrium (mucosa of the uterus), Esophageal mucosa, Gastric mucosa, Intestinal mucosa (gut mucosa), Nasal mucosa, Olfactory mucosa, Oral mucosa, Penile mucosa and/or Vaginal mucosa.

Sampling

The term "sampling" is used herein to refer to the use of a device to generate smoke, vapour or aerosol from a target.

Any of the methods may optionally include automatic sampling, which may optionally be carried out using, e.g., a REIMS device. Any of the methods may optionally comprise using a disposable sampling tip.

Optionally, the target may comprise or consist of a microbial culture cultured on a solid culture medium. The microbial culture may optionally be sampled directly from said culture medium, or it may optionally be sampled from a support onto which it has been transferred. For example, prior to sampling, a microbial culture may be transferred onto a hard support made, e.g., of glass or plastic, such as a microscope slide.

Optionally, the target may comprise or consist of a liquid, which may optionally be a microbial culture cultured in a liquid culture medium, a body fluid or clinical fluid specimen, an environmental sample, a food, or a beverage.

The liquid may optionally be processed prior to sampling, for example by centrifugation or filtration. Optionally, centrifugation may be carried out at a force and for a time suitable to deposit any microbes. The microbes form a pellet and the supernatant may be removed.

The force may optionally be selected from at least 1,000×g, 2,000×g, 3,000×g, 4,000×g, 5,000×g, 6,000×g, 7,000×g, 8,000×g, 9,000×g, 10,000×g, 11,000×g, or at least 12,000×g and optionally less than 15,000×g, 14,000×g, 13,000×g, 12,000×g, 11,000×g, 10,000×g, 9,000×g, 8,000×g, 7,000×g, 6,000×g, or 5,000×g. The centrifugation time may optionally be at least 5, 6, 7, 8, 9, 10, 12, 15, 18, 20, 25, 30, 40 or 50 minutes and optionally less than 60, 50, 40, 30 or 25 minutes. For many microbes, a force of about 5000 g for about 10-20 minutes may typically be used. The skilled person will be able to determine what rotation per minute (rpm) must be selected based on the size of the centrifuge tube to achieve the desired gravitational force g.

The pellet may be sampled straight from the bottom of the centrifuge tube, or it may be sampled from a support onto which it has been transferred. For example, prior to sampling, a pellet may optionally be transferred onto a glass or plastic support, such as a slide, or onto a swab, such as, a cotton swab.

For example, if the microbial pellet contains only small amounts of biomass or excess liquid, the microbial biomass may optionally be transferred to a solid support material such as a common cotton swab. To achieve this, some of the microbial biomass may be picked up from the cell pellet after centrifugation using a swab. Subsequently, parts of the swab may be squeezed between the electrodes of the sampling probe while simultaneously sampling using electrical current. The inventors have determined that such a transfer step does not significantly affect the resulting spectral profiles.

Alternatively, the liquid may be processed by filtration to deposit any microbes on a filter or mesh, which may then be sampled. Thus, the method may further comprise aspirating or passing the liquid through a filter media.

The method may further comprise analysing residue on the filter media which remains after the liquid has been aspirated or passed through the filter media.

Thus, the analysis of a liquid may optionally include, or be preceded by, a processing step to remove excess liquid; thereby providing a target that is devoid of excess liquid. Such a target which was obtained from a liquid but from which excess liquid has been removed may be referred to herein as a "solid" target. It will be understood that the term "solid" is used in biology to refer to samples that appear solid to the naked eye, e.g., form a lump, even if they do not have the physical characteristics of a solid. Thus, a "solid" target includes, for example, microbial colonies, microbial cell pellets, a microbial biofilm, smears of any thereof, or animal tissue.

The analysis of a target may optionally involve the use forceps-based REIMS technology, wherein a sample of the target may be taken between the forceps and the probes may then be drawn together.

The microbial population, e.g., a pellet, may optionally be subjected to one or more washing steps, e.g., to remove the culture medium. Washing may be performed with a suitable buffer. Thus, the method may optionally be performed on a washed microbial population.

Biomarkers

The method may optionally involve the analysis of one or more biomarkers. A biomarker may be an objective, quantifiable characteristic of, e.g., the presence of a microbe, a microbe type, microbe characteristic, compound, and/or biological process.

The term "biomarker" is sometimes used explicitly herein, but it should also be understood that any of the analyses mentioned herein may optionally be the analysis of a biomarker. Thus, e.g., any reference to analysing a "microbe" should be understood optionally to be "analysing a microbial biomarker"; any reference to analysing a "compound" should be understood optionally to be "analysing a biomarker for that compound"; and so on.

The biomarker may optionally be a spectral biomarker. The term "spectral biomarker" is used interchangeably herein with "spectrometric biomarker" and is used herein to refer to spectrometric data that is characteristic of a cell type, disease status, microbe, compound, and/or biological process, but for simplicity, a spectral biomarker may simply be referred to as a "biomarker".

By "characteristic of a microbe type" is meant that the biomarker may optionally be used to analyse, e.g., detect, identify and/or characterise said microbe type. Optionally, the biomarker may be used to distinguish between microbes of different taxa, e.g., kingdoms, phyla, classes, genera, species and/or strains; between genotypically and/or phenotypically different microbes; between an animal cell and a microbial cell; between a normal and an abnormal microbe; and/or between a wild-type and a mutant microbe.

By "characteristic of a microbe" is meant that the biomarker may optionally be used to analyse, e.g., detect, identify and/or characterise said microbe. As discussed elsewhere herein, identification may be on any level, for example, on a taxonomic level. A biomarker that allows identification of a microbe as belonging to a particular taxonomic level may be referred to as a "taxonomic marker" or "taxonomic biomarker". Thus, a taxonomic marker may be specific for a Kingdom, Phylum, Class, Order, Family, Genus, Species and/or Strain.

By "characteristic of a compound" is meant that the biomarker may optionally be used to analyse, e.g., detect, identify and/or characterise said compound.

By "characteristic of a biological process" is meant that the biomarker may optionally be used to analyse a biological process. Optionally, the biomarker may be used to analyse the start, progression, speed, efficiency, specificity and/or end of a biological process.

Different microbe types, compounds, biological progresses and the like may be characterised by the presence or absence, and/or relative abundance, of one or more compounds, which may serve as biomarkers. Any reference herein to a biomarker being a particular compound, or class of compounds, should be understood optionally to be the spectrometric data of that compound, or class of compounds.

For example, a reference to a "C24:1 sulfatide ($C_{48}H_{91}NO_{11}S$)" biomarker should be understood to be a reference to the spectrometric data corresponding to C24:1 sulfatide ($C_{48}H_{91}NO_{11}S$) which may, e.g., be a signal at m/z of about 888.6; whereas a reference to a "glycosylated ceramide" biomarker should be understood to be a reference to the spectrometric data corresponding to glycosylated ceramide, which may, e.g., be a signal at m/z of 842, 844 or 846.

As explained above, a biomarker may be indicative of a cell type, disease status, microbe, compound, and/or biological process. A biomarker which is indicative of *Pseudomonas aeruginosa* may be referred to as a "*Pseudomonas aeruginosa* biomarker" and so on.

Optionally, a spectral biomarker may be identified as being the spectrometric data of a particular compound, or class of compounds. Thus, a signal corresponding to a particular mass, charge state, m/z and/or ion mobility may optionally be identified as being indicative of the presence of a particular compound, or class of compounds.

Optionally, a spectral signal may serve as a biomarker even if a determination has not been made as to which particular compound, or class of compounds gave rise to that signal. Optionally, a pattern of spectral signals may serve as a biomarker even if a determination has not been made as to which particular compounds, or class of compounds, gave rise to one or more signals in that pattern, or any of the signals in a pattern.

The work disclosed herein has led to the identification of a range of biomarkers, as well as allowing the identification of further biomarkers. Optionally, the biomarker may be selected from any of the biomarkers disclosed herein, including in any of the Examples and/or Tables. Optionally, the biomarker may be a biomarker of the substituted or unsubstituted form of any of the biomarkers mentioned herein; and or of an ether, ester, phosphorylated and/or glycosylated form, or other derivative, of any of the biomarkers mentioned herein.

Optionally, the biomarker may be a biomarker of a lipid; a protein; a carbohydrate; a DNA molecule; an RNA molecule; a polypeptide, such as, a ribosomal peptide or a non-ribosomal peptide; an oligopeptide; a lipoprotein; a lipopeptide; an amino acid; and/or a chemical compound, optionally an organic chemical molecule or an inorganic chemical molecule.

A biomarker may optionally be the clear-cut presence or absence of a particular compound, which may optionally manifest itself as the presence or absence of a spectrometric signal corresponding to a specific mass, charge state, m/z and/or ion mobility(e.g. collision cross section).

A biomarker may optionally be the relative abundance of a particular biomolecule or compound, which may optionally manifest itself as the relative intensity of a spectrometric signal corresponding to a specific mass, charge state, m/z and/or ion mobility.

A biomarker may optionally be the relative abundance of more or more compounds, which may optionally manifest itself as the relative intensity of two or more spectrometric signals corresponding to two or more mass, charge state, m/z and/or ion mobility.

Thus, a biomarker may optionally be an increased or decreased level of one or more compounds, e.g., a metabolite, a lipopeptide and/or lipid species, which may optionally manifest itself as an increase and/or decrease in the intensity of two or more spectrometric signals corresponding to two or more mass, charge state, m/z and/or ion mobility.

The presence, absence and relative abundance of a variety of compounds may be referred to as a molecular "fingerprint" or "profile". The totality of the lipids of a cell may be referred to as a lipidomic fingerprint/profile, whereas the totality of metabolites produced by a cell may be referred to as a metabolomic fingerprint/profile.

Thus, the biomarker may be a molecular fingerprint, e.g., a lipid fingerprint and/or a metabolomic fingerprint, more particularly e.g., a (i) a lipidomic profile; (ii) a fatty acid profile; (iii) a phospholipid profile; (iv) a phosphatidic acid (PA) profile; (v) a phosphatidylethanolamine (PE) profile; (vi) a phosphatidylglycerol (PG) profile; (vii) a phosphatidylserines (PS) profile; or (viii) a phosphatidylinositol (PI) profile.

By way of example, phosphatidylglycerol may be found in almost all bacterial types, but it may be present in different bacteria in different relative amounts. Phosphatidylglycerol may be present at a level of only 1-2% in most animal tissues. It may therefore be a biomarker for bacteria in an animal specimen, and/or be a biomarker for specific types of bacteria.

The biomarker may optionally be a direct biomarker or an indirect biomarker. By "direct" biomarker is meant that the spectrometric data is produced directly from the biomarker. For example, if a particular compound has a specific spectrometric signal or signal pattern, then obtaining this signal or signal pattern from a sample provides direct information about the presence of that compound. This may be the case, for example, for a metabolite produced in significant amounts by a cell or microbe. Optionally, in such an example, the spectrometric data from the compound may alternatively or in addition serve as an indirect biomarker for the cell or microbe that produced this compound.

By "indirect" biomarker is meant that the spectrometric data is produced from one or more biomarkers that is/are indicative of a particular compound, biological process, and/or type of microbe or cell. Thus, an indirect biomarker is spectrometric data generated from one or more molecules that provides information about a different molecule. For example, a molecular fingerprint, such as, a lipid fingerprint, may be indicative of the expression of a particular protein, e.g., a receptor; or of a particular cell type or microbial type.

A lipid biomarker may optionally be selected from, e.g., fatty acids, glycerolipids, sterol lipids, sphingolipids, prenol lipids, saccharolipids and/or phospholipids. A brief overview of various lipids is provided below, but it must be appreciated that any particular lipid may fall into more than one of the groups mentioned herein.

A fatty acid is an aliphatic monocarboxylic acid. The fatty acid may optionally have a carbon chain comprising precisely or at least 4, 6, 8, 10, 12, 14, 16, 18, 20, 22, 24, 26, 28, 30, 32, 36, 38 or 40 carbons. It may optionally be monounsaturated, polyunsaturated, or saturated. It may optionally be an eicosanoid. It may, for example, be oleic acid, palmitic acid, arachidonic acid, a prostaglandin, a prostacyclin, a thromboxane, a leukotriene, or an epoxyeicosatrienoic acid.

The glycerolipid may optionally be selected from e.g., monoacylglycerol, diacylglycerol, and/or triacylglycerol.

The sterol may optionally be selected from free sterols, acylated sterols (sterol esters), alkylated sterols (steryl alkyl ethers), sulfated sterols (sterol sulfate), sterols linked to a glycoside moiety (steryl glycosides) and/or acylated sterols linked to a glycoside moiety (acylated sterol glycosides).

The sterol may optionally have an aliphatic side chain of precisely or at least 8, 9, 10, 11, 12, 13, 14, 15, 16, 17, 18, 19, 10, 21, 22, 23, 24, 25, 26, 27, 28, 29, 20, 35 or 40 carbon atoms. The number of carbon atoms in the aliphatic side chain may be expressed by the letter C followed by the number, e.g., C27 for cholesterol. It may, for example, be selected from cholesterol, cholesterol sulphate, ergosterol, lanosterol, dinosterol (4α,23,24-trimethyl-5α-cholest-22E-en-3β-ol), oxysterol and/or a derivative of any thereof.

A phospholipid may comprise two fatty acids, a glycerol unit, a phosphate group and a polar molecule. The Phospholipid may optionally comprise an ester, ether and/or other O-derivative of glycerol. The phospholipid may optionally be selected from, e.g., Phosphatidylglycerol, diphosphatidylglycerol (cardiolipin), Acylphosphatidylglycerol (1,2-diacyl-sn-glycero-3-phospho-(3'-acyl)-1'-sn-glycerol), and/or plasmalogen.

The phosphatidylglycerol lipid may optionally be selected from phosphatidic acids (PAs), phosphatidylethanolamines (PEs), phosphatidylglycerols (PGs), phosphatidylcholines (PCs), phosphatidylinositols (PIs) and/or phosphatidylserines (PSs).

A sphingolipid is a lipid containing a sphingoid. It may optionally be selected from, e.g., a ceramide, i.e. an N-acylated sphingoid; sphingomyelin, i.e. a ceramide-1-phosphocholine; phosphoethanolamine dihidroceramide, and/or a glycosphingolipid, i.e. a lipid containing a sphingoid and one or more sugars. For example, it may optionally be a glycosylated ceramide.

The biomarker may optionally be a metabolite, such as, a primary or a secondary metabolite; an antibiotic; a quorum sensing molecule; a fatty acid synthase product; a pheromone; and/or a biopolymer.

A biomarker compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

For example, it may optionally be a terpene; prenylquinone; sterol; terpenoid; alkaloid; glycoside; surfactin; lichenysin, 2-Heptyl-3-hydroxy-4(1H)-quinolone or 2-heptyl-3,4-dihydroxyquinoline ("PQS" or *Pseudomonas* quinolone signal); 4-hydroxy-2-heptylquinoline ("HHQ"); phenol, such as, a natural phenol; phenazine; biphenyl; dibenzofurans; beta-lactam; polyketide; rhamnolipid; mycolic acids; and/or polyhydroxyalkanoates;

The biomarker may optionally be selected from, e.g., Glycerophosphocholines, Sphingomyelins, Glycerophospholipids, Galactoceramides, Glycerophosphoinositols, Glycerophosphoserines, Glycerophosphoglycerols, Cholesterol sulphate, sulfatides, seminolipids, citric acid, Glycerophosphoethanolamines, Glycerophosphoethanolamines, 2-hydroxygluterate, glutamine, glutamate, succinate, fumarate, palmitoylglycine, ubiquinones, gadoteridol and/or any of the other biomarkers mentioned herein, including any of the Tables.

The inventors have identified inter alia the biomarkers listed in any of the Tables, as well as the following biomarkers:

Mycolic acids for bacteria belonging to the *Corynebacterineae* suborder such as *Mycobacterium* spp., *Corynebacterium* spp. and *Rhodococcus* spp. In particular, the following mycolic acids have been detected from the corresponding genera:

*Mycobacterium* spp.: C77-C81 (even and odd numbered, 0-2 unsaturations);
*Corynebacterium* spp.: C28-C36 (even numbered, 0-2 unsaturations);
*Nocardia* spp.: C48-C56 (even numbered, 0-3 unsaturations);
*Rhodococcus* spp.: C28-C38 (even and odd numbered, 0-4 unsaturations).

A variety of sphingolipid species were found to be specific for members of the Bacteroidetes phylum. These sphingolipids include oxidized ceramides species, phosphoethanolamine dihydroceramides and C15:0-substituted phosphoglycerol dihydroceramides and dihydroceramide. Among those sphingolipid species, a series of galactosylated sphingolipids was found to be specific for *Bacteroides fragilis* (*Bacteroides fragilis* alpha-Galactosylceramides).

Among bacteria, plasmalogens are highly specific for anaerobic bacteria such as *Clostridium* spp. and *Fusobacterium* spp. This is due to the fact that aerobic bacteria lost the biochemical pathway required for plasmalogen synthesis. Humans are able to synthesize plasmalogens (although via a different biochemical pathway from anaerobes), although these were generally found to have longer chain lengths than bacterial plasmalogens.

Other biomarkers that are indicative of a certain group of bacteria include, for instance, lipopeptides that are produced specifically by certain *Bacillus* species, such as, surfactin for *B. subtilis* and lichenysin for *B. licheniformis*. Production of these two molecules also enables straightforward differentiation of these otherwise very closely related bacteria. A further example includes PQS-derived quorum-sensing molecules and mono- and di-rhamnolipid species found for *Pseudomonas aeruginosa*.

Quorum sensing is a form of cell-to-cell communication which relies on the principle that when a single microbe releases quorum sensing molecules into the environment, the concentration of such molecules is too low to be detected. However, when sufficient bacteria are present, quorum sensing molecule concentrations reach a threshold level that allows the microbes to sense a critical cell mass and, in response, to activate or repress particular genes. Quorum sensing molecules may therefore also be referred to as autoinducers. Pathogens may use quorum sensing molecules as virulence factors.

Some examples of quorum sensing molecules are listed above. Additional examples include N-acyl homoserine lactones (N-acyle HSLs), such as, 3-oxo-$C_8$-HSL, 3-oxo-$C_{10}$-HSL, or 3-oxo-$C_{12}$-HSL; diketopiperazines; 3-hydroxypalmitic acid methyl ester; and peptide-based quorum sensing molecules, such as, that of *Staphylococcus aureus*, which is an oligopeptide that has been termed the autoinducing peptide (AIP), encoded by the gene agrD. The active AIP is 7-9 amino acids, with a 5-membered thiolactone ring.

By way of example, sphingomyelin lipids may optionally be a biomarker, e.g., for cancer; ergosterol may optionally be a biomarker, e.g., for fungi; dinosterol may optionally be a biomarker, e.g., for dinoflagellates; cholesterol sulphate may optionally be a biomarker, e.g., for cancer; 2-hydroxygluterate may optionally be a biomarker, e.g., for cancer; and/or one or more sulfatides may optionally be a biomarker, e.g., for cancer, for example, astrocytoma. Optionally, the sulfatide may be selected from $C_{48}H_{91}NO_{11}S$, $C_{48}H_{92}NO_{12}S$, and/or $C_{50}H_{94}NO_{11}S$.

Iso-C15:0-substituted phosphoglycerol dihydroceramides may be specific for the Porphyromonadaceae family. m/z=566.4790 may be a biomarker for members of the Flavobacteria class.

The method provided herein may optionally involve the analysis of an exogenous compound, i.e. a compound that was administered to a subject, brought into contact with a subject or specimen, or to which a microbe was exposed. Thus, the biomarker may be an exogenous compound.

Analysis of Spectrometric Data

Any of the methods provided herein may optionally involve the analysis of spectrometric data; more particularly, the analysis of spectrometric data from a first sample. In particular, the detection, identification and/or characterisation of a microbe and/or a compound may involve the analysis of spectrometric data (from a first sample). The detection, identification and/or characterisation of a microbe and/or a compound may be based solely on the analysis of spectrometric data, or it may optionally involve one or more further analytical tools, details of which are discussed elsewhere herein.

In some embodiments, the spectrometric data provides direct information about the target. For example, if a particular microbe has a specific spectrometric pattern, then obtaining this pattern from a sample provides direct information about the presence of that microbe. For another example, if a particular compound has a specific spectrometric pattern, then obtaining this pattern from a sample provides direct information about the presence of that compound. This may be the case, for example, for a compound which is secreted by a microbe.

However, in other embodiments, spectrometric data provides indirect information about the target. This may be the case, for example, for a compound which is produced but not secreted by a microbe. The presence of this compound may be detected indirectly by detecting a spectrometric pattern which is characteristic of a microbe containing said compound.

Spectrometric data obtained using a sample, e.g., a first sample, may optionally be compared to one or more other spectrometric data, which may conveniently be referred to herein as "reference", "control" or "comparator" spectrometric data.

The term "reference" spectrometric data is used herein to mean spectrometric data from a known microbe or compound. Reference spectrometric data may optionally be publicly available, or the skilled person may generate a library of reference spectrometric data. Any of the methods provided herein may optionally involve comparing the spectrometric data to one or more reference spectrometric data. If the spectrometric data obtained from a sample matches or corresponds sufficiently to a reference spectrometric data, then optionally a positive determination may be made. If the spectrometric data obtained from a sample does not match or correspond sufficiently to a reference spectrometric data, then optionally a negative determination may be made. Optionally, a positive determination may be made if the spectrometric data corresponds more closely to one library entry than any other library entry.

The term "comparator" spectrometric data is used herein to mean spectrometric data obtained from a second sample. The first and second sample may be obtained from different samples, or from the same different locations of the same sample. Any of the methods provided herein may optionally involve comparing the spectrometric data to one or more comparator spectrometric data. If the spectrometric data obtained from a sample matches or corresponds sufficiently to a comparator spectrometric data, then optionally a positive determination may be made. If the spectrometric data obtained from a sample does not match or correspond sufficiently to a comparator spectrometric data, then optionally a negative determination may be made.

The term "control" spectrometric data is used herein to mean spectrometric data obtained from the first sample at an earlier point in time. Control spectrometric data may, for example, be used when monitoring a microbial culture. Any of the methods provided herein may optionally involve comparing the spectrometric data to one or more control spectrometric data. If the spectrometric data obtained from a sample matches or corresponds sufficiently to a control spectrometric data, then optionally a positive determination may be made. If the spectrometric data obtained from a sample does not match or correspond sufficiently to a control spectrometric data, then optionally a negative determination may be made.

By a "positive determination" is meant that the presence, identity and/or characteristics of a particular microbe and/or compound is determined. For example, a positive determination may involve determining that a microbe of a particular taxonomic rank is present; that a particular microbe has a certain characteristic, such as, resistance to a particular drug; and/or that a particular compound is being produced.

Thus, for example, if the spectrometric data of a first sample matches or corresponds sufficiently to a reference spectrometric data, then the presence in the first sample of a microbe corresponding to the microbe from which the reference spectrometric data was obtained may be confirmed. If the spectrometric data of a first sample matches or corresponds sufficiently to a reference spectrometric data, then the microbe present in the first sample may be identified as corresponding to the identity of the microbe from which the reference spectrometric data was obtained. If the spectrometric data of a first sample matches or corresponds sufficiently to a reference spectrometric data, then the microbe present in the first sample may be characterised as having a characteristic corresponding to the characteristic of the microbe from which the reference spectrometric data was obtained. If the spectrometric data of a first sample matches or corresponds sufficiently to a reference spectrometric data, then a determination may be made that the microbe present in the first sample produces the compound produced by the microbe from which the reference spectrometric data was obtained.

As another example, if the spectrometric data of a first sample matches or corresponds sufficiently to a comparator spectrometric data, then the presence in the first sample of a microbe corresponding to the microbe from which the comparator spectrometric data was obtained may be confirmed. If the spectrometric data of a first sample matches or corresponds sufficiently to a comparator spectrometric data, then the microbe present in the first sample may be identified as corresponding to the identity of the microbe from which the comparator spectrometric data was obtained. If the spectrometric data of a first sample matches or corresponds sufficiently to a comparator spectrometric data, then the microbe present in the first sample may be characterised as having a characteristic corresponding to the characteristic of the microbe from which the comparator spectrometric data was obtained. If the spectrometric data of a first sample matches or corresponds sufficiently to a comparator spectrometric data, then a determination may be made that the microbe present in the first sample produces the compound produced by the microbe from which the comparator spectrometric data was obtained.

In other words, a match or sufficient correspondence to a reference or comparator spectrometric data respectively may be used to confirm that the first microbe and the reference or comparator microbe respectively have the same identity, whereas the lack of a match or sufficient correspondence to a reference or comparator spectrometric data respectively may be used to confirm that the first microbe and the reference or comparator microbe respectively do not have the same identity.

By a "negative determination" is meant that the absence of a particular microbe and/or compound is determined; and/or that it is determined that a microbe does not have a particular identity and/or characteristic. For example, a negative determination may involve determining that a microbe of a particular taxonomic rank is not present; that a particular microbe does not have a certain characteristic such as resistance to a particular drug; and/or that a particular compound is not being produced.

Thus, for example, if the spectrometric data of a first sample does not match or have sufficient correspondence to a reference spectrometric data, then the absence or insufficient presence in the first sample of a microbe corresponding to the microbe from which the reference spectrometric data was obtained may be confirmed. If the spectrometric data of a first sample does not match or have sufficient correspondence to a reference spectrometric data, then the microbe present in the first sample may be identified as not corresponding to the identity of the microbe from which the reference spectrometric data was obtained. If the spectrometric data of a first sample does not match or have sufficient correspondence to a reference spectrometric data, then the microbe present in the first sample may be characterised as not having a characteristic corresponding to the characteristic of the microbe from which the reference spectrometric data was obtained. If the spectrometric data of a first sample does not match or have sufficient correspondence to a reference spectrometric data, then a determination may be made that the microbe present in the first sample does not produce, or insufficiently produces, the compound produced by the microbe from which the reference spectrometric data was obtained.

As explained below, by determining or confirming the "identity" of a microbe is meant that at least some information about the identity is obtained, which may, for example, be at any taxonomic level. Thus, for example, if the reference spectrometric data is from *Candida albicans*, then in one embodiment a match or sufficient correspondence may be used to identify the first microbe as belonging to the genus *Candida*, whereas in another embodiment a match or sufficient correspondence may be used to identify the first microbe as belonging to the species *Candida albicans*.

As another example, if the spectrometric data of a first sample matches or sufficiently corresponds to a control spectrometric data, then a determination may be made that no, or no significant, change has taken place, whereas if the spectrometric data of a first sample does not match or correspond sufficiently to a control spectrometric data, then a determination may be made that a change, optionally a significant change, has taken place. Examples of a change may, for example, be the presence of a contaminating microbe and/or compound; or a change in the microbe's behaviour or its environment, such as, a change in the microbe's growth rate, respiration rate; rate of production of a compound, such a secreted compound; environmental temperature, pH, nutrient availability and so on.

Optionally, the analyte giving rise to a particular spectrometric signal, e.g., a particular m/z, may optionally be further characterised, e.g., using MS/MS. Thus, ionic species in the mass spectra may optionally be identified based on exact mass measurements, e.g., with a mass deviation <3 ppm, and/or MS/MS fragmentation patterns. Isobaric lipids with different headgroups may optionally be differentiated by ion mobility.

Thus, optionally, the method may involve analysing the target for the presence of a spectrometric signal of one or more biomarkers, optionally selected from any of the biomarkers mentioned herein.

The spectrometric data may comprise one or more sample spectra. Obtaining the spectrometric data may comprise obtaining the one or more sample spectra. Analysing the spectrometric data may comprise analysing the one or more spectra. Obtaining the one or more sample spectra may comprise a binning process to derive a set of time-intensity pairs and/or a set of sample intensity values for the one or more sample spectra. The binning process may comprise accumulating or histogramming ion detections and/or intensity values in a set of plural bins. Each bin in the binning process may correspond to particular range of times or time-based values, such as masses, mass to charge ratios, and/or ion mobilities. The bins in the binning process may each have a width equivalent to a width in Da or Th (Da/e) in a range selected from a group consisting of: (i) < or >0.01; (ii) 0.01-0.05; (iii) 0.05-0.25; (iv) 0.25-0.5; (v) 0.5-1.0; (vi) 1.0-2.5; (vii) 2.5-5.0; and (viii) < or >5.0. It has been identified that bins having widths equivalent to widths in the range 0.01-1 Da or Th (Da/e) can provide particularly useful sample spectra for classifying some aerosol, smoke or vapour samples, such as samples obtained from tissues. The bins may or may not all have the same width. The widths of the bin in the binning process may vary according to a bin width function. The bin width function may vary with a time or time-based value, such as mass, mass to charge ratio and/or ion mobility. The bin width function may be non-linear (e.g., logarithmic-based or power-based, such as square or square-root based). The bin width function may take into account the fact that the time of flight of an ion may not be directly proportional to its mass, mass to charge ratio, and/or ion mobility. For example, the time of flight of an ion may be directly proportional to the square-root of its mass and/or mass to charge ratio.

Spectrometric Library

The terms "spectrometric library" and "spectrometric database" are used interchangeably herein.

The skilled person may use any publicly available spectrometric data as reference spectrometric data. Examples of useful databases are: LipidMaps, LipidBlast and LipidXplorer, details of which are provided in the following publications: "LipidBlast—in-silico tandem mass spectrometry database for lipid identification" by Kind et al., Nat Methods. 2013 August; 10(8): 755-758; "LipidXplorer: A Software for Consensual Cross-Platform Lipidomics" by Herzog et al. PLoS ONE 7(1): e29851; and "Lipid classification, structures and tools" by Fahy et al. Biochimica et Biophysica Acta (BBA)—Molecular and Cell Biology of Lipids, Volume 1811, Issue 11, November 2011, Pages 637-647, Lipidomics and Imaging Mass Spectrometry, see also http://www.lipidmaps.org/.

Alternatively or in addition, the skilled person may construct a spectrometric library by obtaining spectrometric data from one or more samples, which may optionally include type culture strains and/or clinical and/or environmental microbial isolates; in the case of compound, the sample(s) may optionally be purchased or synthesised.

Type culture strains may optionally be obtained from culture collections, such as, the American Type Culture Collection (ATCC) (10801 University Boulevard, Manassas, Va. 20110 USA).

The present inventors generated a spectrometric library using over 1500 microbial strains, including clinical isolates and type culture strains from the ATCC, encompassing about 95 genera and about 260 species of bacteria and fungi. To expedite the generation of the spectrometric library, the inventors set up high throughput culturing, automated colony imaging, colony picking and REIMS analysis.

The present inventors have also generated spectrometric libraries using tissues and/or cell lines, details of which are provided elsewhere herein, including in the Examples.

The generation of a spectrometric library from microbes, cell lines and/or tissues may optionally be combined with a further analysis, e.g., taxonomic classification and/or histology, e.g., based on any of the further analytical tools discussed elsewhere herein. For example, the tool may be DNA analysis. This may involve DNA sequencing, optionally preceded by DNA isolation and/or amplification using, e.g., PCR. For bacteria, sequencing of all or part of the 16S rRNA gene is particularly suitable, whereas for fungi, sequencing of all or part of the internal transcribed spacer (ITS) region is particularly suitable.

Analysing Sample Spectra

The step of analysing the spectrometric data may comprise analysing one or more sample spectra so as to classify an aerosol, smoke or vapour sample.

Analysing the one or more sample spectra so as to classify the aerosol, smoke or vapour sample may comprise unsupervised analysis of the one or more sample spectra (e.g., for dimensionality reduction) and/or supervised analysis of the one or more sample spectra (e.g., for classification).

Analysing the one or more sample spectra may comprise unsupervised analysis (e.g., for dimensionality reduction) followed by supervised analysis (e.g., for classification).

Analysing the one or more sample spectra may be performed as discussed elsewhere herein.

A list of analysis techniques which are intended to fall within the scope of the present invention are given in the following table:

Analysis Techniques
Univariate Analysis
Multivariate Analysis
Principal Component Analysis (PCA)
Linear Discriminant Analysis (LDA)
Maximum Margin Criteria (MMC)
Library Based Analysis
Soft Independent Modelling Of Class Analogy (SIMCA)
Factor Analysis (FA)
Recursive Partitioning (Decision Trees)
Random Forests
Independent Component Analysis (ICA)
Partial Least Squares Discriminant Analysis (PLS-DA)
Orthogonal (Partial Least Squares) Projections To Latent Structures (OPLS)
OPLS Discriminant Analysis (OPLS-DA)

Support Vector Machines (SVM)
(Artificial) Neural Networks
Multilayer Perceptron
Radial Basis Function (RBF) Networks
Bayesian Analysis
Cluster Analysis
Kernelized Methods
Subspace Discriminant Analysis
K-Nearest Neighbours (KNN)
Quadratic Discriminant Analysis (QDA)
Probabilistic Principal Component Analysis (PPCA)
Non negative matrix factorisation
K-means factorisation
Fuzzy c-means factorisation
Discriminant Analysis (DA)

Combinations of the foregoing analysis approaches can also be used, such as PCA-LDA, PCA-MMC, PLS-LDA, etc.

Analysing the sample spectra can comprise unsupervised analysis for dimensionality reduction followed by supervised analysis for classification.

By way of example, a number of different analysis techniques will now be described in more detail.

Multivariate Analysis—Developing a Model for Classification

By way of example, a method of building a classification model using multivariate analysis of plural reference sample spectra will now be described.

Figure 15:
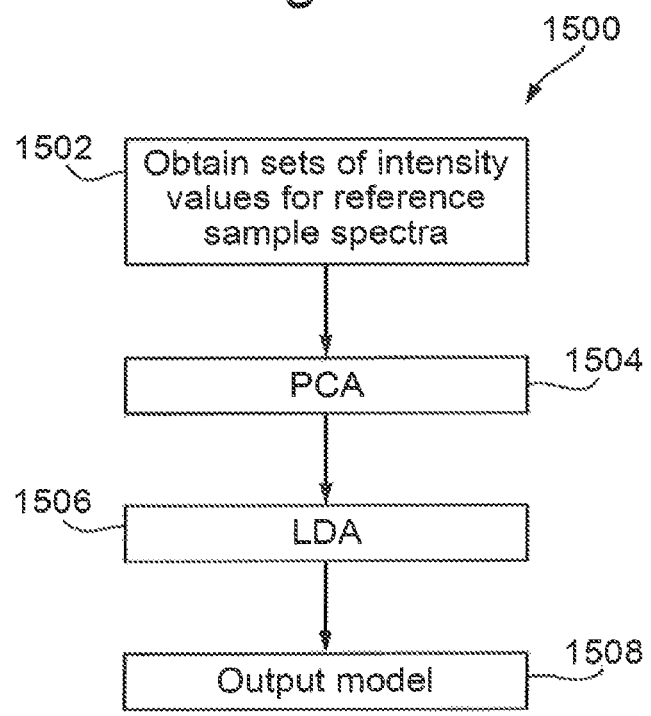
FIG. 15 shows a method of analysis that comprises building a classification model according to various embodiments.

FIG. 15 shows a method 1500 of building a classification model using multivariate analysis. In this example, the method comprises a step 1502 of obtaining plural sets of intensity values for reference sample spectra. The method then comprises a step 1504 of unsupervised principal component analysis (PCA) followed by a step 1506 of supervised linear discriminant analysis (LDA). This approach may be referred to herein as PCA-LDA. Other multivariate analysis approaches may be used, such as PCA-MMC. The PCA-LDA model is then output, for example to storage, in step 1508.

The multivariate analysis such as this can provide a classification model that allows an aerosol, smoke or vapour sample to be classified using one or more sample spectra obtained from the aerosol, smoke or vapour sample. The multivariate analysis will now be described in more detail with reference to a simple example.

Figure 16:
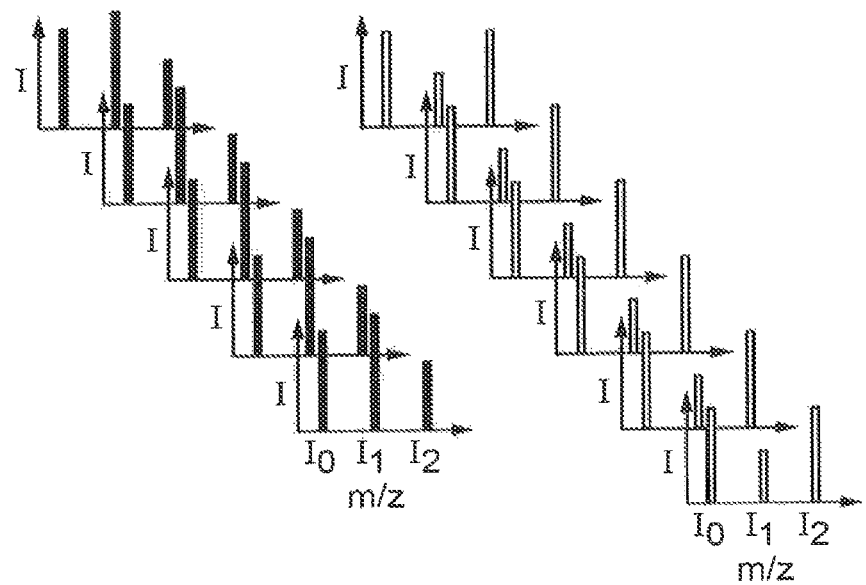
FIG. 16 shows a set of reference sample spectra obtained from two classes of known reference samples.

FIG. 16 shows a set of reference sample spectra obtained from two classes of known reference samples. The classes may be any one or more of the classes of target described herein. However, for simplicity, in this example the two classes will be referred as a left-hand class and a right-hand class.

Each of the reference sample spectra has been pre-processed in order to derive a set of three reference peak-intensity values for respective mass to charge ratios in that reference sample spectrum. Although only three reference peak-intensity values are shown, it will be appreciated that many more reference peak-intensity values (e.g., ~100 reference peak-intensity values) may be derived for a corresponding number of mass to charge ratios in each of the reference sample spectra. In other embodiments, the reference peak-intensity values may correspond to: masses; mass to charge ratios; ion mobilities (drift times); and/or operational parameters.

Figure 17:
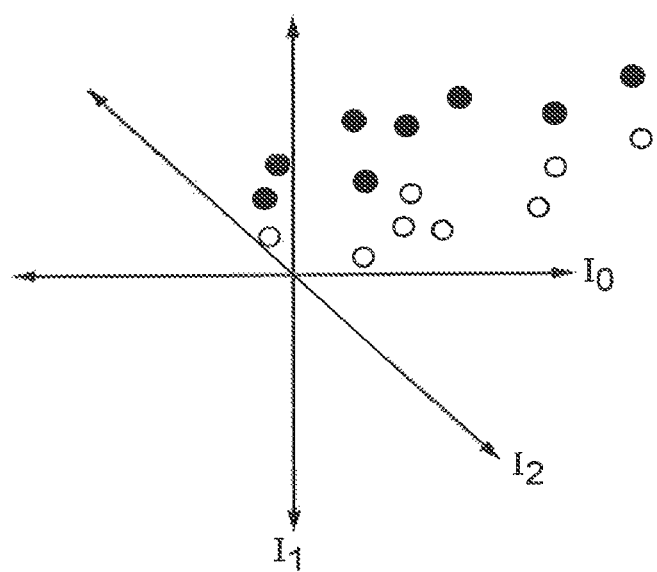
FIG. 17 shows a multivariate space having three dimensions defined by intensity axes, wherein the multivariate space comprises plural reference points, each reference point corresponding to a set of three peak intensity values derived from a reference sample spectrum.

FIG. 17 shows a multivariate space having three dimensions defined by intensity axes. Each of the dimensions or intensity axes corresponds to the peak-intensity at a particular mass to charge ratio. Again, it will be appreciated that there may be many more dimensions or intensity axes (e.g., ~100 dimensions or intensity axes) in the multivariate space. The multivariate space comprises plural reference points, with each reference point corresponding to a reference sample spectrum, i.e., the peak-intensity values of each reference sample spectrum provide the co-ordinates for the reference points in the multivariate space.

The set of reference sample spectra may be represented by a reference matrix D having rows associated with respective reference sample spectra, columns associated with respective mass to charge ratios, and the elements of the matrix being the peak-intensity values for the respective mass to charge ratios of the respective reference sample spectra.

In many cases, the large number of dimensions in the multivariate space and matrix D can make it difficult to group the reference sample spectra into classes. PCA may accordingly be carried out on the matrix D in order to calculate a PCA model that defines a PCA space having a reduced number of one or more dimensions defined by principal component axes. The principal components may be selected to be those that comprise or "explain" the largest variance in the matrix D and that cumulatively explain a threshold amount of the variance in the matrix D.

Figure 18:
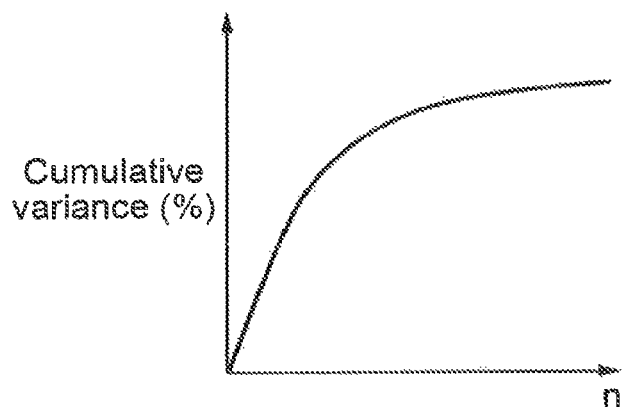
FIG. 18 shows a general relationship between cumulative variance and number of components of a PCA model.

FIG. 18 shows how the cumulative variance may increase as a function of the number n of principal components in the PCA model. The threshold amount of the variance may be selected as desired.

The PCA model may be calculated from the matrix D using a non-linear iterative partial least squares (NIPALS) algorithm or singular value decomposition, the details of which are known to the skilled person and so will not be described herein in detail. Other methods of calculating the PCA model may be used.

The resultant PCA model may be defined by a PCA scores matrix S and a PCA loadings matrix L. The PCA may also produce an error matrix E, which contains the variance not explained by the PCA model. The relationship between D, S, L and E may be:

$$D = SL^T + E \qquad (1)$$

Figure 19:
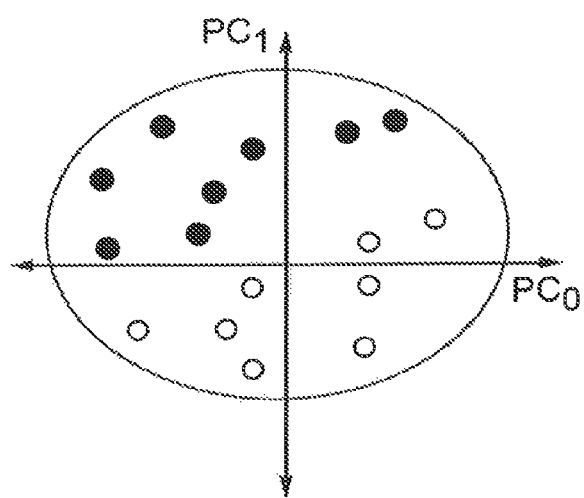
FIG. 19 shows a PCA space having two dimensions defined by principal component axes, wherein the PCA space comprises plural transformed reference points or scores, each transformed reference point or score corresponding to a reference point of FIG. 17.

FIG. 19 shows the resultant PCA space for the reference sample spectra of FIGS. 16 and 17. In this example, the PCA model has two principal components $PC_0$ and $PC_1$ and the PCA space therefore has two dimensions defined by two principal component axes. However, a lesser or greater number of principal components may be included in the PCA model as desired. It is generally desired that the number of principal components is at least one less than the number of dimensions in the multivariate space.

The PCA space comprises plural transformed reference points or PCA scores, with each transformed reference point or PCA score corresponding to a reference sample spectrum of FIG. 16 and therefore to a reference point of FIG. 17.

As is shown in FIG. 19, the reduced dimensionality of the PCA space makes it easier to group the reference sample spectra into the two classes. Any outliers may also be identified and removed from the classification model at this stage.

Further supervised multivariate analysis, such as multi-class LDA or maximum margin criteria (MMC), in the PCA space may then be performed so as to define classes and, optionally, further reduce the dimensionality.

As will be appreciated by the skilled person, multi-class LDA seeks to maximise the ratio of the variance between classes to the variance within classes (i.e., so as to give the largest possible distance between the most compact classes possible). The details of LDA are known to the skilled person and so will not be described herein in detail.

The resultant PCA-LDA model may be defined by a transformation matrix U, which may be derived from the PCA scores matrix S and class assignments for each of the transformed spectra contained therein by solving a generalised eigenvalue problem.

The transformation of the scores S from the original PCA space into the new LDA space may then be given by:

$$Z=SU \qquad (2)$$

where the matrix Z contains the scores transformed into the LDA space.

Figure 20:
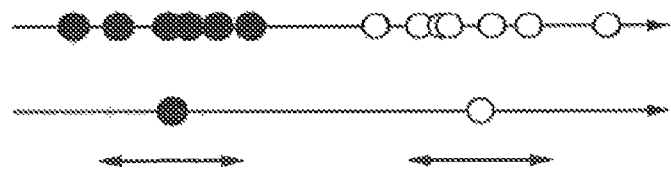
FIG. 20 shows a PCA-LDA space having a single dimension or axis, wherein the LDA is performed based on the PCA space of FIG. 19, the PCA-LDA space comprising plural further transformed reference points or class scores, each further transformed reference point or class score corresponding to a transformed reference point or score of FIG. 19.

FIG. 20 shows a PCA-LDA space having a single dimension or axis, wherein the LDA is performed in the PCA space of FIG. 19. As is shown in FIG. 20, the LDA space comprises plural further transformed reference points or PCA-LDA scores, with each further transformed reference point corresponding to a transformed reference point or PCA score of FIG. 19.

In this example, the further reduced dimensionality of the PCA-LDA space makes it even easier to group the reference sample spectra into the two classes. Each class in the PCA-LDA model may be defined by its transformed class average and covariance matrix or one or more hyperplanes (including points, lines, planes or higher order hyperplanes) or hypersurfaces or Voronoi cells in the PCA-LDA space.

The PCA loadings matrix L, the LDA matrix U and transformed class averages and covariance matrices or hyperplanes or hypersurfaces or Voronoi cells may be output to a database for later use in classifying an aerosol, smoke or vapour sample.

The transformed covariance matrix in the LDA space $V'_g$ for class g may be given by $$V'_g = U^T V_g U \qquad (3)$$

where $V_g$ are the class covariance matrices in the PCA space.

The transformed class average position $z_g$ for class g may be given by $$s_g U = z_g \qquad (4)$$

where $s_g$ is the class average position in the PCA space.
Multivariate Analysis—Using a Model for Classification By way of example, a method of using a classification model to classify an aerosol, smoke or vapour sample will now be described.

Figure 21:
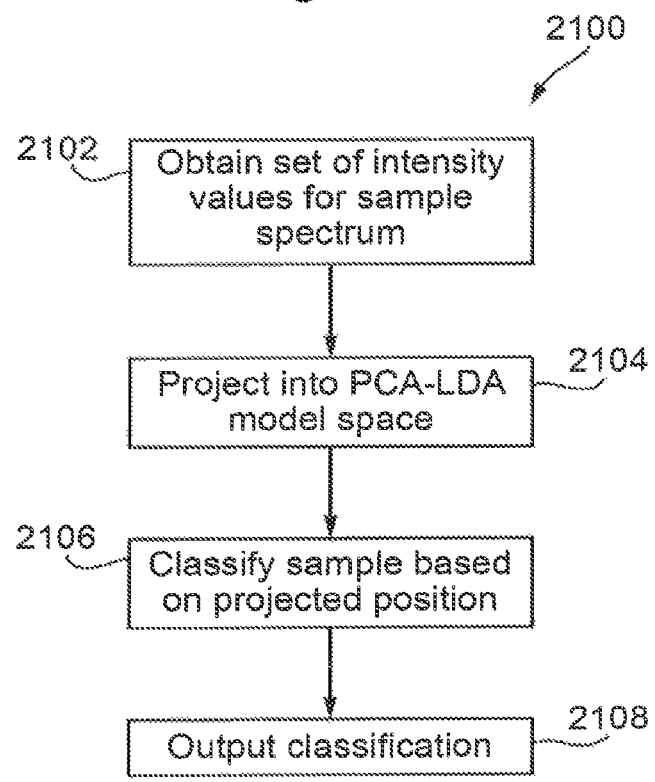
FIG. 21 shows a method of analysis that comprises using a classification model according to various embodiments.

FIG. 21 shows a method 2100 of using a classification model. In this example, the method comprises a step 2102 of obtaining a set of intensity values for a sample spectrum. The method then comprises a step 2104 of projecting the set of intensity values for the sample spectrum into PCA-LDA model space. Other classification model spaces may be used, such as PCA-MMC. The sample spectrum is then classified at step 2106 based on the project position and the classification is then output in step 2108.

Classification of an aerosol, smoke or vapour sample will now be described in more detail with reference to the simple PCA-LDA model described above.

Figure 22:
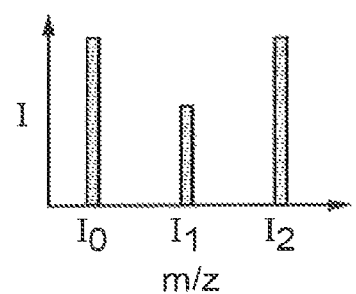
FIG. 22 shows a sample spectrum obtained from an unknown sample.

FIG. 22 shows a sample spectrum obtained from an unknown aerosol, smoke or vapour sample. The sample spectrum has been pre-processed in order to derive a set of three sample peak-intensity values for respective mass to charge ratios. As mentioned above, although only three sample peak-intensity values are shown, it will be appreciated that many more sample peak-intensity values (e.g., ~100 sample peak-intensity values) may be derived at many more corresponding mass to charge ratios for the sample spectrum. Also, as mentioned above, in other embodiments, the sample peak-intensity values may correspond to: masses; mass to charge ratios; ion mobilities (drift times); and/or operational parameters.

The sample spectrum may be represented by a sample vector $d_x$, with the elements of the vector being the peak-intensity values for the respective mass to charge ratios. A transformed PCA vector sX for the sample spectrum can be obtained as follows:

$$d_x L = s_x \qquad (5)$$

Then, a transformed PCA-LDA vector $z_X$ for the sample spectrum can be obtained as follows:

$$s_x U = z_x \qquad (6)$$

FIG. 23 again shows the PCA-LDA space of FIG. 20. However, the PCA-LDA space of FIG. 23 further comprises the projected sample point, corresponding to the transformed PCA-LDA vector $z_x$, derived from the peak intensity values of the sample spectrum of FIG. 22.

In this example, the projected sample point is to one side of a hyperplane between the classes that relates to the right-hand class, and so the aerosol, smoke or vapour sample may be classified as belonging to the right-hand class.

Alternatively, the Mahalanobis distance from the class centres in the LDA space may be used, where the Mahalanobis distance of the point $z_x$ from the centre of class g may be given by the square root of:

$$(z_x - z_g)^T (V'_g)^{-1} (z_x - z_g) \qquad (8)$$

and the data vector $d_x$ may be assigned to the class for which this distance is smallest.

In addition, treating each class as a multivariate Gaussian, a probability of membership of the data vector to each class may be calculated.
Library Based Analysis—Developing a Library for Classification By way of example, a method of building a classification library using plural input reference sample spectra will now be described.

FIG. 24 shows a method 2400 of building a classification library. In this example, the method comprises a step 2402 of obtaining plural input reference sample spectra and a step 2404 of deriving metadata from the plural input reference sample spectra for each class of sample. The method then comprises a step 2406 of storing the metadata for each class of sample as a separate library entry. The classification library is then output, for example to electronic storage, in step 2408.

A classification library such as this allows an aerosol, smoke or vapour sample to be classified using one or more sample spectra obtained from the aerosol, smoke or vapour sample. The library based analysis will now be described in more detail with reference to an example.

In this example, each entry in the classification library is created from plural pre-processed reference sample spectra that are representative of a class. In this example, the reference sample spectra for a class are pre-processed according to the following procedure:

First, a re-binning process is performed. In this embodiment, the data are resampled onto a logarithmic grid with abscissae:

$$x_i = \left\lfloor N_{chan} \log \frac{m}{M_{min}} / \log \frac{M_{max}}{M_{min}} \right\rfloor$$

where $N_{chan}$ is a selected value and $\lfloor x \rfloor$ denotes the nearest integer below x. In one example, $N_{chan}$ is $2^{12}$ or 4096.

Then, a background subtraction process is performed. In this embodiment, a cubic spline with k knots is then constructed such that p % of the data between each pair of knots lies below the curve. This curve is then subtracted from the data. In one example, k is 32. In one example, p is 5. A constant value corresponding to the q % quantile of the intensity subtracted data is then subtracted from each intensity. Positive and negative values are retained. In one example, q is 45.

Then, a normalisation process is performed. In this embodiment, the data are normalised to have mean $\bar{y}_i$. In one example, $\bar{y}_i = 1$.

An entry in the library then consists of metadata in the form of a median spectrum value $\mu_i$ and a deviation value $D_i$ for each of the $N_{chan}$ points in the spectrum.

The likelihood for the i'th channel is given by:

$$Pr(y_i | \mu_i, D_i) = \frac{1}{D_i} \frac{C^{C-1/2} \Gamma(C)}{\sqrt{\pi} \, \Gamma(C - 1/2)} \frac{1}{\left(C + \frac{(y_i - \mu_i)^2}{D_i^2}\right)^C}$$

where $1/2 \leq C < \infty$ and where $\Gamma(C)$ is the gamma function.

The above equation is a generalised Cauchy distribution which reduces to a standard Cauchy distribution for C=1 and becomes a Gaussian (normal) distribution as $C \to \infty$. The parameter $D_i$ controls the width of the distribution (in the Gaussian limit $D_i = \sigma_i$ is simply the standard deviation) while the global value C controls the size of the tails.

In one example, C is 3/2, which lies between Cauchy and Gaussian, so that the likelihood becomes:

$$Pr(y_i | \mu_i, D_i) = \frac{3}{4} \frac{1}{D_i} \frac{1}{(3/2 + (y_i - \mu_i)^2 / D_i^2)^{3/2}}$$

For each library entry, the parameters $\mu_i$ are set to the median of the list of values in the i'th channel of the input reference sample spectra while the deviation $D_i$ is taken to be the interquartile range of these values divided by $\sqrt{2}$. This choice can ensure that the likelihood for the i'th channel has the same interquartile range as the input data, with the use of quantiles providing some protection against outlying data.

Library-Based Analysis—Using a Library for Classification

By way of example, a method of using a classification library to classify an aerosol, smoke or vapour sample will now be described.

FIG. 25 shows a method 2500 of using a classification library. In this example, the method comprises a step 2502 of obtaining a set of plural sample spectra. The method then comprises a step 2504 of calculating a probability or classification score for the set of plural sample spectra for each class of sample using metadata for the class entry in the classification library. The sample spectra are then classified at step 2506 and the classification is then output in step 2508.

Classification of an aerosol, smoke or vapour sample will now be described in more detail with reference to the classification library described above.

In this example, an unknown sample spectrum y is the median spectrum of a set of plural sample spectra. Taking the median spectrum y can protect against outlying data on a channel by channel basis.

The likelihood $L_s$ for the input data given the library entry s is then given by:

$$L_s = Pr(y | \mu, D) = \prod_{i=1}^{N_{chan}} Pr(y_i | \mu_i, D_i)$$

where $\mu_i$ and $D_i$ are, respectively, the library median values and deviation values for channel i. The likelihoods $L_s$ may be calculated as log likelihoods for numerical safety.

The likelihoods $L_s$ are then normalised over all candidate classes 's' to give probabilities, assuming a uniform prior probability over the classes. The resulting probability for the class s is given by:

$$Pr(s | y) = \frac{L_s^{(1/F)}}{\sum_s L_s^{(1/F)}}$$

The exponent (1/F) can soften the probabilities which may otherwise be too definitive. In one example, F=100. These probabilities may be expressed as percentages, e.g., in a user interface.

Alternatively, RMS classification scores $R_s$ may be calculated using the same median sample values and derivation values from the library:

$$R_s(y, \mu, D) = \sqrt{\frac{1}{N_{chan}} \sum_{i=1}^{N_{chan}} \frac{(y_i - \mu_i)^2}{D_i^2}}$$

Again, the scores $R_s$ are normalised over all candidate classes 's'.

The aerosol, smoke or vapour sample may then be classified as belonging to the class having the highest probability and/or highest RMS classification score.

Microbial Detection, Identification and/or Characterisation

The terms "detect" and "detection" and derivations of these terms are used interchangeably herein to mean that the presence or absence of a target entity is determined.

Any of the methods in which the target entity is a microbe may optionally be used to determine whether or not a particular target or region thereof is sterile or non-sterile. Thus, in one embodiment, a microbe is detected and optionally based on this detection a determination is made that the target or region is non-sterile. In one embodiment, a microbe is not detected and optionally based on this detection a determination is made that the target or region is sterile.

Any of the methods in which the target entity is a microbe may be used to determine that one or more different types of microbes are present. The detection of only 1 type of microbe may indicate that no other types of microbes are present in the sample. Thus, in one embodiment, the presence of only 1 type of microbe is determined. In the case of a sample from a microbial culture, optionally a determination is made that a microbial culture is free of contaminating microbes. In the case of a clinical or food sample, optionally a determination is made that an infection is, or is likely to be, only caused by a single microbial pathogen.

In one embodiment, the presence of 1, 2, 3, 4, 5, 6, 7, 8, 9, 10, 15, 20, 25, 30, 35, 40, 45 or 50 different types of microbes is determined. In one embodiment, the presence of 1 or more, 2 or more, 3 or more, 4 or more, 5 or more, 6 or more, 7 or more, 8 or more, 9 or more, 10 or more, 15 or more, 25 or more or 30 or more different types of microbes is determined. In the case of a sample from a microbial culture, optionally a determination is made that a microbial culture contains contaminating microbes. In the case of a clinical or food sample, optionally a determination is made that an infection is, or is likely to be, caused by a plurality of microbes.

Some microbes are pathogenic, whereas others are non-pathogenic. A pathogenic microbe may be defined as a microbe that is able to cause disease in a host, such as a plant or animal. A pathogen may be an obligate pathogen or an opportunistic pathogen.

The ability of a microbe to cause disease depends both on its intrinsic virulence factors and on the ability of the host to fight off the microbe. The distinction between non-pathogens and opportunistic pathogens is therefore not clear-cut, because, for example, immuno-compromised hosts will be susceptible to infection by microbes that may be unable to infect a host with a healthy immune system. Antibiotic use can also create an environment in which a microbe will flourish as an opportunistic pathogen.

For example, *Neisseria gonorrhoeae* is an obligate pathogen, *Pseudomonas aeruginosa* and *Candida albicans* are typically referred to as opportunistic pathogens, and *Lactobacillus acidophilus* and *Bifidobacterium bifidum* are typically considered to be non-pathogens or "commensal" bacteria.

Pathogenic microbes may optionally be characterised by the expression of one or more virulence factors, i.e. factors that allow or facilitate infection of a host. Virulence factors may optionally be selected from factors that mediate cell adherence, cell growth, the ability to bypass or overcome host defence mechanisms, and/or the production of toxins. Toxins may be selected from exotoxins and endotoxins.

Thus, the method may be used to determine whether one or more pathogenic microbes are present. In one embodiment, the presence of 1 or more, 2 or more, 3 or more, 4 or more, 5 or more, 6 or more, 7 or more, 8 or more, 9 or more, 10 or more, 15 or more, 25 or more or 30 or more different pathogenic microbes is determined.

It is often desirable to identify a microbial population present in or on a target. The identity of microbial populations in/on clinical and/or environmental specimens is often unknown and identification is therefore desired. With regard to microbial cultures, human error and/or other circumstances can lead to misidentification, mislabelling, mix-ups, and the like, of microbial populations.

Thus, the identity of a particular microbial population may be unknown, uncertain and/or unconfirmed. Optionally, the method may be used to identify a microbial population, and/or to confirm the identity of a microbial population.

The terms "determine identity" "identify" and "identification" and derivations of these terms are used interchangeably herein By "identifying" a microbial population is meant that at least some information about the type(s) of microbes present in the microbial population is obtained. This may optionally be the determination of the identity, and/or the confirmation of the identity of one or more microbial types in the microbial population. Confirming the identity of a microbial population may, e.g., in the context of a microbial culture, also be referred to as confirming the authenticity of a microbial population. However, "identifying" may alternatively include information that allows the microbe to be identified as falling into a particular classification.

Thus, optionally the method may be performed on a microbial population whose identity is unknown, to determine the identity of the microbial population.

Optionally, the method may be performed on a microbial population suspected of having a particular identity, to confirm or refute the identity of the microbial population.

Optionally, the method may be performed on a microbial population in need of authentication, to confirm the authenticity of the microbial population.

Optionally, the microbial population may be identified as comprising or consisting of one or more of the microbes listed elsewhere herein, e.g., having the identity of any one of the microbes listed elsewhere herein.

Optionally, the microbial population may be identified as comprising or consisting of pathogenic microbes. Optionally, the microbial population may be identified as comprising or consisting of commensal microbes, e.g., non-pathogenic microbes.

Optionally, the microbial population may be identified as comprising or consisting of mutant and/or transgenic microbes.

Optionally, the microbial population may be identified as comprising or consisting of microbes that are sensitive and/or resistant to one or more antimicrobials.

Optionally, the microbial population may be analysed (i) to confirm the identity or authenticity of said microbial population; (ii) to detect a mutation in said microbial population; and/or (iii) to detect an undesired variation in said microbial population.

Optionally, the method may be used to analyse the spread of an infection. For example, the method may be used to analyse whether two or more different subjects have been infected by the same type of microbe or by two different types of microbes. This may optionally involve the analysis of the genotype and/or phenotype of the microbe, particularly if each infection is caused by the same microbial species. Thus, optionally, the method may be used to determine the identity and/or genotype and/or phenotype of a first microbial population causing an infection in a first subject, as well as the identity and/or genotype and/or phenotype of a second or further microbial population causing an infection in a second or further subject. A determination may then be made as to whether the first and the second or further microbial population are identical, and, if not, to what extent or how significantly they differ from one another. If a determination is made that the first and the second microbial population are identical or significantly similar, then optionally a determination may be made that the first and the second subject have, or are likely to have, acquired the same infection, e.g., acquired the infection from the same source. Conversely, if a determination is made that the first and the second microbial population are not identical or significantly similar, then optionally a determination may be made that the first and the second subject have, or are likely to have, acquired different infections, e.g., acquired the infection from different sources. This may, e.g, help to analyse whether a patient acquired an infection prior to entering a hospital, or whether a patient has a hospital-acquired infection.

Microbial identification may optionally be on any taxonomic level, for example, at the Kingdom, Phylum or Division, Class, Order, Family, Genus, Species and/or Strain level.

"Taxonomy" is the classification of organisms, and each level of classification may be referred to as a "taxon" (plural: taxa). Organisms may be classified into the following taxa in increasing order of specificity: Kingdom, Phylum or Division, Class, Order, Family, Genus, Species and Strain. Further subdivisions of each taxon may exist. It must be appreciated that within the vast scientific community there are some discrepancies within some taxonomic classifications. There may also be a lack of consensus with regard to the nomenclature of certain microbes, resulting in a particular microbe having more than one name or in two different microbes having the same name.

Taxonomic classification is illustrated below by reference to *Pseudomonas aeruginosa*, which belongs to the Kingdom: bacteria; Phylum: Proteobacteria; Class: Gammaproteobacteria; Order: Pseudomonadales; Family: Pseudomonadaceae; Genus: *Pseudomonas*; and Species: *Pseudomonas aeruginosa*.

A microbe, also known as a micro-organism, is an organism which is too small to be visible to the naked eye, i.e. is microscopic. A microbe may be selected from bacteria, fungi, archaea, algae, protozoa, and viruses. Although the terms bacteria, fungi, archaea, algae, protozoa and viruses technically denote the plural form, it is common practice to use them also to denote the singular form. Consequently, the terms "bacteria" and "bacterium" are used interchangeably herein; the terms "fungi" and "fungus" are used interchangeably herein; the terms "archaea" and "archaeum" are used interchangeably herein; the terms "protozoa" and "protozoum" are used interchangeably herein; and the terms "viruses" and "virus" are used interchangeably herein.

In some embodiments, the microbe may be selected from bacteria, fungi, archaea, algae and protozoa. In some embodiments, it may be selected from bacteria and fungi. In some embodiments, it may be selected from bacteria.

The microbe may be single-cellular or multi-cellular. If the microbe is a fungus, it may optionally be filamentous or single-cellular, e.g., a yeast.

A fungus may optionally be yeast. It may optionally be selected from the genus *Aspergillus, Arthroascus, Brettanomyces Candida, Cryptococcus, Debaryomyces, Geotrichum, Pichia, Rhodotorula, Saccharomyces, Trichosporon*, and *Zygotorulaspora*.

It may optionally be selected from the species *Arthroascus schoenii, Brettanomyces bruxellensis, Candida albicans, C. ascalaphidarum, C. amphixiae, C. antarctica, C. argentea, C. atlantica, C. atmosphaerica, C. blattae, C. bromeliacearum, C. carpophila, C. carvajalis, C. cerambycidarum, C. chauliodes, C. corydali, C. dosseyi, C. dubliniensis, C. ergatensis, C. fructus, C. glabrata, C. fermentati, C. guilliermondii, C. haemulonii, C. insectamens, C. insectorum, C. intermedia, C. jeffresii, C. kefyr, C. keroseneae, C. krusei, C. lusitaniae, C. lyxosophila, C. maltosa, C. marina, C. membranifaciens, C. milleri, C. mogii, C. oleophila, C. oregonensis, C. parapsilosis, C. quercitrusa, C. rugosa, C. sake, C. shehatea, C. temnochilae, C. tenuis, C. theae, C. tolerans, C. tropicalis, C. tsuchiyae, C. sinolaborantium, C. sojae, C. subhashii, C. viswanathii, C. utilis, C. ubatubensis, C. zemplinina, Cryptococcus neoformans, Cryptococcus uniguttulatus, Debaryomyces carsonii, Geotrichum capitatum, Trichosporon asahii, Trichosporon mucoides, Trichosporon inkin, Saccharomyces cerevisiae, Pichia acaciae, Pichia anomala, Pichia capsulata, Pichia farinosa, Pichia guilliermondii, Pichia spartinae, Pichia ohmeri, Rhodotorula glutinous, Rhodotorula mucilaginosa, Saccharomyces boulardii, Saccharomyces cerevisiae*, and/or *Zygotorulaspora florentinus*.

The protozoa may be selected from the group of amoebae, flagellates, ciliates or sporozoa. It may be selected from the genus *Acanthamoeba, Babesia, Balantidium, Cryptosporidium, Dientamoeba, Entamoeba, Giardia, Leishmania, Naegleria, Plasmodium Paramecium, Trichomonas, Trypanosoma, Typanosoma, Toxoplasma*

The protozoa may be of the species *Balantidium coli, Entamoeba histolytica, Giardia lamblia* (also known as *Giardia intestinalis*, or *Giardia duodenalis*), *Leishmania donovani, L. tropica, L. brasiliensis, Plasmodium falciparum, P. vivax, P. ovale, P. malariae, P. knowlesi, P. reichenowi, P. gaboni, P. mexicanum, P. floridense Trypanosoma brucei, Typanosoma evansi, Trypanosoma rhodesiense, Trypanosoma cruzi, Toxoplasma gondii*.

The algae may optionally be selected from *Chlamydomonas*.

The bacteria may optionally be selected from the phylum Aqufice, Thermotogae, Thermodesulfobacteria, Deinococcus-Thermus, Chrysiogenetes, Chloroflexi, Thermomicrobia, Nitrospira, Deferribacteres, Cyanobacteria, Chlorobi, Proteobacteria, Firmicutes, Actinobacteria, Planctomycetes, Chlamydiae, Spirochaetes, Fibrobacteres, Acidobacteria, Bacteroidetes, Fusobacteria, Verrucomicrobia, Dictyoglomi, Gemmatomonadetes, and Lentisphaerae.

The bacteria may optionally be selected from the class Actinobacteria, Alphaproteobacteria, Bacilli, Betaproteobacteria, Clostridia, Deltaproteobacteria, Epsilonproteobacteria, Flavobacteriaceae, Fusobacteria, Gammaproteobacteria, Mikeiasis, Mollicutes, or Negativicutes.

The bacteria may optionally be of the Order Aeromonadales, Actinomycetales, Bacillales, Bacteroidales, Bifidobacteriales, Burkholderiales, Campylobacterales, Caulobacterales, Cardiobacteriales, Clostridiales, Enterobacteriales, Flavobacteriales, Fusobacteriales, Lactobacillales, Micrococcales, Neisseriales, Pasteurellales, Pseudomonadales, Rhizobiales, Rhodospirillales, Selenomonadales, Vibrionales, Xanthomonadales.

The bacteria may optionally be selected from the Family Acetobacteraceae, Alcaligenaceae, Bacillaceae, Bacteroidaceae, Burkholderiaceae, Caulobacteraceae, Comamonadaceae, Enterobacteriaceae, Flavobacteriaceae, Fusobacteriaceae Nocardiaceae, Prevotellaceae, Porphyromonadaceae, Pseudomonadaceae, Rikenellaceae, Rhizobiaceae, Sutterellaceae.

The bacteria may optionally be of a genus selected from, e.g., *Abiotrophia, Achromobacter, Acidovorax, Acinetobacter, Actinobacillus, Actinomadura, Actinomyces, Aerococcus, Aeromonas, Anaerococcus, Anaplasma, Bacillus, Bacteroides, Bartonella, Bifidobacterium, Bordetella, Borrelia, Brevundimonas, Brucella, Burkholderia Campylobacter, Capnocytophaga, Chlamydia, Citrobacter, Chlamydophila, Chryseobacterium, Clostridium, Comamonas, Corynebacterium, Coxiella, Cupriavidus, Delftia, Dermabacter, Ehrlichia, Eikenella, Enterobacter, Enterococcus, Escherichia, Erysipelothrix, Facklamia, Finegoldia, Francisella, Fusobacterium, Gemella, Gordonia, Haemophilus, Helicobacter, Klebsiella, Lactobacillus, Legionella, Leptospira, Listeria, Micrococcus, Moraxella, Morganella, Mycobacterium, Mycoplasma, Neisseria, Nocardia, Orientia, Pandoraea, Pasteurella, Peptoniphilus, Peptostreptococcus, Plesiomonas, Porphyromonas, Pseudomonas, Prevotella, Proteus, Propionibacterium, Rhodococcus, Ralstonia, Raoultella, Rickettsia, Rothia, Salmonella, Serratia, Shigella, Staphylococcus, Stenotrophomonas, Streptococcus, Tannerella, Treponema, Ureaplasma, Vibrio* or *Yersinia*.

The bacteria may optionally be of a species selected from, e.g., *Abiotrophia defective, Achromobacter xylosoxidans, Acidovorax avenae, Acidovorax citrulli, Bacillus anthracis, B. cereus, B. subtilis, B. licheniformis, Bacteroides fragilis, Bartonella henselae, Bartonella quintana, Bordetella pertussis, Borrelia burgdorferi, Borrelia garinii, Borrelia afzelii, Borrelia recurrentis, Brucella abortus, Brucella canis, Brucella melitensis, Brucella suis, Burkholderia cepacia, Burkholderia genomovars, Campylobacter jejuni, Chlamydia pneumoniae, Chlamydia trachomatis, Chlamydophila psittaci, Citrobacter koseri, Clostridium botulinum, Clostridium difficile, C. perfringens, C. tetani, Corynebacterium diphtherias, C. striatum, C. minutissimum, C. imitans, C. amycolatum, Delftia acidovorans, Enterobacter aerogenes, E. cloacae Enterococcus faecalis, Enterococcus faecium, Escherichia coli, Francisella tularensis, Fusobacterium nucleatum, Haemophilus influenzae, Helicobacter pylori, Klebsiella oxytoca, K. pneumonia, Legionella pneumophila, Leptospira interrogans, Leptospira santarosai, Leptospira weilii, Leptospira noguchii, Listeria ivanovii, Listeria monocytogenes, Micrococcus luteus, Morganella morganii, Moraxella catarrhalis, Mycobacterium avium, M. fortuitum, M. leprae, M. peregrium, M. tuberculosis, M. ulcerans, Mycoplasma pneumoniae, Neisseria gonorrhoeae, N. lactamica, N. meningitidis, Nocardia asteroids, Proteus mirabilis, Pseudomonas aeruginosa, Rhodococcus equi, Rhodococcus pyridinivorans, Rickettsia rickettsii, Salmonella typhi, Salmonella typhimurium, Serratia marcescens, Shigella sonnei, Staphylococcus aureus, S. capitis, S. epidermidis, S. haemolyticus, S. hominis, S. saprophyticus, Stenotrophomonas maltophilia, Streptococcus agalactiae, S. pyogenes, S. pneumonia, Treponema pallidum, Ureaplasma urealyticum, Vibrio cholerae, Yersinia pestis, Yersinia enterocolitica* and *Yersinia pseudotuberculosis*.

The virus may optionally be a DNA virus, and RNA virus or a retrovirus. It may optionally be a single stranded (ss) or a double stranded (ds) virus. More particularly, it may optionally be a ssDNA, dsDNA, dsRNA, ssRNA(positive strand), ssRNA (negative strand), ssRNA (reverse transcribed) or dsDNA (reverse transcribed) virus.

It may optionally be selected from one or more of the Herpesviridae, optionally selected from Simplexvirus, Varicellovirus, Cytomegalovirus, Roseolovirus, Lymphocryptovirus, and/or Rhadinovirus; the Adenoviridae, optionally selected from Adenovirus and/or Mastadenovirus; Papillomaviridae, optionally selected from Alphapapillomavirus, Betapapillomavirus, Gammapapilloma-virus, Mupapillomavirus, and/or Nupapillomavirus; Polyomaviridae, optionally selected from Polyomavirus; Poxviridae, optionally selected from Molluscipoxvirus, Orthopoxvirus and/or Parapoxvirus; Anelloviridae, optionally selected from Alphatorquevirus, Betatorquevirus, and/or Gammatorquevirus; Mycodnaviridae, optionally selected from Gemycircular-viruses; Parvoviridae, optionally selected from Erythrovirus, Dependovirus, and/or Bocavirus; Reoviridae, optionally selected from Coltivirus, Rotavirus, and/or Seadornavirus; Coronaviridae, optionally selected from Alphacoronavirus, Betacoronavirus, and/or Torovirus; Astroviridae, optionally selected from Mamastrovirus; Caliciviridae, optionally selected from Norovirus, and/or Sapovirus; Flaviviridae, optionally selected from Flavivirus, Hepacivirus, and/or Pegivirus; Picornaviridae, optionally selected from Cardiovirus, Cosavirus, Enterovirus, Hepatovirus, Kobuvirus, Parechovirus, Rosavirus, and/or Salivirus; Togaviridae, optionally selected from Alphavirus and/or Rubivirus; Rhabdoviridae, optionally selected from Lyssavirus, and/or Vesiculovirus; Filoviridae optionally selected from Ebolavirus, and/or Marburgvirus; Paramyxoviridae, optionally selected from Henipavirus, Morbilivirus, Respirovirus, Rubulavirus, Metapneumovirus, and/or Pneumovirus; Arenaviridae, optionally selected from Arenavirus; Bunyaviridae, optionally selected from Hantavirus, Nairovirus, Orthobunyavirus, and/or Phlebovirus; Orthomyxoviridae, optionally selected from Influenzavirus A, Influenzavirus B, Influenzavirus C and/or Thogotovirus; Retroviridae, optionally selected from Gammaretrovirus, Deltaretrovirus, Lentivirus, Spumavirus; Epadnaviridae, optionally selected from Orthohepadnavirus; Hepevirus; and/or Deltavirus.

Thus, optionally, the spectrometric data may be used to microbe to be identified as: (i) being a prokaryote or a eukaryote; (ii) belonging to a particular Kingdom, such as, any of those listed herein; (iii) belonging to a particular Phylum or Division, such as, any of those listed herein; (iv) belonging to a particular Class, such as, any of those listed herein; (v) belonging to a particular Order, such as, any of those listed herein; (vi) belonging to a particular Family, such as, any of those listed herein; (vii) belonging to a particular Genus, such as, any of those listed herein; (viii) belonging to a particular Species, such as, any of those listed herein; and/or (ix) belonging to a particular Strain, such as, any of those listed herein.

The terms "characterise" and "characterisation" and derivations of these terms are used interchangeably herein to mean that information about the characteristics of a target entity is obtained.

Information about the characteristics of a microbe may, for example, be selected from one or more of the following: virulence, antimicrobial sensitivity or resistance, ability to produce a particular compound, growth rate, production rate with regard to a particular compound, respiration rate, and/or response to/level of stress. Thus, characterisation may involve the analysis of the genotype and/or phenotype of a microbe, and/or the analysis of a property of a microbe.

Analysis of Phenotype, Genotype and/or Homogeneity

Genetic mutations may alter the structure of a protein, e.g., by coding for a different amino acid, and/or by resulting in a shortened or elongated protein. Genetic mutations may alternatively or in addition result in a reduced output or absence of a gene product.

The term "phenotype" is used to refer to the physical and/or biochemical characteristics of a microbe whereas the term "genotype" is used to refer to the genetic constitution of a microbe.

The term "phenotype" may be used to refer to a collection of a microbe's physical and/or biochemical characteristics, which may optionally be the collection of all of the microbe's physical and/or biochemical characteristics; and/or to refer to one or more of a microbe's physical and/or biochemical characteristics. For example, a microbe may be referred to as having the phenotype of a particular microbial type, e.g., a *Bacillus subtilis* strain, and/or as having the phenotype of being antibiotic-resistant.

The term "genotype" may be used to refer to genetic information, which may include genes, regulatory elements and/or junk DNA. The term "genotype" may be used to refer to a collection of a microbe's genetic information, which may optionally be the collection of all of the microbe's genetic information; and/or to refer to one or more of a microbe's genetic information. For example, a microbe may be referred to as having the genotype of a particular microbial type, e.g., a *Bacillus subtilis* strain, and/or as having the genotype of being antibiotic-resistant.

The genotype of a microbe may or may not affect its phenotype, as explained below.

The relationship between a genotype and a phenotype may be straightforward. For example, if a microbe includes a functional gene encoding a particular protein, such as the adhesion protein FimH adhesin, then it will typically be phenotypically FimH adhesin-positive, i.e. have the FimH adhesin protein on its surface, whereas if a microbe lacks a functional FimH adhesin gene, then it will have a FimH adhesin-negative phenotype.

A mutant genotype may result in a mutant phenotype. For example, if a mutation destroys the function of a gene, then the loss of the function of that gene may result in a mutant phenotype. However, factors such as genetic redundancy may prevent a genotypic trait to result in a corresponding phenotypic trait. For example, a microbe may have multiple copies of a particular gene, or have genes encoding alternative pathways that lead to the same result.

It must also be borne in mind that many genotypic changes may have no phenotypic effect, e.g., because they are in junk DNA, i.e. DNA which seems to serve no sequence-dependent purpose, or because they are silent mutations, i.e. mutations which do not change the coding information of the DNA because of the redundancy of the genetic code.

The phenotype of a microbe may be determined by its genotype in that a cell requires genetic information to carry out cellular processes and any particular protein may only be generated within a cell if the cell contains the relevant genetic information. However, the phenotype of a microbe may also be affected by environmental factors and/or stresses, such as, temperature, nutrient and/or mineral availability, toxins and the like. Such factors may influence how the genetic information is used, e.g., which genes are expressed and/or at which level. Environmental factors and/or stresses may also influence other characteristics of a microbe, e.g., heat may make membranes more fluid.

If a functional transgene is inserted into a cell at the correct genomic position, then this may result in a corresponding phenotype.

The insertion of a transgene may affect a microbe's phenotype, but an altered phenotype may optionally only be observed under the appropriate environmental conditions. For example, the insertion of a transgene encoding a protein involved in a synthesis of a particular substance will only result in microbes that produce that substance if the microbes are provided with the required starting materials.

Optionally, the method may involve the analysis of the phenotype and/or genotype of a microbial population.

The genotype and/or phenotype of a microbial population may be manipulated, e.g., to analyse a cellular process, to make a microbial population more suitable for drug screening and/or production, and the like. Optionally, the method may involve the analysis of the effect of such a genotype and/or phenotype manipulation on the microbial population, e.g., on the genotype and/or phenotype of the microbial population.

The method may optionally be used to analyse a microbial population after mutagenesis. Conventional methods for confirming whether or not a microbe has been mutated can be difficult and/or time consuming. Optionally, the method may be used to analyse whether a microbe has been mutated. A mutation may, e.g., be the introduction of a new gene, the silencing of a gene, an alteration in the expression of a gene, or give rise to an altered protein. Silencing may, e.g., be achieved via gene knock-out.

Optionally, the method may be used to analyse the effect of mutagenesis on a microbe, e.g., on the genotype and/or phenotype of a microbe.

Optionally, the method may analyse a microbe at 2 or more time points, e.g., before and after mutagenesis, and/or at 2 or more time points after mutagenesis.

Optionally, the microbial population may be homogeneous or heterogeneous. By "homogeneous", "homogeneity" and derivatives of these terms is meant that the population is uniform, and by "heterogeneous", "heterogeneity" and derivatives of these terms is meant that the population is non-uniform.

By "degree of homogeneity" or "degree of heterogeneity" is meant the extent to which a microbial population is homogeneous or heterogeneous, which may be expressed as a percentage. For example, a microbial population may be considered to have a high degree of homogeneity if at least 60, 70, 75, 80, 85, 90, 91, 92, 93, 94, 95, 96, 97, 98, 99 or 100% of the microbes are homogenous. A microbial population may be considered to have a high degree of heterogeneity if at least 40, 45, 50, 55, 60, 70, 75, 80, 85, 90, 91, 92, 93, 94, 95, 96, 97, 98, 99 or 100% of the microbes are heterogeneous.

The homogeneity and/or heterogeneity may be with respect to one or more genotypic and/or phenotypic features, e.g., at least 1, 2, 3, 4, 5, 6, 7, 8, 9 or 10 genotypic and/or phenotypic features, optionally with respect to the microbes' entire genotype and/or phenotype.

Optionally, the method may involve the analysis of the degree of homogeneity and/or heterogeneity of the microbial population.

During culture of a microbial population, microbes may grow and replicate. Replication may involve self-renewal, i.e. the production of a daughter cell having the same genotype and/or phenotype as the mother cell, and/or differentiation, i.e. the production of a daughter cell having a different genotype and/or phenotype compared to the mother cell.

Alternatively or in addition, microbes may acquire one or more mutations and thus acquire a different genotype, which may manifest itself as a different phenotype.

In a heterogeneous microbial population, one type may grow and/or replicate better or in a different way to another microbial type, and/or one cell type may become dormant and/or die.

For these and/or other reasons, microbial population may become more or less heterogeneous, so the method may optionally involve monitoring for any changes in the homogeneity and/or heterogeneity of the microbial population.

Optionally, if the degree of homogeneity and/or heterogeneity of the microbial population is higher or lower than desired, the method may involve a step of influencing the degree of homogeneity and/or heterogeneity. This may, e.g., involve the adjustment of culture conditions and/or the addition of a substance, to affect, e.g., the growth and/or differentiation rate of one or more of the microbial types present in the microbial population.

Manipulation of Genotype and/or Phenotype

Optionally, a microbial population may be manipulated, e.g., the phenotype and/or genotype of some or all of the microbes that make up the microbial population may be manipulated.

The manipulation may optionally involve the exposure of a microbial population or a portion thereof to a compound and/or radiation.

The manipulation may optionally be genetic manipulation.

Genetic manipulation may alter one or more genomic region(s) of a microbe, which genomic region may be in the coding region of a gene, the non-coding region of a gene, a regulatory region, e.g., a promoter or enhancer, and/or in a region called "junk" DNA.

Genetic manipulation may optionally involve random mutagenesis. For example, microbes may be exposed to a mutagen, which may, e.g., be selected from a chemical mutagen and/or radiation.

A compound, which may optionally be a chemical mutagen, may optionally be selected from, e.g., an alkylating agent, cross-linking agent, and/or polycyclic aromatic hydrocarbons (PAHs). Alkylating agents act by adding molecular components to DNA bases, which alters the protein product. Cross-linking agents create covalent bonds with DNA bases, while PAHs are metabolized by the human body into other potentially mutagenic molecules.

Radiation may optionally be selected from, e.g., light of a suitable wavelength, heat, and/or ionizing radiation. Ionizing radiation can penetrate microbes and create ions in the cell contents. These ions can cause permanent alterations in DNA. Ionizing radiation may optionally be selected from, e.g., x rays, gamma rays, neutrons, electrons ("beta" particles), and/or alpha particles (helium nuclei). Ionizing radiation can alter the way two strands of DNA interact. It can rearrange entire sections of the chromosomes, altering relatively long stretches of DNA. Light may optionally be, e.g., UV light. This can cause covalent bonds to form between neighbouring thymine bases in the DNA, thereby altering the DNA at that location.

Alternatively or in addition to random mutagenesis, genetic manipulation may optionally involve targeted mutagenesis, which may optionally, e.g., be the knock-out, alteration, and/or insertion of genetic information. A cell that has been manipulated via targeted mutation may be referred to as a "transformed" cell, particularly if a new gene or gene variant, i.e. a "transgene" has been inserted. Similarly, a microbial population comprising or consisting of cells that have been manipulated via targeted mutation may be referred to as a "transformed" microbial population. Similarly, an organoid comprising or consisting of cells that have been manipulated via targeted mutation may be referred to as a "transformed" organoid.

Mutagenesis may optionally involve, e.g., one or more of the following techniques to introduce the desired genetic material, such as a transgene, into a cell: microinjection into the nucleus of a cell; a viral vector, e.g., an adenoviral or lentiviral vector; a liposome; calcium phosphate; a dendrimer; a cationic polymer, such as DEAE-dextran and/or polyethylenimine; sonication; electroporation; magnet-assisted transfection with magnetic particles; and/or particle bombardment.

Mutagenesis may optionally involve genome editing, e.g., using programmable nucleases, such as zinc-finger nucleases (ZFNs), transcription activator-like effector nucleases (TALENs), and/or clustered regularly interspaced short palindromic repeats (CRISPR)/CRISPR-associated protein 9 (Cas9).

Optionally, the method may involve a step of random and/or targeted mutagenesis, e.g., via any of the methods mentioned herein.

Analysis of Contamination

A microbial population may be at risk of contamination with another microbe type. In particular, a microbial culture, such as a microbial type culture, should be free of contamination. By "contamination" is meant that the microbial culture is not pure, i.e. that one or more further (unwanted) microbial types are present.

Contamination can be difficult to detect with conventional methods, because two microbial types may be visually indistinguishable from one another.

Optionally, the method may be used to analyse whether contamination is present in a microbial population.

Optionally, the method may be used (i) to determine whether or not said microbial population suffers from contamination; (ii) to determine whether or not said microbial population is contamination free; (iii) to determine whether or not said microbial population has been cured of contamination; (iv) to determine the progression or stage of contamination of a microbial population; or (v) to determine the progression or stage of a treatment for contamination of a microbial population.

Optionally, if contamination is determined, the contaminating microbe may be identified.

Optionally, if contamination is determined, the method may involve a step of treating/removing the contamination, e.g., through contacting the microbial population with an appropriate substance that is effective at selectively killing, or inhibiting the growth of, the contamination microbe. For example, if contamination with a bacterium is determined, a suitable antibiotic may be used.

Properties of Microbial Populations

The method may be carried out on a microbial population having a desired property by selecting an existing microbial population with the desired property. Alternatively or in addition, a microbial population may be manipulated to impart a desired property unto the microbial population. The method may optionally involve the analysis of one or more properties of a microbial population.

Properties of a microbial population that may be selected, manipulated, analysed or the like may optionally be selected from any of the properties listed below.

The microbial population may optionally be auxotrophic with respect to one or more substances. Auxotrophy is the inability, or reduced ability, of a microbe to synthesize a particular substance required for its growth. An auxotroph is a microbe that displays this characteristic; auxotrophic is the corresponding adjective. For example, an auxotroph may have a deficiency in a metabolic enzyme required to make tryptophan, in which case it may be referred to as a trp-auxotroph.

The microbial population may optionally have the ability to produce a desired substance, e.g., a drug. Thus, the microbial population may optionally have the ability to utilise a substance, e.g., to metabolise a substrate molecule to form a desired compound or precursor. Utilisation of a first substance may involve using a first substance as a substrate to produce a second substance; using a first substance as a general nutrient; and/or breaking down a first substance.

The microbial population may optionally have a high specific productivity with respect to the production of a desired substance. The microbial population may optionally have a high efficiency with respect to the utilisation and/.or breakdown of a desired substance. It may optionally comprise high levels of, or have the ability to generate high levels of, one or more key metabolites linked to energy generation, regulation of cellular redox potential, and precursors for glycosylation. The method may optionally be used to determine whether a low productivity/efficiency microbial population exhibits a different metabolic profile than its high productivity/efficiency counterpart. The method may optionally be used to analyse the specific productivity potential and/or or efficiency with respect to the utilisation and/or breakdown of a desired substance, of a microbial population.

The microbial population may optionally have the ability to secrete a produced substance.

The microbial population may optionally have the ability to replicate rapidly.

The method may optionally be used to analyse the metabolome, lipidome and/or proteome of a microbial population.

The metabolome is a collection of some or all of the small-molecule metabolites present in a cell. The lipidome is a collection of some of all of the lipids present in a microbe. The proteome is a collection of some of all of the proteins present in a microbe. Although many proteins and some metabolites may not necessarily be analysed directly via the method provided herein, they may optionally be analysed indirectly, by analysing an indirect biomarker therefor.

The method may optionally involve the analysis of the state of a microbial population or one or more microbe types present therein. By "state" is meant the condition of a microbial population or one or more microbe types present therein, which may, e.g., be healthy and growing; healthy and not growing; stressed and growing; stressed and not growing; dying; or dead.

The method may optionally involve the analysis of the viability of a microbial population. By "viability" is meant the minimum length of time that the microbial population will continue to live. The viability may also be referred to as the "robustness", as robust microbial populations are likely to live longer than non-robust microbial populations.

The method may optionally involve the analysis of a cellular process. A cellular process may, e.g., be the production of a substance; the utilisation of a nutrient; a response to exposure to a substance; a response to exposure to an environmental condition and the like.

The method may optionally involve the identification of a spectrometric biomarker for a microbial type, phenotype, genotype and/or a microbial property. The identity and characteristics of many microbial populations, e.g., E. coli, are known, and the method provided herein allows the identification of spectrometric biomarkers of these microbial types or microbial characteristics. Thus, the method may be used, e.g., to correlate a characteristic with spectrometric data, e.g., a spectrometric biomarker. The characteristic may, e.g., be the sensitivity to a particular substance.

Drug Discovery and Screening of Agents, e.g., Antimicrobial Agents

It is known to use microbe-based platforms to advance drug discovery, and it will be understood by those skilled in the art that microbe-based compound screens and bioassays are essential for such drug discovery.

Optionally, the method provided herein may be used for drug discovery and/or drug analysis. Thus, it may, e.g., be used as a screening method to screen potential therapeutic agents; or to screen known therapeutics to analyse their effects. For example, the method may be used to analyse the efficacy of a substance; the mechanism of action of a substance; and/or the safety of a substance. The efficacy may optionally be the therapeutic efficacy. The safety may optionally be the pharmacological safety.

Optionally the screening may be high-throughput screening. Optionally, the screening may be for, or of, a therapeutic agent effective against any of the diseases listed elsewhere herein, e.g., an infection.

Thus, the method may optionally comprise exposing a microbial population to a first substance and using the method to analyse the effect of said substance on the microbial population. Details of suitable substances are discussed elsewhere herein.

Optionally, a second substance may be used, e.g., for comparison or control purposes. For example, the method may comprise exposing a first microbial population to a first substance and a second microbial population may be exposed to a second substance, analysing the first and the second microbial population via mass spectrometry and/or ion mobility spectrometry as discussed elsewhere herein and analysing any differences between the two microbial populations. Optionally, the second substance may be a control substance, which may, e.g., be a negative control such as water or a buffer, or a positive control, such as an agent with a known effect, e.g., a known antimicrobial effect. Optionally, the first and the second microbial population may be identical prior to performance of the method. For example, two samples may be taken from a single microbial population to generate 2 microbial populations. Optionally, the first and the second microbial population may be isogenic. Optionally, the first and the second microbial population may be phenotypically and/or genotypically different, e.g., they may be different microbe types.

Analysing the effect of said substance on the microbial population may comprise analysing a change in one or more properties of the microbial population, details of which are discussed elsewhere herein.

Thus, optionally the method may comprise analysing said spectrometric data in order to determine whether or not said microbial population has interacted with said substance in a manner which is of potential interest.

An "interaction in a manner which is of potential interest" is meant that the interaction results in a phenotypic and/or genotypic change. Optionally, the phenotypic and/or genotypic change may be a change in one or more properties of the microbial population, details of which are provided elsewhere herein.

Optionally, the $EC_{50}$ of a test substance may be tested. $EC_{50}$ is the concentration of a drug that gives half-maximal response.

For example, the toxicity of a test substance may be tested, e.g., the percentage of surviving microbes as a function of the concentration of the test substance may be measured and microbial populations which are sensitive and/or resistant to a test substance may be identified.

Optionally, the method may comprise analysing the susceptibility of a microbial population to a substance, e.g., the susceptibility of a microbial population to a known or potential therapeutic agent. For example, the susceptibility of a microbial population to an anti-microbial drug may be analysed.

Optionally, the method may also comprise a step of analysing the effect of an environmental condition of the microbial population on the response of a microbial population to said substance. Details of environmental conditions of the microbial population are provided elsewhere herein. Thus, said method may optionally comprise the steps of (i) exposing the microbial population to a substance; and (ii) changing an environmental condition of the microbial population.

Optionally, the steps of (i) exposing the microbial population to a substance; and (ii) changing an environmental condition of the microbial population may be carried out simultaneously or sequentially in any order. Any of these steps, alone and/or in combination, may optionally be repeated, e.g., at least 2, 3, 4, 5, 6, 7, 8, 9 or 10 times.

Thus, a microbial population may optionally, e.g., be exposed to a substance, and an environmental condition of the microbial population may subsequently be changed; an environmental condition of the microbial population may be changed, and a microbial population may subsequently be exposed to a substance; and/or a microbial population may be exposed to a substance, and an environmental condition of the microbial population may simultaneously be changed.

It will be understood that optionally, one or more different substances and/or one or more different environmental conditions may be used in any of these methods. For example, a panel of different substances may optionally be used. The panel may, e.g., comprise or consist of members of a single class of drugs and/or members of two or more classes of drugs, e.g., known and unknown drugs.

For example, optionally, the substance may be an antimicrobial drug. Thus, e.g., one or more microbial populations may be tested with one or more known antimicrobial drugs. Optionally, one or more microbial populations may, e.g., be tested using one or more potentially new therapeutic agents or antimicrobial drugs.

Optionally, one or more microbial populations may be genetically modified and the modified microbial population may be tested, e.g., with a known cytotoxic/cytostatic drug, and/or against a panel of potentially new therapeutic agents or cytotoxic/cytostatic drugs.

Optionally, one or more microbial populations may be tested against a first substance and subsequently be tested against a second substance and optionally one or more further substances.

Analysis of a Change

The optional analysis of a change may be carried out in one or more different ways.

Optionally, a microbial population may be analysed via the method provided herein at a first time and at a subsequent further time, e.g., second time, third, fourth, fifth, sixth, seventh, eighth, ninth, tenth, etc. time.

Thus, optionally, the method may comprise generating said aerosol, smoke or vapour from said target at a first time so as to obtain said first spectrometric data;

generating aerosol, smoke or vapour from said target, at a subsequent time;

mass analysing and/or ion mobility analysing the aerosol, smoke or vapour generated at the subsequent time, or ions derived therefrom, so as to obtain second spectrometric data; and comparing the first and subsequent spectrometric data to determine changes in the target. The subsequent time may be a second time, third, fourth, fifth, sixth, seventh, eighth, ninth, tenth, etc. time.

Optionally, between the first and a subsequent time, the microbial population may be manipulated and/or exposed to a substance, which may optionally be selected from any of the agents listed herein, such as, a test agent.

Optionally, 2 or more, e.g., at least 2, 3, 4, 5, 6, 7, 8, 9, 10, 15, 20, 30, 40, 50, 60, 70, 80, 90, 100, 150, 200, 300, 400, 500, 600, 700, 800, 900, 1000, 2000, 3000, 4000, 5000, 6000, 7000, 8000, 9000, or 10000 identical and/or non-identical microbial populations may be analysed simultaneously and/or sequentially. If a group of 3 or more microbial populations are analysed, then the group may optionally comprise, e.g., 2 or more microbial populations that are identical to one another, as well as 2 or more microbial populations that are non-identical to one another.

Optionally, one or more further test agents and/or reference or control agents may be used. For example, a first microbial population may be exposed to a first test agent and a second microbial population may be exposed to a further test agent, a reference agent or a control agent.

Environmental Conditions

The method allows the analysis of a microbial population under a defined environmental condition. This may optionally allow, e.g., microbial populations to be analysed under conditions that mimic in vivo conditions, e.g., the conditions of a host microenvironment.

By "defined environmental condition" is meant that at least one environmental factor is controlled. For example, a controlled temperature or temperature range, or a controlled level of a particular nutrient, may be referred to as a defined environmental condition.

Optionally, the method may involve the analysis of the effect of one or more defined environmental conditions on a microbial population. Optionally, the analysis may be of the effect of a change in one or more environmental conditions on a microbial population.

The environmental condition may optionally be a condition that can influence microbial population growth; differentiation; migration; microbe state; and/or phenotype and/or genotype. Thus, the environmental condition may, e.g., be the nature and/or concentration of culture media components, particularly nutrient and/or mineral concentrations; the nature and extent of cell-cell contacts; temperature; pH; fluid balance; pressure; flow volume; and/or oxygen pressure. For example, the microbial population may be exposed to hypoxia.

The environmental condition may optionally be altered by introducing the microbial population into a host organism or a specimen thereof. Thus, optionally, the microbial population may be introduced into a host organism or specimen thereof. The host organism may optionally be selected from a human or non-human animal. Optionally, it may be a livestock, domestic or laboratory animal, e.g., be a rodent. Optionally, it may be murine, guinea pig, hamster, rat, goat, pig, cat, dog, sheep, rabbit, cow, horse, alpaca, ferret, fowl, buffalo, and/or monkey. Thus, optionally the cell population may be exposed to, e.g., maintained and/or grown in, the in vivo environment of a host organism or the or ex vivo environment of a host organism specimen. The effect of such an exposure may optionally be analysed by the method provided herein.

Prior to and/or after analysis of a target, one or more of these conditions may optionally be appropriately modified. Such modification is within the competencies of one of ordinary skill in the art.

Thus, optionally the method may comprise one or more of the following: changing or varying the concentration of a nutrient which is supplied to a microbial population; changing or varying the concentration of a mineral which is supplied to a microbial population; changing or varying a pH level at which said microbial population is maintained; changing or varying a temperature at which said microbial population is maintained; changing or varying an oxygen, carbon dioxide or other gas level to which said microbial population is exposed; changing or varying the concentration of a contamination control substance or an antibiotic to which said microbial population is exposed; changing or varying the concentration of a catalyst, inducer or agent which prompts said microbial population to generate a therapeutic or other product; and/or changing or varying a light level to which said microbial population is exposed. Optionally, the effect of any of these changes may be analysed.

For example, the environmental condition may be a culture medium which has a low concentration of one or more lipids, and/or a low overall lipid concentration.

Isotope Studies

Optionally, the method may be used in or with isotope studies.

Isotopes are variants of a particular chemical element which differ in neutron number, whilst having the same number of protons in each atom. Isotope studies may, e.g., involve the use of stable isotopes, i.e. non-radioactive isotopes. For example, isotopes of hydrogen (H), carbon (C), nitrogen (N), oxygen (O), fluorine (F) and/or sulphur (S) may be used. The term "different types of isotopes" is used to mean isotopes of different elements, so an isotope of C is a different type of isotope from an isotope of N.

In nature, one isotope of each element is typically most abundant, and any other stable isotopes of the element that may exist are typically far less abundant. For example, $_1$H is far more abundant than $_2$H, $_{12}$C is far more abundant than $_{13}$C, $_{14}$N is far more abundant than $_{15}$N, $_{16}$O is far more abundant than $_{17}$O or $_{18}$O, and $_{32}$S is far more abundant than $_{34}$S. The less abundant isotopes are the heavier ones, so they may be referred to as a "heavy isotope". In isotope studies, cells may be exposed to one or more heavy isotopes and cellular processes may then be analysed by analysing the fate of the heavy isotope(s).

Different nonradioactive stable isotopes can be distinguished by mass spectrometry or ion mobility spectrometry, so the method provided herein may optionally be used in or with isotope studies.

Thus, optionally, the microbial population may be exposed to one or more heavy isotopes, e.g., to one or more substances comprising or consisting of one or more heavy isotopes. The substance may optionally be selected from any of the substances listed elsewhere herein, e.g., any nutrients, e.g., glucose, glutamine o the like. A substance comprising or consisting of one or more heavy isotopes may be referred to as a "heavy-isotope substance". A heavy-isotope substance may optionally comprise a single heavy-isotope, 2 or more heavy-isotopes, or consist of heavy-isotopes. A heavy-isotope substance may optionally comprise a single type of heavy isotope or 2 or more, e.g., at least 2, 3, 4, 5, or 6 different types of heavy isotopes.

A substance may optionally be isotopically defined, i.e. it may be possible to use a substance in which one or more specific atoms are replaced with one or more heavy isotopes, which may allow an analysis of the fate of specific parts of a substance. Optionally, an analysis with a substance having a first atom replaced with a heavy isotope may be compared to an analysis with the corresponding substance having a different atom replaced with a heavy isotope.

For example, a heavy-isotope substance, such as, a nutrient, e.g., carbon source, may be used and the method may optionally be used to analyse whether and/or how the nutrient is used by the microbial population. Thus, optionally, lipid, carbon and/or protein metabolism, e.g., anabolism and/or catabolism may be analysed. In particular, the method may optionally be used to analyse the depletion or enrichment of a heavy isotope type in one or more metabolites, such as, fatty acid type(s). Thus, e.g., the presence or absence, and/or relative abundance, of one or more metabolites, fatty acids, lipids and/or biomarkers may be analysed prior to and/or after exposure of a microbial population to a heavy isotope. Optionally, the analysis may be carried out at 2 or more time points, e.g., to monitor a change over time in the presence or absence, and/or relative abundance, of one or more metabolites, fatty acids, lipids and/or biomarkers.

Optionally, a microbial population may be exposed to at least 2 types of heavy isotopes and/or at least 2 types of heavy isotope substances simultaneously and/or sequentially. Optionally, a microbial population may be exposed to a first type of heavy isotope at a first time point and to a second type of heavy isotope at a second time point. Optionally, a microbial population may be exposed to a first type of heavy isotope substance at a first time point and to a second type of heavy isotope substance at a second time point. For example, a microbial population may be exposed to a heavy-isotope glucose at a first time point and to a heavy-isotope glutamine at a second time point.

Isogenic Microbial Populations

Optionally, the method may involve the use of 2 or more microbial populations that are isogenic except for one or more genetic regions of interest. The term "isogenic" is used in the art to indicate that 2 microbial populations are genetically identical or share essentially the same genetic information, except for one or more genetic regions of interest. Typically, 2 isogenic microbial populations will differ in a single gene, which may optionally be linked to a reporter gene in which the isogenic microbial populations may also differ.

Optionally, isogenic microbial populations may differ with respect to an endogenous gene, e.g., one microbial population may have a wild-type endogenous gene and another microbial population may have a mutant version of said gene. Optionally, the mutant version may have an altered functionality or be a knock-out.

Optionally, isogenic microbial populations may differ with respect to an exogenous gene, e.g., one microbial population may comprise a first version of an exogenous gene and another microbial population may have a second version of said exogenous gene; or one microbial population may comprise a first exogenous gene and another microbial population may have a second exogenous gene.

The method may thus optionally be used to analyse differences between 2 or more isogenic microbial populations. The use of isogenic microbial populations may be useful, e.g., to analyse the effect of a modification or change, e.g., to analyse the effect of a substance on a microbial population; to analyse the effect of an environmental change on a microbial population; and/or to analyse the production of a substance by a microbial population.

Isogenic microbial populations may be obtained, e.g., by transfecting a first microbial population with a first vector that encodes a first transgene and a first marker and transfecting a second microbial population with a second vector that encodes a second transgene and a second marker, the second being different from the first.

Optionally, the marker may, e.g., be a fluorescent marker, details of which are provided elsewhere herein.

Culture and analysis via the method provided herein of both microbial population allows, e.g., screening for compounds with selective activity, e.g., toxicity, towards a gene of interest. Such drug screening is broadly applicable for mining therapeutic agents targeted to specific genetic alterations responsible for disease development.

Substance Production and/or Utilisation by Microbial Populations

Microbes may produce substances, such as quorum sensing molecules, virulence factors and the like, so the analysis of the production of substances by a microbial population may provide useful information regarding the identity and/or characteristics of the microbial population, such as, their virulence, their interaction with their environment and the like. Details of suitable substances are provided elsewhere herein.

Microbial populations may be used for the production of substances, such as, therapeutics, fuel, food etc. For example, the substance may be a biopharmaceutical, e.g., antibody, hormone and/or cytokine. Microbial populations may utilise a first substance as a substrate to produce a second substance. Microbial populations may be used to break down substances, optionally into useful and/or less harmful substances. They may, e.g., be used to break down industrial waste products, pollutants, herbicides, pesticides, explosives, and the like.

The method may therefore optionally be used to analyse the ability of a microbial population to utilise and/or produce a substance, and/or to analyse the utilisation and/or production of a substance by a microbial population. Details of suitable substances are provided elsewhere herein.

Optionally, the method may involve the purification of a substance, so it may include a step of purifying a substance. A step of purifying the substance may, e.g., comprise one or more of lysis of cells; centrifugation, e.g., to achieve isopycnic banding and/or non-equilibrium settling; filtration; membrane separation, which may, e.g., be microfiltration, ultrafiltration, and/or dialysis; extraction, which may, e.g., be fluid extraction, and/or liquid/liquid extraction; precipitation, which may, e.g., be fractional precipitation; chromatography, which may, e.g., be ion-exchange chromatography, gel filtration chromatography, affinity chromatography, hydrophobic interaction chromatography, high performance liquid chromatography ("HPLC"), and/or adsorption chromatography. Optionally, it may involve precipitation of a free acid form of said substance, and, optionally, conversion of a free acid form of said substance to a salt of said compound.

Microbial populations may be used for the breakdown of substances, optionally into useful and/or less harmful substances. They may, e.g., be used to break down industrial waste products, pollutants, herbicides, pesticides, explosives, and the like. Details of suitable substances are provided elsewhere herein.

Identification of Utilisation/Production/Breakdown Microbial Populations

Optionally, the method may be used as a screening method, e.g., to identify a suitable utilisation/production/breakdown microbial population, and/or to distinguish between microbial populations with different utilisation/production/breakdown properties.

Cells may optionally be manipulated, e.g., genetically manipulated, to generate a microbial population having one or more desired properties. Optionally, the method may involve an analysis to identity/select a microbial population which has successfully been manipulated, e.g., to identify a microbial population having the desired genotype and/or phenotype.

Conventional methods for deriving a suitable utilisation/production/breakdown microbial population, e.g., a high-turnover population from parental population, may be quite time-consuming and laborious and may, e.g., take more than six months in industrial settings. The first step may be genetic manipulation, which is exemplified in the discussion below by the insertion of a transgene. Once the transgene enters the microbe, the integration site of the gene may be random, and expression of the transgene may, in part, be dictated by the surrounding genetic structure. High expression of the transgene may be very desirable. Optionally, the method provided herein may be used to speed up the process of identifying/selecting a suitable production/breakdown microbial population.

A large number, e.g., a pool of at least or about 50,000, 40,000, 30,000, 20,000, 10,000, 5000, 1000 or 500 microbial populations may be screened to select a small number, e.g., about or no more than 1, 2, 3, 4, 5, 6, 7, 8, 9, 10, 20, 30, 40, 50, 80, 100 or 200 candidate populations.

Optionally, one or more strategies may be used to improve the generation and/or selection of microbes that have a transgene integrated at a transcriptionally active site. For example, the transgene construct may optionally include one or more antibiotic resistance gene(s). If an antibiotic resistance gene is used, then, following mutagenesis, microbes stably expressing the transgene construct and hence the antibiotic resistance factor, may optionally be selected using the relevant antibiotic.

A selection strategy, e.g., one of the ones mentioned herein, may yield a heterogeneous population of microbes having different transgene construct integration sites, copy numbers and the like.

Optionally, a series of limiting dilutions, e.g., in multi-well plates, may be carried out to isolate uniform microbial populations, which may optionally be screened to select candidate microbial populations.

Optionally, candidate microbial populations may be evaluated in more detail and/or on a larger scale to select one or more final candidates.

Optionally, the method provided herein may be used to analyse microbes at any stage of such a process of deriving a suitable utilisation/production microbial population. Optionally, expression of the transgene and/or one or more factors that influence the growth, efficiency and/or productivity of a cell may be analysed. This allows the rapid selection of a small number of candidates. For example, the pool of cells may be reduced by a factor of about or at least 10, 20, 30, 40, 50, 60, 70, 80, 90, 100, 200, 500 or 1000.

Thus, optionally, the method may involve analysing a plurality of microbial cultures, each microbial culture comprising one or more microbial populations. This may optionally involve generating a plurality of spectrometric data and determining from said plurality of spectrometric data a first subset of microbial cultures which are of potential interest for utilising a substance and/or producing/breaking down a substance of interest.

The method may optionally further involve the use of liquid chromatography based analysis, e.g., liquid chromatography mass spectrometry ("LCMS") analysis; liquid chromatography ion mobility spectrometry ("LCIMS") analysis; liquid chromatography tandem mass spectrometry ("LCMS/MS") analysis; liquid chromatography followed by $MS^E$ spectrometry ("LCMS$^E$") analysis; liquid chromatography followed by ion mobility separation and then mass spectrometry ("LC-IMS-MS") analysis; and/or liquid chromatography followed by ion mobility separation and then $MS^E$ spectrometry ("LC-IMS-MS$^E$") analysis. Such a liquid chromatography based analysis may optionally be used to analyse said first subset of microbial cultures, e.g., to generate a second subset of microbial cultures. Optionally, the method may comprise classifying or dividing cell populations into subsets based on spectrometric data, liquid chromatography based analysis data, or a combination of spectrometric data and liquid chromatography based analysis data.

However, the ambient ionisation mass spectrometry and/or ion mobility spectrometry methods mentioned herein are much faster than liquid chromatography based analysis, so, optionally, the method optionally does not involve the use of a liquid chromatography based analysis, e.g., any of the ones listed above.

Thus, optionally, the method may be used in the process of drug manufacture and production.

Conventionally, a very large number (e.g., approximately 50,000) of potential batches of a microbial culture may be produced. Liquid chromatography analysis, e.g., LCMS may then be performed on each of the microbial cultures in order to determine a small subset of microbial cultures which are of greatest interest in terms of taking on into full production.

However, it will be appreciated that subjecting approximately 50,000 separate batches of microbial populations to LCMS analysis is a complex and time consuming process.

One particular advantage of the method provided herein is that the method provided herein enables experimental results to be produced on essentially an instantaneous basis. Furthermore, the method provided herein lends itself to automation and a large number of microbial cultures can be analysed either in sequence and/or in parallel in a comparatively short period of time. Certainly, it is possible to analyse approximately 50,000 separate batches of microbial cultures on a timescale which is several orders of magnitude faster than conventional LCMS approaches.

Accordingly, one particular application of REIMS and related ionisation techniques is the ability to analyse a large number of microbial cultures in a short period of time.

This analysis enables the large number of microbial cultures, e.g., 50,000, to be reduced to a very small candidate list of, for example, just ten microbial cultures which can then be taken on to full production/utilisation.

Alternatively, other embodiments are contemplated wherein REIMS analysis may be performed on the approximately 50,000 batches enabling a first subset of microbial cultures to be established. The first subset of microbial cultures may comprise, for example, approximately 1000 batches. Liquid chromatography analysis, e.g., LCMS can then be performed on this reduced number of 1000 samples in order to determine a second subset of microbial cultures (e.g., 10) which are the most promising to be taken on to full production. Although this alternative approach still involves using liquid chromatography analysis, e.g., LCMS, the two-stage process still results in considerable time savings since only e.g., 1000 batches need to be analysed by liquid chromatography analysis, e.g., LCMS (c.f. approximately 50,000 as per the conventional approach).

Determining or establishing one or more subsets may optionally involve a classification and/or a physical separation.

Substance Utilisation/Production/Breakdown and Quality Control

A general process of utilising, producing and/or breaking down substance, such as a (bio)therapeutic product, via microbial culture may include one or more of the following steps:

1. Set up microbial culture apparatus with suitable microbial culture conditions;
2. Inoculate with microbial population, e.g., starter culture grown on smaller scale;
3. Allow microbes to grow
4. If utilisation/production/breakdown of substance is not automatic (e.g., if dependent on a particular temperature or nutrient), adjust conditions to induce utilisation/production/breakdown;
5. Monitor culture conditions and adjust as required;
6. Monitor substance utilisation/production/breakdown; 7. Harvest substance
   from culture medium, if substance or breakdown product is secreted
   from microbes, if substance or breakdown product accumulates within microbes
8. Purify substance, e.g., by removing any contaminants During a process of utilising and/or producing a substance via microbial culture, analysis may be carried out, e.g., via the method described herein described herein, e.g., for monitoring the culture conditions and/or substance utilisation/production. This may optionally involve obtaining a sample from the microbial population for analysis. The skilled person will be aware of suitable sample acquisition methods, such as pipetting, using a swab or the like. The sample may optionally be processed, e.g., a liquid sample may be filtered or processed to generate a pellet as mentioned elsewhere herein. Optionally, a swab may be used, which may optionally be analysed without further processing using the method with a REIMS ion source.

Optionally, any adjustments to the culture conditions may be made, e.g., if the analysis reveals the necessity for an adjustment. The culture pH may be measured, e.g., with a pH meter, and optionally adjusted, e.g., by adding an acid or a base as required. Nutrient use may be monitored by analysing, e.g., respiration. The Respiratory Quotient, i.e. the ratio of the Carbon Dioxide Evolution Rate to the Oxygen Uptake Rate, may be analysed. Metabolic products, e.g., the substance of interest, a breakdown product and/or contaminants, may be analysed.

Thus, optionally, the method may involve analysing, e.g., monitoring, a process of utilising/producing/breaking down a substance via culture of a microbial population. Optionally, the invention provides a method of utilising/producing/breaking down a substance via culture of a microbial population, wherein said method includes a step of analysing the utilisation/production/breakdown process via a method of analysis of the invention. Optionally, said method further comprises a step of adjusting the culture conditions on the basis of the analysis.

Thus, the method may optionally comprise analysing the utilisation, production and/or breakdown of a substance by a microbial population. There is provided a method of producing and/or breaking down a substance, comprising (a) using a first device to generate smoke, aerosol or vapour from a target in vitro or ex vivo microbial population; (b) mass and/or ion mobility analysing said smoke, aerosol or vapour, or ions derived therefrom, in order to obtain spectrometric data; and (c) analysing said spectrometric data in order to analyse the production and/or break down of a substance by said target microbial population. Also provided is a method of identifying a microbial population capable of utilising, producing and/or breaking down a substance, comprising (a) using a first device to generate an smoke, aerosol or vapour from a target in vitro or ex vivo microbial population; (b) mass and/or ion mobility analysing said smoke, aerosol or vapour, or ions derived therefrom, in order to obtain spectrometric data; and (c) analysing said spectrometric data in order to identify a microbial population capable of utilising, producing and/or breaking down a substance.

Any of these methods may optionally comprise analysing said spectrometric data in order to (i) determine whether said microbial population utilises, produces and/or breaks down said substance; (ii) determine the rate at which said microbial population utilises, produces and/or breaks down said substance; (iii) determine whether said microbial population produces any by-products; and/or (v) determine the mechanism by which said microbial population utilises, produces and/or breaks down said substance. Optionally, two or more microbial populations may be analysed in order to determine which microbial population utilises, produces and/or breaks down said substance at a higher rate and/or at a higher purity. Optionally, a plurality of microbial populations may be analysed and divided into 2 or more subsets based on said analysis. For example, microbial populations may be divided based on said analysis into subsets based on (i) their ability or inability to utilise, produce and/or break down said substance; (ii) the rate of utilisation, production and/or breakdown of said substance; (iii) the production and/or breakdown of any by-products; and/or (iv) the mechanism of utilisation, production and/or breakdown. Optionally, based on the analysis microbial populations may be divided into (i) a first subset capable of utilising, producing and/or breaking down said substance and a second subset incapable of utilising, producing and/or breaking down said substance; (ii) a first subset and a second subset, wherein said first subset utilises, produces and/or breaks down the substance at a higher rate compared to the second subset; (iii) a first subset and a second subset, wherein said first subset produces no by-products, or fewer by-products compared to the second subset; and/or (iv) a first subset and a second subset, wherein said first subset utilises, produces and/or breaks down the substance via a different mechanism compared to the second subset.

Optionally, the method may further comprise a step of subjection the microbial population or microbial population subset to liquid chromatography mass spectrometry ("LCMS") analysis prior to and/or after the method of analysis. Optionally, based on said LCMS analysis, microbial population may be divided into subsets, or a said microbial population subset as mentioned above may be divided into further subsets.

Optionally, the microbial population or microbial population subset may be cultured under conditions suitable to utilise, produce and/or break down said substance.

Optionally, the method does not comprise a step of subjection a microbial population, or microbial population subset, to liquid chromatography mass spectrometry ("LCMS") analysis.

Optionally, the method may be used to monitor the utilisation and/or production of a substance, particularly to monitor the production of by-products. This may involve analysing a sample from a microbial population at various time points, as discussed elsewhere herein.

Click Chemistry

"Click Chemistry" is a term that was introduced by K. B. Sharpless in 2001 to describe reactions that are high yielding, wide in scope, create only by-products that can be removed without chromatography, are stereospecific, simple to perform, and can be conducted in easily removable or benign solvents.

A typical click chemistry (click reaction) is the copper-catalyzed 1,3-dipolar cycloadditions between azides and acetylenes.

A click reaction may, e.g., happen between a fluorescent probe comprising an alkyne and a biomolecule comprising an azide.

Thus, click chemistry may be used for attaching a probe or substrate of interest to a specific biomolecule, a process called bioconjugation. The possibility of attaching fluorophores and other reporter molecules has made click chemistry a very powerful tool for identifying, locating and characterizing both old and new biomolecules.

One of the earliest and most important methods in bioconjugation was to express a reporter on the same open reading frame as a biomolecule of interest. Notably, green fluorescent protein ("GFP") is expressed in this way at the N- or C-terminus of many proteins. However, this approach comes with several difficulties. For instance, GFP is a very large unit and can often affect the folding of the protein of interest. Moreover, by being expressed at either terminus, the GFP adduct can also affect the targeting and expression of the desired protein. Finally, using this method, GFP can only be attached to proteins, and not post-translationally, leaving other important biomolecular classes (nucleic acids, lipids, carbohydrates, etc.) out of reach.

To overcome these challenges, chemists have opted to proceed by identifying pairs of bioorthogonal reaction partners, thus allowing the use of small exogenous molecules as biomolecular probes. A fluorophore can be attached to one of these probes to give a fluorescence signal upon binding of the reporter molecule to the target—just as GFP fluoresces when it is expressed with the target.

Optionally, the method provided herein may involve monitoring a click chemistry reaction, e.g., to detect the end-products and/or any by-products of a click chemistry reaction. Optionally, the method may be used in combination with click chemistry, e.g., before or after a click chemistry reaction. Optionally, the method may be used instead of click chemistry. For example, the method may allow the analysis of biomarkers that would conventionally be analysed by using click chemistry, thus obviating the need for a click chemistry reaction.

Diseases

The analysis may optionally relate to a disease or condition, such as any of the diseases or conditions listed in this section and/or elsewhere herein. The terms "disease" and "condition" are used interchangeably herein. For example, the target may be a subject having a disease, or a specimen derived from such a subject.

The disease may optionally be, or associated with, injury, infection, cancer, infarction, toxins, inflammation, lack of proper care to a wound site, frostbite, diabetes, and/or arteriosclerosis. The disease may optionally be an autoimmune disorder, an inflammatory disease, tropical sprue, and/or a food intolerance.

Optionally, it may be an infection of any of the tissues mentioned elsewhere herein, e.g., a vaginal, lung, respiratory tract, brain, skin and/or gastrointestinal infection.

Optionally, it may be thrush, malaria, measles, meningitis, diarrhoea, Bronchitis, pharyngitis, laryngitis, Chronic obstructive pulmonary disease (COPD), Pneumonia, sepsis, and/or Cystic fibrosis.

The disease may optionally be a cancer or tumour, which may optionally be selected from, for example, carcinomas, sarcomas, leukaemias, lymphomas and gliomas. The disease may optionally be necrosis, which may optionally be, for example, coagulative, liquefactive, caseous, fat necrosis, fibrinoid necrosis and/or gangrenous necrosis.

More particularly, the disease may optionally be selected from, for example, asthma, Coeliac disease, gastritis, peptic duodenitis, Gluten-sensitive enteropathy; allergy and/or intolerance to an allergen, e.g., to milk, soy, tree nut(s), egg, wheat, meat, fish, shellfish, peanut, seed, such as sesame, sunflower, and/or poppy seeds, garlic, mustard, coriander, and/or onion; Hashimoto's thyroiditis; Irritable bowel syndrome; Graves's disease; reactive arthritis; psoriasis; multiple sclerosis; Systemic lupus erythematosus (SLE or lupus); ankylosing spondylitis; progressive systemic sclerosis (PSS); glomerulonephritis; autoimmune enteropathy; IgA deficiency; common variable immunodeficiency; Crohn's disease; colitis, such as, lymphocytic colitis, collagenous colitis and/or ulcerative colitis; diffuse lymphocytic gastroenteritis; ulcer; intestinal T-cell lymphoma.

Optionally, one or more of the microbes in the microbial population may be (i) the cause of the disease; (ii) associated with the disease; and/or (iii) aggravating the disease.

Diagnosis and/or Treatment

Optionally, the method may be a method of treatment. Thus, the method may optionally comprise a step of administering a therapeutically effective amount of a therapeutic agent to a subject in need thereof.

Optionally, the method may comprise obtaining spectrometric data from a target in or from a subject as described elsewhere herein and analysing the spectrometric data in order to assess the effectiveness of a substance, optionally a therapeutic or test substance. Optionally, the method may further comprise a step of determining whether the subject should receive a treatment. Optionally, the method may further comprise a step of treating the subject. The treatment may optionally be with an anti-microbial agent, e.g., any of the antimicrobial agents listed elsewhere herein, and/or with any of the compounds listed elsewhere herein.

Optionally, the method may be a method of diagnosis. Thus, the method may optionally comprise a step of making a diagnosis based on the analysis of said spectrometric data.

Optionally, the method may include a step of diagnosis and a step of treatment.

As mentioned elsewhere herein, the method involves the analysis of a target entity, which may be a microbe and/or a compound. In the context of diagnosis and/or treatment, the target entity may, e.g., be a pathogenic microbe and/or a virulence factor.

The terms "diagnosis" or "diagnosing" and derivations of these terms as used herein refer to the determination whether or not a subject is suffering from a disease. Optionally, the method may involve analysing a target and, on the basis of one or more of the following making a diagnosis that a subject is or is not suffering from a particular disease: detecting a target entity; identifying a target entity; detecting an increase in a target entity; detecting a decrease in a target entity.

An increase or decrease may be determined by reference to a suitable reference, comparator or control.

The term "monitoring" and derivations of this term as used herein refer to the determination whether any changes take place/have taken place. Typically, it is determined whether any changes have taken place over time, i.e. since a previous time point. The change may, for example, be the development and/or progression of a disease, such as, any of the diseases mentioned. Optionally, the method may involve analysing a target and, on the basis of one or more of the following monitoring a subject or disease: detecting a target entity; identifying a target entity; detecting an increase in a target entity; detecting a decrease in a target entity.

The term "prognosis" and derivations of this term as used herein refer to risk prediction of the severity of disease or of the probable course and clinical outcome associated with a disease. Thus, the term "method of prognosis" as used herein refers to methods by which the skilled person can estimate and/or determine a probability that a given outcome will occur. The outcome to which the prognosis relates may be morbidity and/or mortality. In particular, the prognosis may relate to "progression-free survival" (PFS), which is the length of time that a subject lives with the disease without the disease progressing. Thus, PFS may, for example, be the time from the start of therapy to the date of disease progression, or the time from the end of therapy to the date of disease progression.

Optionally, the method may involve analysing a target and, on the basis of one or more of the following making a prognosis: detecting a target entity; identifying a target entity; detecting an increase in a target entity; detecting a decrease in a target entity.

By "progressing" or "progression" and derivations of these terms is meant that the disease gets worse, i.e. that the severity increases. For example, in the case of a pathogenic infection, it may mean that the pathogen burden increases, for example a pathogen multiplies and/or acquires resistance to one or more antimicrobials.

The prognosis may relate to overall survival. By "overall survival" (OS) is meant the length of time that a subject lives with the disease before death occurs. Overall survival may, for example, be defined as the time from diagnosis of the disease; the time of treatment start; or the time of treatment completion, until death. Overall survival is typically expressed as an "overall survival rate", which is the percentage of people in a study or treatment group who are still alive for a certain period of time after they were diagnosed with, or started treatment for, or completed treatment for, a disease. The overall survival rate may, for example, be stated as a one-year survival rate, which is the percentage of people in a study or treatment group who are alive one year after their diagnosis or the start or completion of treatment.

Statistical information regarding the average (e.g., median, mean or mode) OS and PFS of subjects having a particular type of disease is available to those skilled in the art. A determination whether a subject has, or is likely to have, an increased or decreased OS or PFS compared to such an average may therefore be made.

A determination that the likelihood and/or length of PFS and/or overall survival is decreased means that the prognosis is poor or adverse. The terms "poor" and "adverse" are used interchangeably herein. A "poor" prognosis may be defined as a prognosis that is worse than the reference prognosis for a subject, so it may also be referred to as a "worse" prognosis, and a "good" or "non-adverse" prognosis may be defined as a prognosis that is better than the reference prognosis for a subject so it may also be referred to as a "better" prognosis. The skilled person will appreciate that for the "reference prognosis" subjects having the same type of disease, optionally the same stage of disease, should be used. The "reference prognosis" may be the average prognosis or a typical prognosis determined by any other suitable method.

An adverse or worse prognosis may be defined as a shorter overall survival or an increased likelihood of shorter overall survival and/or shorter PFS or an increased likelihood of shorter PFS.

By "regressing" or "regression" is meant that the disease improves, i.e. that the severity decreases. For example, in the case of an infection, it may mean that the pathogen burden decreases.

By "development" is meant the onset of a disease.

The term "prediction" or "predicting" as used herein refers to determining the likelihood of a particular outcome.

The term "stratification" or "stratifying" as used herein refers to the division of a population into subpopulations on the basis of specified criteria. More particularly, it refers to the division of a cohort of subjects into at least two groups on the basis of specific criteria, which in the context of the present invention comprise or consist of the results of the method of analysis. Optionally, subjects may be stratified into those likely to respond to a particular treatment and those unlikely to respond; and/or subjects may be stratified based on their diagnosis, prognosis and/or the response that they have presented to treatment.

Optionally, the method may involve analysing a target and, on the basis of one or more of the following, stratifying subjects: detecting a target entity; identifying a target entity; detecting an increase in a target entity; detecting a decrease in a target entity.

The term "treatment" or "treating" as used herein refers to a course of action which is aimed at bringing about a medical benefit for a subject. The treatment may be prophylactic or therapeutic.

By "prophylactic" is meant that the treatment is preventative, i.e. it is applied before the onset of disease. By "therapeutic" is meant that the treatment is applied after the onset of disease.

Optionally, the method may involve analysing a target and, on the basis of one or more of the following, determining that a subject should or should not receive a particular treatment: detecting a target entity; identifying a target entity; detecting an increase in a target entity; detecting a decrease in a target entity.

Optionally, the method may involve analysing a target and, on the basis of one or more of the following, determining that a subject has or has not responded a particular treatment: detecting a target entity; identifying a target entity; detecting an increase in a target entity; detecting a decrease in a target entity.

Optionally, the method may involve analysing a target and, on the basis of one or more of the following, administering a particular treatment to a subject: detecting a target entity; identifying a target entity; detecting an increase in a target entity; detecting a decrease in a target entity.

The treatment may optionally be treatment with any of the compounds listed elsewhere herein, e.g., with one or more antimicrobial compounds.

Thus, optionally, the method may comprise determining or diagnosing on the basis of the spectrometric data that a subject (i) has a microbial infection; (ii) has an infection with a particular type of microbe; and/or (iii) has an infection with a microbe having sensitivity or resistance to one or more antimicrobials.

Determining which antimicrobial a microbe is sensitive to allows a determination to be made as to which treatment a subject needs to receive, and/or how urgently a subject needs to receive treatment.

Optionally, alternatively or in addition, the method may comprise determining or diagnosing, e.g., on the basis of the spectrometric data, that a or the subject (i) is in need of treatment with an antimicrobial agent; and/or (ii) is in need to treatment with an antimicrobial agent selected from an agent to which said microbe is sensitive.

Optionally, alternatively or in addition, the method may comprise administering an antimicrobial agent to a or the subject, which may optionally be an antimicrobial agent to which the microbe causing the infection is sensitive, as determined by the method provided herein.

Compounds

As discussed elsewhere herein is often desirable to analyse a compound. For example, the method may optionally be used to (i) detect the presence of a compound; (ii) identify a compound; (iii) characterise a compound; and/or (iv) analyse the spatial distribution of a compound. This may optionally allow, e.g., the detection, identification and/or characterisation of a microbe that produces said compound; the analysis of the response to a microbial population to exposure to a compound and/or environmental condition; the analysis of the production and/or breakdown of a compound.

For example, the identity of compounds produced by microbes, e.g., in a response to a substance, environmental condition etc, is often unknown, so it may be desired to analyse such a compound. In the context of fermentation, it may be desired to analyse the production of a primary compound and/or any by-products.

Thus, the method may optionally involve the direct or indirect analysis of one or more substances. Unless otherwise stated, the terms "substance", "compound", "molecule" and "biomolecule" are used interchangeably herein.

As mentioned elsewhere herein, the method may also optionally involve a step of administering a treatment to a subject, e.g., a subject suffering from an infection by said microbial population. Such a treatment step may, e.g., involve the administration of a therapeutic agent, which may optionally comprise or consist of any of the substances mentioned herein.

The compound may optionally be intracellular and/or extracellular. It may optionally be endogenous, i.e. produced by the microbial population, and/or exogenous, i.e. added to the microbial population.

The compound may, e.g., comprise or consist of a biomolecule, an organic compound, and/or an inorganic compound. Optionally, it may be a microbially-produced compound. It may optionally be an industrial waste product, pollutant, herbicide, pesticide, explosive, therapeutic, fuel, food, and the like. For example, the substance may be a biopharmaceutical, e.g., antibody, hormone and/or cytokine.

The compound may optionally comprise or consist of any of the compounds or classes of compounds mentioned herein, e.g., any of the biomarker compounds mentioned herein. Thus, for example, it may optionally be a terpene; prenylquinone; sterol; terpenoid; alkaloid; glycoside; surfactin; 2-Heptyl-3-hydroxy-4(1H)-quinolone or 2-heptyl-3, 4-dihydroxyquinoline ("PQS" or *Pseudomonas* quinolone signal); 4-hydroxy-2-heptylquinoline ("HHQ"); phenol, such as, a natural phenol; phenazine; biphenyl; dibenzofurans; beta-lactam; polyketide; rhamnolipid; cardiolipin; phosphatidylglycerol lipid; phosphatidic acids (PAs); phosphatidylethanolamines (PEs); phosphatidylglycerols (PGs); phosphatidylcholines (PCs); phosphatidylinositols (PIs); phosphatidylserines (PSs); sphingolipid; mycolic acids; ceramides, polyhydroxyalkanoates; diacylglycerol (DAG); and/or triacylglycerol (TAG).

Optionally, it may comprise or consist of, for example, a lipid, such as, a glycolipid or phospholipid; carbohydrate; DNA; RNA; protein, e.g., an antibody, enzyme or hormone; polypeptide, such as, a ribosomal peptide or a non-ribosomal peptide; oligopeptide; lipoprotein; lipopeptide; amino acid; and/or chemical molecule, optionally an organic chemical molecule.

The compound may optionally be linear, cyclic or branched.

The compound may optionally be a metabolite, such as, a primary or a secondary metabolite; an antibiotic; a quorum sensing molecule; a fatty acid synthase product; a pheromone; a protein; a peptide; and/or a biopolymer. It may optionally be an antibody or hormone.

The compound may optionally be characterised by one or more of the following functional groups: alcohol, ester, alkane, alkene, alkyne, ether, ketone, aldehyde, anhydride, amine, amide, nitrile, aromatic, carboxylic acid, alkyl halide, and/or carbonyl. Optionally, it may additionally be identified as being primary, secondary or tertiary, e.g., a primary alcohol, a secondary amine, or the like.

The substance may optionally be a test agent or a drug.

The substance may optionally be a known drug, e.g., an anti-cancer drug, e.g., a cytostatic and/or cytotoxic agent, which may optionally be selected from any of the substances listed below.

The substance may optionally be, e.g., an aromatase inhibitor; an anti-angiogenic agent; a Tubulin-binding agent; an inhibitor of lipogenic pathways; and/or a cytostatic agent; optionally selected from an alkylating agent, a cross-linking agent, an intercalating agent, a nucleotide analogue, an inhibitor of spindle formation, and/or an inhibitor of topoisomerase I and/or II.

It may, for example, be an antibody specific for a receptor expressed by cancer cells, which may optionally be conjugated to a chemotherapy drug or to a radioactive particle.

The antibody may optionally, for example, be selected from a HER-2/neu specific monoclonal antibody, such as, Trastuzumab (Herceptin); Adecatumumab, alemtuzumab, Blinatumomab, Bevacizumab, Catumaxomab, Cixutumumab, Gemtuzumab, Rituximab, Trastuzumab, and/or Ibritumomab.

The substance may optionally be, e.g., an anthracycline, an Epipodophyllotoxin, a Dactinomycin, a Campthothecin, a Taxane, a Vinca alkaloid, Soraphen A, and/or Simvastatin Cytotoxic anticancer drugs (sometimes known as antineoplastics) describe a group of medicines that contain chemicals which are toxic to cells. The cytotoxic drugs prevent cell replication and growth and hence are useful in the treatment of cancer. Most of the commonly used cytotoxic anticancer drugs were discovered through random high-throughput screening of synthetic compounds and natural products in cell-based cytotoxicity assays. Most of the compounds are DNA-damaging agents with a low therapeutic index.

The substance may optionally be selected from, e.g., anastrozole; azathioprine; bcg; bicalutamide; chloramphenicol; ciclosporin; cidofovir; coal tar containing products; colchicine; danazol; diethylstilbestrol; dinoprostone; dithranol containing products; dutasteride; estradiol; exemestane; finasteride; flutamide; ganciclovir; gonadotrophin, chorionic; goserelin; interferon containing products (including peginterferon); leflunomide; letrozole; leuprorelin acetate; medroxyprogesterone; megestrol; menotropins; mifepristone; mycophenolate mofetil; nafarelin; oestrogen containing products; oxytocin (including syntocinon and syntometrine); podophyllyn; progesterone containing products; raloxifene; ribavarin; sirolimus; streptozocin; tacrolimus; tamoxifen; testosterone; thalidomide; toremifene; trifluridine; triptorelin; valganciclovir; and/or zidovudine. These substances may optionally be referred to as non-chemotheraphy approved cytotoxic/cytostatic drugs.

The substance may optionally be selected from, e.g., aldesleukin; alemtuzumab; amsacrine; arsenic trioxide; asparaginase; bleomycin; bortezomib; busulphan; capecitabine; carboplatin; carmustine; cetuximab; chlorambucil; cisplatin; cladribine; cyclophosphamide; cytarabine; dacarbazine; dactinomycin; daunorubicin; dasatinib; docetaxel; doxorubicin; epirubicin; estramustine; etoposide; fludarabine; fluorouracil; gemcitabine; gemtuzumab; hydroxycarbamide; idarubicin; ifosfamide; imatinib mesylate; irinotecan; lomustine; melphalan; mercaptopurine; methotrexate; mitomycin; mitotane; mitoxantrone; oxaliplatin; paclitaxel; pentamidine; pentostatin; procarbazine; raltitrexed; rituximab; temozolomide; thiotepa; topotecan; trastuzumab; vidaradine; vinblastine; and/or vincristine. These substances may optionally be referred to as non-chemotheraphy approved cytotoxic/cytostatic drugs.

The substance may optionally be selected, e.g., from Mescaline, PCP (Phencyclidine), Psilocybin, LSD, Heroin, Morphine, Codeine, dextroamphetamine, bupropion, cathinone, lisdexamfetamine, Allobarbital, Alphenal (5-allyl-5-phenylbarbituric acid), Amobarbital, Aprobarbital, Brallobarbital, Butobarbital, Butalbital, Cyclobarbital, Methylphenobarbital, Mephobarbital, Methohexital, Pentobarbital, Phenobarbital, Secobarbital, Talbutal, Thiamylal, and/or Thiopental. Ranitidine, phenylalanine PKU, dimethylamylamine, cocaine, diazepam, androstadienedione, stigmastadienone, androsteronehemisuccinate, 5α-androstan-3β,17β-diol-16-one, androsterone glucuronide, epitestosterone, 6-dehydrocholestenone, phenylalanine, leucine, valine, tyrosine, methionine, sitamaquine, terfenadine, prazosin, methadone, amitripyline, nortriptyline, pethidine, DOPA, ephedrine, ibuprofen, propranolol, atenolol, acetaminophen, bezethonium, citalopram, dextrorphan, paclitaxel, proguanil, simvastatin, sunitinib, telmisartan, verapamil, amitriptyline, pazopanib, tamoxifen, imatinib, cyclophosphamide, irinotecan, docetaxel, topotecan, acyl-carnitines (C2-C18), nicotine, cotinine, trans-3'-hydroxycotinine, anabasine, amphetamine, amphetamine-like stimulants, methamphetamine, MDA, MDMA, MDEA, morphine, $\Delta^9$-THC, tacrolimus, benzethonium, meprobamate, O-desmethyl-cis-tramadol, carisoprodol, tramadol, nordiazepam, EDDP, norhydrocodone, hydromorphone, codeine, temazepam, noroxycodone, alprazolam, oxycodone, buprenorphine, norbuprenorphine, fentanyl, propoxyphene, 6-monoacetylmorphine, caffeine, carbadox, carbamazepine, digoxigenin, diltiazem, diphenhydramine, propanolol, sulfadiazine, sulfamethazine, sulfathiazole, thiabendazole, ketamine, norketamine, BZE, AMP, MAMP, and/or 6-MAM.

The methods of the invention may optionally involve the use of an antimicrobial, for example, to test for antibiotic resistance, or to prevent the growth of certain microbes, for example to prevent contamination.

The methods of the invention may optionally involve the detection and/or characterisation of antimicrobials, of microbes that produce antimicrobials, and/or of microbes that are sensitive or resistant to antimicrobials.

The substance may, e.g., be an antimicrobial. The term "antimicrobial" includes any agents that act against any type of microbe. Thus, the antimicrobial may optionally be selected from antibacterial, an antiviral, an antifungal, and an antiprotozoal. More particularly, it may optionally be selected from aminoglycosides, beta-lactam antibiotics, chloramphenicol, fluroquinolones, glycopeptides, lincosamides, macrolides, polymixins, rifampins, streptogramins, sulphonamides, tetracyclines, and/or diaminopyrimidines.

The Aminoglycoside may optionally be selected from gentamicin, tobramycin, amikacin, streptomycin, kanamycin. The beta-lactam antibiotic may optionally be selected from a penicillin such as methicillin, penicillin, amoxicillin, ampicillin, carbenicillin, oxacillin or nafcillin; a cephalosporin, such as, cephalothin, cefamandole, cefotaxime, ceftazidime, cefoperazone, or ceftriaxone; a carbapenem, such as, imipenem, meropenem, ertapenem, ordoripenem; or a monobactam, such as, aztreonam. The fluroquinolone may optionally be selected from Enrofloxacin, ciprofloxacin, Danofloxacin, Difloxacin, Ibafloxacin, Marbofloxacin, Pradofloxacin and Orbifloxacin. The glycopeptide may optionally be selected from vancomycin, teicoplanin and avoparcin. The lincosamide may optionally be selected from Lincomycin, Clindamycin and Pirlimycin. The macrolide may optionally be selected from Erythromycin, Tylosin, Spiramycin, Tilmicosin and Tulathromycin. The polymixin may optionally be selected from Polymixin B and colistin (Polymixin E). The rifampin may optionally be selected from Rifampin, Rifabutin and Rifapentine. The Streptogramin may optionally be selected from Virginiamycin. The sulfonamide may optionally be selected from Sulfadiazine, sulfamethoxazole and sulfadoxine. The tetracycline may optionally be selected from Chlortetracycline, oxytetracycline, demethylchlortetracycline, rolitetracycline, limecycline, clomocycline, methacycline, doxycycline and minocycline. The Diaminopyrimidine may optionally be selected from Trimethoprim, Aditoprim, Baquiloprim and/or Ormetoprim.

The substance may, e.g., be an anti-viral drug.

The substance may, e.g., be an anti-inflammatory drug, optionally selected from, e.g., steroids, diclofenac, ibuprofen, naproxen, celecoxib, mefenamic acid, etoricoxib, indomethacin, and/or aspirin.

Optionally, one or more microbial populations may be tested with a known antimicrobial drug. Optionally, one or more microbial populations may be tested using a panel of potentially new therapeutic agents or antimicrobial drugs.

Optionally, one or more microbial populations may be genetically modified and the modified microbial populations may be tested with a known antimicrobial drug or against a panel of potentially new therapeutic agents or antimicrobial drugs.

Automation and/or Optical Recognition

Optionally, the method may include automation. Optionally, the method may include the acquisition of an optical (or other) image of a sample, followed by (e.g., optical) recognition of one or more microbial populations, e.g., colonies, followed by sampling of one or more microbial populations (e.g., using the first device). Optionally, one or more, e.g., all of these steps may be automated. Thus, the method may optionally include automatic sampling, which may optionally be carried out using, e.g., a REIMS device. Any of the methods may optionally comprise using a disposable sampling tip.

Imaging

The method provided herein may optionally comprise determining the spatial distribution of one or more microbes and/or compounds.

The method provided herein may optionally comprise determining the spatial distribution of one or more excreted substances emanating from one or more microbes.

According to the various embodiments herein, ion imaging may be used to generate an image or map of one or more properties of the target. This may be achieved by using the first device to generate aerosol, smoke or vapour from multiple different regions of the target; ionising analytes in the smoke, aerosol or vapour originating from the different regions to produce analyte ions (or ions derived therefrom, e.g., fragment ions); and then analysing the analyte ions (or ions derived therefrom) to obtain spectrometric data for each of the regions of the target. The spectrometric data is correlated to the region of the target to which it relates (i.e. from where the smoke, aerosol or vapour that generated the spectrometric data originated from) so as to generate image or map data. An image or map of the target can then be generated based on the image or map data. For example, one or more properties of each region of the target may be determined from the spectrometric data and this may be included in the image or map data and hence mapped as a function of location within the target. The image or map data may then be displayed to a user.

The first device may be stepped between multiple spaced apart regions of the target so as to generate the aerosol, smoke or vapour from discrete regions of the target. Alternatively, a plurality of devices may be used to generate the aerosol, smoke or vapour from discrete regions of the target, optionally simultaneously. These plurality of devices may not move across the target, although may move into and out of engagement with the target. Alternatively, the first device may be moved across or through the target continuously so as to generate aerosol, smoke or vapour from the different regions of the target. Any movements of the first device, or the plurality of devices, may be automated and controlled by a machine.

The spectrometric data for each region may be analysed and converted into data representative of the type, condition or constituent(s) of the material at that region in the target.

The representative data may then be displayed as an image or map showing the type, condition or constituents of the material as a function of location in the target.

For example, the representative data may indicate the type, level, presence and/or absence of a microbe and/or compound at each of the regions in the target. For example, the spectrometric data may be used to identify and/or display the locations of margins of infected and/or non-infected tissue in the target.

Additionally, or alternatively, the spectrometric data may be used to identify and/or display the location of one or more microbe type of interest.

The representative data may indicate the different type of microbe and/or compound in the target.

Additionally, or alternatively, the representative data may indicate the presence and/or distribution of one or more types of microbes within the target.

Additionally, or alternatively, the representative data may indicate the presence and/or distribution of one or more types of compounds within the target.

Additionally, or alternatively, the representative data may indicate the type or level of biomarker in the target, and the distribution of the type or level of biomarkers within a target may be identified and/or displayed.

The ion imaging and map data may be generated and/or displayed in real-time. This may be useful, for example, to determine action to be taken during surgical procedures. The position of at least a portion of the first device and/or another tool relative to the target may be displayed on the image or map, e.g., in real time. For example, the position of a surgical tool, such as a tool for resecting or ablating tissue, may be displayed on the map of the target. This enables the surgeon to selectively resect or ablate tissue based on the representative data displayed in the image or map.

Ion imaging mass spectrometry technology, such as DESI-MS and/or REIMS technology, may optionally be used to obtain the spectrometric data for the different regions of the target. A REIMS technology device may optionally be used in cutting and/or pointing mode.

This ion imaging analysis may optionally be combined with a further analysis of the target. Details of further analysis methods and tools are provided elsewhere herein. Optionally, the results of mass spectrometry imaging may be correlated with the results of a further analysis.

More details as to how to perform ion imaging are discussed below with reference to a particular example of DESI imaging. It will be understood that the specific parameters discussed were those used in an assay by the inventor, and that any of these parameters may be varied.

Specimens, such as tissue sections or microbes smeared onto the surface of a standard glass microscope slide, were subjected to DESI-MS imaging analysis using an Exactive mass spectrometer (Thermo Fisher Scientific Inc., Bremen, Germany). Exactive instrument parameters are listed in the table below.

| Thermo Exactive instrumental parameters used for DESI-MS imaging. ||
|---|---|
| Parameter | Setting. |
| Polarity | negative |
| Resolution | 100,000 |
| Mass range | 200-1050 |
| Spray voltage | −4.5 kV |
| Capillary temperature | 250° C. |
| Capillary voltage | −50 V |
| Tube lens voltage | −150 V |
| Skimmer Voltage | −24 V |
| Max. injection time | 1000 ms |
| Microscans | 1 |
| AGC target | 5e6 |

Methanol/water (95:5 v/v) was used as the electrospray solvent at a flow-rate of 1.5 □L/min. Nitrogen N4.8 was used as nebulising gas at a pressure of 7 bars. All solvents used were of LC-MS grade (Chromasolv, Sigma Aldrich, St Louis, Mo., USA). The height distance between the DESI sprayer and the sample surface was set to 2 mm with the distance between the sprayer and sniffer set to 14 mm. The distance between the sample surface and the inlet capillary of the mass spectrometer was <<1 mm. The angle between the sprayer tip and the sample surface was set at 80°. The collection angle between inlet capillary and sample was set to 10°.

The general principle underlying imaging processes using DESI MS is that rather than point-by-point sampling, horizontal line scans are performed over the specimen surface by moving the automated sampling platform at a speed that covers the area determined as a pixel (spatial resolution) in the time the mass spectrometer requires to complete one scan (acquire one mass spectrum). This results in each one file per row of the resulting image (number of rows determined by sample height divided by spatial resolution).

For image analysis, individual horizontal line scans were converted into .imzML files using the imzML Converter Version 1.1.4.5 (www.maldi-msi.org). Single ion images and RGB images were generated using MSiReader Version 0.05(146) with linear interpolation (order 1) and 0.005 Da bin size.

Culture Media

The microbial population may be a microbial culture, so it may be maintained in a culture medium. The culture medium may optionally comprise a complex component, such as blood or a derivative thereof, e.g., serum, or be a serum-free defined medium. Unless it is desired to test an environmental factor relating to the culture medium, the culture medium may optionally be sterile, isotonic, have a suitable pH, and/or comprise all of the minerals and nutrients required by the microbial population.

The microbe may optionally be cultured on a solid culture medium and it may optionally be sampled directly from its solid culture medium. It will be understood that in the art the term "solid culture medium" is used to refer to non-liquids, which may, for example, be true solids or be in gel form.

The microbe may optionally be cultured in liquid medium and it may optionally be processed to provide a solid sample as discussed elsewhere herein.

The culture medium may optionally comprise minerals; nutrients; indicators, such as, phenol red, and/or selective agents, such as a specific antibiotic.

The culture medium may, for example, optionally comprise blood, serum, carbohydrate, and/or yeast extract.

The solid culture medium may optionally comprise a solidifying agent or a matrix selected from agar, which is a phycocolloid that may be extracted from a group of red-purple marine algae; cassava starch powder; methylcellulose; a collagen matrix; or any other suitable polymer. Agar may, for example, optionally be used in a final concentration of 1-2% for solidifying culture media.

The culture medium may, for example, optionally be selected from a liquid or solid (such as agar) form of any of the following commonly known media: Luria Bertani (LB), Brain-heart infusion, Columbia horse blood, Chocolate, Mueller-Hinton, Trypticase soy, Aztreonam, Braziers media, Fastidious anaerobe, Eosin methylene blue, Mannitol salt, and/or MacConkey.

One or more of the following culture medium components may optionally be optimised or altered: (i) Nutrients, which may be optimised to include all essential nutrients at sufficient levels, or which may be altered, e.g., to insufficient levels of one or more nutrients; minerals which may be optimised to include all essential minerals at sufficient levels, or which may be altered, e.g., to insufficient levels of one or more minerals; (ii) pH; (iii) temperature; and/or (iv) levels of gases, e.g., oxygen and/or $CO_2$, to which the microbial population is exposed. Optimum culture conditions will depend on the type of microbe. For example, a pathogenic microbe may have an optimum growth temperature of about 30-37° C., whereas a thermophilic microbe may have higher optimum growth temperature.

Nutrients

Microbial populations require nutrients for survival and/or growth. One or more suitable nutrients may therefore be used to culture a microbial population. Optionally, a mixture of different nutrients may be used, e.g., a mixture comprising one or more of the nutrients listed below. As discussed elsewhere herein, the type and/or level of any nutrients may be altered, e.g., when analysing the effect of environmental conditions.

Any nutrient may optionally be a heavy-isotope nutrient.

Suitable nutrients are well known, but a nutrient may optionally comprise or consist of, e.g., a carbohydrate, optionally selected from monosaccharides, disaccharides, oligosaccharides, and/or polysaccharides. It may optionally be selected from sucrose, glucose, fructose, maltose, starch, lactose, galactose, lactulose, and/or trehalose.

A nutrient may optionally comprise or consist of, e.g., an amino acid, a peptide, a polypeptide, or protein, optionally selected from an essential amino acid, a non-essential amino acid, and/or a peptide, polypeptide or protein comprising one or more essential and/or non-essential amino acids. Essential amino acids may be selected from phenylalanine, valine, threonine, tryptophan, methionine, leucine, isoleucine, lysine, and/or histidine. Optionally, a nutrient may be glutamine.

A nutrient may optionally comprise or consist of a vitamin, e.g., vitamin A, B, C, D, or E.

A nutrient may optionally comprise or consist of a lipid, e.g., a fatty acid, lecithin, and/or a sterol.

Flow Cytometry

Optionally, the method may additionally include a step of flow cytometry, e.g., prior to and/or after the mass and/or ion mobility spectrometric analysis. For example, the method may optionally be carried out on a microbial population that was previously analysed via flow cytometry, e.g., it may optionally be carried out on a sub-population of microbes sorted via fluorescence-assisted cell sorting ("FACS").

Optionally, the method may comprise separating labelled microbes from unlabelled microbes prior into a first and a second subset, optionally a labelled and an unlabelled subset. This separation may optionally be before and/or after the generation of spectrometric data. Thus, optionally, the target may be a subset of a microbial population, wherein the subset has been generated using flow cytometry, e.g., FACS.

Optionally, said steps of separating labelled cells from unlabelled microbes may be carried out prior to performing the method provided herein. Optionally, (i) at least one of said subsets may be analysed directly via the method of any preceding claim; (ii) at least one subset may be introduced directly into a mass spectrometer and/or ion mobility spectrometer; and/or (iii) a FACS device may be coupled, optionally directly, to a device, optionally as defined elsewhere herein, e.g., a mass spectrometer and/or ion mobility spectrometer.

In biotechnology, flow cytometry is a laser-based biophysical technology employed, e.g., in cell counting, cell sorting, biomarker detection and protein engineering. Flow cytometry may optionally be used, e.g., for analysing the expression of microbial cell surface and/or intracellular molecules, characterizing and/or identifying different microbe types in a heterogeneous microbe population, assessing the purity of isolated subpopulations, and/or analysing cell size and volume. It allows simultaneous multi-parameter analysis of single microbial cells.

It may particularly be used to measure fluorescence intensity produced by ligands that bind to specific cell-associated molecules, e.g., (i) fluorescent-labelled antibodies detecting proteins; or (ii) propidium iodide binding to DNA.

The staining procedure may involve making a single-cell suspension from a microbe culture or sample. The microbes may then incubated, e.g., in tubes and/or microtiter plates, with unlabelled or fluorochrome-labelled antibodies. Microbes may be suspended in a stream of fluid and passed by an electronic detection apparatus.

Flow cytometers are able to analyse several thousands or particles per second. A flow cytometer comprises a flow cell in which a liquid stream carries and aligns cells so that they pass single file through a light beam for sensing. The impedance or conductivity of the cells and various optical properties of the cells may be measured.

Flow cytometry is routinely used in the diagnosis of health disorders, especially blood cancers, but has many other applications in basic research, clinical practice and clinical trials. A common variation is to physically sort particles based on their properties, so as to purify populations of interest, e.g., by fluorescence-assisted cell sorting ("FACS").

Fluorescence-activated cell sorting (FACS) is a method of sorting a heterogeneous mixture of biological cells, e.g., microbial cells, into two or more containers, one cell at a time, based upon the specific light scattering and fluorescent characteristics of each cell. Thus, FACS allows the physical sorting of a heterogeneous mixture of cells into 2 or more different sub-populations.

As mentioned above, microbial cells may be labelled with fluorescent labels that are specific for a particular cellular marker. If a cell population is heterogeneous for that marker only the marker-positive subpopulation of the cells will become labelled.

A FACS apparatus may then be used to sort the cells. The cell suspension is entrained in the centre of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains charge of the same sign as the stream. The stream is then returned to neutral after the droplet breaks off.

Fluorescent Labelling

Optionally, a molecule on or within one or more of the microbial cells may be labelled. The label may, e.g., be a fluorescent label.

The following table details a list of fluorochromes for immunofluorescence microscopy:

| Fluorochromes | excitation (nm) | emission (nm) |
| --- | --- | --- |
| AMCA | 347 | 445 |
| Alexa Fluor 350 | 345 | 440 |
| Alexa Fluor 488 | 488 | 520 |
| Cy2 | 492 | 510 |
| FITC | 496 | 518 |
| Bodipy-FL | 503 | 511 |
| TRITC | 544 | 572 |
| Cy3 | 550 | 570 |
| LRSC | 572 | 590 |
| Rhodamine Red-X | 570 | 590 |
| Texas Red | 596 | 620 |
| Cy5 | 650 | 670 |
| Alexa Fluor 647 | 650 | 668 | wherein AMCA is aminomethylcoumarin acetic acid, Cy2 is cyanine, FITC is fluorescein isothiocyanate, TRITC is tetramethylrhodamine isothiocyanate, Cy3 is indocarbocyanine, LRSC is lissamine rhodamine sulfonyl chloride and Cy5 is indodicarbocyanine.

Further Analytical Tools

Any of the methods of the invention may optionally include a step of using one or more additional analytical tools to detect, identify and/or characterise a microbe. Such a tool may, for example, be selected from microscopic examination; Gram-staining; examination of the morphology of a microbial colony or an individual microbe; nucleic acid analysis, for example, using restriction enzymes, hybridisation, polymerase chain reaction (PCR) amplification and/or sequencing; morphological examination; culture-based screening for nutrient requirements and/or antimicrobial sensitivity; fatty acid profiling; and/or testing for antigens. Such tools are well known in the art, but brief details are provided below.

Microscopic examination may, for example, optionally involve mounting a microbial sample on a microscopic slide, for example, by placing a drop of microbe-containing solution onto the slide or by smearing a sample from a microbial colony or other microbial-containing material onto a slide together with a drop of water.

Gram-staining may, for example, optionally involve heat-fixing a microbial sample on a microscopic slide, for example, by gently moving the slide over a heat source such as a Bunsen-burner. A dye, typically Crystal Violet, may then be applied. This dye typically penetrates through the cell wall and cell membrane of both Gram-positive and Gram-negative cells and stains the bacterial cells purple. Iodine may then be added. Iodine acts as a mordant and as a trapping agent. A mordant is a substance that increases the affinity of the cell wall for a stain by binding to the primary stain, thus forming an insoluble complex which gets trapped in the cell wall. In the Gram stain reaction, the crystal violet and iodine form an insoluble complex which serves to turn the smear a dark purple colour. At this stage, all cells will turn purple. A suitable alcohol, such as 95% ethyl alcohol, or acetone, may then be added to dissolve the lipid outer membrane of Gram negative bacteria, thus leaving the peptidoglycan layer exposed and increasing the porosity of the cell wall. The Crystal Violet-Iodine complex is then washed away from the thin peptidoglycan layer of Gram negative bacteria, leaving them colourless. By contrast, in Gram positive bacteria the Crystal Violet-Iodine complex gets tightly bound into the multi-layered, highly cross-linked Gram positive cell wall, thus staining the cells purple. Optionally, any decolorized Gram negative cells can then be rendered visible with a suitable counterstain, such as positively charged safranin, which stains them pink.

Nucleic acid analysis may optionally involve isolation and purification of DNA and/or RNA.

Nucleic acid analysis via PCR amplification may, for example, optionally involve amplification of all or part of a suitable gene, such as the bacterial 16S rRNA gene, using universal or species-specific primers. Other examples of suitable genes which may optionally be analysed alternatively or in addition include, for example, species-specific genes or virulence genes, for example, Shiga toxin (stx), intimin (eae), flagellar H-antigen genes fliC-fliA, hsp65, rpoB and/or recA. For fungi, PCR amplification of all or part of the internal transcribed spacer (ITS) is particularly suitable.

Nucleic acid analysis with restriction enzymes may, for example, optionally involve restriction-fragment length polymorphism (RFLP) analysis. RFLP, is a technique that exploits variations in the length of homologous DNA sequences. RFLP analysis may involve a restriction digest, i.e. incubating a DNA with a suitable restriction enzyme such as BamHI, HindIII or EcoRI. Each restriction enzyme can recognise and cut a specific short nucleic acid sequence. The resulting DNA fragments may then be separated by length, for example, through agarose gel electrophoresis. The DNA fragments in the gel may optionally be stained, for example, with ethidium bromide, and the pattern of the fragments of different length may be determined.

Optionally, the DNA fragment may be transferred to a membrane via the Southern blot procedure. The membrane may then be exposed to a labelled DNA probe to allow hybridisation to occur. The label may, for example, be or comprise a radioactive isotope or digoxigenin (DIG). Any unhybridised probe may then be washed off. The label may then be detected and the pattern of the fragments which have hybridised to the labelled probe may be determined.

Sequencing may, for example, optionally involve the dideoxy or chain termination method. In this method, the DNA may be used as a template to generate a set of fragments that differ in length from each other by a single base. The fragments may then be separated by size, and the bases at the end may be identified, recreating the original sequence of the DNA.

Hybridisation analysis may, for example, optionally include DNA-DNA hybridization of one or more selected DNA fragments, genes or whole genomic DNA from a first microbe to a labelled DNA probe to determine the genetic similarity between the first microbe and the known or comparator microbe. Hybridisation analysis may, for example, involve transfer of the DNA to a membrane via the Southern blot procedure, labelling and detection as described above.

Fatty acid profiling of microbes may, for example, optionally be carried out using gas-chromatography coupled to a flame ionisation detector (GC-FID), or high performance liquid chromatography (HPLC).

With respect to the colony morphology, one or more of the following may, for example, optionally be examined: size; whole colony shape, which may, for example, be circular, irregular, or rhizoid; colony edge, which may, for example, be smooth, filamentous, or undulating; elevation, which may, for example, be flat, raised, convex or crateriform; surface, which may, for example, be wrinkled, rough, waxy, or glistening; opacity, which may, for example, be transparent, translucent, or opaque; pigmentation; colour, which may, for example, be red, yellow, or white; and/or water solubility.

With respect to the morphology of individual microbes, this may, for example, optionally be determined to be a *coccus* (spherical), *bacillus* (rod-shaped), spiral (twisted), or pleomorphic. *Cocci* may optionally be a single *coccus*, diplococcic, streptococci, tetrads, sarcinae or staphylococci. Bacilli may optionally be a single *bacillus*, diplobacilli, streptobacilli or coccobacilli. Spirals may optionally be *vibrio, spirilla* or Spirochetes.

Culture-based screening for nutrient requirements may optionally involve inoculating microbes onto on into one or more different growth media, such as different selective media, and observing in/on which media microbial growth occurs, and to what extent the growth differs between different media.

Culture-based screening for antimicrobial sensitivity may optionally involve inoculating microbes onto one or more different growth media, which may be done, for example, by streaking or plating the microbes onto a petri dish containing a suitable nutrient agar. An antimicrobial agent may then be added, which may be done, for example, by placing a filter paper disk impregnated with the antimicrobial onto the growth medium. Several disks each containing a different antimicrobial agent may be added onto a single petri dish. A determination may then be made as to whether a zone of growth inhibition occurs around any of the disk(s), and, if so, how large this zone is.

Testing for antigens may also be referred to as serotyping. The presence of specific antigens, particularly on the cell surface of the microbe, may be tested for by using specific antibodies. The antibodies may be polyclonal or monoclonal. The test may optionally involve simply detecting the presence or absence of agglutination, i.e. the formation of complexes of microbes and antibodies. Alternatively or in addition, the antibodies may be Labelled and the assay may involve, for example, an enzyme-linked immunosorbent assay ("ELISA") and/or fluorescence activated cell sorting ("FACS").

Further aspects and embodiments are set out below.

According to an aspect there is provided a method of ion imaging. The method includes automatically sampling using a rapid evaporation ionization mass spectrometry ("REIMS") device a plurality of different locations of a bacterial and/or a fungal sample which has been cultured on to a culture medium; obtaining spectrometric data corresponding to each location; and using the obtained spectrometric data to identify one or more bacterial strains and/or one or more fungal strains at each the location.

Optionally, the method may additionally include a step of flow cytometry, e.g., prior to and/or after the mass and/or ion mobility spectrometric analysis. For example, the method may optionally be carried out on a cell population that was previously analysed via flow cytometry, e.g., it may optionally be carried out on a sub-population of cells sorted via fluorescence-assisted cell sorting ("FACS").

Strittmatter discloses a manual approach wherein as described on p. 6556 two hand-held electrodes in the form of a forceps were used as a sampling probe. Strittmatter does not disclose a method of automatically sampling.

WO 2010/136887 (Takats) does not disclose automatically sampling different locations on a cultured medium.

The approach according to an embodiment was validated using samples of human liver with metastases and bacterial strains, cultured on solid medium, belonging to the species *P. aeruginosa, B. subtilis* and *S. aureus*. For both sample types, spatially resolved spectral information were obtained that resulted in clearly distinguishable multivariate clustering between the healthy/cancerous liver tissues and between the bacterial species.

The culture medium may comprise an agar-based medium, a carbohydrate matrix or another solid growth medium, as discussed elsewhere herein.

The method may further comprise determining the spatial distribution of one or more excreted substances emanating from one or more bacterial colonies and/or fungal colonies which have been cultured on the medium.

The one or more excreted substances may be selected from any of the compounds discussed elsewhere herein, optionally more particularly the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; and (xx) one or more ribosomal peptides.

The step of automatically sampling a plurality of different locations of a bacterial and/or fungal sample may comprise sampling using a disposable tip.

According to another aspect there is provided an ion imager. The ion imager includes a rapid evaporation ionization mass spectrometry ("REIMS") device which is arranged to automatically sample a plurality of different locations of a bacterial and/or a fungal sample which has been cultured on to a culture medium; and a mass analyser arranged and adapted: (i) to obtain spectrometric data corresponding to each the location; and (ii) to use the obtained spectrometric data to identify one or more bacterial strains and/or one or more fungal strains at each the location.

The culture medium may comprise an agar-based medium, a carbohydrate matrix or another solid growth medium.

The ion imager may be arranged and adapted to determine the spatial distribution of one or more excreted substances emanating from one or more bacterial colonies and/or fungal colonies which have been cultured on the medium.

The one or more excreted substances may be selected from the group consisting of: (i) one or more metabolites; (ii) one or more primary metabolites; (iii) one or more secondary metabolites; (iv) one or more lipopeptides; (v) surfactin; (vi) one or more quorum sensing molecules; (vii) 2-Heptyl-3-hydroxy-4(1H)-quinolone or 2-heptyl-3,4-dihydroxyquinoline ("PQS" or *Pseudomonas* quinolone signal); (viii) 4-hydroxy-2-heptylquinoline ("HHQ"); (ix) one or more antibiotics; (x) one or more alkaloids; (xi) one or more terpenoids; (xii) one or more glycosides; (xiii) one or more natural phenols; (xiv) one or more phenazines; (xv) one or more biphenyls and dibenzofurans; (xvi) one or more beta-lactams; (xvii) one or more polyketides; (xviii) one or more fatty acid synthase products; (xix) one or more nonribosomal peptides; and (xx) one or more ribosomal peptides.

The ion imager may be arranged and adapted to use a disposable tip to automatically sample a plurality of different locations of a bacterial and/or a fungal sample.

According to another aspect there is provided a method of Rapid Evaporation Ionization Mass Spectrometry ("REIMS"). The method includes using a REIMS ionisation source to analyse a biological liquid for the presence or absence of bacteria in the biological liquid.

The biological liquid may be selected from the group consisting of: (i) blood; (ii) urine; (iii) saliva; (iv) sputum; or (v) serum.

The method may further comprise using a disposable sampling tip to sample the biological liquid.

The method may further comprise aspirating or passing the biological liquid through a filter media.

The method may further comprise analysing residue on the filter media which remains after the biological liquid has been aspirated or passed through the filter media.

According to another aspect there is provided an apparatus. The apparatus comprises a Rapid Evaporation Ionization Mass Spectrometry ("REIMS") device which is arranged and adapted to analyse a biological liquid for the presence or absence of bacteria in the biological liquid.

The biological liquid may be selected from the group consisting of: (i) blood; (ii) urine; (iii) saliva; (iv) sputum; or (v) serum.

The apparatus may further comprise a disposable sampling tip to sample the biological liquid.

The apparatus may further comprise a device which is arranged and adapted to aspirate or pass the biological liquid through a filter media.

The apparatus may further comprise an analyser which is arranged and adapted to analyse residue on the filter media which remains after the biological liquid has been aspirated or passed through the filter media.

According to another aspect there is provided a method. The method includes obtaining an optical image of a substrate and determining on the basis of the optical image if one or more areas of interest exist on the substrate; wherein if one or more areas of interest are determined to exist, then the method further comprises the steps of: (i) automatically sampling at least one location within at least one determined area of interest using a rapid evaporation ionization mass spectrometry ("REIMS") device and obtaining spectrometric data corresponding to the at least one location; and (ii)

using the obtained spectrometric data to identify one or more bacterial strains and/or one or more fungal strains at the one or more locations.

The substrate may comprise a food product.

According to another aspect there is provided an apparatus. The apparatus includes a rapid evaporation ionization mass spectrometry ("REIMS") device; a device arranged and adapted to obtain an optical image of a substrate; and a control system arranged and adapted: (i) to determine on the basis of the optical image if one or more areas of interest exist on the substrate, wherein if one or more areas of interest are determined to exist, then the control system is further arranged and adapted to: (ii) to automatically sample at least one location within at least one determined area of interest using the rapid evaporation ionization mass spectrometry ("REIMS") device and to obtain spectrometric data corresponding to the at least one location; and (iii) to use the obtained spectrometric data to identify one or more bacterial strains and/or one or more fungal strains at the one or more locations.

The substrate may comprise a food product.

According to another aspect there is provided a method of ion imaging. The method includes dispensing a bacterial and/or fungal sample onto a culture medium, wherein one or more antibiotic and/or antifungal substances are embedded within and/or on the culture medium; automatically sampling using a rapid evaporation ionization mass spectrometry ("REIMS") device a plurality of different locations of the bacterial and/or a fungal sample which has been cultured on the culture medium; obtaining spectrometric data corresponding to each the location; and determining from the spectrometric data information concerning the resistance or otherwise of the sample to the one or more antibiotic and/or antifungal substances.

According to another aspect there is provided an ion imager. The ion imager includes a rapid evaporation ionization mass spectrometry ("REIMS") device; and a control system arranged and adapted: (i) to automatically sample using the rapid evaporation ionization mass spectrometry ("REIMS") device a plurality of different locations of a bacterial and/or a fungal sample which has been cultured on a culture medium, wherein one or more antibiotic and/or antifungal substances are embedded within and/or on the culture medium; (ii) to obtain spectrometric data corresponding to each the location; and (iii) to determine from the spectrometric data information concerning the resistance or otherwise of the sample to the one or more antibiotic and/or antifungal substances.

According to another aspect there is provided a method of ion imaging. The method includes automatically sampling a plurality of different locations on a sample using a rapid evaporation ionization mass spectrometry ("REIMS") device and obtaining spectrometric data corresponding to each location; and using the obtained spectrometric data to construct, train or improve a sample classification model.

According to an embodiment the sample may comprise a biological sample, biological tissue, human tissue, animal tissue, one or more bacterial strains or one or more fungal stains.

A sample classification model may be used comprising a biological sample classification model, a biological tissue classification model, a human tissue classification model, an animal tissue classification model, a bacterial strain classification model or a fungal strain classification model.

The method may further comprise automatically translating a sample relative to the REIMS device optionally before, optionally during and optionally after obtaining spectrometric data from at least some of the locations on the sample.

The REIMS device may comprise one or more electrodes or one or more electrosurgical tips.

The one or more electrodes or the one or more electrosurgical tips may comprise a monopolar device.

According to an embodiment a separate return electrode may be provided.

The one or more electrodes or the one or more electrosurgical tips may comprise a bipolar device.

The step of automatically sampling a plurality of different locations on the sample may further comprise applying an RF voltage to the one or more electrodes or the one or more electrosurgical tips.

The RF voltage may have an amplitude, a peak to peak voltage or a RMS voltage selected from the group consisting of: (i) about <100 V; (ii) about 100-200 V; (iii) about 200-300 V; (iv) about 300-400 V; (v) about 400-500 V; (vi) about 500-600 V; (vii) about 600-700 V; (viii) about 700-800 V; (ix) about 800-900 V; (x) about 900-1000 V; and (xi) about >1 kV.

The RF voltage may have a frequency selected from the group consisting of: (i) about <1 kHz; (ii) about 1-2 kHz; (iii) about 2-3 kHz; (iv) about 3-4 kHz; (v) about 4-5 kHz; (vi) about 5-6 kHz; (vii) about 6-7 kHz; (viii) about 7-8 kHz; (ix) about 8-9 kHz; (x) about 9-10 kHz; (xi) about 10-20 kHz; (xii) about 20-30 kHz; (xiii) about 30-40 kHz; (xiv) about 40-50 kHz; (xv) about 50-60 kHz; (xvi) about 60-70 kHz; (xvii) about 70-80 kHz; (xviii) about 80-90 kHz; (xix) about 90-100 kHz; (xx) about 100-200 kHz; (xxi) about 200-300 kHz; (xxii) about 300-400 kHz; (xxiii) about 400-500 kHz; (xxiv) about 500-600 kHz; (xxv) about 600-700 kHz; (xxvi) about 700-800 kHz; (xxvii) about 800-900 kHz; (xxviii) about 900-1000 kHz; (xxix) about 1-2 MHz; and (xxx) about >2 MHz.

The method may further comprise aspirating analyte, smoke, fumes, liquid, gas, surgical smoke, aerosol or vapour produced from a sample.

The method may comprise aspirating the analyte, smoke, fumes, liquid, gas, surgical smoke, aerosol or vapour in a substantially pulsed manner.

The method may comprise aspirating the analyte, smoke, fumes, liquid, gas, surgical smoke, aerosol or vapour substantially only when an electrosurgical voltage or potential is supplied to one or more electrodes or one or more electrosurgical tips.

The method may comprise varying an aspiration duty cycle during the course of a surgical, non-surgical or other procedure.

The method may comprise passing the analyte, smoke, fumes, liquid, gas, surgical smoke, aerosol or vapour into a vacuum chamber of a mass spectrometer.

The method may comprise causing at least some of the analyte, smoke, fumes, liquid, gas, surgical smoke, aerosol or vapour to impact upon a collision surface located within a vacuum chamber of the mass spectrometer.

At least some of the analyte, smoke, fumes, liquid, gas, surgical smoke, aerosol or vapour may be ionised upon impacting the collision surface so as to form analyte ions.

The method may comprise heating the collision surface.

The step of heating the collision surface may comprise heating the collision surface to a temperature selected from the group consisting of: (i) about <100° C.; (ii) about 100-200° C.; (iii) about 200-300° C.; (iv) about 300-400° C.; (v) about 400-500° C.; (vi) about 500-600° C.; (vii) about 600-700° C.; (viii) about 700-800° C.; (ix) about 800-900° C.; (x) about 900-1000° C.; (xi) about 1000-1100° C.; and (xii) about >1100° C.

The method may comprise mass analysing the analyte ions.

The method may comprise adding a matrix to the analyte, smoke, fumes, liquid, gas, surgical smoke, aerosol or vapour.

The matrix may be added to the analyte, smoke, fumes, liquid, gas, surgical smoke, aerosol or vapour prior to the analyte, smoke, fumes, liquid, gas, surgical smoke, aerosol or vapour impacting upon the collision surface.

The matrix may be selected from the group consisting of: (i) a solvent for the analyte, smoke, fumes, liquid, gas, surgical smoke, aerosol or vapour; (ii) an organic solvent; (iii) a volatile compound; (iv) polar molecules; (v) water; (vi) one or more alcohols; (vii) methanol; (viii) ethanol; (ix) isopropanol; (x) acetone; and (xi) acetonitrile.

The matrix may comprise a lockmass or calibration compound.

The method may comprise operating the REIMS device in a cutting mode of operation wherein the REIMS device forms one or more substantially continuous cuts in the sample.

The method may comprise maintaining the REIMS device at substantially the same height whilst performing the one or more substantially continuous cuts in the sample.

The method may comprise maintaining the REIMS device in substantially continuous contact with the sample whilst performing the one or more substantially continuous cuts in the sample.

The method may comprise operating the REIMS device in a pointing mode of operation.

The method may comprise lowering the REIMS device so as to contact the sample and to acquire spectrometric data and then raising the REIMS device after contacting the sample and prior to acquiring further spectrometric data.

The method may comprise obtaining an optical image of the sample.

The method may comprise substantially co-registering the optical image and an ion image.

The method may comprise defining one or more regions of interest in the optical image and/or the ion image.

The method may comprise determining a class or classification of one or more regions of interest.

The class or classification may comprise a healthy status, a pre-cancerous status, a cancerous status, a bacterial strain or a fungal strain.

According to another aspect there is provided a method. The method includes sampling a plurality of different locations of a sample using a rapid evaporation ionization mass spectrometry ("REIMS") device and to obtain spectrometric data at each the location; and using a sample classification model which was previously constructed, trained or improved in order to classify the sample at each the location.

According to another aspect there is provided an ion imager. The ion imager includes a rapid evaporation ionization mass spectrometry ("REIMS") device; and a control system arranged and adapted: (i) to automatically sample a plurality of different locations on a sample using the rapid evaporation ionization mass spectrometry ("REIMS") device and to obtain spectrometric data corresponding to each the location; and (ii) to use the obtained spectrometric data to construct, train or improve a sample classification model.

According to another aspect there is provided an apparatus. The apparatus includes a rapid evaporation ionization mass spectrometry ("REIMS") device; and a control system arranged and adapted: (i) to sample a plurality of different locations of a sample using the rapid evaporation ionization mass spectrometry ("REIMS") device and to obtain spectrometric data at each the location; and (ii) to use a sample classification model which was previously constructed, trained or improved in order to classify the sample at each the location.

Automatic Ion Imaging of Bacterial Samples

For the analysis of human samples, ethical approval was obtained from the National Healthcare Service Research Ethics Committee (Study ID 11/LO/1686).

According to various embodiments an automatic ion imager was provided which was arranged to automatically sample different locations of a target (e.g., a bacterial or fungal sample which had been culture on a culture medium).

Figure 1:
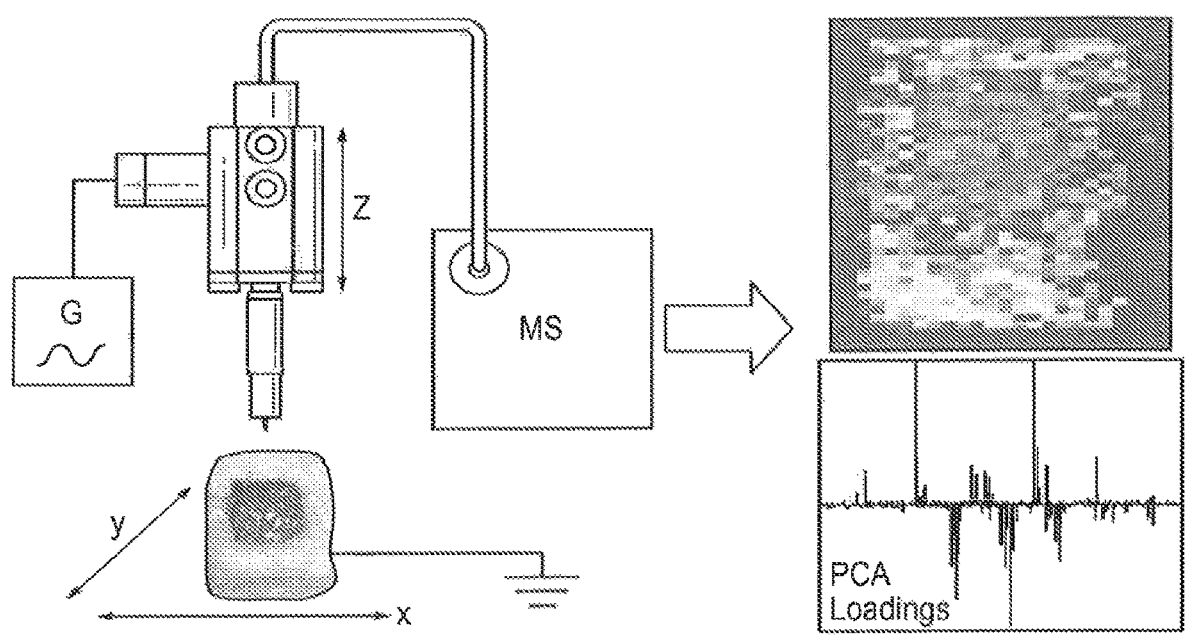
FIG. 1 shows an embodiment wherein a REIMS imaging platform is located above a sample, e.g., tissue sample to be imaged.

FIG. 1 shows a related embodiment wherein a REIMS imaging platform is located above a tissue sample to be imaged.

Figure 2:
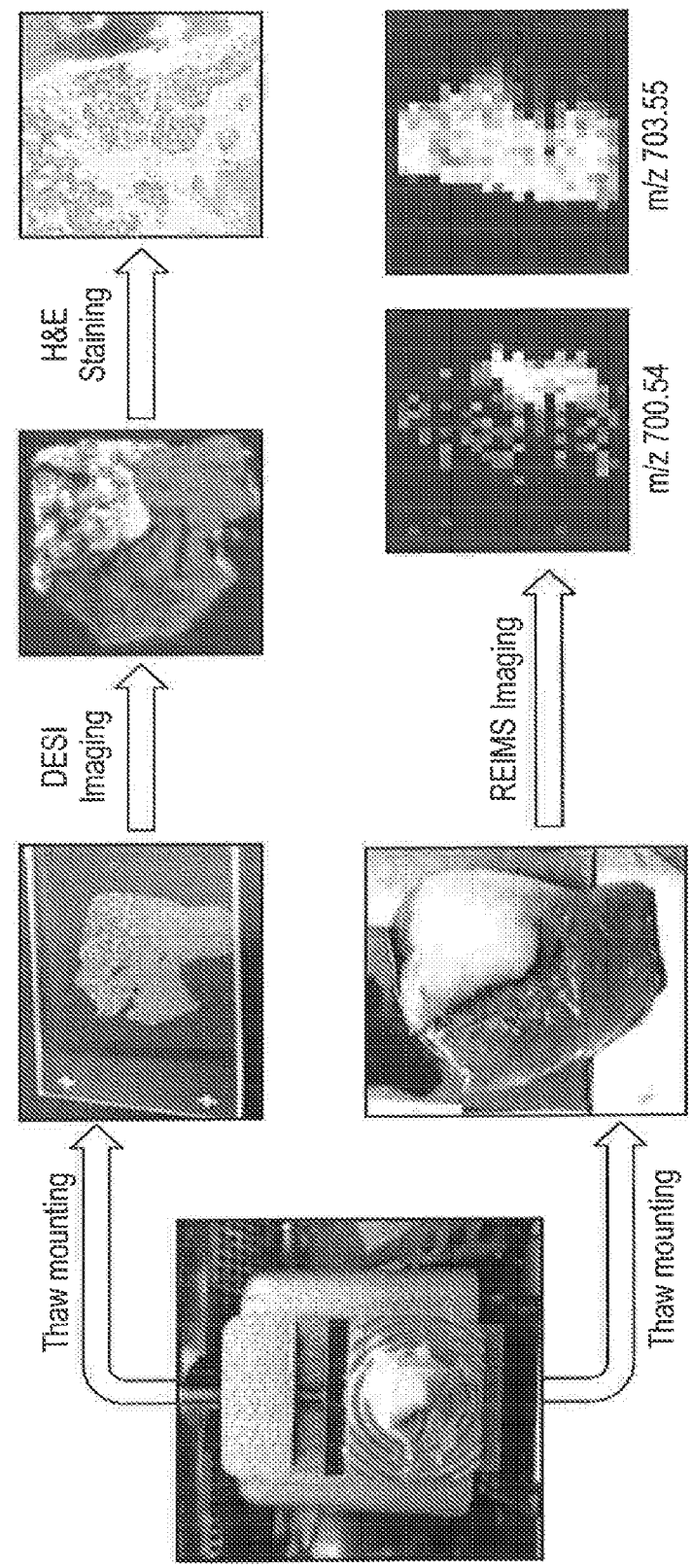
FIG. 2 shows a workflow of a combined DESI and REIMS imaging platform analysis for co-registration of histological features between an optical image and DESI and REIMS data.

FIG. 2 shows a workflow illustrating various aspects an embodiment wherein fresh human liver metastasis samples were obtained from surgical resection specimens and immediately frozen to −80° C. The tissue samples were cryosectioned (Thermo Microm HM550 Cryostat, Thermo Fisher Scientific®, Germany) to 10 μm thickness and thaw mounted onto glass slides for Desorption Electrospray Ionisation ("DESI") analysis. The remaining bulk tissue was used for REIMS analysis.

DESI analysis was carried out using an in-house built DESI stage and REIMS analysis was performed using a modified Prosolia® flowprobe stage (Prosolia®, USA).

DESI analysis of tissues was carried out using a mass spectrometer operated in negative ion mode.

The DESI imaging pixel size was set to 100 μm, the electrospray solvent was methanol:water (95:5 vol/vol) at a solvent flow rate of 1.5 μL/min and zero-grade nitrogen nebulizing gas at a pressure of 4 bar was used. Following DESI analysis, tissue sections were stained with H&E (haematoxylin and eosin) and digitally scanned (NanoZoomer 2.0-HT, Hamamatsu®, Japan) to create optical images for comparison with MS images.

A line scan mode (cutting mode) REIMS analysis of one liver metastasis sample was performed on a mass spectrometer and a spot sampling (pointing mode) analysis of another liver metastasis sample and a microorganism culture were performed on a Waters Xevo G2-S Q-TOF instrument® (Waters Micromass®, U.K.) in negative ion mode.

Figure 3:
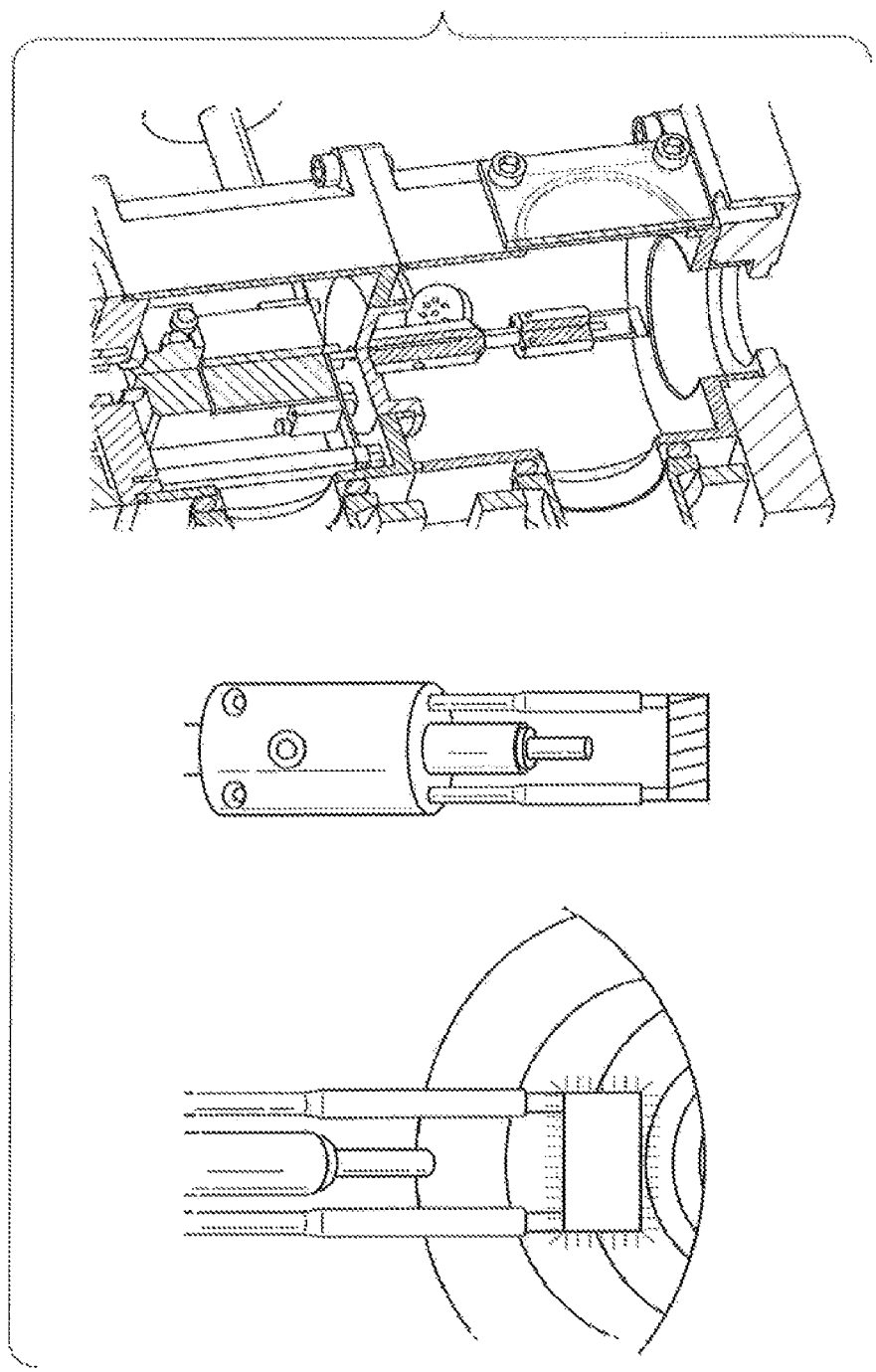
FIG. 3 shows a heated coil interface used on a Waters Xevo G2-S® instrument for improved sensitivity and robustness towards contamination.

The Waters Xevo G2-S® mass spectrometer was equipped with a modified atmospheric interface combining an orthogonal Venturi-pump for aerosol transfer and a heated capillary inlet as shown in FIG. 3.

REIMS imaging analysis of liver metastasis was carried out in a (first) cutting mode at about 1 bar Venturi gas pressure and about 4 kV p-p amplitude at about 50 kHz alternating current frequency (AC). A blade-shaped electrosurgical tip was used, about 500 μm pixel size, about 1 mm/s cutting speed and about 1 mm cutting depth.

Analysis of liver metastasis in a (second) pointing mode was carried out at about 0.25 bar Venturi gas pressure, about 2 kV amplitude at about 50 kHz AC and using a wire-shaped electrosurgical tip at about 750 μm pixel size, about 0.1 s time remaining inside the sample and a pointing depth of about 1 mm.

Aerosol was transferred using a ⅛" OD, 2 mm ID PTFE tubing. Since the used power settings were sufficiently high such as potentially to cause severe injury, the instrumental setup was handled with high caution and insulating gloves were worn.

Parameter optimization of the REIMS imaging platform was carried out using porcine liver samples. For comparison of spectrometric patterns between REIMS imaging and iKnife, porcine liver, porcine kidney cortex, lamb liver and chicken skeletal muscle were analysed using an electrosurgical handpiece (Meyer-Haake GmbH®, Germany) with incorporated PTFE tubing (⅛" OD, 2 mm ID) which was connected to the Venturi pump. Liver, kidney and muscle were food grade and purchased as such. The iKnife was operated in a cutting mode at 4 about 0 W and about 1 bar gas pressure in combination with a Valleylab SurgiStat II® power-controlled electrosurgical generator (Covidien, Ireland).

Data Processing

Raw spectral profiles were loaded into a MATLAB® environment (Version R2014a, Mathworks, USA) for pre-processing, MS-image visualization and pattern recognition analysis. All mass spectra were linearly interpolated to a common interval of 0.1 Da and individually normalized to the total ion count ("TIC") of each mass spectrum. The data was used for univariate comparison of intensity levels across liver tissue types and ionization techniques and for bacterial MS-image visualization of single ions. Peak annotation for liver metastasis samples was based on m/z accuracy obtained from the unprocessed raw files, while bacterial peak annotation was based on mass accuracy and on tandem-MS spectra obtained using bipolar forceps.

Multivariate MS-image visualization was performed on mass spectra additionally binned to 1 Da intervals in the mass range of m/z 600-1000 Da for biological tissue and m/z 400-2000 for bacteria. For multivariate image visualization, MS-images and optical images were co-registered to define regions of interest ("ROIs") for building a supervised training model. Defined ROIs (classes) were healthy and cancerous tissue for the liver samples and one region for each bacterium plus agar, resulting overall in 2 classes for liver samples and 4 classes for bacterial samples.

The training model was used to classify each pixel of the same sample and colour code the obtained score-values into red-green-blue colour scale. This supervised strategy for image visualization is based on an algorithm that combines recursive maximum margin criterion ("RMMC") with linear discriminant analysis ("LDA"). For unsupervised analysis, principal component analysis ("PCA") was performed on the mass spectra defined by the regions of interest.

Concordance correlation coefficients were used to measure the agreement between REIMS imaging platform ("RIP") mass spectra and iKnife mass spectra. This quantitative measure is defined as:

$$\rho_c = \frac{2\rho\sigma_{RIP}\sigma_{iKnife}}{\sigma_{RIP}^2 + \sigma_{iKnife}^2 + (\mu_{RIP} - \mu_{iKnife})^2} \quad (1)$$

wherein $\rho_c$ is the concordance correlation coefficient, $\rho$ is Pearson's correlation coefficient and $\sigma_{RIP/iKnife}$ is the standard deviation of the mean intensity values of $\mu_{RIP/iKnife}$.

A low concordance correlation coefficient close to the value of zero indicates low agreement while a value close to the value of one suggests high similarity between spectral profiles.

Boxplots show the median at the central mark within the box with $25^{th}$ and $75^{th}$ percentiles at the edges of the box. The upper and lower whiskers account for approximately 2.7 standard deviations (99.3% data coverage). Mass spectra were standardized to 100% intensity scale before their data was visualized with boxplots.

Figure 4:
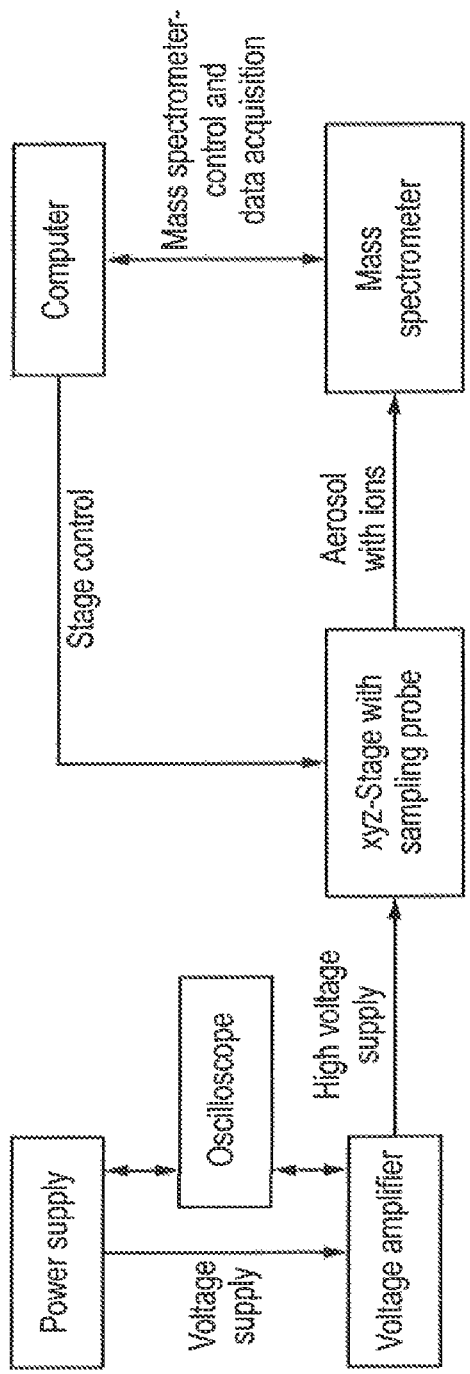
FIG. 4 shows a setup of REIMS imaging instrumentation.

FIG. 4 shows in further detail a REIMS imaging platform which comprises three major functional elements that all influence the quality of mass spectra. The imaging platform comprises a power generator, a xyz-stage with a sampling probe and a mass spectrometer.

The power supply setup used for the platform comprises a Tektronix® AFG 3022 arbitrary function generator (Tektronix®, USA), a Tektronix® DPO 3014 Oscilloscope and a Trek 10/40A High Voltage Amplifier (Trek®, USA).

The arbitrary function generator was used to generate sinus waveforms with amplitudes between about 1 V and 6 V at frequencies in the range of about 10 to 60 kHz. The high voltage power amplifier multiplied the voltage by a factor of about 1000 and supplied the connected sampling probe with the electric current. The oscilloscope provided feedback to ensure correct working parameters.

Figure 5:
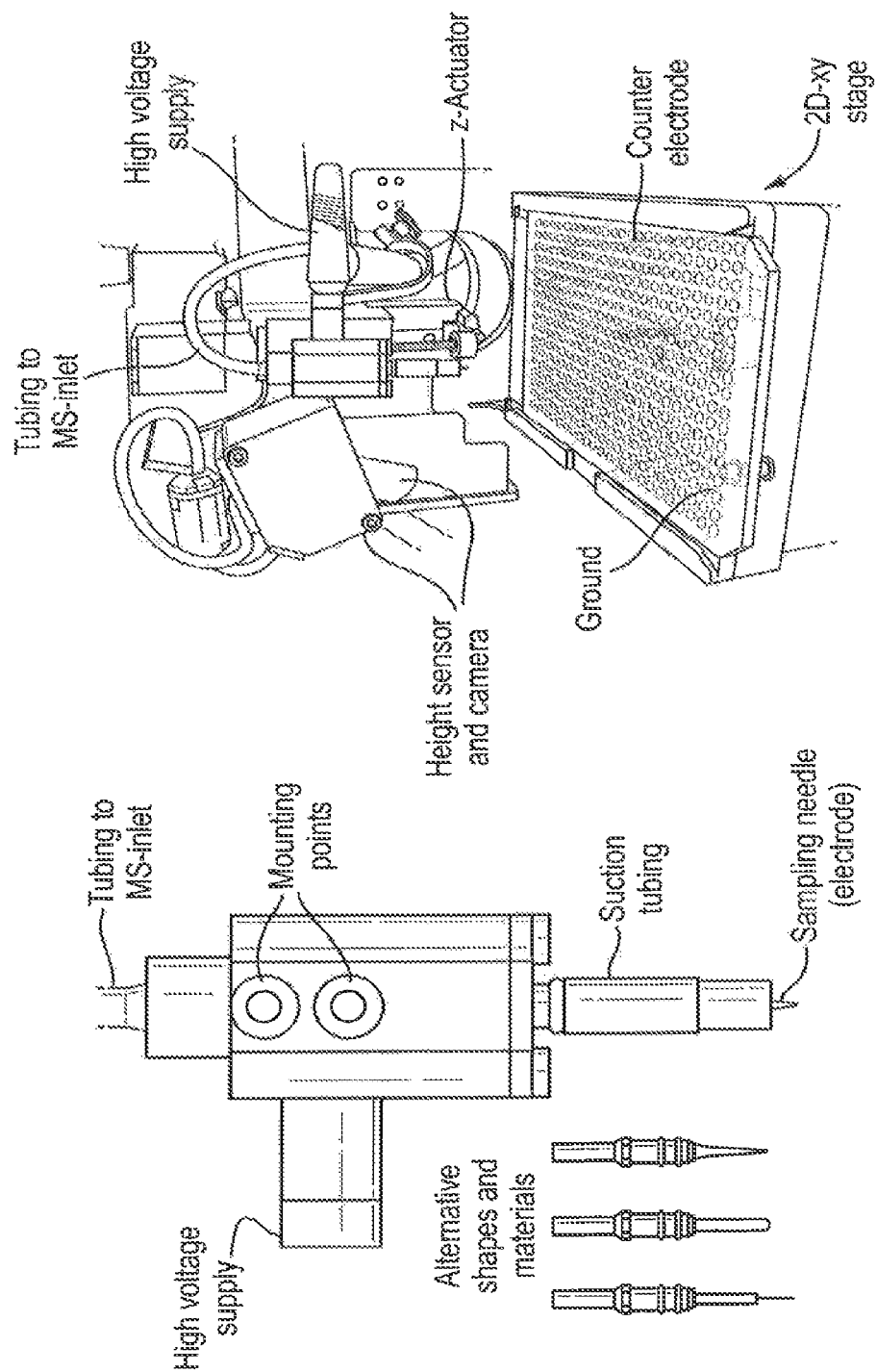
FIG. 5 shows a REIMS imaging sampling probe and setup of a xyz-stage wherein a sampling probe is mounted onto a z-actuator and is connected to a high voltage power supply and wherein evaporated aerosol is captured by suction tubing and is transported to a mass and/or ion mobility spectrometer.

The xyz-stage comprises a modified Prosolia® 2D DESI stage including Flowprobe® upgrade (Prosolia®, USA) with a high precision z-axis actuator. The sampling probe is mounted onto the actuator and is connected to the power generator setup as well as a MS inlet capillary (as shown in FIG. 5).

A laser height sensor may be provided to measure the distance between the electrosurgical tip and the sample surface and ensures an equal penetration depth of the tip into the sample which is particularly useful for an uneven sample surface. The electrosurgical tip can be exchanged for other materials or shapes depending on the field of application. In case of high precision sampling, a small diameter wire may be used, whereas a large surface tip is suitable to maximize mass spectrometric signal intensity. The electrosurgical tip is surrounded by a tubing which is connected to a Venturi air jet pump.

Bacterial Identification/Imaging

Tissue ion imaging has been described above to assist in the understanding of ion imaging of microbial populations.

REIMS imaging analysis of bacteria was carried out at about 1 bar Venturi gas pressure, about 2 kV, about 40 kHz AC, with a blade-shaped electrosurgical tip, about 1 mm pixel size, about 0.1 s time remaining inside the sample and about 1 mm pointing depth.

Bacterial strains of *P. aeruginosa* ATCC 27853, *B. subtilis* ATCC 6633 and *S. aureus* ATCC 25923 were cultured in a single petri dish on solid agar-based media (Oxoid®, U.K.). Incubation was carried out under atmospheric conditions at 37° C. overnight. REIMS analysis was carried out directly from solid culture medium on the Waters Xevo G2-S® mass spectrometer. Peak identifications were carried out on isolated strains using tandem mass spectrometry and the REIMS bipolar forceps approach.

Imaging mass spectrometric techniques such as MALDI-MSI and (nano-)DESI-MSI are increasingly applied in microbiological context as they offer the unique opportunity to study the spatially-resolved distribution of metabolites in a microbial colony. Additionally, microbial cultures cannot only be studied individually but the interactions of different microorganisms can be analysed directly and in many cases in vivo in 2D and after sectioning of the growth medium in 3D. This can reveal novel insights into defence mechanisms of certain types of bacteria and can be extended to the imaging of microbial infections and the study of microbe-host interactions.

Figure 6:
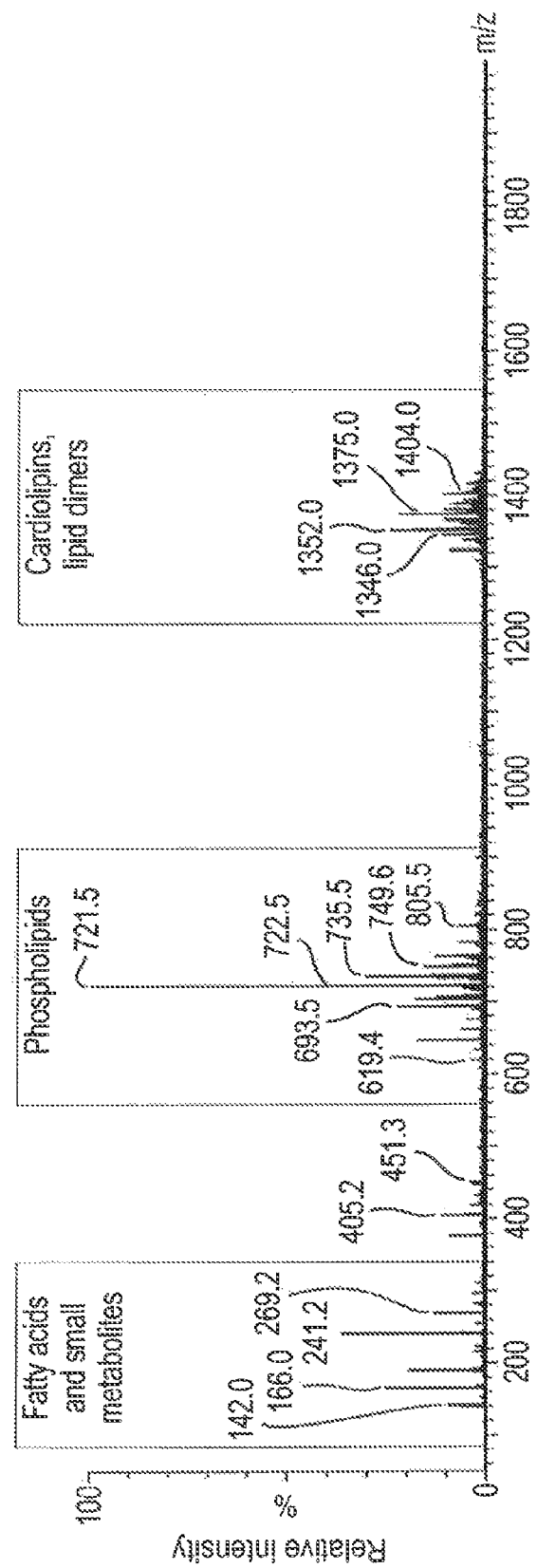
FIG. 6 shows an example mass spectrum of *P. aeruginosa* bacterium with most prominent metabolite classes for distinct mass ranges.
Figure 7:
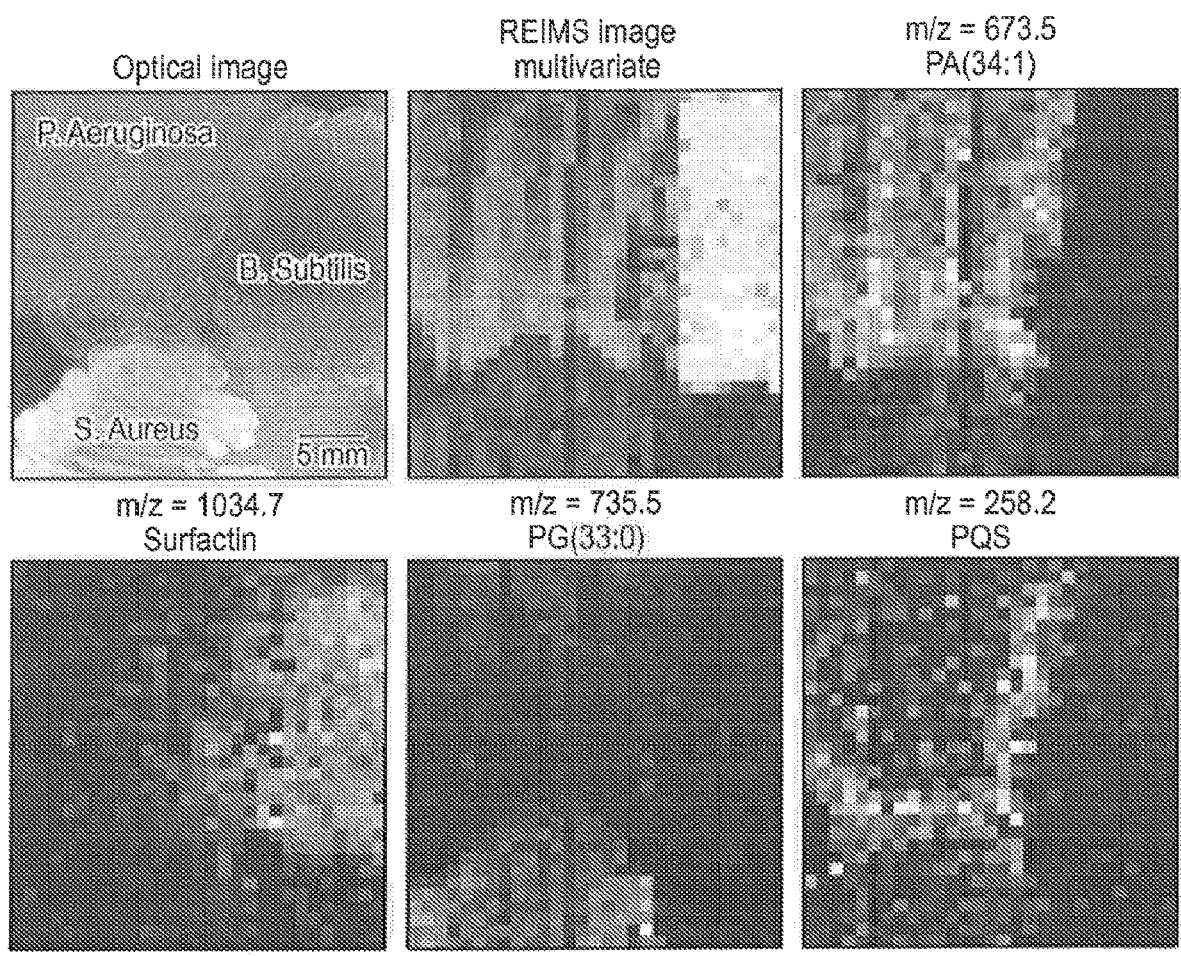
FIG. 7 shows optical, mass spectrometric multivariate and ion images of three different bacterial species wherein the multivariate image shows clear distinction between the species, while ion images show metabolites of current interest, including phospholipids. Molecules were ionized as [M-H] wherein PA: phosphatidic acid, PG: phosphatidyl-glycerol, PQS: 2-Heptyl-3hydroxy-4(1H)-quinolone.
Figure 8:
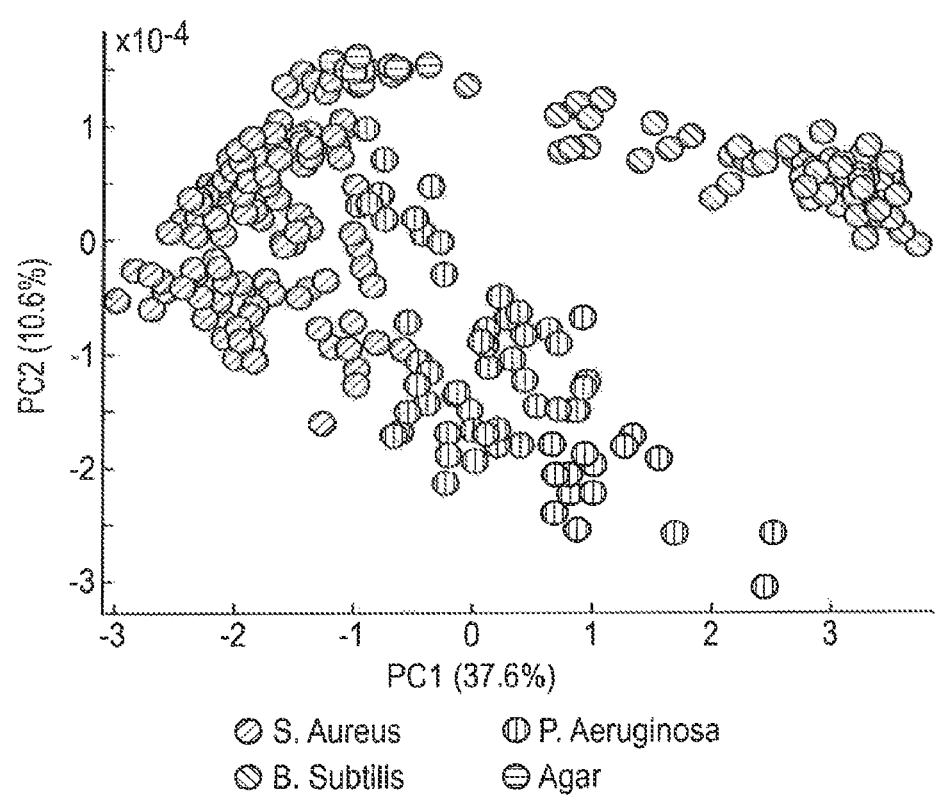
FIG. 8 shows a principal components analysis plot of three different bacterial strains together with agar medium and wherein PC is the principal component and percentage values are explained variance.

REIMS imaging analysis of the bacterial strains *P. aeruginosa*, *B. subtilis* and *S. aureus* was carried out directly from the colonies growing on agar plates in vivo. The detected spectrometric species show high resemblance with those of the same strains obtained using bipolar REIMS. The mass spectra are each dominated by intact phospholipid species in the mass range of m/z 600 to 1000, identified as phosphatidic acid ("PA"), phosphatidyl-glycerol ("PG") and phosphatidyl-ethanolamine ("PE") species. Fatty acids are mostly present in the lower mass range, whereas cardiolipins give strong signal in the higher mass range (see FIG. 6). Using the mass range of m/z 400 to 2000, all three strains are distinguishable from each other using both supervised and unsupervised multivariate methods (see FIGS. 7 and 8). The multivariate images show distinct separation of each of the three species, with agar not grouping into any of the three strains.

Unlike in bipolar REIMS, where the agar surface remains intact, with a monopolar REIMS imaging setup the sampling probe is directly immersed into the agar culturing medium during analysis. However, the ion yield from agar was generally low, devoid of all the lipid peaks observed in bacteria. This low ion yield might be associated with the carbohydrate-based agar matrix undergoing condensation reactions by losing water, resulting in charring and therefore hindering ion formation via the REIMS mechanism.

Single ion images reveal the spatial distribution of excreted metabolites such as the lipopeptide surfactin in *B. subtilis*. Surfactin was reported to exhibit antibacterial, antiviral and antifungal properties. The surfactin signal was equally distributed over the *B. subtilis* culture. However, excretion of surfactin into neighbouring areas not directly inhabited by *B. subtilis* can be observed in FIG. 7.

In the case of *Pseudomonas aeruginosa*, a range of PQS-derived quorum sensing molecules were observed with similar distributions to each other.

Figure 9:
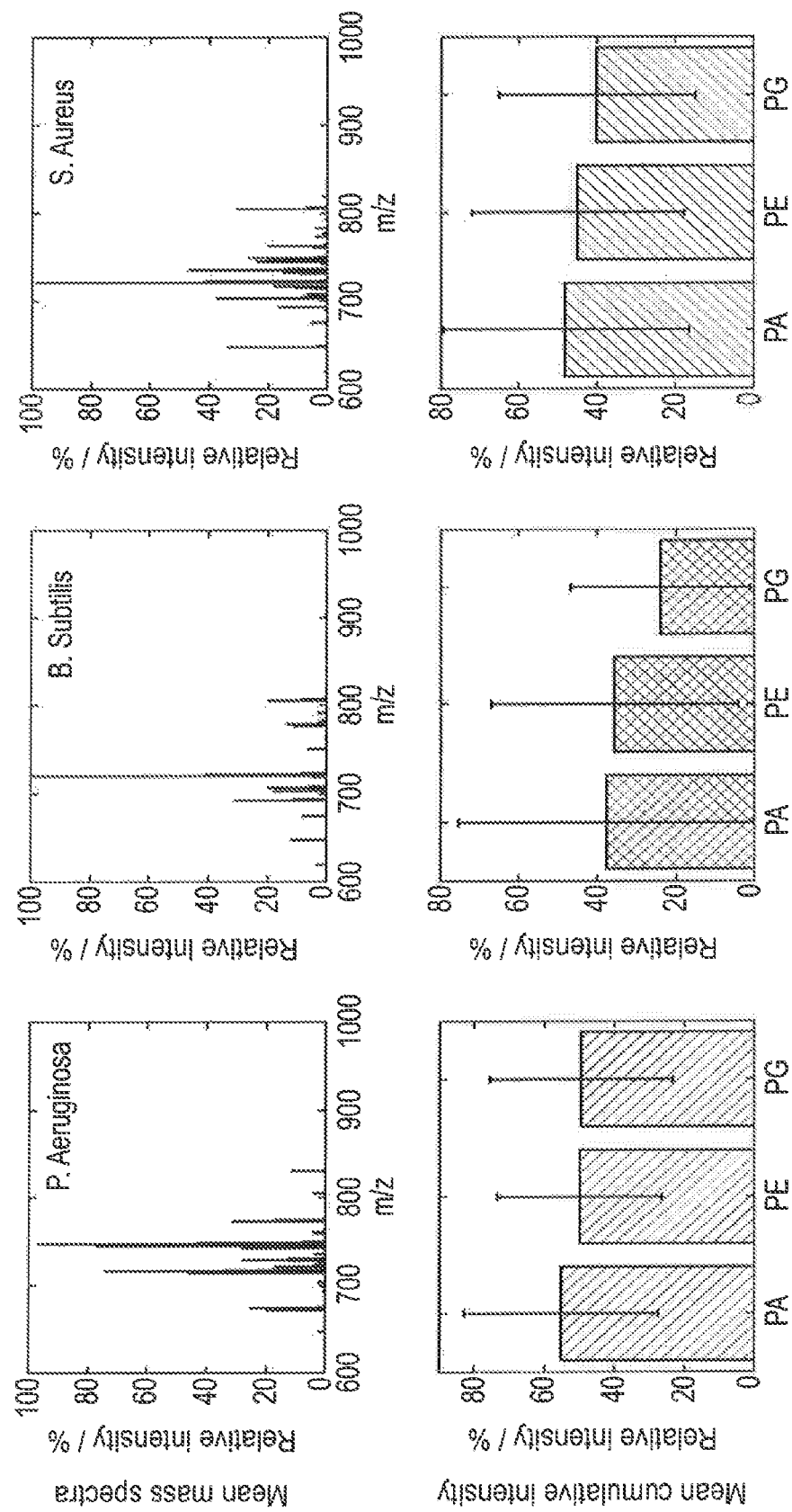
FIG. 9 shows mean mass spectra and mean phospholipid-class intensity levels for each lipid species wherein mean intensities of phospholipid classes are stable across the species, with highest level for PA class and lowest level for PG class and wherein PA: phosphatidic acid, PE: phosphatidyl-ethanolamine, PG: phosphatidyl-glycerol and wherein n(*P. aeruginosa*)=48, n(*B. subtilis*)=45, n(*S. aureus*)=52.

While structural cell membrane components such as PA(34:1) are equally distributed over the whole area covered by *P. aeruginosa*, the extracellular quorum-sensing metabolites are found in significantly higher abundance on the outer edge of the *P. aeruginosa* growth area as visualized for PQS (*Pseudomonas* quorum signal, 2-Heptyl-3-hydroxy-4(1H)-quinolone) in FIG. 9.

The area with high concentration of quorum-sensing molecules seems to correlate to the *P. aeruginosa* bacterial cells that were swarming from the main growth area. Quorum sensing molecules such as PQS are excreted by a wide variety of bacteria for both cell-to-cell communication within the same or between bacterial species. Quorum-sensing has been related to a wide variety of behaviours in *P. aeruginosa* including swarming and biofilm production. A comparison of the mean intensity levels of the phospholipid classes shows similar relative intensity distributions for PA, PE and PG classes across all bacterial strains (see FIG. 9). Cumulative intensity of PA ion species is slightly elevated compared to the other classes, being approximately 5% higher in intensity compared to PG class for *P. aeruginosa* and *S. aureus* and about 15% higher for *B. subtilis*.

The results demonstrate successful multivariate differentiation and identification of endogenous and exogenous bacterial species, while simultaneously allowing the spatially-resolved localization of metabolic features, eventually giving information on biochemical pathways and interactions between microbial species. A REIMS-based imaging platform additionally marks the first step towards an automated sampling system for microbial cultures for colony-to-colony sampling on a plate containing multiple organisms.

The automated nature of the REIMS imaging platform enables the systematic collection of reference mass spectra for use in spectral libraries necessary for classification of unknown tissue or bacteria. In both cases, REIMS imaging technology was able to clearly distinguish between healthy/cancerous tissue and between three bacterial strains. This enables the localization of metabolites within the growth area of bacteria as well as an automated identification system for microorganisms.

The ability to arbitrarily choose the material and the shape of the electrode provides a versatile application of the technology depending on the needs of the user, while the availability of two modes of sampling (pointing and cutting) adds another layer of flexibility. Principally, any conductive material with biological origin can be systematically analysed without pre-preparation by this technology, enabling a wide range of applications such as, tissue matrix analysis, bacterial identification or food quality management. Since REIMS mass spectrometric profiles varies across histological tumour types and bacteria, underlying biochemical information together with a large spectrometric database may provide additional information for future biomarker discovery or bacterial pathway exploration.

Analysis Using REIMS Technology

In embodiments disclosed herein, for analysis using REIMS technology, two handheld electrodes in form of a forceps were used as the sampling probe (bipolar forceps, obtained from Erbe Elektromedizin, Tübingen, Germany). A Valleylab Force EZc power-controlled electrosurgical unit (Covidien, Dublin, Ireland) was used at 60 W power setting in bipolar mode as RF alternating current power supply (470 kHz, sinusoid). An approximately 1.5 m long ⅛ in. outer diameter, 1/16 in. inner diameter PTFE tubing (Fluidflon PTFE tubing; LIQUID-scan GmbH Co. KG, Überlingen, Germany) was applied to connect the embedded fluid line of the bipolar forceps and the inlet capillary of either an LTQ Orbitrap Discovery instrument (Thermo Scientific GmbH, Bremen, Germany), a Thermo Exactive instrument (Thermo Scientific GmbH), or a Xevo G2-S Q-TOF instrument (Waters Corporation, Manchester, UK). In each case the inherent vacuum system of the mass spectrometer was used for aspiration of the aerosol. This setup is shown in FIG. 10A-C while instrumental settings are given in the Table below.

| Instrumental parameters of Orbitrap Discovery and Xevo G2-S instruments used in this study. | | | | |
| --- | --- | --- | --- | --- |
| | Thermo Orbitrap Discovery | Exactive | Waters Xevo G2-S | |
| Parameter | Setting | Setting | Parameter | Setting |
| Injection time | 1000 ms | 1000 ms | Scan time | 1000 ms |
| Microscans | 1 | 1 | Scan Mode | Sensitivity |
| Mass analyser | $FTMS^a$ | $FTMS^b$ | Mass analyser | TOF |
| Ion mode | negative | negative | Ion mode | negative |
| Mass range | 150-2000 | 150-2000 | Mass range | 150-2000 |
| Tube Lens Voltage | −120 V | −160 V | Sampling Cone | 30 V |
| Capillary Voltage | −40 V | −50 V | Source Offset | 80 V |

Instrumental parameters of Orbitrap Discovery
and Xevo G2-S instruments used in this study.

| Parameter | Thermo Orbitrap Discovery Setting | Exactive Setting | Waters Xevo G2-S Parameter | Setting |
|---|---|---|---|---|
| Skimmer Voltage | na | −24 V | Source Temperature | 150° C. |
| Capillary Temperature | 250° C. | 250° C. | | |
| Automatic Gain Control | Off | On | | |

[a]Orbitrap Discovery instrument is working at a resolution of 30,000 at m/z = 400,
[b]Mass analyser was used at a resolution of 50,000 (m/z = 200)

Mass spectrometric analysis of the microorganisms was typically performed directly from the solid culture medium, in which case about 0.1-1.5 mg of microbial biomass was scraped off the agar surface using one of the electrodes of the bipolar forceps. The two electrodes were subsequently brought into close proximity (i.e. by pinching the biomass between the tips of the forceps) and the RF power supply was triggered using a foot switch. The microbial biomass is rapidly heated up due to its non-zero impedance and an aerosol containing the analytes is produced and transferred directly into the mass spectrometer. Where possible, five individual measurements were performed for each strain and averaged as a database entry.

Culturing of Microorganisms

All clinical isolates analysed in some embodiments disclosed herein were routinely isolated during clinical microbiology work by trained NHS staff. Most of the microorganisms analysed during this study were previously isolated from blood cultures, identified using a Bruker Biotyper instrument, and stored on beads in a −80° C. freezer. For REIMS analysis, microorganisms were, for example, grown on a range of solid agar-based media commonly used in clinical microbiology settings. Media were purchased from Oxoid (Basingstoke, UK) or E&O Laboratories Ltd. (Bonnybridge, UK). The bacteria were incubated under appropriate atmospheric conditions at 37° C. overnight before analysis. Atmospheric conditions included aerobic (hot room), anaerobic (incubator), microaerophilic (jar in hot room), and aerobic containing 5% $CO_2$ (humidified incubator). Microaerophilic conditions were generated using a Whitley Jar Gassing System (Don Whitley Scientific Ltd., Shipley, UK).

Analysis of Bacteria Using REIMS Technology

When applying the method provided herein using REIMS technology to bacteria, the majority of phospholipid species detected can be ascribed to PAs, PEs and PGs. This can clearly be seen in Table 1, which shows the qualitative phospholipid distribution as obtained for nine different bacterial pathogenic species using exact mass measurements and tandem mass spectrometry measurements acquired during REIMS technology measurements. Only high abundance signals (>5% relative abundance) were included. Distinct peak patterns can be obtained for all bacterial species, even for those that are closely related such as different *Streptococcus* spp. or members of the Enterobactereaceae family (*E. coli, C. koseri, K. pneumoniae, S. marcescens, P. mirabilis*). Most spectral patterns for both Gram-negative and Gram-positive species are seen to be dominated by high abundance quasi-molecular PG signals.

Generally, Gram-negative species display a higher amount of unsaturated phospholipid species and a higher relative amount of PEs. This is in good agreement with literature published about the bacterial phospholipid composition. *Staphylococcus aureus* (and other *Staphylococcus* spp.) are clearly distinguished from other bacterial species by the fact that they exclusively show signals arising from saturated phospholipid species.

Metabolite Identification

Bacterial metabolites were primarily identified based on exact mass measurements and literature references on compounds with the same exact mass that were found in the same bacterial species. Mass deviations were calculated using the following formula $$\Delta m [ppm] = \left| \frac{m_{exp} - m_{th}}{m_{th}} 10^6 \right|$$

with $\Delta m$ = mass deviation (in ppm)

$m_{exp}$ = experimental exact mass, 4 decimal places accuracy $m_{th}$ = theoretical exact mass, 4 decimal places accuracy Mass accuracies of <3 ppm were regarded to be confirming the proposed the sum formula. Further structural identifications were only made by additional literature references, confirmed by additional tandem mass spectrometry measurements if signal intensity was found sufficiently high and reference spectra were available. Fragmentation experiments were performed on either on a Thermo LTQ XL or Xevo G2-S instrument and using collision induced dissociation as fragmentation mechanism.

Distinction Between Bacteria and Yeast

There are marked differences in the phospholipid composition between bacteria and fungi. The inventors have determined that REIMS spectral profiles of bacteria differ extensively between different bacteria, whereas the REIMS spectra of fungi have an overall very conserved appearance with differences largely arising from different phospholipid ratios, rather than the presence or absence of certain lipid species. Thus, the method provided herein was successfully used to distinguish between bacteria and fungi.

Thus, optionally, the method may be used to detect the presence or absence of bacteria in a sample. Optionally, the method may be used to detect the presence or absence of fungi in a sample. Optionally, the method may be used to determine whether a microbe is a bacterium or a fungus. Optionally, the method may be used to detect the presence of bacterial contamination in a non-bacterial culture, such as, a fungal culture or an animal cell line culture. Optionally, the method may be used to detect the presence of fungal contamination in a non-fungal culture, such as, a bacterial culture or an animal cell line culture.

*Candida* Speciation

*Candida* species are found within the environment, soil and on surfaces. They can cause a range of infections from thrush to sepsis, and be a problem, e.g., in immune-compromised patients such as those suffering from HIV or cystic fibrosis. In the UK they are the 9th most common cause of bloodstream infections and 90% of these are due to *C. albicans*. It is clinically useful to speciate *Candida* species because *Candida* species other than *C. albicans* are typically more drug resistant and are often intrinsically resistant to azole antifungals.

Identification of yeasts using MALDI TOF MS requires the pre-treatment of the yeast sample prior to mass spectrometric analysis in order to give reliable identification performances (score >2.0). While the recommended sample pre-treatment for MALDI TOF MS comprises the complete extraction of the fungal material using formic acid and acetonitrile, intact yeast species can directly be analysed by the method provided herein without any modifications in experimental setup or analysis workflow.

Seven different *Candida* species were sampled and examined using the forceps method and REIMS.

Figure 26A:
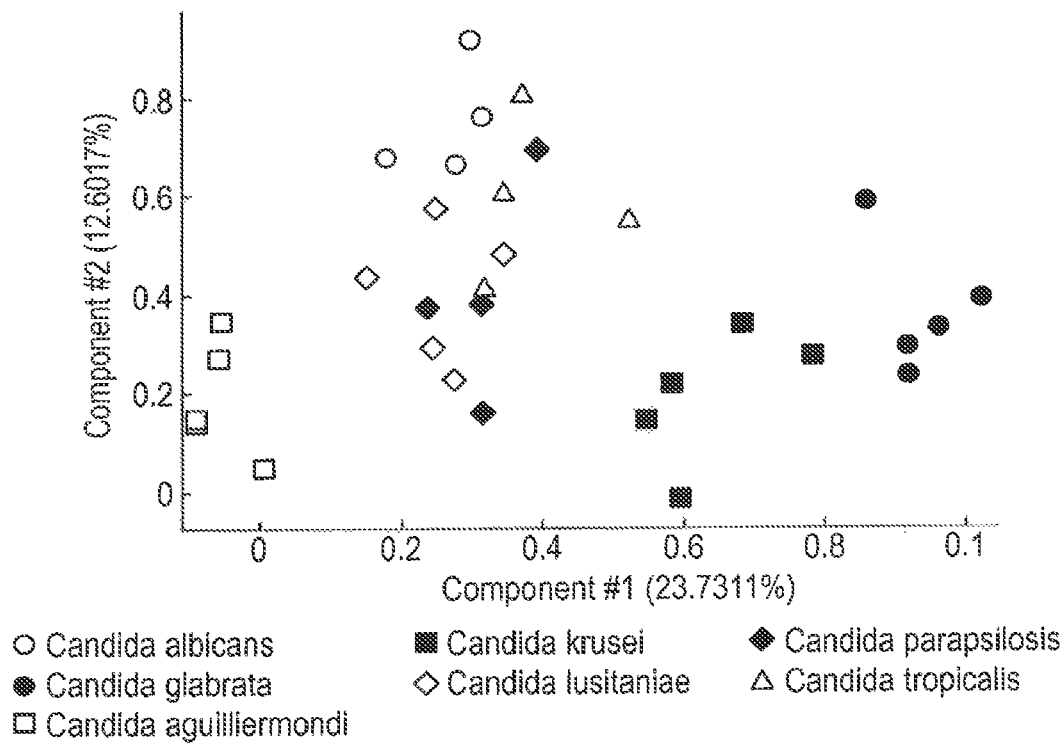
FIG. 26A shows PCA analysis of 7 *Candida* species using the method provided herein with REIMS technology.
Figure 26B:
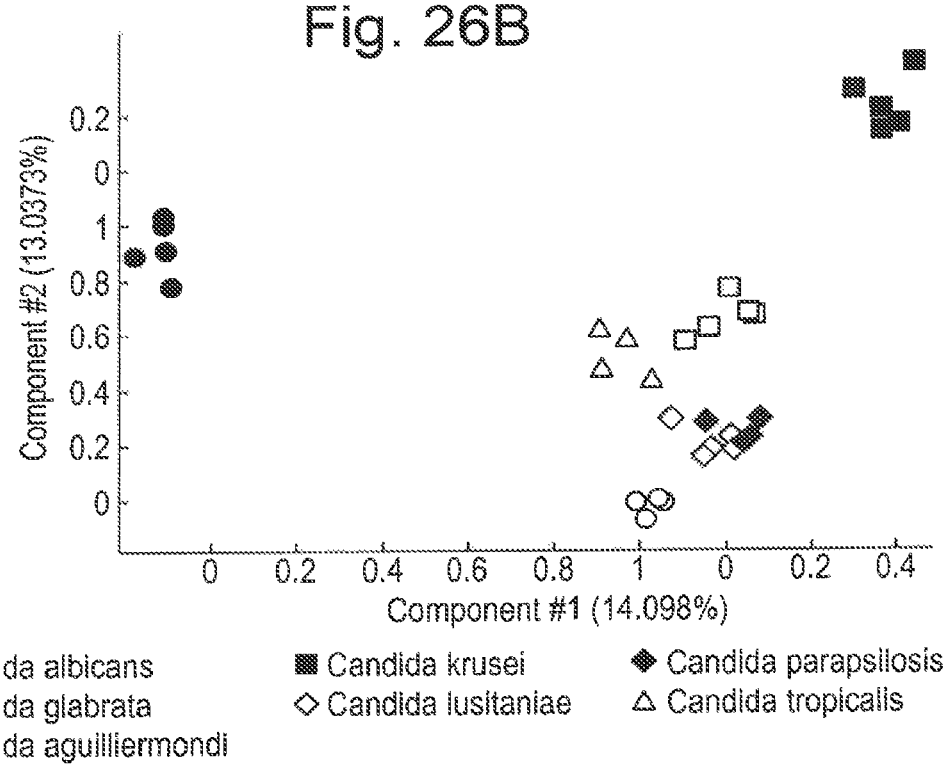
FIG. 26B shows LDA analysis of 7 *Candida* species using the method provided herein with REIMS technology.

As shown in FIG. 26, it was possible to distinguish all species. Leave one out cross validation scores were 100%. In this Example, the spectrometric data of any of the tested *Candida* species may serve as a "comparator" spectrometric data with respect of each of the other tested species. Alternatively or in addition, the spectrometric data of any of these species may be compared to "reference" spectrometric data of one or more known *Candida* species.

Thus, optionally, the method may be used to detect, identify and/or characterise one or more *Candida* species. Optionally, the method may be used to detect or confirm the presence or absence of *C. albicans* in a sample, for example by comparing the spectrometric data from the sample to a reference spectrometric data of *C. albicans*.

Optionally, the method may be used to detect or confirm the presence or absence of one or more *Candida* species selected from *C. albicans, C. galbrata, C. krusei, C. guilliermondii, C. lusitaniae, C. parapsilosis* and/or *C. tropicalis*.

Optionally, the method may be used to detect or confirm the presence or absence of one or more *Candida* species selected from those listed elsewhere herein.

The sample may optionally be known to contain at least one yeast species, e.g., one *Candida* species.

Analysis of Microbial Mixtures

To determine whether species specific peaks could be observed from mixed cultures, known quantities of bacteria were amalgamated and analysed using forceps based REIMS. For example, as shown in FIGS. 27A-C, when 10 μl of *E. coli* and *C. albicans* were mixed together and analysed using REIMS, species specific peaks could be observed within the mixed spectra.

Figure 27A:
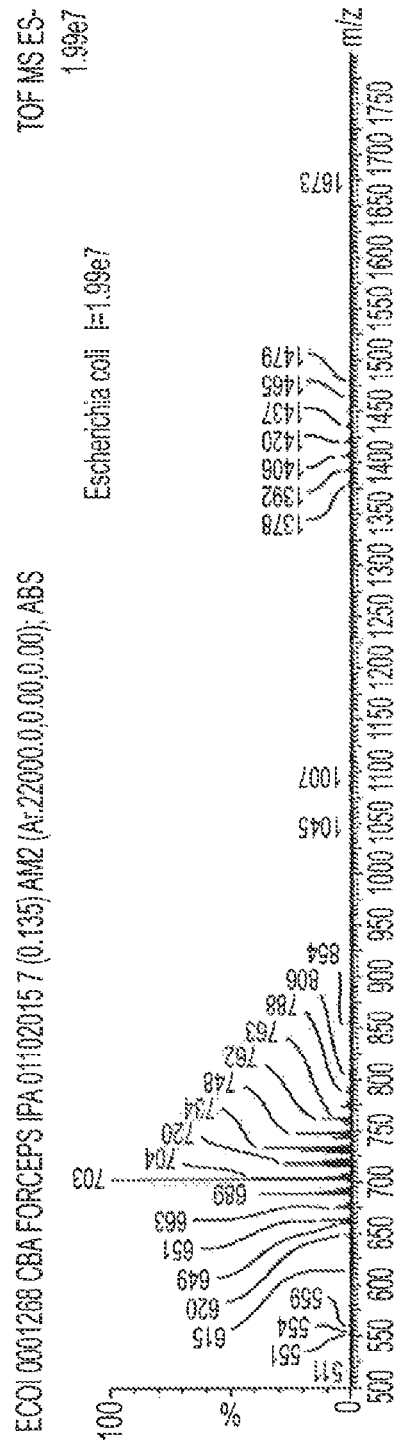
FIG. 27A shows spectral profiles of a pure *Escherichia coli* isolate.
Figure 27B:
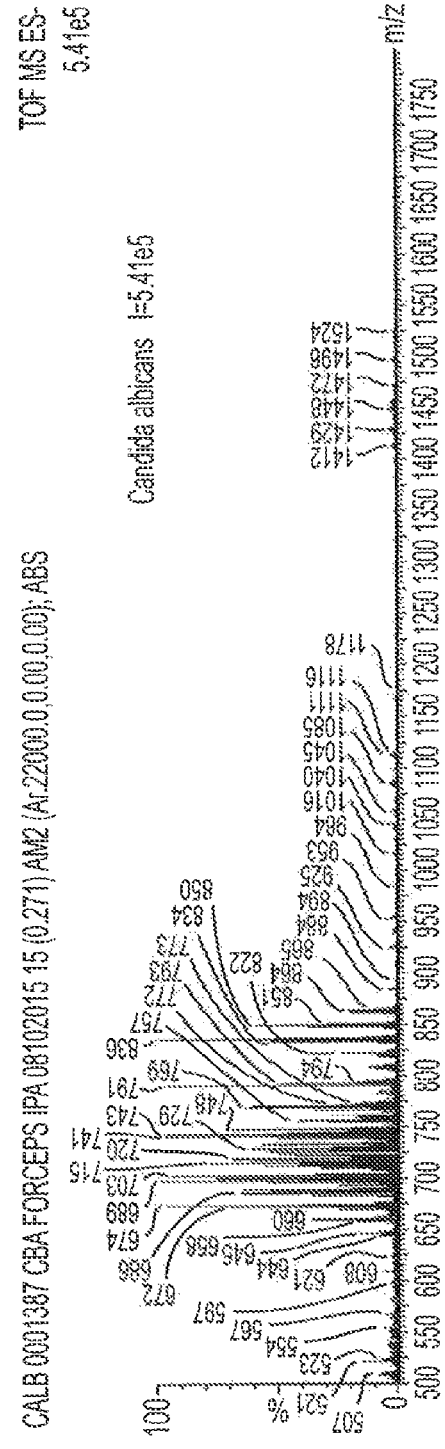
FIG. 27B shows spectral profiles of a pure *Candida albicans* isolate.

FIG. 27A shows a mass spectrum of *Escherichia coli*, FIG. 27B shows a mass spectrum of *Candida albicans* and FIG. 27C shows a mass spectrum of a mixture of *Escherichia coli* and *Candida albicans*.

Thus, in one embodiment, the method provided herein may be used to detect, identify and/or characterise a sample comprising a microbial mixture. By "microbial mixture" is meant that at least 2 different microbes are present in a sample, so a first and a second microbe may be present. Optionally, at least 3, 4, 5, 6, 7, 8, 9 or at least 10 different microbes are present in the sample. Optionally, the different microbes are taxonomically different, e.g., different strains, species, genera, classes or the like. In another embodiment, the different microbes differ at least in one characteristic, such as drug sensitivity or the ability to produce a particular compound. Thus, optionally, the different microbes may be identical or different at a taxomonic level such as Gram stain, class, family, genus, species and/or strain.

Optionally, the method may be used to detect, identify and/or characterise 1, 2, 3, 4, 5, 6, 7, 8, 9 or 10, or at least 1, at least 2, at least 3, at least 4, at least 5, at least 6, at least 7, at least 8, at least 9 or at least 10 of the microbes present in a sample comprising a microbial mixture.

Optionally, the method provided herein may be used to confirm the presence or absence of *E. coli* and/or *C. albicans* in a sample. Optionally, the sample may comprise a microbial mixture.

Subtyping of Microbes

Microbial typing provides information on the genetic relationships between strains. This process is critical for tracking the spread of infectious diseases, informing infection control practices and, in some instances, providing useful information about the nature of the microbe, for example whether it is a highly pathogenic variant. The suitability of the method provided herein using REIMS technology to provide accurate strain level discrimination was shown using various examples as discussed below.

Ribotyping of *C. difficile*

*Clostridium difficile* is a Gram-positive anaerobic bacterium and its derived infections are often nosocomially (i.e. in a hospital) acquired infections obtained after broad-band antibiotic treatment, which allows excessive growth of this more hardy and spore-forming species. *Clostridium difficile* is an important cause of antibiotic associated diarrhoea and has a case fatality rate of up to 30%. Typing information is used clinically to understand the epidemiology of disease and to determine whether an isolate has been transferred from one patient to another. In routine clinical microbiology, severe *C. difficile* outbreaks are often associated with certain ribotypes such as ribotype 027 or 078 which are thought to be especially pathogenic. Therefore, it is especially interesting for clinical microbiology labs to establish whether an infection was acquired during the hospital stay (nosocomial—all patients would be expected to have been infected by a strain of the same ribotype) or whether the infection was caused by a strain acquired before entering the hospital (different patients may be expected to be infected by strains of different ribotypes).

Ribotyping of *C. difficile* is routinely performed by isolating *C. difficile* on specific media, such as Braziers medium, and subsequently performing PCR amplification of the 16S-23 S intergenic spacer region to determine the ribotype pattern. This process is very time consuming and labour intensive, so the specificity of the REIMS technique was investigated for this particular problem.

As *C. difficile* sporulates in adverse conditions, this may affect the cell membrane lipids in turn affecting spectral profiles. Culture conditions should be standardised to reduce any confounding factors that may introduce differences in the spectral patterns.

Figure 28:
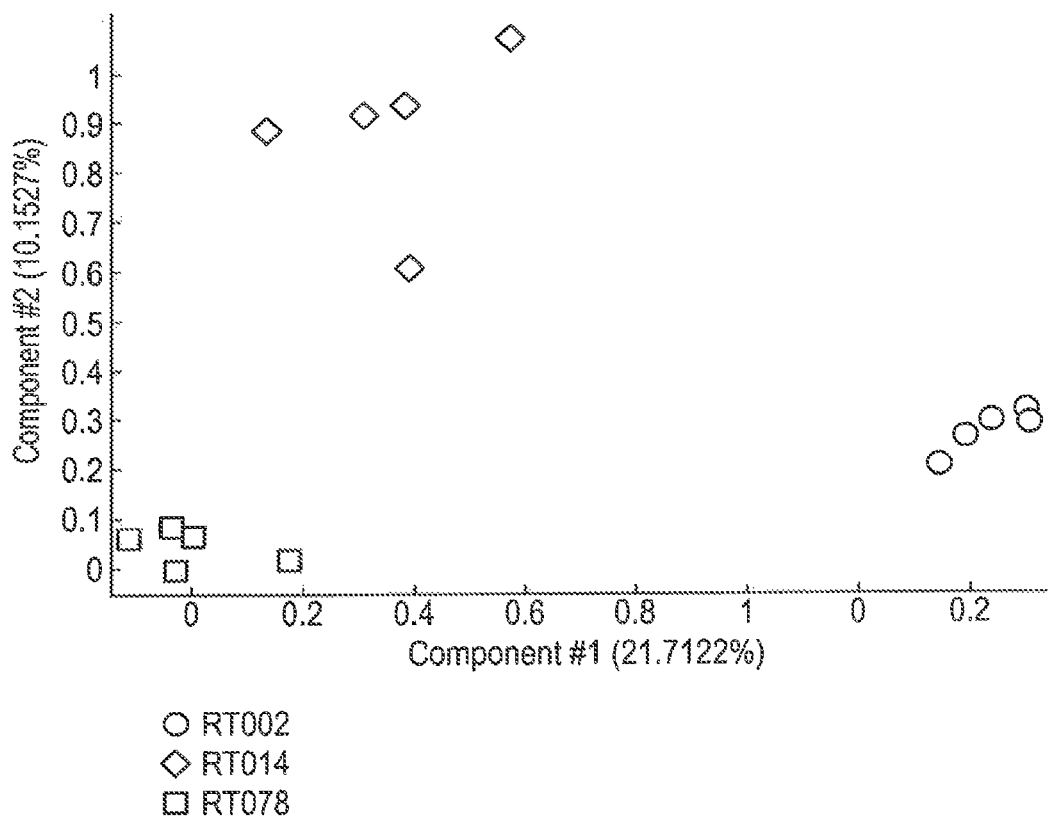
FIG. 28 shows LDA analysis of spectrometric data obtained using an embodiment of the method provided herein with REIMS with *C. difficile* ribotyped isolates.

10 strains of each of three different ribotypes of *C. difficile* were cultured on Columbia blood agar for 24 hrs under anaerobic conditions. The ribotypes included 002 and 014 which are thought to be less pathogenic and the more pathogenic ribotype 078. Clear separation trends can be observed (see FIG. 28). Overall cross-validation accuracy was 90%. Thus, the method provided herein using REIMS can provide strain level information.

Typing of *Pseudomonas aeruginosa*

*Pseudomonas aeruginosa* (*P. aeruginosa*) is an organism that while ubiquitous and generally not pathogenic, can cause severe infections including sepsis and pneumonia. It is also a significant pathogen for Cystic Fibrosis ("CF") patients where it can lead to exacerbations. Currently *P. aeruginosa* isolates are commonly typed by Variable Number Tandem Repeat (VNTR) testing, e.g., at the Public Health England reference laboratory.

The method provided herein using REIMS was successfully used to distinguish between two different *P. aeruginosa* strains obtained from CF patients (data not shown).

Typing of *Escherichia coli*

The method provided herein using REIMS was successfully used to distinguish between two different *E. coli* strains: OP50, derived from parent strain B, and C600 derived from parent strain K-12 (data not shown).

Serotyping of *Streptococcus pneumoniae*

*Streptococcus pneumoniae* is a Gram-positive bacterium that causes a variety of infectious diseases in children and adults, including bacteremia, meningitis and infections of the respiratory tract. Young children and the elderly are most affected and it is estimated that about one million children die of pneumococcal disease every year, especially in developing parts of the world. *Streptococcus pneumoniae* cells are covered with layers of polysaccharides forming a capsule which is an essential factor in virulence. 91 distinct pneumococcal serotypes have been identified, however, only a comparably small number of these serotypes are accounting for most diseases in infants. Identification of *S. pneumoniae* serotypes is most commonly performed using the Quellung reaction which involves adding an antibody solution to a broth of *S. pneumoniae* and observing a positive reaction indicated by "swelling" of the bacterial cells. This test is laborious and time-consuming and consists of a range of subsequent individual tests until a serotype is unambiguously identified. Usually antibody solutions are added in mixtures of several antibodies at a time to reduce amount of tests necessary. Molecular serotyping methods involving PCR are rather expensive and need extensive sample processing. Therefore, a straightforward way to distinguish between different pneumococcal serotypes without the need to introduce further sample processing steps besides those needed for species-level identification would have a huge impact on daily microbiological practice.

The method provided herein using REIMS was successfully used to distinguish between two different *Streptococcus pneumonia* serotypes, serotype 14 and serotype 3 (data not shown).

Thus, in one embodiment, the method provided herein may be used for microbial typing, such as strain typing, ribotyping and/or serotyping, optionally *C. difficile* ribotyping *Streptococcus pneumonia* serotyping, typing of *E. coli* and/or typing of *P. aeruginosa* strains.

Conventionally, ribotyping is the characterization or classification of bacteria on the basis of their rRNA gene sequences. It can be done, e.g., by 16S rRNA gene PCR-RFLP and sequencing. Optionally, the method provided herein may be used to analyse, e.g., whether a microbe has a particular ribotype, to distinguish between 2 or more microbes having different ribotypes, to detect a microbe having a particular ribotype, and the like.

Conventionally, serotyping is the characterization or classification of microbes on the basis of particular surface structures. Optionally, the method provided herein may be used to analyse, e.g., whether a microbe has a particular serotype, to distinguish between 2 or more microbes having different serotypes, to detect a microbe having a particular serotype, and the like.

Analysis of Inter-Species Variance Versus Intra-Species Variance

The general requirement that needs to be fulfilled for a methodology to serve as a general identification tool is that the inter-species variance is larger than intra-species variance. The biological variance introduced to the overall spectral appearance by different strains of the same species was assessed and the results can be seen in FIG. 30, for the three most common and most extensively studied pathogenic species encountered in clinical microbiology, namely *Pseudomonas aeruginosa*, *Staphylococcus aureus* and *Escherichia coli*.

Figure 30:
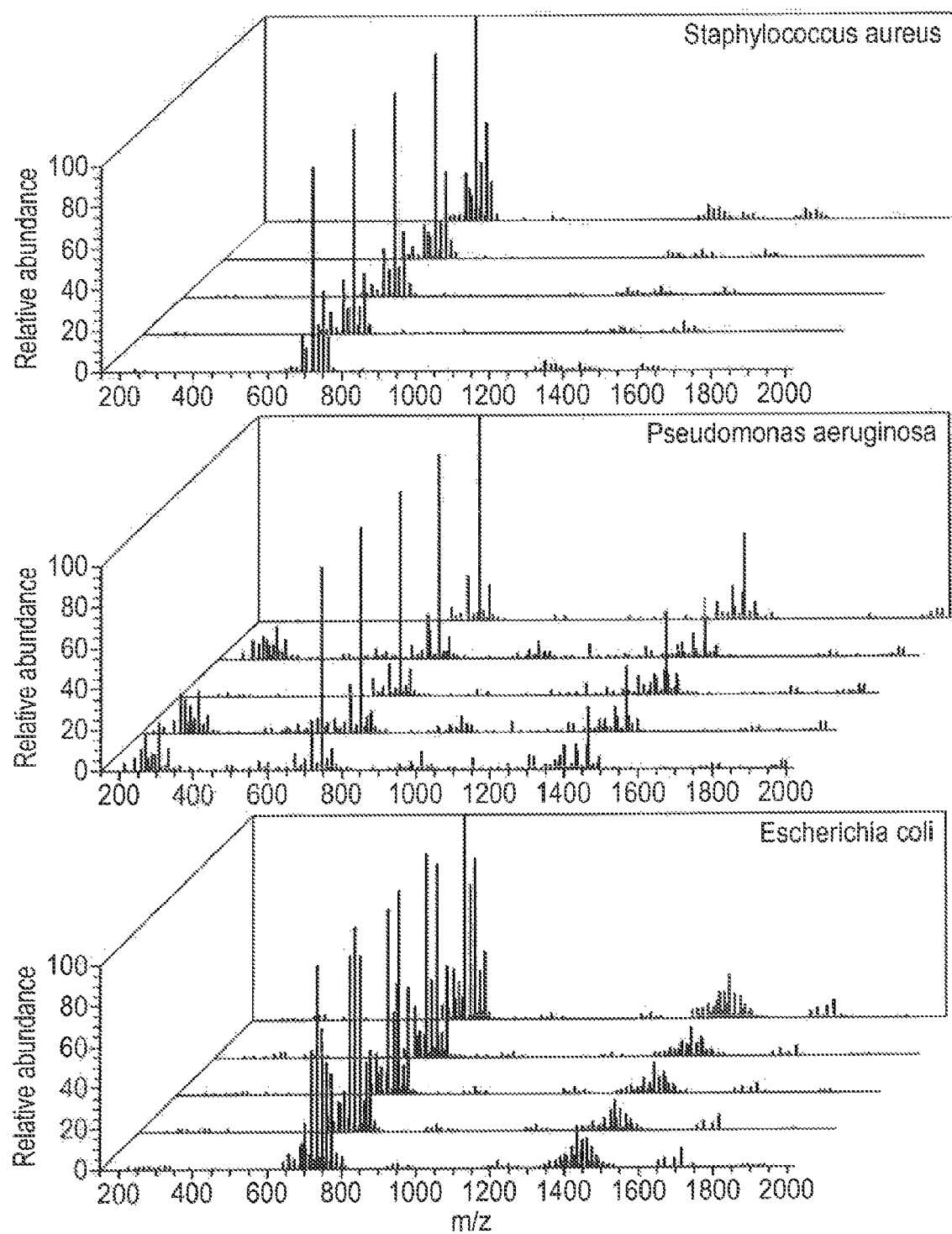
FIG. 30 shows spectrometric data obtained using an embodiment of the method provided herein with REIMS for five different clinical isolates of each of *Staphylococcus aureus* (top), *Pseudomonas aeruginosa* (middle) and *Escherichia coli* (bottom) cultured on Columbia blood agar.

FIG. 30 shows REIMS spectral profiles as obtained for five different clinical isolates of the respective species. Excellent pattern stability can be observed for *S. aureus*. For *E. coli*, some changes in relative signal intensity can be observed between major phosphatidylglycerol phospholipid species in the mass range m/z 600-800. A very high degree of similarity is observed for the high mass range. In case of *P. aeruginosa*, three of five strains exhibit production of extracellular metabolites such as quorum-sensing molecules and rhamnolipids in the mass range of m/z 200-350 and m/z 500-680, respectively. Identical strains furthermore exhibit a group of signals in the range of m/z 900-1100. However, the phospholipid region between m/z 680-800 and masses above m/z 1100 show good agreement between all five clinical isolates of *P. aeruginosa*.

In all of these cases it is apparent that large parts of the spectral information remains conserved, especially for masses above m/z 1100. This highly conserved nature of signals at m/z >1000 has been largely ignored by other lipidomics technologies in the past, which might be due to difficulties in detection for technologies such as DESI.

Thus, in one embodiment, the method provided herein may be used to detect, identify and/or characterise a microbe selected from *Pseudomonas*, *Staphylococcus* and/or *Escherichia*, optionally *Pseudomonas aeruginosa*, *Staphylococcus aureus* and/or *Escherichia coli*.

A further data set was created comprising 28 different bacterial species represented by 15 different clinical isolates each as detailed in following table:

| Gram-stain | Family | Genus | Species | Growth conditions |
|---|---|---|---|---|
| negative | Pseudomonadaceae | *Pseudomonas* | *aeruginosa* | CBA, aerobic |
| | Enterobacteriaceae | *Citrobacter* | *koseri* | CBA, aerobic |
| | | *Enterobacter* | *aerogenes* | CBA, aerobic |
| | | | *cloacae* | CBA, aerobic |
| | | *Klebsiella* | *oxytoca* | CBA, aerobic |
| | | | *pneumoniae* | CBA, aerobic |
| | | *Escherichia* | *coli* | CBA, aerobic |
| | | *Proteus* | *mirabilis* | CBA, aerobic |
| | | *Morganella* | *morganii* | CBA, aerobic |
| | | *Serratia* | *marcescens* | CBA, aerobic |
| | Pasteurellaceae | *Haemophilus* | *influenzae* | CHOC, aerobic (5% $CO_2$) |
| | Burkholderiaceae | *Burkholderia* | *cepacia complex* | CBA, aerobic (5% $CO_2$) |
| | Xanthomonadaceae | *Stenotrophomonas* | *maltophilia* | CBA, aerobic |
| | Bacteroidaceae | *Bacteroides* | *fragilis* | CBA, anaerobic |
| | Moraxellaceae | *Moraxella* | *catarrhalis* | CBA, aerobic |
| | Neisseriaceae | *Neisseria* | *gonorrhoeae* | CBA, aerobic (5% $CO_2$) |

-continued

| Gram-stain | Family | Genus | Species | Growth conditions |
|---|---|---|---|---|
| positive | Staphylococcaceae | Staphylococcus | aureus | CBA, aerobic |
| | | | epidermidis | CBA, aerobic |
| | | | capitis | CBA, aerobic |
| | | | haemolyticus | CBA, aerobic |
| | | | hominis | CBA, aerobic |
| | Enterococcaceae | Enterococcus | faecalis | CBA, aerobic (5% $CO_2$) |
| | | | faecium | CBA, aerobic (5% $CO_2$) |
| | Clostridiaceae | Clostridium | difficile | CBA, anaerobic |
| | Micrococcaceae | Micrococcus | luteus | CBA, aerobic |
| | Streptococcaceae | Streptococcus | agalactiae | CBA, aerobic(5% $CO_2$) |
| | | | pyogenes | CBA, aerobic (5% $CO_2$) |
| | | | pneumoniae | CBA, aerobic (5% $CO_2$) |

The generated datasets were analysed using supervised and unsupervised analysis. Generally the plots resulting from the supervised and unsupervised analysis of REIMS technology data showed high similarity to each other. This is due to the fact that REIMS technology features exclusively signals originating from the sample (i.e. not from any chemical background). This is an advantage compared to MALDI MS where matrix related signals significantly contribute to the overall spectral information.

The results demonstrate that REIMS technology spectral profiles largely follow taxonomical trends. Cross-validation revealed 95.9%, 97.8% and 100% correct classification at species-, genus- and Gram-level.

Gram-positive and Gram-negative species were found to separate along the first multivariate component in both PCA and RMMC analysis. Compared to Gram-negative species, Gram-positive bacteria generally showed a higher amount of saturated phospholipid species and lower relative abundance of phosphatidylethanolamines. These observations are in agreement with the bacterial cell membrane composition reported in the literature. Hierarchical cluster analysis was performed in order to investigate how well the REIMS spectral profiles follow the bacterial taxonomy as determined by 16S rRNA gene sequences. Hierarchical Cluster Analysis (HCA) was performed using Euclidean pairwise distance calculation with a complete linkage metric. 3×3 strains of the original dataset were averaged for each bacterial species to form the dataset which was then subjected to HCA. This step was undertaken in order to facilitate visualization while still incorporating a maximum of the biological variance among strains of a certain species. The inventor found that spectral profiles of closely related bacterial species were grouped closely together while rather unrelated bacterial species grouped separately. For the Gram-positive species this was determined for each the Staphylococcus spp. (S. aureus, S. capitis, S. epidermidis, S. hominis and S. haemolyticus), Streptococcus spp. (S. agalactiae, S. pneumoniae, S. pyogenes) and two Enterococcus spp. (E. faecalis and E. faecium). Streptococcus and Enterococcus spp. which both belong to the Lactobacillales order were further situated on the same cluster in the HCA.

Regarding Gram-negative species, all members of the Enterobacteriaceae family (members of the genera Escherichia, Citrobacter, Enterobacter, Proteus, Morganella, Klebsiella and Serratia) grouped closely together. Furthermore, Pseudomonas aeruginosa, Moraxella catarrhalis and Burkholderia cepacia complex strains were all located together in a separate cluster when compared to the other Gram-negative species. Pseudomonas spp. and Moraxella spp. are both part of the Pseudomonadales order. Although Burkholderia cepacia complex strains belong to □-Proteobacteria today, they were previously classified into the Pseudomonas genus, thus indicating a high phenotypic similarity between Pseudomonas spp. and Burkholderia spp. which explains their proximity on the HCA dendrogram. The same trends were observed in PCA plots for Gram-positive and Gram-negative-species only. Similarly to HCA, these results demonstrate that REIMS technology spectral profiles largely follow taxonomical trends.

Effect of Growth Conditions

Pseudomonas aeruginosa, Staphylococcus aureus and Escherichia coli are all facultative anaerobes and can thus survive and grow under a variety of different atmospheres. REIMS technology profiles were obtained after culturing the bacteria under the four most commonly used atmospheres. For P. aeruginosa and E. coli the different culture conditions did not result in any significant differences in the spectrometric data (data not shown).

Figure 31C:
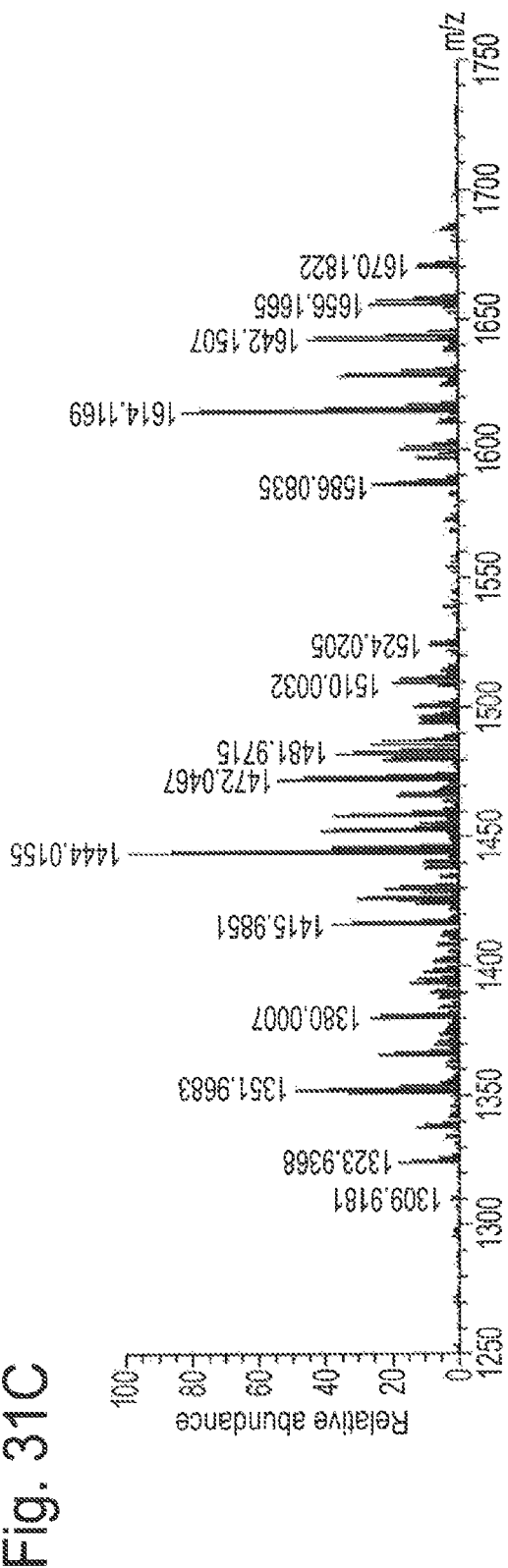
Figure 31D:
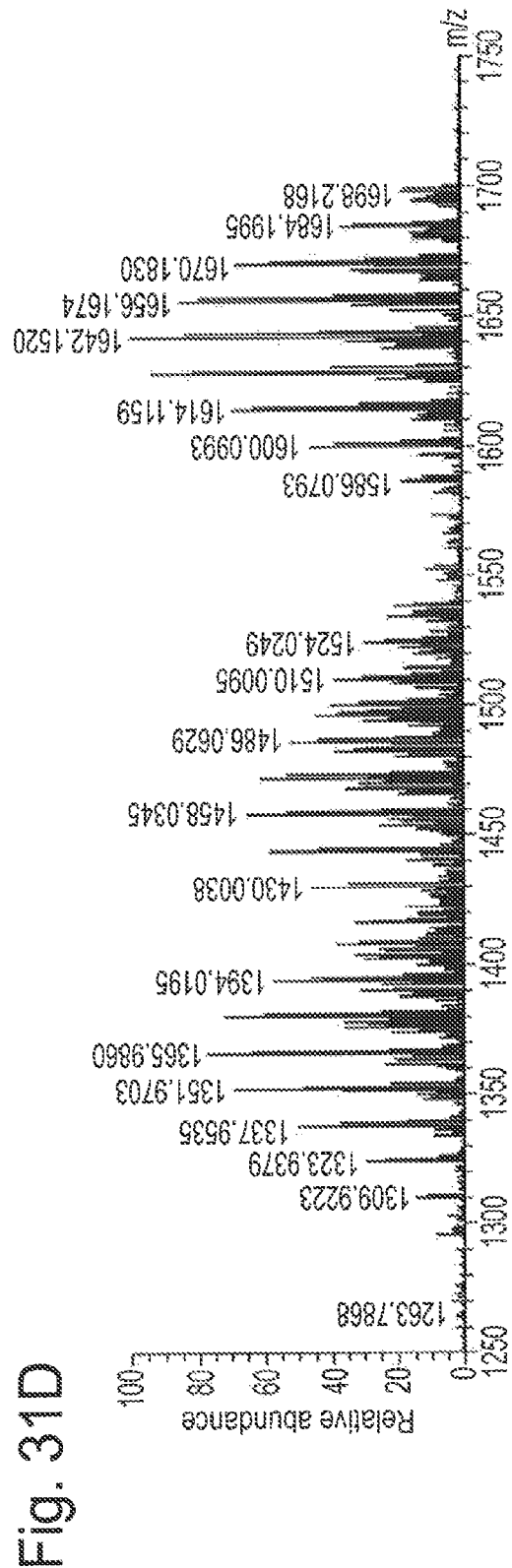

FIG. 31A shows zoomed regions of mass spectra of S. aureus grown under aerobic conditions in the mass range m/z 650-800, FIG. 31B shows zoomed regions of mass spectra of S. aureus grown under anaerobic conditions in the mass range m/z 650-800, FIG. 31C shows zoomed regions of mass spectra of S. aureus grown under aerobic conditions in the mass range m/z 1250-1750 and FIG. 31D shows zoomed regions of mass spectra of S. aureus grown under anaerobic conditions in the mass range m/z 1250-1750.

Significant changes can be observed in the spectral profile of S. aureus with a strong shift of phosphatidylglycerols expression towards lipid species with longer chain lengths, both for phosphatidylglycerols at m/z 650-800 as for higher mass species in the range of m/z 1300-1700, as shown in the zoomed spectrometric regions in FIGS. 31A-D.

Similar results were obtained in a study analysing the fatty acid composition of S. aureus grown under aerobic and anaerobic conditions using gas-liquid chromatography. While under aerobic conditions, fatty acids with 15, 18, and 20 carbon atoms account for 40.86%, 3.7%, and 21.84% of the overall fatty acid content, under anaerobic conditions these numbers change to 16.26%, 22.38% and 37.65%, respectively (D. C. White, F. E. Frerman, Fatty Acid Composition of the Complex Lipids of Staphylococcus aureus During the Formation of the Membrane-bound Electron Transport System. Journal of Bacteriology 95, 2198-2209 (1968)). This was associated with the membrane-bound electron transport system being inactive under anaerobic conditions. As S. aureus was found to contain less than 1% free fatty acids, these fatty acids are predominantly built into membrane lipid species and thus leads to a significant increase in heaver phospholipid species which can be confirmed using the spectrometric data obtained via the method herein using REIMS technology.

The effect of different media on bacteria was determined by growing ten distinct isolates of *Staphylococcus epidermidis* on three commonly used agars; aztreonam, blood and chocolate agar. The agar type did not affect the lipid profiles (data not shown).

Mycolic Acids in Corynebacterinaceae Suborder

The suborder Corynebacterineae forms a large group of actinomycete species characterized by the presence of mycolic acids. Mycolic acids long fatty acids that are generally composed of a longer beta-hydroxy chain (meromycolate chain) and shorter alpha-alkyl side chain (α-branch). The variability of their chain lengths and the complexity of their structures contribute to the definition of the genera, from the simplest corynomycolic acids of *Corynebacterium* to the most complex mycolic acids of the *Mycobacterium* genus. The number of carbon atoms and the degree of desaturation (refers to the number of double bonds and/or cyclopropane rings) of main and side chains vary according to the genus considered. Using the method provided herein with REIMS technology, spectral profiles were obtained for members of the four most common genera of the Corynebacterineae suborder as encountered in clinical microbiology. The inventors determined that *Corynebacterium aftermentans* displays mycolic acids of chain lengths ranging from C28 to C36; whereas *Rhodococcus equi* displays mycolic acids of chain lengths ranging from C28 to C39; *Nocardia ateroides* displays mycolic acids of chain lengths ranging from C48 to C60; and *Mycobacterium avium* displays mycolic acids of chain lengths ranging from C77 to C81.

Mycolic acids constituents were determined for *Rhodococcus equi* ATCC 6939. *Rhodococcus* spp. are reportedly known to contain mycolic acids between 30-54 carbon chain lengths and 0-2 unsaturations. For the analysed *Rhodococcus* strain, mycolic acids with overall chain length of 28-39 were found with 0-3 unsaturations. The overall chain length for this particular strain is in good agreement for *R. equi* species as reported in literature. However, a higher amount of unsaturations were found in the presented study (see Table 4). This might be due to a lack of sensitivity in the literature source, i.e. due to a higher sensitivity of the method provided herein compared to conventional methods, because the highly unsaturated species detected in the REIMS technology spectra are of low spectral intensity.

*Nocardia* spp are reportedly known to contain mycolic acids with chain lengths between C48-60 with a degree of unsaturation between 0-3. These findings could be confirmed using the method provided herein for a *Nocardia* sp. isolated from a sample of respiratory origin and type-strain *Nocardia asteroides* ATCC 19247. Detected mycolic acid species are listed in Table 5.

Strains of *Mycobacterium avium*, *M. fortuitum* and *M. peregrium* were obtained from clinical respiratory specimens and analysed using the method herein using REIMS technology. The detected mycolic acid species are listed in Table 6. Mycobacteria are reportedly known to contain mycolic acids with chain lengths between 60-90 carbons and 1-2 unsaturations. While other members of the Corynebacterineae suborder mainly contain unfunctionalised mycolic acids, there is a larger structural variability in Mycobacteria ranging from unfunctionalised alpha-mycolic acids to methoxy-, keto- and epoxy-functionalities as part of the beta-hydroxy side chain. Apart from *Segniliparus* spp., no other member of the Corynebacterineae suborder contains similarly long mycolic acids. However, while lower chain length mycolic acids were found with high intensity, mycolic acids in case of *Mycobacterium* spp. were found with comparably low spectral intensity. This might either be due to lower general abundance in the membrane of Mycobacteria as compared to other genera or more likely decreasing ionisation efficiency with increasing mycolic acid chain length.

Sphingolipids in Bacteroidetes Class

Sphingolipid production is ubiquitous among eukaryotes but present in only a few bacterial genera. Species of *Bacteroidetes*, a Gram-negative bacterial phylum whose members often comprise around 50% of the human gut community, are unusual in that they produce sphingolipids with up to 40-70% of their total membrane phospholipid content.

Sphingolipids are signaling molecules that play a key role in modulating the host immune response. Genera that are comprised within the Bacteroidetes phylum include *Bacteroides, Parabacteroides, Prevotella, Tannerella* and *Porphyromonas* spp.

The method provided herein using REIMS technology was used to analyse members of the Bacteroidetes phylum. Spingolipids that were described in literature and identified in spectra generated via this method include free ceramides, phosphoethanolamine dihydroceramides, as well as substituted and unsubstituted phosphoglycerol dihydroceramides. An overview of these compounds is given in Table 7, wherein a) denotes: see Fragmentation spectra in FIG. 13; and b) denotes: see fragmentation spectra in FIG. 14.

Figure 13:
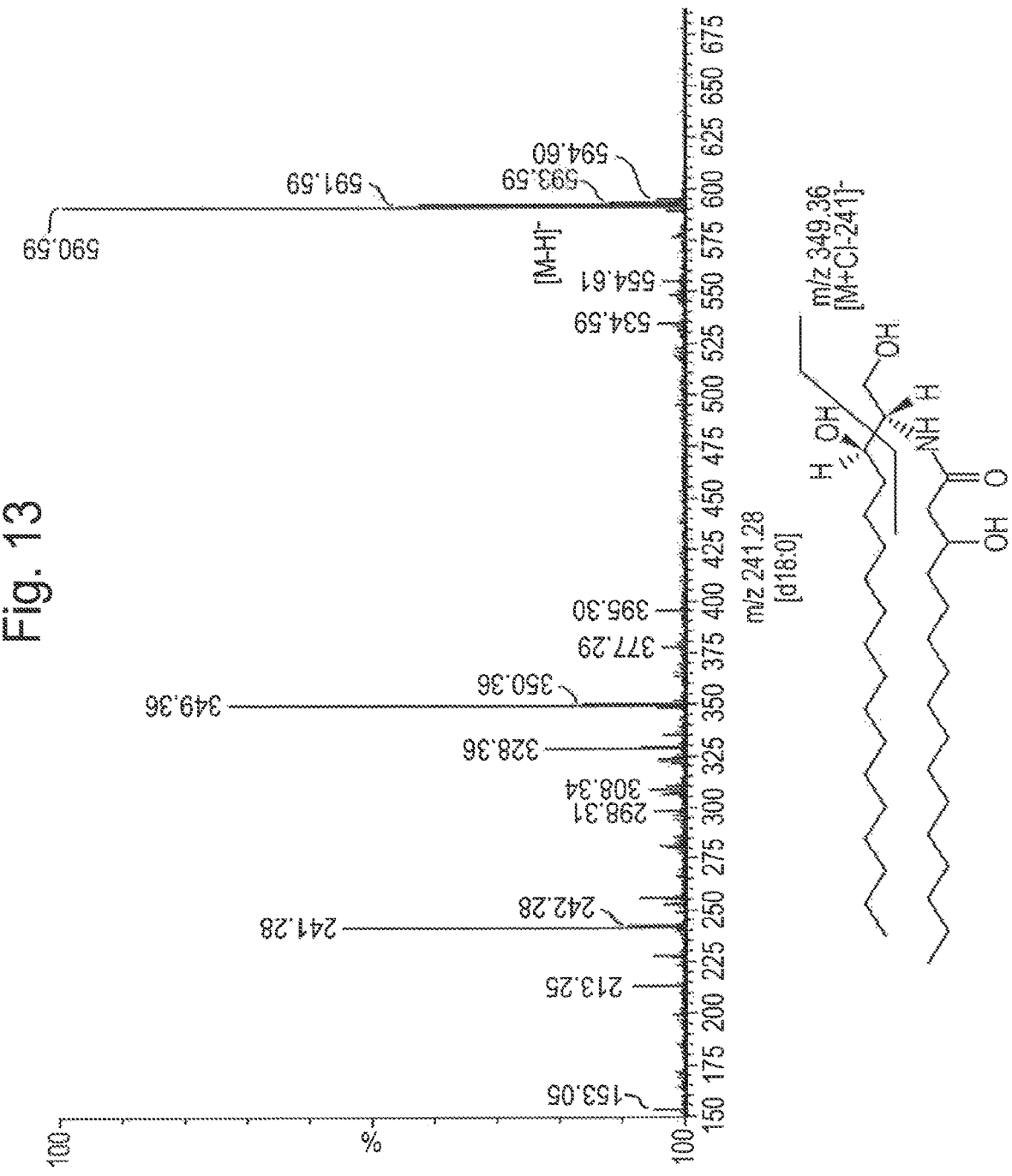
FIG. 13 shows a fragmentation spectrum and scheme of fragmentation for an oxidised ceramide signal at m/z 590 obtained from *B. fragilis*.
Figure 14:
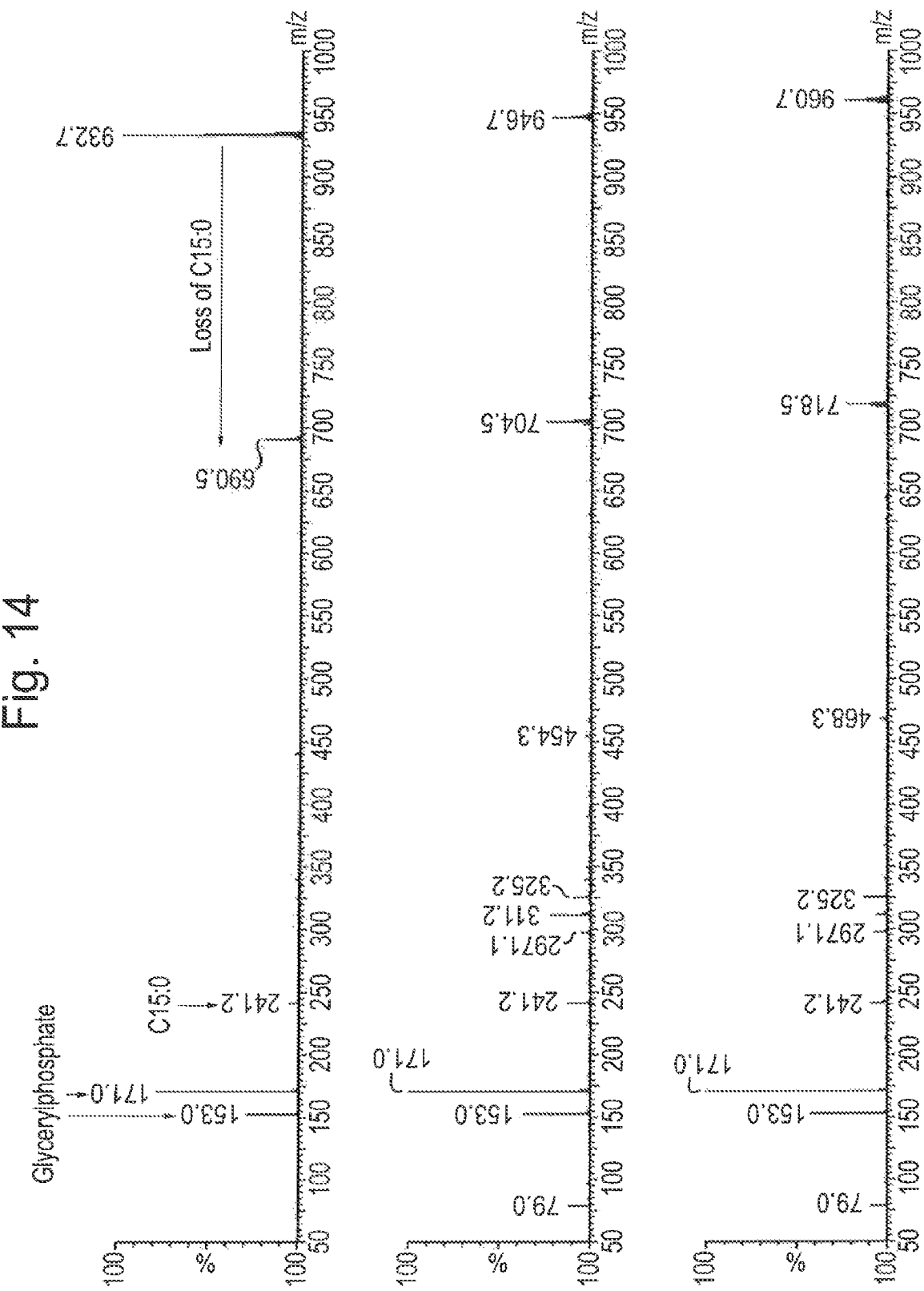
FIG. 14 shows fragmentation spectra obtained for peaks at m/z 932, 946 and 960 from *Parabacteroides distonasis* assigned as C15:0 substituted phosphoglycerol dihydroceramides (subPG-DHC)

Ceramides were not found to be identical with those observed for samples of mammalian origin but were found to contain an additional oxygen molecule. A fragmentation mechanism of the $[M+Cl]^-$ ion at m/z 590 is shown in FIG. 13 explaining the two major fragments observed from collision induced dissociation of the parent ion. FIG. 14 shows fragmentation spectra obtained for C15:0 substituted phosphoglycerol dihydroceramides that were produced by members of the *Parabacteroides* genus. Main fragments at m/z 153 and 171 can be ascribed to the glycerolphosphate headgroup while m/z 241 can be attributed to C15:0 acyl chains. A neutral loss of 242 Da form the parent ion can additionally be ascribed to the C15:0 acyl chain. These compounds have been described for *Porphyromonas gingivalis* (not part of the present database) and thus seem specific for the Porphyromonadaceae family. These compounds were furthermore reported to penetrate into human tissues and were found in blood, vasculature tissues and brain.

It was recently reported that *Bacteroides fragilis* NCTC 9343 additionally produces an isoform of α-galactosylceramides, a sponge-derived sphingolipid that serves as ligand for the host immune receptor CD1d. The inventor determined that these compounds can be found in REIMS technology spectra of *B. fragilis* strains at m/z 752, 766 and 780 cannot be found in any other analysed species within the Bactoidetes class.

Corynebacterium Speciation

Species identification within the *Corynebacterium* genus can be challenging using existing methods. For example, partial 16S rRNA sequencing does not lead to sufficient specificity, so ideally the less commonly used full sequence is needed. Corynebacteria typically contain mycolic acids, so REIMS may be used to identify *Corynebacterium* species, or to differentiate between *Corynebacterium* species, for example, on the basis of spectrometric data pertaining to mycolic acids.

Figure 32:
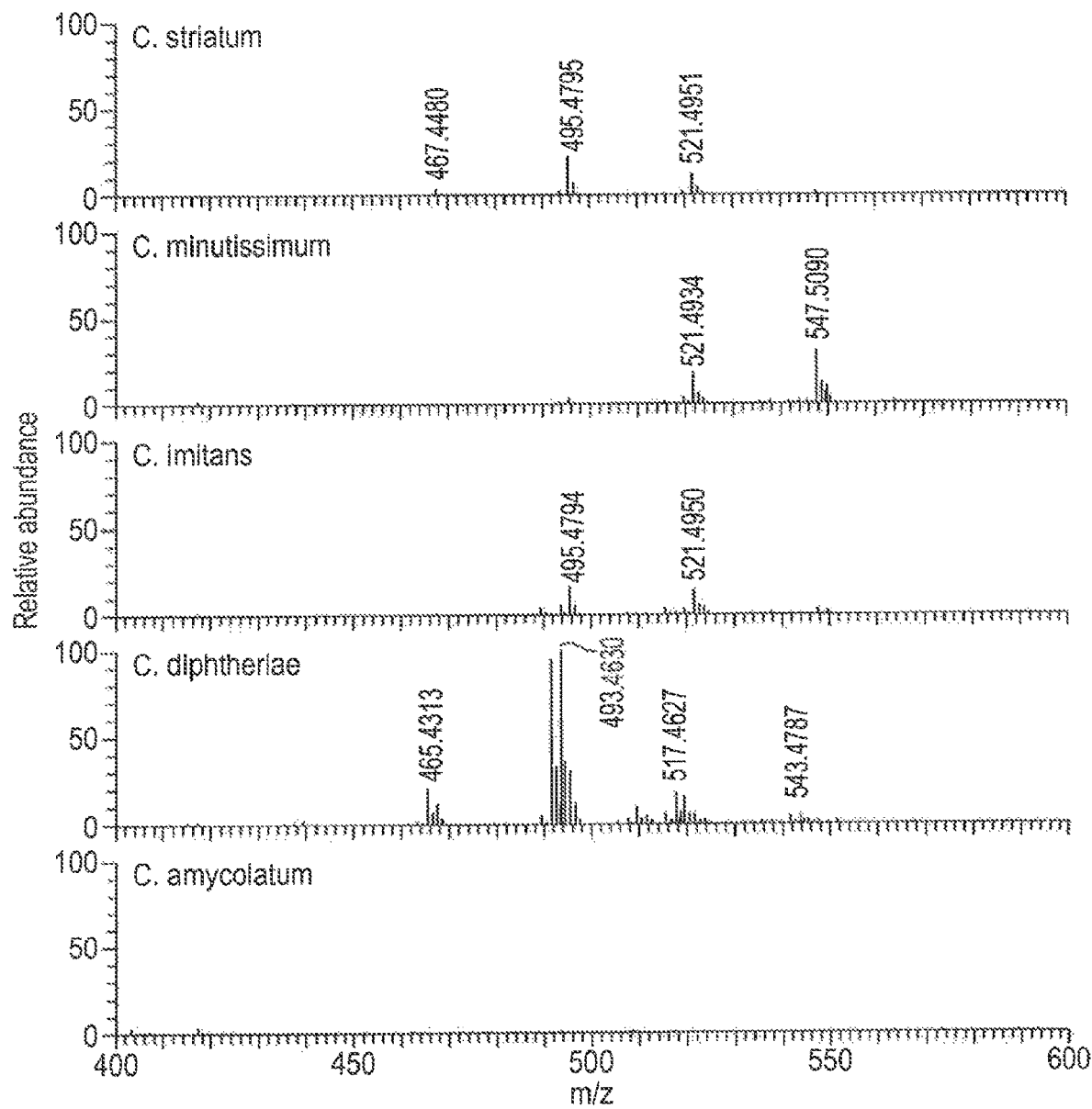
FIG. 32 shows zoomed spectrometric data obtained using the method provided herein provided herein with REIMS for five different *Corynebacterium* species, which reveals different mycolic acid patterns; spectra normalised to base peak.

The method provided herein using REIMS technology was successfully used to distinguish between five different *Corynebacterium* species: *C. striatum, C. minutissimum, C. imitans, C. diphtheria, C. amycolatum* (FIG. 32). Most strikingly, *Corynebacterium amycolatum*, an emerging opportunistic pathogen, can be easily distinguished by its absence of mycolic acid signals.

Using collision induced dissociation, mycolic acids fragment at the bond between the meromycolate chain and the a-branch. While the meromycolate chain forms an aldehyde and leaves the parent ion as a neutral entity, the a-branch of the mycolic acid forms a negatively charged carboxylate ion, allowing for structural assignment of the parent ion. Fragment ions observed (see Table 3) were in good agreement with those reported in literature for *C. glutamicum* and confirm chemical assignment.

Thus, in one embodiment, the method provided herein may be used to detect, identify and/or characterise one or more *Corynebacterium* species. In one embodiment, the method provided herein may be used to detect or confirm the presence or absence of *C. amycolatum* in a target, for example by comparing the spectrometric data from said target to a reference spectrometric data of *C. amycolatum*. In one embodiment, the method provided herein may be used to detect or confirm the presence or absence of one or more *Corynebacterium* species selected from *C. striatum*, *C. minutissimum*, *C. imitans*, *C. diphtheria*, and/or *C. amycolatum*.

In any of these embodiments, the sample may optionally be known to contain at least one bacterial species, e.g., one *Corynebacterium* species.

Antimicrobial Susceptibility Testing ("AST")

Antibiotic resistance of microbes is a global problem of increasing significance that often can significantly complicate treatment of infections. The protein profiles that are acquired during routine MALDI TOF analysis do not contain information on the antibiotic sensitivity and resistance pattern. As discussed elsewhere herein, culture-based methods for testing antibiotic sensitivity are time-consuming.

*Staphylococcus aureus* can cause a range of infections including pneumonia, bacteraemia and skin and soft tissue infections. Methicillin resistant *Staphylococcus aureus* (MRSA) strains are resistant to beta-lactam antimicrobials and result in increased length of hospital stays, higher economic costs and poorer clinical outcomes. Moreover, it is a leading cause of Hospital Acquired Infections (HAIs) and is estimated to account for 44% of HAIs in the EU each year. Because MRSA colonisation has been identified as a major risk factor in the development of an MRSA infection, and to curb nosocomial spread, universal or targeted screening programmes are often adopted.

30 MRSA and 30 methicillin susceptible *S. aureus* (MSSA) isolates were examined using the method provided herein using REIMS technology. LDA and cross validation analysis (FIG. 29) revealed a clear separation of MSSA and MRSA isolates indicating that the method provided herein provides a useful tool for MRSA screening.

The method provided herein using REIMS technology was also successfully used to distinguish between some antimicrobial-resistant (cabapenemase-producing) and antimicrobial-sensitive (not cabapenemase-producing) strains of *Klebsiella pneumonia*.

Thus, in one embodiment, the method provided herein may be used to detect, identify or characterise a microbe having sensitivity to an antimicrobial. In one embodiment, the method provided herein may be used to detect, identify or characterise a microbe having resistance to an antimicrobial. In one embodiment, the method may be used to distinguish between antimicrobial-resistant and antimicrobial-sensitive microbes.

Optionally, the antimicrobial may be selected from any of the antimicrobials disclosed elsewhere herein.

Optionally, the antimicrobial-resistant microbe may be selected from a producer of β-lactamase, such as cabapenemase or TEM-1 β-lactamase; a producer of chloramphenicol acetyltransferase, a producer of a tetracycline efflux system, a producer of AmpC cephalosporinase; and/or an over-producer of DHF (dihydrofolate) reductase.

Optionally, the antimicrobial-resistant microbe may be MRSA and/or the antimicrobial-sensitive microbe may be MSSA.

Analysis of Liquids and Microbial Mixtures

Direct analysis of a liquid such as a microbial culture medium or a body fluid is not advisable as evaporation temperatures are restricted by the boiling point of water and thus cannot exceed 100° C. This, together with dilution of cells by the culturing medium considerably limits sensitivity. Thus, the analysis of liquid cultures may optionally include, or be preceded by, a processing step to remove excess liquid to prepare a solid sample. Suitable processing steps, such as centrifugation and/or filtration, are discussed elsewhere herein.

For most bacterial species, a centrifugation step of 10 mins at 3500 rpm is sufficient to form a cell pellet suitable for REIMS technology analysis. However, certain bacterial species such as *Klebsiella pneumoniae* or *Pseudomonas aeruginosa* may need to be centrifuged at more rigorous conditions such as 10 mins at 12500 rpm to allow effective removal of the supernatant. The skilled person is aware of, or can easily determine, which centrifugation conditions are appropriate to allow effective removal of the supernatant. The resulting pellet may be analysed directly, e.g., using REIMS technology, or it may be transferred onto a solid support such as a swab or a slide. The inventors have determined that such a transfer does not impact on the analysis.

In one set of Examples, binary mixtures of bacteria were created at different ratios and analysed using the method provided herein using REIMS technology.

For this purpose, bacterial biomass was cultured for 48 hrs on blood agar and subsequently scraped off using a 10 uL loop and collected in an Eppendorf tube for *Pseudomonas aeruginosa*, *Bacteroides fragilis*, *Staphylococcus aureus* and *Escherichia coli*. Using an analytical balance, bacteria were weighed into a fresh Eppendorf in ratios of 1:5, 1:3, 1:1, 3:1, and 5:1 (weight: weight). The method allowed the detection of each species within each mixture.

Thus, optionally, the method provided herein may be used to detect, identify and/or characterise a microbe present in a liquid. Optionally, the method may be used to analyse a liquid to determine whether any microbes are present; and/or to identify and/or characterise a microbe present in said liquid. As explained above, the method optionally includes a processing step to prepare a solid sample. Optionally, the method may be used to analyse a target comprising or consisting of a microbial mixture, e.g., to detect, identify and or characterise one or more or all of the different microbes present in said mixture.

Cardiolipins

Cardiolipins (1,3-bis(sn-3'-phosphatidyl)-sn-glycerols) are complex diphosphatidylglycerol lipids containing four fatty acid chains that can differ in length and degree of unsaturation. They are predominantly distributed in bacterial plasma membranes and in eukaryotic mitochondrial inner membranes. Although there is significant potential for complexity in cardiolipin structure considering the presence of four fatty acyl chains, the cardiolipin profiles are generally found to comparably simple and reproducible. Bacterial cardiolipins predominantly exhibit shorter carbon chain lengths with mostly saturated or mono-unsaturated fatty acids. However, eukaryotic cells feature predominantly longer chain polyunsaturated fatty acids as building blocks of their cardiolipins. Using the method provided herein with a REIMS technology device, cardiolipins were detected and identified in a wide range of both Gram-positive and Gram-negative bacteria, based on exact mass measurements. They were typically detected in the mass range between m/z=1300-1450 which corresponds to overall chain lengths of CL(60:0)-CL(72:0).

For example, for *Staphylococcus epidermidis* ATCC 12228, the presence of cardiolipins was further confirmed using fragmentation patterns. For this purpose, the strain was cultured on BHI medium which was found to increase the relative spectral intensity for cardiolipins as compared to blood agar. The identified cardiolipins species and fragmentation results are listed in Table 2. In good agreement with the phosphatidylglycerol species in case of the *Staphylococcus* genus (see Table 1), only cardiolipins with saturated fatty acyl groups were detected. This is expected as phosphatidylglycerols moieties form the building blocks of cardiolipins.

Quorum-Sensing Molecules in *P. aeruginosa*

Figure 34:
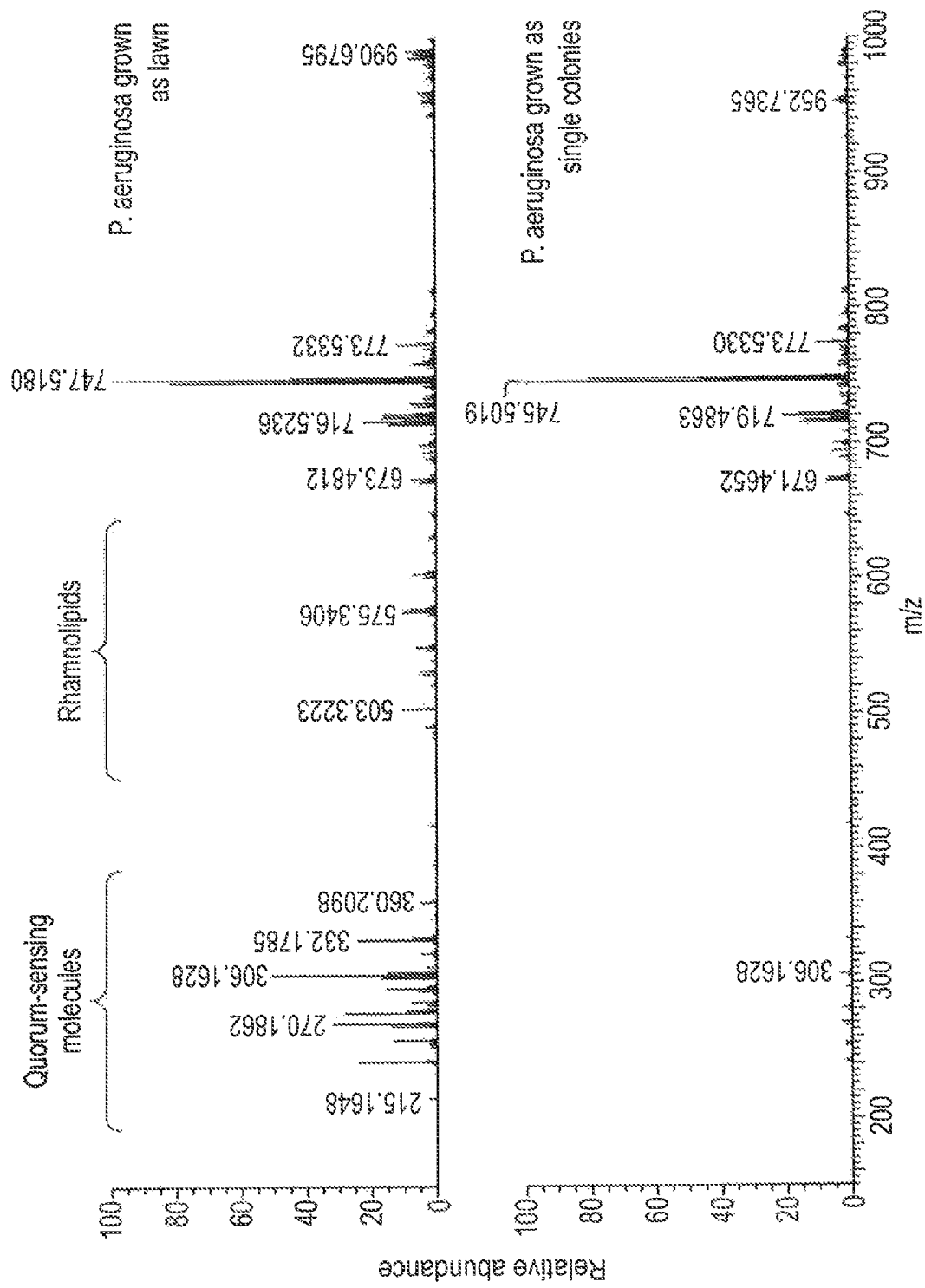
FIG. 34 Shows spectrometric data obtained using an embodiment of the method provided herein with REIMS for a clinical isolate of *Pseudomonas aeruginosa* grown as a lawn (top) and as single colonies (bottom), with spectrometric data for quorum sensing molecules and rhamnolipids highlighted.

Cell-to-cell communication via so-called quorum-sensing (QS) mechanisms is ubiquitous in the bacterial world. These systems rely on synthesis of small molecules that diffuse in and out of cells where they promote collective behaviour by facilitating gene expression. These molecules are also called autoinducers as among others they also promote expression of genes that lead to their own synthesis. QS signal molecules are also known to cross the procaryote-eucaryote border where they may aid bacterial survival by promoting collective advantageous behaviour. Several chemically distinct molecular families of QS molecules have been described of which the N-acylhomoserine lactone (AHL) family in Gram-negative bacteria have arguably been best studied. *P. aeruginosa* is known to employ both AHL and a more unique system which is linked to the first and which utilises 2-heptyl-3-hydroxy-4(1H)-quinolone as main functional entity (*Pseudomonas* quinolone signal, PQS). PQS and structurally similar derivatives are known to regulate the production of virulence determinants such as elastase, rhamnolipids, the galactophilic lectin, LecA, and the pigment pyocyanin. It was further reported to influence biofilm development and maturation Using the method provided herein with REIMS technology, abundant signals were observed in *P. aeruginosa* that correlate with the PQS-based quorum-sensing system. These were found in different abundances and compositions based on culturing medium, culture age, growth mode and strain. An example for different growth modes observed in a number of *P. aeruginosa* strains is given in FIG. 34 and shows spectra for cells acquired from cells of the same strain grown on the same plate in small single colonies (<1 mm diameter) and from cells grown as a lawn. While no signals corresponding to quorum-sensing molecules were observed in case of spectra obtained from single colonies, abundant quorum-sensing molecules were observed for those cells grown in a lawn pattern. Production of quorum-sensing molecules and resulting gene expression is known to be depending on cell density and was found increased in biofilms of *P. aeruginosa*; the observed findings were thus correlated with this effect. The same effect was observed in case of rhamnolipid production (see below).

Compounds 2-heptylquinoline-4(1H)-one and 2-heptyl-3-hydroxy-4(1H)-quinolone (PQS) have been confirmed by the inventor by comparison with tandem mass spectra of standard compounds. Hydroxynonenylquinoline (m/z=268), hydroxynonylquinoline (m/z=270) and hydroxyundecenylquinoline (m/z=296) show similar fragmentation patterns and can thus be ascribed to structurally similar compounds. Common fragments include m/z 143, 157 and 170. Tandem mass spectra of these compounds featured in the literature are only reported for the $[M+H]^+$ quasi-molecular ion. However, the fragments observed in negative ion mode (m/z=157 and 170) seem to correlate with the fragments observed in positive ion mode (m/z=159 and 172) and are indicative of 4-hydroxy-2-alkylquinolines.(170) Structurally confirmed quorum-sensing molecules are listed in Table 8. Furthermore, m/z signals at 306 and 332 show fragments at m/z 270 and 296 (and a common fragment at m/z 157), respectively (loss of 36 Da) and a isotopic pattern indicative of $[M+Cl]^-$ adducts.

Rhamnolipids in *P. aeruginosa*

Microorganisms like bacteria, yeasts, and fungi are known to produce various types of biosurfactants. Rhamnolipids are a class of surface-active glycolipids containing one or two 3-hydroxy fatty acids of various lengths, linked to a mono- or dirhamnose (Rha) moiety. They can be found as secondary metabolites and in different concentrations and composition patterns in a variety of *Pseudomonas* species. Other bacterial species as some *Burkholderia* sp. have been reported to produce rhamnolipids with longer alkyl chains than those produced by *P. aeruginosa*. Rhamnolipid production could be linked to physiological functions such as biofilm formation, uptake and biodegradation of poorly soluble substrates, surface motility as well as displaying antimicrobial activity against both Gram-negative and Gram-positive species and a range of fungal species.

Rhamnolipids probably contribute to the inflammatory-related tissue damage observed in lungs of cystic fibrosis (CF) patients. In fact, rhamnolipid concentrations in CF patients are high: up to 8 μg/mL rhamnolipid concentration was reportedly found in sputum samples obtained from *P. aeruginosa* colonised CF patients and as much as 65 μg/mL were reportedly found in secretions of a lung removed from a CF patient.

Although initially described as a mixture of four congeners, the development of more sensitive analytical techniques has led to the further discovery of about 60 rhamnolipids homologues.

The method provided herein was used with REIMS to analyse rhamnolipid production by *Pseudomonas aeruginosa* isolates. Identified rhamnolipid species are listed in Table 9. The inventor determined that overall spectral intensity of rhamnolipids depends on a number of factors: single colonies were observed to display less rhamnolipids than when grown as a lawn (this effect was correlated with the detection and production of quorum-sensing molecules, see previous point). Rhamnolipid intensity was also seen to increase significantly with increasing age of the culture. However, not all *P. aeruginosa* strains analysed were observed to produce rhamnolipids. Rhamnolipid production is linked to the quorum-sensing apparatus, a fact that can be observed in REIMS spectra of *P. aeruginosa* as well where high abundance of rhamnolipids are usually accompanied by abundant quorum-sensing signals.

Figure 35:
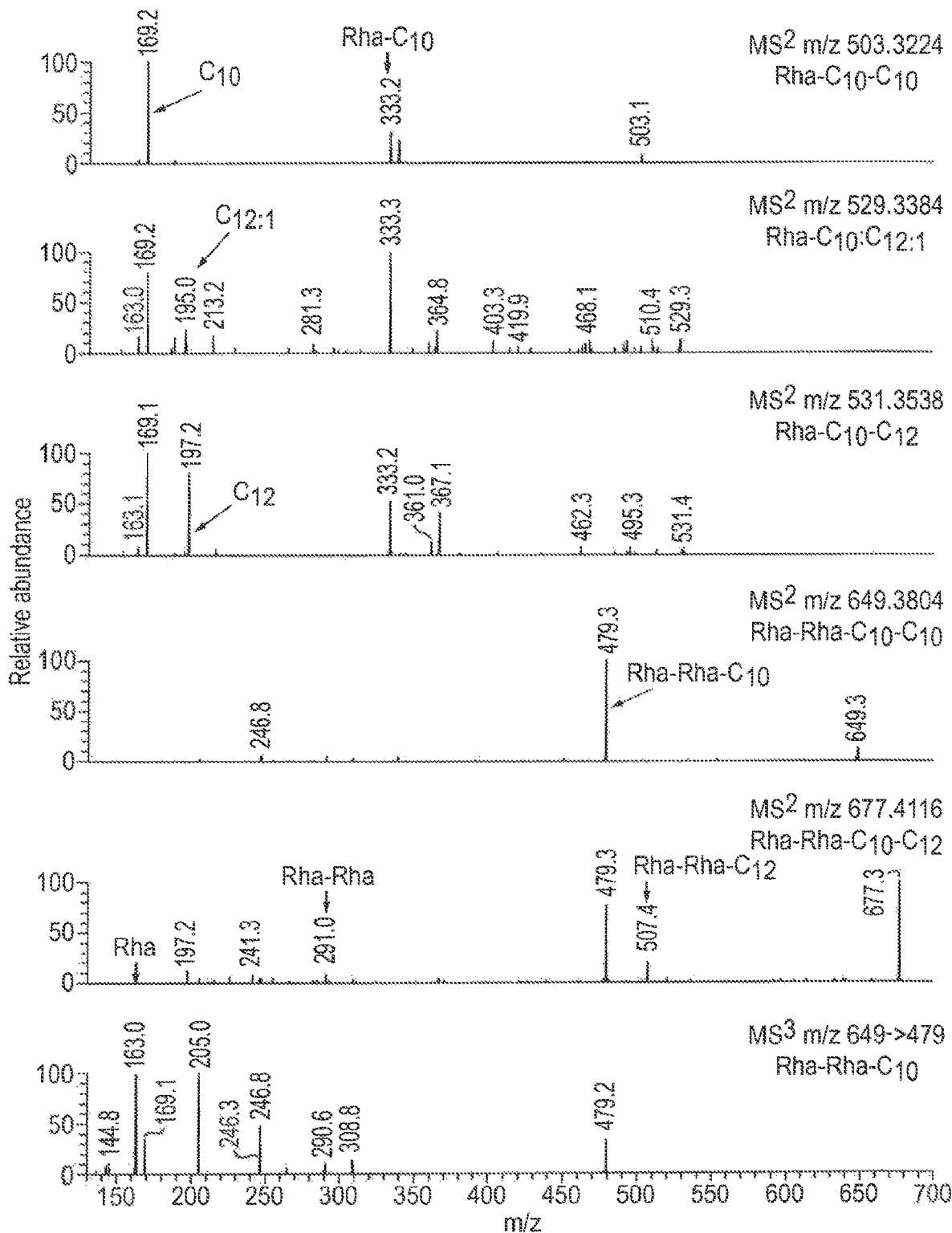
FIG. 35 shows fragmentation spectra for rhamnolipids species detected in *Pseudomonas aeruginosa* recorded using Thermo LTQ XL ion trap instrument using collision induced dissociation at collision energy setting of 25.

Fragmentation spectra of rhamnolipids species listed in Table 9 can be seen in FIG. 35. Rhamnolipids at m/z=503 and m/z=649 were confirmed by comparison to tandem mass spectra published in literature. Other rhamnolipids were assigned based on similar fragmentation patterns such as the loss of rhamnose moieties and the loss of one of the acyl chains and exact mass measurements.

Rhamnolipids have several potential biotechnological applications, especially as biodegradable surfactants for use in industry or medicine or as a possible alternative for production of rhamnose. Therefore, a screening method according to the present invention may optionally be applied for the identification of optimal rhamnolipid producers.

Lipopeptides in *Bacillus* Species

*Bacillus subtilis* is an important Gram-positive model organism that produces a variety of antibiotics of which the most important one is surfactin, a cyclic lipoheptapeptide ($C_{13}H_{27}$HCO|$CH_2$CO-Glu-Leu-D-Leu-Val-Asp-D-Leu-Leu|, where the symbols '|' represent the two cyclic bonding sites. Surfactin and its isomers are cyclic lipopeptide biosurfactants consisting of seven amino acid units and one β-hydroxyl fatty acid side chain. The carbon length of the side chain can range from 13-15 carbons. Due to their hydrophobic side chains, surfactins can incorporate into the phospholipid bilayer where they lead to perturbation of the cells. They showed a variety of activities such as anticoagulants and immunosuppressives as well as against cancer, viruses, and inflammation. The various polar functional groups of the surfactin molecule allow ready ionisation in both positive and negative ion mode. Other minor related antibiotic compounds produced by *B. subtilis* include fengycin and iturin, however, these compounds were not observed in the REIMS spectra, presumably due to concentrations below the limit of detection in the tested strains.

The inventor determined, using the method provided herein with REIMS technology, that *Bacillus subtilis* mass spectra are dominated by species clustering around m/z=1034 in negative ion mode and m/z=1059 in positive ion mode. These cluster can be ascribed to [Surfactin(C15)-H]$^-$ and [Surfactin(C15)+Na]$^+$ and C13 and C14 homologues, respectively, as shown in Table 10. The protonated quasi-molecular ions corresponding to [M+H]$^+$ adducts were not observed in positive ion mode. This is due to the high affinity of surfactin for sodium cations and high abundance of sodium in all living organisms and the culturing medium. The presence of surfactin and its homologues was further confirmed by tandem mass spectrometry measurements. Fragmentation patterns observed in negative ion mode correspond well with fragmentation patterns reported in literature.

Table 11 provides details of Lichenysin compounds detected using the method provided herein with REIMS technology in *Bacillus licheniformis*. Thus, the method provided herein may optionally be used to distinguish between various *Bacillus* species. In particular, between *B. subtilis* and *B. licheniformis*. This is difficult to achieve using conventional methods.

Polyhydroxyalkanoate Polymers

Polyhydroxyalkanoates or PHAs are linear polyesters produced in nature by bacterial fermentation of sugar or lipids, usually under in combination to a shortage in a non-carbonous nutrient, e.g., nitrogen. They are produced by the bacteria to store carbon and energy. These plastics are biodegradeable and are used in the production of bioplastics. The simplest and most commonly occurring form of PHA is the fermentative production of poly-beta-hydroxybutyrate (poly-3-hydroxybutyrate, P3HB). However, more than 100 different monomers have been reported as PHA constituents. Generally, PHAs are classified into three different classes according to monomer carbon chain length: short (C3-C5), medium (C6-C14) and long (C>14) chain PHAs. More than 90 genera of archae and eubacteria (both Gram-positive and Gram-negative) have been reported to produce PHAs.

The inventor detected, using the method provided herein with REIMS technology, polymers consisting of $C_4H_6O_2$ (polyhydroxybutyrate) monomers, in different amounts in strains of *Bacillus cereu*), *Delftia acidovorans*, *Burkholderia cepacia* and *Achromobacter xylosoxidans*. The ability of the method provided herein with REIMS technology to detect polymer production in several bacterial species offers an opportunity for biotechnological applications to rapidly screen organisms for successful production of polymers, average polymer chain lengths and modifications and/or best polymer producers.

Derivatisation of Taxon-Specific Markers

Figure 33:
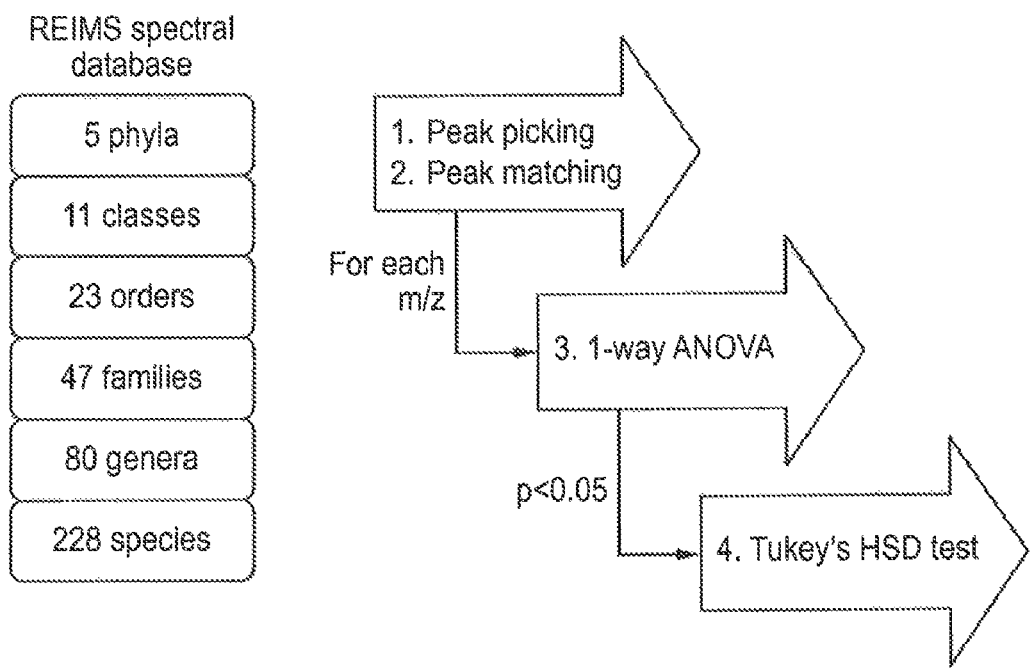
FIG. 33 shows the general workflow applied for finding taxon-specific markers.

The general workflow applied for finding taxon-specific markers is displayed in FIG. 33. All data was compiled and a representative subset of the >4,000 bacterial and fungal strains recorded was generated. This was followed by a peak-picking and peak-matching routine and an ANOVA-based biomarker discovery to derive taxon-specific markers.

A large dataset was created comprising 228 different bacterial species belonging to 80 genera, 47 families, 23 orders, 11 classes and 5 phyla. A maximum of five to seven individual strains was used for calculations for badly represented genera, while a maximum of 3 strains per species was used for well represented genera (10 species or more). Different culturing media, culturing ages and culturing atmospheres were included into the sample set.

For the derivatisation of taxon-specific markers, the data was processed in centroid rather than profile mode. For this, raw mass spectrometric files were transcoded to mzXML format by the ProteoWizard msconvert tool (version 3.0.4043).

Peak picking was performed on individual spectra within each separate file, with processing being performed on each set of m/z values and corresponding intensity values. Local maxima and peak boundaries are determined according to local minima or zero intensity values to either side of the maximum. Peak intensity is calculated as its sum between the two boundaries, with boundary intensities being halved (important only for un-resolved peaks; resolved peak boundaries are 0). The peak's 'centre of mass' is determined by means of an intensity-weighted average. After processing all spectra of a single mzXML file, the individual m/z and intensity vectors are aligned using a dynamic programming algorithm. The user specifies maximum peak shift (in ppm) that acts as the maximum distance over which peaks can be matched. If multiple files are to be compared, the peak-matching algorithm is re-run using the same parameters.

Each variable was analysed independently, initially by 1-way analysis of variance (ANOVA), to determine if there is a significant difference between the means of the defined groups (for example, bacterial species). Significant differences (e.g., p<0.05) are further analysed by Tukey's honestly significant difference (HSD) post-hoc method. HSD provides information about confidence intervals and if this interval spans across zero then the difference between two means is regarded as insignificant. A difference for each variable between all groups is determined. Thus, a variable that differs significantly between one and all other groups is considered a likely biomarker candidate. Results for each variable are returned as the ANOVA p-value (i.e. is there a significant difference in group means. NB that it does not identify the actual difference) and the number of significantly different group means. The emphasis has been placed on variables that are significantly higher in one group than in others, rather than variables that are absent in all but one taxonomical group.

For each taxonomical level, both a list of the top 20 most significant peaks per taxon and 150 most significant peaks in the dataset were created and manually compiled into markers that are specific on different taxonomical levels. Mass spectrometric signals were tentatively assigned using exact mass measurements, literature research and tandem mass spectrometry measurements as obtained during LC/MS experiments of total lipid extracts or using REIMS on a Waters Xevo G2-XS instrument. A list of most specific markers at different taxonomical levels was compiled and subsequently these markers were visualised in colorectal tumour resection samples and gastrointestinal biopsy samples to test for the presence or absence of these taxa. As these imaging data sets were recorded using a mass range of m/z 200-1000, the identification of taxon-specific markers was restricted to the same mass range.

Single ion images and RGB images were generated using MSiReader Version 0.05(135) with linear interpolation (order 1) and 0.005 Da bin size.

PCA was applied to initially assess the similarity between REIMS spectral profiles and bacterial species on different higher taxonomical levels such as Gram-, phylum-, class- and order-level.

An overall good separation was obtained for Gram-positive and Gram-negative species along the first principal component. Good taxonomic markers were also identified for the lower taxa, such as order, family, genus, species or strain.

For example, m/z=618.5233 (hydroxylated ceramide species, C36H73NO4Cl as [M+Cl]—) is indicative of a member of the Bacteroidales order being present, while m/z=820.7522 is indicative of a member of the Bacteroidaceae family. m/z=752.5449, corresponding to α-Galactosylceramide, is indicative of *Bacteroides fragilis*.

The following examples of biomarkers were identified.

Firstly, mycolic acids for bacteria belonging to the Corynebacterineae suborder such as *Mycobacterium* spp., *Corynebacterium* spp. and *Rhodococcus* spp. In particular, the following mycolic acids have been detected from the corresponding genera:

*Mycobacterium* spp.: C77-C81 (even and odd numbered, 0-2 unsaturations); *Corynebacterium* spp.: C28-C36 (even numbered, 0-2 unsaturations);
*Nocardia* spp.: C48-056 (even numbered, 0-3 unsaturations);
*Rhodococcus* spp.: C28-C38 (even and odd numbered, 0-4 unsaturations).

Secondly, a variety of sphingolipid species were found to be specific for members of the Bacteroidetes phylum. These sphingolipids include oxidized ceramides species, phosphoethanolamine dihydroceramides and C15:0-substituted phosphoglycerol dihydroceramides and dihydroceramide. Among those sphingolipid species, a series of galactosylated sphingolipids was found to be specific for *Bacteroides fragilis* (*Bacteroides fragilis* alpha-Galactosylceramides).

Thirdly, among bacteria, plasmalogens are highly specific for anaerobic bacteria such as *Clostridium* spp. and *Fusobacterium* spp. This is due to the fact that aerobic bacteria lost the biochemical pathway required for plasmalogen synthesis. Humans are able to synthesize plasmalogens (although via a different biochemical pathway from anaerobes), although these were generally found to have longer chain lengths than bacterial plasmalogens.

Other biomarkers that are indicative of a certain group of bacteria include, for instance, lipopeptides that are produced specifically by certain *Bacillus* species, such as, surfactin for *B. subtilis* and lichenysin for *B. licheniformis*. Production of these two molecules also enables straightforward differentiation of these otherwise very closely related bacteria. A further example includes PQS-derived quorum-sensing molecules and mono- and di-rhamnolipid species found for *Pseudomonas aeruginosa*.

Results are shown in Tables 1 et seq.

Analysis of Mycoplasma-Infected Cell Lines

Cell cultures frequently get infected by Mycoplasma, a genus of bacteria that lack a cell wall around their cell membrane. Mycoplasma infection can alter many physiological processes and thus lead to misleading experimental results if a study is performed using infected cells. Plasmocin® (InvivoGen, San Diego, Calif., USA) is a commercially available antibiotic treatment that is frequently used to eradicate mycoplasma infection in cell cultures. The method provided herein using REIMS technology was used to generate spectrometric data from Mycoplasma-free, Mycoplasma-infected and plasmocin® cured HeLa and HEK cell lines.

Figure 36:
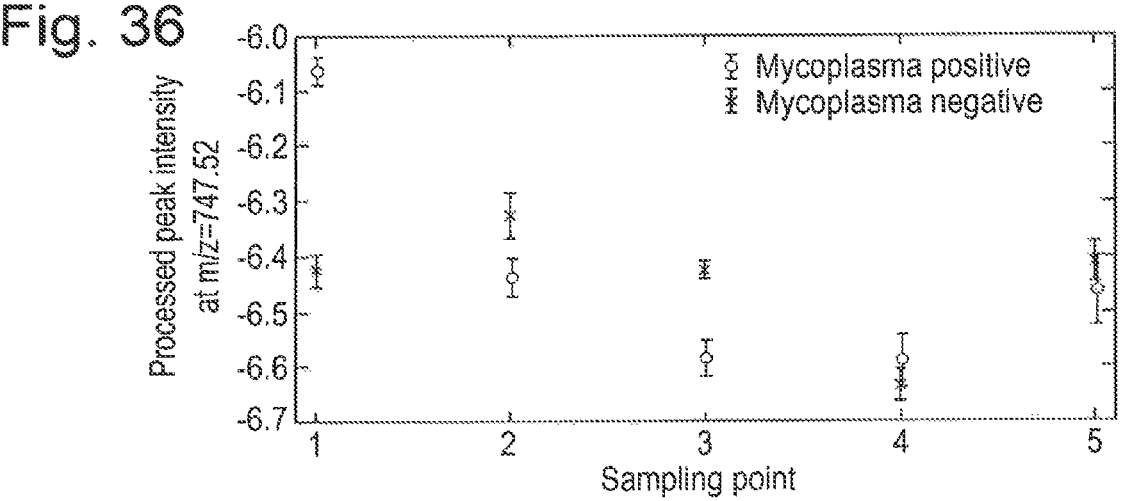
FIG. 36 shows peak intensities for m/z=747.52 in mycoplasma infected and mycoplasma-free cell lines during the duration of the Plasmocin® treatment wherein day 1 corresponds with the original (Mycoplasma positive or negative)

ANOVA tests were performed to determine significant differences between Mycoplasma positive and negative samples. Adjusted p-values were obtained using the adaptive Benjamini-Hochberg (BH) procedure to correct for multiple testing. FIG. 36 shows the time-dependent raw intensities in course of plasmocin® treatment of the mycoplasma infection in case of m/z=747.5183.

Sampling point #1 corresponds with day 1 and the original mycoplasma positive or negative sample and sampling point #2 corresponds with day 2 and the addition of plasmocin® antibiotic. Sampling point #3 corresponds with day 3. Sampling point #4 corresponds with the removal of plasmocin® antibiotic. Sampling point #5 corresponds with all samples being plasmocin® free.

Figure 23:
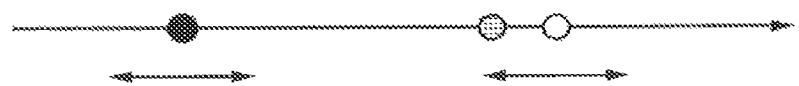
FIG. 23 shows the PCA-LDA space of FIG. 20, wherein the PCA-LDA space further comprises a PCA-LDA projected sample point derived from the peak intensity values of the sample spectrum of FIG. 22.

As shown in FIG. 37A, 23 and 386 binned m/z signals were significantly higher in Mycoplasma-infected HEK and HeLa cells, respectively. The higher number of significantly increased peaks may be explained with a higher number of sampling points (contributing to higher power in significance testing) or may reflect the increased reactivity of HeLa cells to Mycoplasma infection. Interestingly, we found no signals showing reduced intensity in Mycoplasma-infected cell lines (p=0.15). Table 13 lists the annotation of the 18 m/z signals that were found to be significantly increased across all Mycoplasma-infected cells (p=1.37E-20). As an example, changes in the intensity of m/z 819.52 (identified as PG(40:7) based on exact mass measurements) are shown in Mycoplasma-free, Mycoplasma-infected and Plasmocin™-treated HEK and HeLa cells (FIGS. 38A and B). This m/z value, along with the signal corresponding to its isotope, was found to be increased in Mycoplasma-infected HeLA and HEK cells, whereas the intensity returned to pre-infection levels upon successful Plasmocin™ treatment. Similar results were obtained for the other m/z signals shown in Table 13.

Figure 37B:
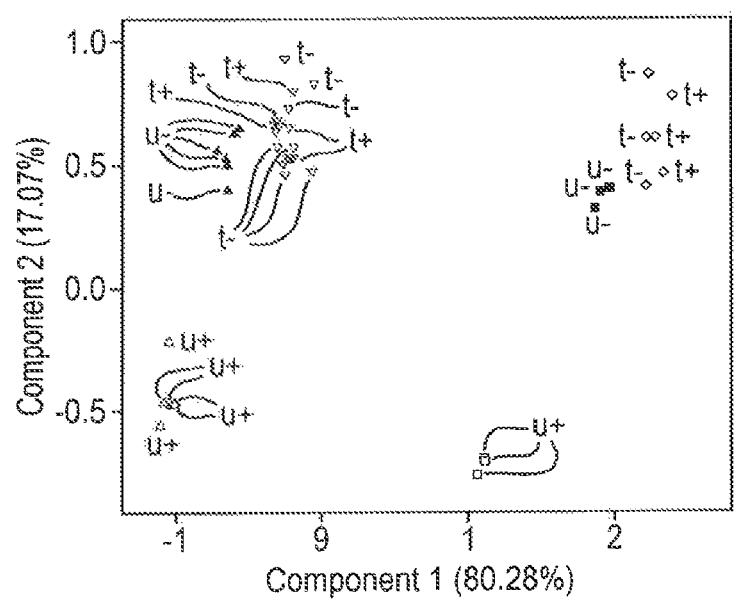

In the 18 dimensional space of these m/z signals, Mycoplasma-infected and Mycoplasma-free HEK and HeLa samples were analyzed by PCA (FIG. 37B). The first principal component (PC1) reveals differences between the two different cell lines while the second PC separates Mycoplasma-free and Mycoplasma-infected samples.

Trends in the spectral intensities of these species were found to be significantly different in case of the healthy and infected cell lines, suggesting that the lipid metabolism has been perturbed by mycoplasma infection. The above approach demonstrates the applicability of the method provided herein to study changes during Mycoplasma infection and as possible use for Mycoplasma screening.

Detection of Bacteria in Human Colorectal Tissue Specimens

The inventors attempted to visualise the presence and distribution of bacteria in human colorectal tissue specimens. Bacteria are known to cover the mucosal membranes in the gut and the gut microbial community is arguably most extensively studied and characterised. The analysis was performed by generating single ion images for the taxonomical markers that are listed in Table 14. Bacteria could be visualised in >90% of analysed colorectal specimens, including healthy and cancerous tissue specimens. Among cancerous specimens, bacteria were largely found localised in areas that were identified as necrotic by histopathological examination of the H&E stained tissue sections. However, bacteria were also frequently detected along healthy mucosa.

Analysis of Necrotic Tissue

FIG. 39 shows the tissue type-distribution of a cancerous tissue specimen that originated from the centre of tumour dissected during a right hemicolectomy. Histopathological examination revealed the presence of cancerous and stromal tissue.

Mass spectra of the necrotic tissue area as well as surrounding cancerous and stromal tissue are shown in FIG. 39 and display a markedly different phospholipid composition for the necrotic area compared to viable human tissue, namely a significantly reduced glycerophospholipid content and a variety of lower molecular weight sphingolipid-derived taxonomic marker species in the mass range of m/z=500-700.

When visualising these taxonomical markers, the respective single ion images were found to largely display co-localisation of the taxonomical marker molecules and thus bacterial cells. An array of co-localised single ion images of homologous molecules are displayed in FIG. 40 and could be attributed to the Bacteroidetes phylum. Iso-C15:0-substituted phosphoglycerol dihydroceramides were found to be specific for the Porphyromonadaceae family (part of Bacteroidetes phylum), which in this study were only represented by *Parabacteroides* spp., however, named compounds were reported present in high abundance in *Porphyromonas gingivalis*, suggesting general applicability of this marker for this family. Members of the Bacteroidetes phylum were reported in metagenomic studies to be accountable for up to 50% of the gut microbial community. However, taxon-specific markers for *Bacteroidetes fragilis* were not detected suggesting that the Bacteroidetes bacteria present do not contain a high amount of the opportunistic pathogen *B. fragilis*.

FIG. 41 shows single ion images of further taxonomical markers which were found to be specific for the Bacteroidetes phylum, among those dihydroceramide and a related compound with two more double-bonds (or equivalents). The compound at m/z=639.4954 was found to be a homologue of the lipid species at m/z=653.5113 mentioned earlier. A signal at m/z=566.4790 indicates the presence of members of the Flavobacteria class. Specific plasmalogen species for Clostridiales and Fusobacteria were additionally found, as well as an odd numbered PE that shows specificity for the Enterobacteriales order. All of these bacterial classes are capable of living under anaerobic conditions and were reported to be major components of the human gut microbiome.

While members of the Bacteroidetes phylum largely cluster around the left hand side of the tissue section where necrotic areas were identified, Clostridiales and Fusobacteria were additionally detected in at a spot more centred within the tissue section, thus confirming the expectation that not all bacterial species show identical localisation. The large bacterial presence observed in the necrotic tissue areas is tentatively associated with the lack of immunoresponse of the human body, which enables bacteria to multiply largely uncontrolled.

Detection of Bacteria in Healthy Mucosa

FIG. 39 shows the tissue type-distribution of a healthy tissue specimen that originated from a right hemicolectomy. It originated from healthy colon tissue 5 cm distance from the centre of tumour. Histopathological examination revealed healthy mucosa and submucosa, divided by the muscularis mucosae layer. Additionally, two lymphoid aggregates (inflammation) can be observed.

FIG. 40 shows single ion images for those taxon-specific markers that were detected in this sample. Generally, far fewer and less intense signals were observed than for necrotic tissue. This is tentatively attributed to the healthy immune response that restricts unlimited bacterial growth as was observed in the necrotic tissue specimen. However, the two main bacterial components of the commensal human microbiome could still be detected, namely members of the Bacteroidetes phylum and Clostridiaceae family.

Metagenomic characterisations were performed for this sample and confirmed the presence of large amounts of Bacteroidetes, Proteobacteria and Firmicutes which on class level were largely attributable to Clostridia, Bacteroidia, and Gamma-Proteobacteria, respectively.

This study demonstrates that molecular species differ significantly between microbial lipidomes and the human tissue lipidome. Taxon-specific markers for a variety of bacterial types were shown to be absent in human lipidomes/metabolome and can thus be used to visualize the presence of bacteria in human samples, as shown for human colorectal tissues. It was further demonstrated that taxonomic markers derived by the REIMS technique can be used in conjunction with other mass spectrometric ionization techniques detecting lipid profiles, such as, DESI.

Detection of Bacteria Using DESI

FIG. 43A shows desorption electrospray ionisation ("DESI") mass spectrometry analysis of a bacteria (*Klebsiella pneumonia*) sample on a swab in accordance with an embodiment. The data illustrated in FIG. 43A shows that bacterial samples can be detected using desorption electrospray ionisation ("DESI") mass spectrometry on swabs, according to various embodiments. FIG. 43B shows for comparison rapid evaporative ionisation mass spectrometry ("REIMS") time of flight ("TOF") mass spectrometry data of a corresponding bacterial sample measured directly from an agar plate. The peaks highlighted by stars were detected with both ionisation techniques.

Desorption electrospray ionisation ("DESI") swab analysis for microorganism detection was further tested on six cultivated species including *Candida albicans, Pseudomonas montelli, Staphylococcus epidermis, Moraxella catarrhalis, Klebsiella pneumonia* and *Lactobacillus* sp. These are all important bacteria and fungi species that were isolated from vaginal mucosal membranes of pregnant patients and which were identified by sequence analysis such as 16S rRNA gene sequencing.

A swab was quickly dipped into a solution of diluted biomass from each species in 10 µL methanol, followed by desorption electrospray ionisation ("DESI") mass spectrometry analysis of the swab surface.

FIGS. 44A-C show microorganism analysis using desorption electrospray ionisation ("DESI") mass spectrometry on swabs.

FIG. 44A shows averaged desorption electrospray ionisation ("DESI") mass spectra of diverse analysed microorganism species including *Candida albicans, Pseudomonas montelli, Staphylococcus epidermis, Moraxella catarrhalis, Klebsiella pneumonia* and *Lactobacillus* sp.

FIGS. 44B and 44C show PCA plots showing a separation between the vaginal mucosa (pregnant and non-pregnant group) and the microorganism species within the first two components. In addition, a separation can be observed between the different bacteria and fungi species.

Unique spectral features were observed in the mass spectra as shown in FIG. 44A resulting in the ability to separate between different microorganism classes as well as from the vaginal mucosa in the PCA score plots (FIGS. 44B and 44C) within the first two components.

This result shows the potential to characterise microbe, e.g., bacteria-specific and host-response metabolite biomarkers and signatures from specific microbial, e.g., bacterial communities from the animal, e.g., human mucosal membrane using desorption electrospray ionisation ("DESI") mass spectrometry on medical swabs.

Example of Data Analysis

Raw mass spectrometric files were converted into mzML format and subsequently imported as imzML format (REF) into MATLAB (Mathworks, Natick, Mass.; http://www.mathworks.co.uk/) for data pre-processing. REIMS spectra were linearly interpolated to a common sampling interval of 0.01 Da. Recursive segment wise peak alignment was then used to remove small mass shifts in peak positions across spectral profiles. The aligned data were subjected to total ion count (TIC) data normalization and log-based transformation. Pattern recognition analysis and visualization were performed either in Matlab or in RStudio (Boston, Mass., USA, see also www.r-project.com). Only the mass range of m/z 150-1000 was used for data analysis. For self-identity experiments, the data set was filtered to keep a reduced set of m/z values: a m/z value was kept, if the difference between the available samples were significantly different at alpha=0.01 threshold level based on the Kruskal-Wallis test.

Ionic species in the mass spectra were identified based on exact mass measurements (mass deviation <3 ppm) and MS/MS fragmentation patterns.

Faecal Analysis Using REIMS

1. Take a sample, e.g., a 10 µl loop of fresh or, if frozen, a defrosted sample of stool.
2. If using forceps based REIMS, take a small amount between the forceps and draw the probes together.
3. Perform REIMS analysis, e.g., using previously described parameters for REIMS.

REIMS Analysis of Blood Culture Pellets

Objective: This protocol describes a specific example of a procedure for analysing blood culture samples using REIMS analysis.

Initially, inoculate 10 ml of defibrinated horse blood with a single microbial colony. Grow this aerobically at 37° C. for 24 hours. Next, inoculate 1 l of horse blood with 1 ml of the overnight culture. Grow aerobically at 37° C. and at time 0 and each hour thereafter remove 25 ml to analyse in the following way:

a. Transfer 10 ml into a 50 falcon tube and centrifuge the sample for 10 mins at 3,2000 g. Use REIMS to analyse the pellet as described below.

b. Make a 2.5% Microbiology grade agar solution using HPLC water and heat until the solution reaches 50° C. Leave to stand for 1 minute to remove air bubbles. Next, add 2 ml of this to 8 ml of the blood culture described above and mix gently by pipetting. Pour into a small agar plate and allow to set for 15 minutes. Use this to perform REIMS analysis.

c. With 1 ml of this solution make serial dilutions to 10-6 using molecular grade water, and plate 100 µl of each onto a blood agar plate. Incubate for 24 hours and after count the number of colonies to determine the CFU.

d. Use a further 2 ml of the blood culture and freeze at −80° C. for LC-MS analysis. REIMS analysis may be performed on the centrifuged pellet and/or the agarose block.

Although the present invention has been described with reference to preferred embodiments, it will be understood by those skilled in the art that various changes in form and detail may be made without departing from the scope of the invention as set forth in the accompanying claims.

TABLE 1

Table of biomarkers: phospholipids and their mass spectral signals
Identified phospholipids detected in the mass range m/z = 600-900 for several analysed microbial species. Only phospholipids with relative abundances >5% and only the most abundant acyl chain combination were included. Solid growth media on which bacteria were grown is given in parentheses. ID based solely on exact mass when lipid composition given as sum carbon number rather than individual acyl chains.

| Nominal mass m/z | C. koseri (CBA) | E. coli (CBA) | K. pneumoniae (LB) | P. mirabilis (MCC) | P. aeruginosa (LB) | S. marascens (MCC) | S. aureus (CBA) | S. agalactiae (CBA) | S. pyogenes (CBA) |
|---|---|---|---|---|---|---|---|---|---|
| 645 | | | | | | | | | |
| 659 | | PA(16:0/17:1) | | PA(16:0/17:1) | | PA(16:0/17:1) | | | |
| 661 | | | | | | | | | PA(32:1)* |
| 665 | | | | | | | PA(33:0)* | | |
| 671 | | | | | | | | | PG(12:0/16:0) |
| 673 | | | | | PA(16:0/18:1) | | | | PA(34:2)* |
| 675 | | | | | | | | | PA(16:0/18:1)* |
| 688 | PE(16:1/16:0) | | | | | | PG(15:0/15:0-H$_2$O) | | PG(30:0-H$_2$O)* |
| 691 | | | | | | | | | |
| 693 | | PG(16:0/14:0) | | PE(16:1/16:0) | | | | | PG(14:0/16:1) |
| 697 | | | | | | | PG(15:0/15:0) | PG(15:0/15:0) | PG(14:0/16:0) |
| 699 | | | PG(16:0/14:0) | | | | | | PA(36:3)* |
| 701 | | | | | | | | | PA(18:1/18:1)* |
| 702 | PE(16:0/17:1) | PE(16:0/17:1) | PE(16:0/17:1) | PE(16:0/17:1) | | PE(16:0/17:1) | | PG(32:1)-H$_2$O | PG(32:1)-H$_2$O* |
| 707 | PE(18:1/16:0) | | | PE(18:1/16:0) | PE(18:1/16:0) | PE(17:0/17:1) | PG(15:0/16:0) | | |
| 716 | | | | | | | | PG(32:2)* | PG(16:1/16:1) |
| 717 | | | | | | | | PG(16:0/16:1) | PG(16:0/16:1) |
| 719 | PG(16:1/16:0) | PG(16:1/16:0) | | | | | | | PG(16:0/16:0) |
| 721 | | | PG(16:0/16:1) | PG(16:0/16:1) | PG(16:0/16:1) | PG(16:0/16:1) | PG(15:0/17:0) | PG(15:0/17:0) | PA(16:1/18:2) |
| 725 | | | | | | | | | PG(16:1/18:1)-H$_2$O |
| 727 | | | | | | | | | PG(16:0/18:1)-H$_2$O |
| 729 | | | | | | | | PG(16:0/18:1)-H$_2$O* | |
| 730 | | | | PE(16:0/19:1) | | | | | |
| 733 | PG(16:0/17:1) | PG(16:0/17:1) | PG(16:0/17:1) | PG(16:0/17:1) | PG(16:0/17:1) | PG(16:0/17:1) | | | |
| 735 | | | | | | | PG(15:0/18:0) | | |
| 743 | | | | | | | | PG(16:0/18:3) | PG(16:1/18:2) |
| 745 | PG(16:1/18:1) | PG(16:1/18:1) | PG(16:1/18:1) | PG(16:1/18:1) | PG(16:1/18:1) | | | PG(16:0/18:2)* | PG(16:1/18:1) |

TABLE 1-continued

Table of biomarkers: phospholipids and their mass spectral signals
Identified phospholipids detected in the mass range m/z = 600-900 for several analysed microbial species. Only phospholipids with relative abundances >5% and only the most abundant acyl chain combination were included. Solid growth media on which bacteria were grown is given in parentheses. ID based solely on exact mass when lipid composition given as sum carbon number rather than individual acyl chains.

| Nominal mass m/z | C. koseri (CBA) | E. coli (CBA) | K. pneumoniae (LB) | P. mirabilis (MCC) | P. aeruginosa (LB) | S. marascens (MCC) | S. aureus (CBA) | S. agalactiae (CBA) | S. pyogenes (CBA) |
|---|---|---|---|---|---|---|---|---|---|
| 747 | PG(16:0/18:1) | PG(16:0/18:1) | PG(16:0/18:1) | PG(16:0/18:1) | PG(16:0/18:1) | PG(16:0/18:1) | | PG(16:0/18:1) | PG(16:0/18:1) |
| 749 | | | | | | | PG(15:0/19:0) | PG(15:0/19:0) | PG(16:0/18:1)* |
| 752 | | | | | | | | | |
| 759 | | PG(17:1/18:1) | PG(17:1/18:1) | | PG(17:1/18:1) | PG(17:1/18:1) | | | |
| 761 | | PG(16:0/19:1) | PG(16:0/19:1) | PG(16:0/19:1) | PG(16:0/19:1) | PG(16:0/19:1) | | | |
| 763 | | | | | | | PG(15:0/20:0) | | |
| 770 | | | | | | | | | PE(38:2)* |
| 771 | | | | | | | | PG(36:3)* | PG(18:1/18:1)* |
| 773 | PG(18:1/18:1) | PG(18:1/18:1) | PG(17:1/19:1) | | PG(17:1/19:1) | PG(18:1/18:1) | | PG(36:2)* | PG(18:1/18:1) |
| 775 | | | | | | | | PG(36:1)* | PG(18:0/18:1) |
| 787 | | | PG(18:1/19:1) | | | | | | |
| 801 | | | PG(19:1/19:1) | | | | | | |

*Signal intensity not sufficient to obtain meaningful MS/MS data;
Abbreviations:
PG = phosphatidylglycerol,
PE = phosphatidylethanolamine,
CBA = Columbia blood agar,
LB = lysogenic broth agar,
MCC = McConkey agar.

TABLE 2

Table of biomarkers: cardiolipins and their mass spectral signals
Cardiolipin species that were identified for *Staphylococcus epidermidis* ATCC 12228.

| Compound | Sum formula | Exact mass [M − H]− | Exp. mass | Mass Deviation |
|---|---|---|---|---|
| CL(62:0) | $C_{71}H_{138}O_{17}P_2$ | 1323.9335 | 1323.9268 | 5.0 ppm |
| CL(63:0) | $C_{72}H_{140}O_{17}P_2$ | 1337.9492 | 1337.9426 | 4.9 ppm |
| CL(64:0) | $C_{73}H_{142}O_{17}P_2$ | 1351.9649 | 1351.9601 | 3.6 ppm |
| CL(65:0) | $C_{74}H_{144}O_{17}P_2$ | 1365.9806 | 1365.9758 | 3.5 ppm |
| CL(66:0) | $C_{75}H_{146}O_{17}P_2$ | 1379.9962 | 1379.9913 | 3.5 ppm |
| CL(67:0) | $C_{76}H_{148}O_{17}P_2$ | 1394.0119 | 1394.0070 | 3.5 ppm |
| CL(68:0) | $C_{77}H_{150}O_{17}P_2$ | 1408.0275 | 1408.0238 | 2.6 ppm |
| CL(69:0) | $C_{78}H_{152}O_{17}P_2$ | 1422.0432 | 1422.0400 | 2.3 ppm |
| CL(70:0) | $C_{79}H_{154}O_{17}P_2$ | 1436.0588 | 1436.0561 | 1.9 ppm |
| CL(71:0) | $C_{80}H_{156}O_{17}P_2$ | 1450.0745 | 1450.0748 | 0.2 ppm |
| CL(72:0) | $C_{81}H_{158}O_{17}P_2$ | 1464.0900 | 1464.0970 | 4.8 ppm |

TABLE 3

Table of biomarkers: mycolic acids and their mass spectral signals
Identified mycolic acids as detected in different *Corynebacterium* species.

| Compound | Sum formula | Exact mass [M − H]− | Exp. mass | Mass Deviation | MS/MS fragments |
|---|---|---|---|---|---|
| alpha-Mycolic acid C28:0 | $C_{28}H_{55}O_3$ | 439.415669 | 439.4159 | 0.5 ppm | — |
| alpha-Mycolic acid C30:0 | $C_{30}H_{59}O_3$ | 467.446969 | 467.4473 | 0.7 ppm | 227 (C14:0), 255 (C16:0) |
| alpha-Mycolic acid C32:1 | $C_{32}H_{61}O_3$ | 493.462619 | 493.4634 | 1.6 ppm | — |
| alpha-Mycolic acid C32:0 | $C_{32}H_{63}O_3$ | 495.478269 | 495.4786 | 0.7 ppm | 255 (C16:0) |
| alpha-Mycolic acid C34:2 | $C_{34}H_{63}O_3$ | 519.478269 | 519.4788 | 1.0 ppm | — |
| alpha-Mycolic acid C34:1 | $C_{34}H_{65}O_3$ | 521.493919 | 521.4942 | 0.5 ppm | 255 (C16:0), 281 (C18:1) |
| alpha-Mycolic acid C36:2 | $C_{36}H_{67}O_3$ | 547.509569 | 547.5102 | 1.2 ppm | 281 (C18:1) |

TABLE 4

Table of biomarkers: mycolic acids and their mass spectral signals
Identified mycolic acids as detected in *Rhodococcus* species.

| Compound | Sum formula | Exact mass [M − H]− | Exp. mass | Mass Deviation |
|---|---|---|---|---|
| alpha-Mycolic acid C28:0 | $C_{28}H_{56}O_3$ | 439.4157 | 439.4159 | 0.5 ppm |
| alpha-Mycolic acid C30:1 | $C_{30}H_{58}O_3$ | 465.4313 | 465.4315 | 0.4 ppm |
| alpha-Mycolic acid C30:0 | $C_{30}H_{60}O_3$ | 467.4470 | 467.4472 | 0.4 ppm |
| alpha-Mycolic acid C31:1 | $C_{31}H_{60}O_3$ | 479.4470 | 479.4473 | 0.6 ppm |
| alpha-Mycolic acid C31:0 | $C_{31}H_{62}O_3$ | 481.4626 | 481.4630 | 0.8 ppm |
| alpha-Mycolic acid C32:2 | $C_{32}H_{60}O_3$ | 491.4470 | 491.4475 | 1.0 ppm |
| alpha-Mycolic acid C32:1 | $C_{32}H_{62}O_3$ | 493.4626 | 493.4634 | 1.6 ppm |
| alpha-Mycolic acid C32:0 | $C_{32}H_{64}O_3$ | 495.4783 | 495.4786 | 0.6 ppm |
| alpha-Mycolic acid C33:2 | $C_{33}H_{62}O_3$ | 505.4626 | 505.4630 | 0.8 ppm |
| alpha-Mycolic acid C33:1 | $C_{33}H_{64}O_3$ | 507.4783 | 507.4785 | 0.4 ppm |
| alpha-Mycolic acid C33:0 | $C_{33}H_{66}O_3$ | 509.4939 | 509.4943 | 0.8 ppm |
| alpha-Mycolic acid C34:3 | $C_{34}H_{62}O_3$ | 517.4626 | 517.4632 | 1.2 ppm |
| alpha-Mycolic acid C34:2 | $C_{34}H_{64}O_3$ | 519.4783 | 519.4788 | 1.0 ppm |
| alpha-Mycolic acid C34:1 | $C_{34}H_{66}O_3$ | 521.4939 | 521.4944 | 1.0 ppm |
| alpha-Mycolic acid C34:0 | $C_{34}H_{68}O_3$ | 523.5096 | 523.5100 | 0.8 ppm |
| alpha-Mycolic acid C35:3 | $C_{35}H_{64}O_3$ | 531.4783 | 531.4784 | 0.2 ppm |
| alpha-Mycolic acid C35:2 | $C_{35}H_{66}O_3$ | 533.4939 | 533.4946 | 1.3 ppm |
| alpha-Mycolic acid C35:1 | $C_{35}H_{68}O_3$ | 535.5096 | 535.5100 | 0.7 ppm |
| alpha-Mycolic acid C35:0 | $C_{35}H_{70}O_3$ | 537.5252 | 537.5259 | 1.3 ppm |
| alpha-Mycolic acid C36:3 | $C_{36}H_{66}O_3$ | 545.4939 | 545.4944 | 0.9 ppm |
| alpha-Mycolic acid C36:2 | $C_{36}H_{68}O_3$ | 547.5096 | 547.5102 | 1.1 ppm |
| alpha-Mycolic acid C36:1 | $C_{36}H_{70}O_3$ | 549.5252 | 549.5260 | 1.5 ppm |
| alpha-Mycolic acid C36:0 | $C_{36}H_{72}O_3$ | 551.5409 | 551.5424 | 2.7 ppm |
| alpha-Mycolic acid C37:3 | $C_{37}H_{68}O_3$ | 559.5096 | 559.5102 | 1.1 ppm |
| alpha-Mycolic acid C37:2 | $C_{37}H_{70}O_3$ | 561.5252 | 561.5257 | 0.9 ppm |
| alpha-Mycolic acid C37:1 | $C_{37}H_{72}O_3$ | 563.5409 | 563.5418 | 1.6 ppm |
| alpha-Mycolic acid C37:0 | $C_{37}H_{74}O_3$ | 565.5565 | 565.5573 | 1.4 ppm |
| alpha-Mycolic acid C38:4 | $C_{38}H_{74}O_3$ | 571.5096 | 571.5098 | 0.3 ppm |
| alpha-Mycolic acid C38:3 | $C_{38}H_{74}O_3$ | 573.5252 | 573.5261 | 1.6 ppm |
| alpha-Mycolic acid C38:2 | $C_{38}H_{74}O_3$ | 575.5409 | 575.5415 | 1.0 ppm |
| alpha-Mycolic acid C38:1 | $C_{38}H_{74}O_3$ | 577.5565 | 577.5579 | 2.4 ppm |
| alpha-Mycolic acid C39:2 | $C_{38}H_{76}O_3$ | 589.5565 | 589.5578 | 2.2 ppm |

TABLE 5

Table of biomarkers: mycolic acids and their mass spectral signals
Identified mycolic acids as detected in *Nocardia* species.

| Compound | Sum formula | Exact mass [M − H]− | Exp. mass | Mass Deviation |
|---|---|---|---|---|
| alpha-Mycolic acid C48:3 | $C_{48}H_{90}O_3$ | 713.6817 | 713.6797 | 2.8 ppm |
| alpha-Mycolic acid C48:2 | $C_{48}H_{92}O_3$ | 715.6974 | 715.6959 | 2.1 ppm |
| alpha-Mycolic acid C50:3 | $C_{50}H_{94}O_3$ | 741.7130 | 741.7114 | 2.2 ppm |
| alpha-Mycolic acid C50:2 | $C_{50}H_{96}O_3$ | 743.7287 | 743.7285 | 0.3 ppm |
| alpha-Mycolic acid C52:3 | $C_{52}H_{94}O_3$ | 769.7443 | 769.7430 | 1.7 ppm |
| alpha-Mycolic acid C52:2 | $C_{52}H_{96}O_3$ | 771.7600 | 771.7588 | 1.6 ppm |
| alpha-Mycolic acid C53:3 | $C_{53}H_{96}O_3$ | 783.7600 | 783.7596 | 0.5 ppm |
| alpha-Mycolic acid C53:2 | $C_{53}H_{94}O_3$ | 785.7756 | 785.7754 | 0.3 ppm |
| alpha-Mycolic acid C54:4 | $C_{54}H_{96}O_3$ | 795.7600 | 795.7594 | 0.8 ppm |
| alpha-Mycolic acid C54:3 | $C_{54}H_{98}O_3$ | 797.7756 | 797.7739 | 2.1 ppm |
| alpha-Mycolic acid C54:2 | $C_{54}H_{100}O_3$ | 799.7913 | 799.7902 | 1.4 ppm |
| alpha-Mycolic acid C55:4 | $C_{54}H_{102}O_3$ | 809.7756 | 809.7748 | 1.0 ppm |
| alpha-Mycolic acid C55:3 | $C_{54}H_{104}O_3$ | 811.7913 | 811.7907 | 0.7 ppm |
| alpha-Mycolic acid C55:2 | $C_{54}H_{106}O_3$ | 813.8069 | 813.8061 | 1.0 ppm |
| alpha-Mycolic acid C56:5 | $C_{56}H_{102}O_3$ | 821.7756 | 821.7748 | 1.0 ppm |
| alpha-Mycolic acid C56:4 | $C_{56}H_{104}O_3$ | 823.7913 | 823.7907 | 0.7 ppm |
| alpha-Mycolic acid C56:3 | $C_{56}H_{106}O_3$ | 825.8069 | 825.8053 | 1.9 ppm |
| alpha-Mycolic acid C56:2 | $C_{56}H_{108}O_3$ | 827.8226 | 827.8213 | 1.6 ppm |
| alpha-Mycolic acid C57:4 | $C_{57}H_{106}O_3$ | 837.8069 | 837.8050 | 2.3 ppm |
| alpha-Mycolic acid C57:3 | $C_{57}H_{108}O_3$ | 839.8226 | 839.8215 | 1.3 ppm |
| alpha-Mycolic acid C58:5 | $C_{58}H_{106}O_3$ | 849.8069 | 849.8068 | 0.1 ppm |
| alpha-Mycolic acid C58:4 | $C_{58}H_{108}O_3$ | 851.8226 | 851.8218 | 0.9 ppm |
| alpha-Mycolic acid C58:3 | $C_{58}H_{110}O_3$ | 853.8382 | 853.8375 | 0.8 ppm |
| alpha-Mycolic acid C59:3 | $C_{59}H_{112}O_3$ | 867.8539 | 867.8537 | 0.2 ppm |
| alpha-Mycolic acid C60:4 | $C_{60}H_{112}O_3$ | 879.8539 | 879.8537 | 0.2 ppm |
| alpha-Mycolic acid C60:3 | $C_{60}H_{114}O_3$ | 881.8695 | 881.8683 | 1.4 ppm |

TABLE 6

Table of biomarkers: mycolic acids and their mass spectral signals
Identified mycolic acids as detected in different *Mycobacterium* species.

| Compound | Sum formula | Exact mass [M − H]− | Exp. mass | Mass Deviation |
|---|---|---|---|---|
| alpha-Mycolic acid C77:2 | $C_{77}H_{150}O_3$ | 1122.1512 | 1122.1525 | 1.2 ppm |
| alpha-Mycolic acid C78:2 | $C_{78}H_{152}O_3$ | 1136.1669 | 1136.1684 | 1.3 ppm |
| alpha-Mycolic acid C79:2 | $C_{79}H_{154}O_3$ | 1150.1825 | 1150.1833 | 0.7 ppm |
| Epoxy/keto-Mycolic acid C79:1 or Methoxy-Mycolic acid C79:2 | $C_{79}H_{154}O_4$ | 1166.1774 | 1166.1769 | 0.4 ppm |
| Epoxy/keto-Mycolic acid C80:1 or Methoxy-Mycolic acid C80:2 | $C_{80}H_{156}O_4$ | 1180.1931 | 1180.1897 | 2.9 ppm |
| Epoxy/keto-Mycolic acid C81:1 or Methoxy-Mycolic acid C81:2 | $C_{81}H_{158}O_3$ | 1194.2087 | 1194.2102 | 1.3 ppm |

TABLE 7

Table of biomarkers: sphingolipids and their mass spectral signals.
Identified sphingolipid species in members of the Bacteroidetes phylum

| Formula | Experimental mass | Exact mass | Mass Deviation | Observed in |
|---|---|---|---|---|
| Ceramide Phosphorylethanolamine/Phosphoethanolamine Dihydroceramides (PE-DHC) | | | | |
| $C_{36}H_{74}N_2O_7P^-$ | 677.5253 | 677.5239 | 2.0 | *B. fragilis, B. ovatus, B. thetaiotaomicron,* |
| $C_{37}H_{76}N_2O_7P^-$ | 691.5411 | 691.5396 | 2.2 | *B. uniformis, B. vulgatus, P. bivia,* |
| $C_{38}H_{78}N_2O_7P^-$ | 705.5569 | 705.5552 | 2.4 | *P. distonasis* |
| Ceramides | | | | |
| $C_{34}H_{69}NO_4Cl^-$ | 590.4934[a] | 590.4921 | 2.2 | *B. fragilis, B. ovatus, B. thetaiotaomicron,* |
| $C_{35}H_{71}NO_4Cl^-$ | 604.5090 | 604.5077 | 2.1 | *B. uniformis, B. vulgatus, P. bivia,* |
| $C_{36}H_{73}NO_4Cl^-$ | 618.5246 | 618.5234 | 1.9 | *P. distonasis* |

TABLE 7-continued

Table of biomarkers: sphingolipids and their mass spectral signals.
Identified sphingolipid species in members of the Bacteroidetes phylum

| Formula | Experimental mass | Exact mass | Mass Deviation | Observed in |
|---|---|---|---|---|
| Bacteroides fragilis α-Galactosylceramides | | | | |
| $C_{40}H_{79}NO_9Cl^-$ | 752.5465 | 752.5449 | 2.1 | B. fragilis |
| $C_{41}H_{81}NO_9Cl^-$ | 766.5623 | 766.5605 | 2.3 | |
| $C_{42}H_{83}NO_9Cl^-$ | 780.5781 | 780.5762 | 2.4 | |
| C15:0 substituted Phosphoglycerol Dihydroceramides (subPG-DHC) | | | | |
| $C_{50}H_{100}O_{10}NP$ | 904.7007 | 904.7028 | 2.3 | B. fragilis, B. ovatus, B. thetaiotaomicron, |
| $C_{51}H_{102}O_{10}NP$ | 918.7163 | 918.7185 | 2.4 | B. uniformis, B. vulgatus, P. distonasis |
| $C_{52}H_{104}O_{10}NP$ | 932.7324[b] | 932.7337 | 1.4 | |
| $C_{53}H_{106}O_{10}NP$ | 946.7481[b] | 946.7484 | 0.3 | |
| $C_{54}H_{108}O_{10}NP$ | 960.7637[b] | 960.7624 | 1.3 | |
| Unsubstituted Phosphoglycerol Dihydroceramides (unPG-DHC) | | | | |
| $C_{37}H_{76}O_9NP$ | 708.5184 | 708.5199 | 2.1 | P. distonasis |
| $C_{39}H_{80}O_9NP$ | 736.5497 | 736.5484 | 1.8 | |

TABLE 8

Table of biomarkers: quorum-sensing molecules and their mass spectral signals
Identified quorum-sensing molecules in Psuedomonas aeruginosa.

| Compound | Sum formula | Exact mass | Exp. mass | Mass Deviation |
|---|---|---|---|---|
| 2-Heptylquinoline-4(1H)-one | $C_{16}H_{21}NO$ | $[M - H]^- = 242.1550$ | 242.1552 | −0.8 ppm |
| 2-Heptyl-3-hydroxy-4(1H)-quinolone (PQS) | $C_{16}H_{21}NO_2$ | $[M - H]^- = 258.1499$ | 258.1502 | −1.2 ppm |
| Hydroxynonenylquinoline | $C_{18}H_{23}NO$ | $[M - H]^- = 268.1707$ | 268.1711 | −1.5 ppm |
| Hydroxynonylquinoline | $C_{18}H_{25}NO$ | $[M - H]^- = 270.1863$ | 270.1868 | −1.9 ppm |
| Hydroxyundecenylquinoline | $C_{20}H_{26}NO$ | $[M - H]^- = 296.2020$ | 296.2023 | −1.0 ppm |

TABLE 9

Table of biomarkers: Rhamnolipids and their mass spectral signals.
Rhamnolipid species commonly produced by P. aeruginosa strains.

| Compound | Sum formula | Exact mass [M − H]- | Exp. mass | Mass Deviation |
|---|---|---|---|---|
| Rha-$C_{20}$ | $C_{26}H_{48}O_9$ | 503.3225 | 503.3224 | 0.2 ppm |
| Rha-$C_{22:1}$ | $C_{28}H_{50}O_9$ | 529.3382 | 529.3384 | −0.4 ppm |
| Rha-$C_{22}$ | $C_{28}H_{52}O_9$ | 531.3539 | 531.3538 | 0.2 ppm |
| Rha-Rha-$C_{20}$ | $C_{32}H_{58}O_{13}$ | 649.3805 | 649.3804 | 0.2 ppm |
| Rha-Rha-$C_{22}$ | $C_{34}H_{62}O_{13}$ | 677.4118 | 677.4116 | −0.3 ppm |
| Rha-Rha-$C_{22:1}$ | $C_{34}H_{60}O_{13}$ | 675.3961 | 675.3965 | −0.6 ppm |

TABLE 10

Table of biomarkers: Surfactins and their mass spectral signals. Surfactin species detected in positive and negative ion mode for Bacillus subtilis.

| | Negative ion mode | | | Positive ion mode | | |
|---|---|---|---|---|---|---|
| Compound | Exp. Mass | Exact mass [M − H]- | Δppm | Exp. mass | Exact mass [M + Na]+ | Δppm |
| Surfactin (C13) | 1006.6453 | 1006.6440 | 1.3 | 1030.6389 | 1030.6416 | 2.6 |
| Surfactin (C14) | 1020.6604 | 1020.6597 | 0.7 | 1044.6545 | 1044.6573 | 2.7 |
| Surfactin (C15) | 1034.6754 | 1034.6753 | 0.1 | 1058.6702 | 1058.6729 | 2.6 |

TABLE 11

Table of biomarkers: Lichenysins and their mass spectral signals
Lichenysin compounds detected in Bacillus licheniformis.

| Compound | Exp. mass | Exact mass [M − H]- | Δppm |
|---|---|---|---|
| Lichenysin (C13) | 1005.6594 | 1005.6600 | 0.6 |
| Lichenysin (C14) | 1019.6748 | 1019.6756 | 0.8 |
| Lichenysin (C15) | 1033.6906 | 1033.6913 | 0.7 |
| Lichenysin (C16) | 1047.7055 | 1047.7070 | 1.4 |

TABLE 12

Table of biomarkers
Mass spectrometric signals that show strong positive correlation with the ugcg gene expression for a cell line (NCI60) dataset.

| Exp. mass | Exact mass | Δppm | Tentative ID | Formula | Adduct | Correlation coefficient |
|---|---|---|---|---|---|---|
| 734.5355 | 734.5343 | 0.2 | GlyCer (d18:1/16:0) | $C_{40}H_{77}NO_8$ | [M + Cl]- | 0.552 |
| 818.6295 | 818.6282 | 0.2 | GlyCer (d18:1/22:0) | $C_{46}H_{89}NO_8$ | [M + Cl]- | 0.662 |
| 842.6312 | 842.6332 | −0.2 | GlyCer (d18:1/24:2) | $C_{48}H_{89}NO_8$ | [M + Cl]- | 0.602 |
| 844.6451 | 844.6439 | 0.1 | GlyCer (d18:1/24:1) | $C_{48}H_{91}NO_8$ | [M + Cl]- | 0.668 |
| 846.6627 | 846.6595 | 0.4 | GlyCer (d18:1/24:0) | $C_{48}H_{93}NO_8$ | [M + Cl]- | 0.688 |

TABLE 12-continued

Table of biomarkers
Mass spectrometric signals that show strong positive correlation
with the ugcg gene expression for a cell line (NCI60) dataset.

| Exp. mass | Exact mass | Δppm | Tentative ID | Formula | Adduct | Correlation coefficient |
|---|---|---|---|---|---|---|
| 872.6733 | 872.6752 | −0.2 | GlyCer (d18:1/26:1) | $C_{50}H_{95}NO_8$ | $[M + Cl]^-$ | 0.707 |

TABLE 13

Table of biomarkers for Mycoplasma
List of m/z peak that are significantly higher in Mycoplasma infected samples compared to Mycoplasma free samples in both HEK and HeLa cell lines. Column 2 displays the corresponding binned peak, column 2 highlights putative isotope peaks, while column 4 shows the tentative annotation of the binned peak. Phosphatidylglycerol and sphingomyelin species, that are main Mycoplasma constituents are written in bold.

| significantly different binned m/z | corresponding m/z signal | Annotation |
|---|---|---|
| 687.54 | 687.5468 | |
| 722.51 | 722.5156 | PE(P-36:4) |
| 733.53 | 733.5231 | PE(P-38:4) |
| 747.52 | 747.5193 | PG(34:1) |
| 748.53 | 748.5243 | Isotope of m/z = 747.52 |
| 753.51 | 753.5090 | PG(P-36:4) |
| 764.52 | 764.5264 | PE(38:5) |
| 764.53 | 764.5262 | PE(38:5) |
| 766.53 | 766.5412 | PE(38:4) |
| 773.54 | 773.5359 | PG(36:2) |
| 774.54 | 774.5391 | PG(36:2), Isotope of m/z = 773.54 |
| 774.55 | 774.5391 | PG(36:2), Isotope of m/z = 773.54 |
| 775.56 | 775.5520 | PG(36:1) |
| 776.56 | 776.5564 | PG(36:1), Isotope of m/z = 775.56 |
| 776.57 | 776.5564 | PG(36:1), Isotope of m/z = 775.56 |
| 819.52 | 819.5189 | PG(40:7) |
| 820.53 | 820.5268 | PG(40:7), Isotope of m/z = 819.52 |
| 820.54 | 820.5268 | PG(40:7), Isotope of m/z = 819.52 |

TABLE 14

Taxon-specific biomarkers.
No markers were calculated where the size of sample set was insufficient.

| | Phylum | Class | Order | Family | Genus | Species | No. |
|---|---|---|---|---|---|---|---|
| Gram-negative | Bacteroidetes 381.2765 393.2764 590.4923 591.4963 592.4883 604.5083 605.5113 606.5033 616.4724 623.5024 624.5054 637.5044 639.4954 640.4993 653.5113 654.5143 677.5238 691.5395 705.5562 | Bacteroidetes 616.5094 617.5124 618.5233 619.5273 620.5184 627.4883 628.4913 635.5004 636.5044 637.5044 644.5033 648.5003 697.5743 698.5763 711.5902 712.5933 | Bacteroidales | Bacteroidaceae 576.4764 820.7522 | *Bacteroides* | *Bacteroides acidifaciens* | 2 |
| | | | | | | *Bacteroides caccae* | 2 |
| | | | | | | *Bacteroides eggerthii* | 2 |
| | | | | | | *Bacteroides fragilis* | 5 |
| | | | | | | *Bacteroides helcogenes* | 1 |
| | | | | | | *Bacteroides ovatus* | 3 |
| | | | | | | *Bacteroides pyogenes* | 1 |
| | | | | | | *Bacteroides thetaiotaomicron* | 3 |
| | | | | | | *Bacteroides uniformis* | 3 |
| | | | | | | *Bacteroides vulgatus* | |
| | | | | Porphyromonadaceae 814.7063 815.7112 828.7232 829.7262 840.6842 841.6942 843.7432 854.7022 858.6972 872.7072 908.7401 909.7431 910.7471 918.7191 921.7912 932.7332 933.7362 934.7422 944.7342 945.7372 946.7472 947.7502 948.7562 949.7592 958.7461 959.7501 960.7611 | *Parabacteroides* | *Parabacteroides distasonis* | 5 |
| | | | | | | *Parabacteroides johnsonii* | 2 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | | | 961.7661 962.7691 Prevotellaceae 661.5283 675.5453 676.5503 870.8002 908.7401 922.7552 923.7612 953.5113 Rikenellaceae | *Prevotella* *Alistipes* | *Prevotella bivia* *Alistipes onderdonkii* | 7 1 |
| | Flavobacteria 324.2545 333.2084 390.2324 392.2484 393.2504 552.4643 553.4674 553.4674 554.4714 556.4034 565.4654 566.4794 567.4834 568.4864 600.4664 601.4723 618.4773 619.4813 620.4883 651.4953 651.4953 891.7411 | Flavobacteriales | Flavobacteriaceae | *Chryseobacterium* *Elizabethkingia* *Myroides* | *Chryseobacterium indologenes* *Chryseobacterium* sp *Elizabethkingia meningoseptica* *Myroides odoratimimus* | 3 1 4 2 |
| Fusobacteria 227.2015 644.4652 645.4633 646.4833 647.4812 648.4832 673.4443 696.4953 714.5492 856.6782 865.6632 884.7083 | Fusobacteria | Fusobacteriales | Fusobacteriaceae | *Fusobacterium* | *Fusobacterium gonidiaformans* *Fusobacterium necrophorum* *Fusobacterium peridontiam* *Fusobacterium* sp | 3 7 4 1 |
| Proteobacteria 768.5182 782.5342 783.5293 | Alpha-Proteobacteria | Caulobacterales 769.5502 770.5562 771.5582 795.5572 797.5723 818.5673 957.6261 | Caulobacteraceae | *Brevundimonas* | *Brevundimonas diminuta* | 2 |
| | | Rhizobiales 439.4155 440.4195 739.5313 784.5902 785.5932 799.5132 | Rhizobiaceae | *Rhizobium* | *Rhizobium radiobacter* | 5 |
| | | Rhodospirillales 662.5393 722.5753 729.5813 733.5752 733.6173 734.5753 747.6283 757.6173 | Acetobacteraceae | *Roseomonas* | *Roseomonas mucosa* *Roseomonas* sp | 6 1 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | Beta-Proteobacteria | Burkholderiales | Alcaligenaceae | Achromobacter | Achromobacter sp | 3 |
| | | | | | Achromobacter xylosoxidans | 3 |
| | | | | Alcaligenes | Alcaligenes faecalis | 3 |
| | | | Burkholderiaceae 589.4013 590.4083 591.4184 592.4214 | Burkholderia | Burkholderia cepacia complex | 7 |
| | | | Comamonadaceae 520.3044 | Acidovorax | Acidovorax temperans | 2 |
| | | | | Comamonas | Comamonas kerstersii | 2 |
| | | | | | Comamonas sp | 1 |
| | | | | Delftia | Delftia acidovorans | 4 |
| | | | | | Delftia dentocariosa | 1 |
| | | | | | Delftia sp | 2 |
| | | | Sutterellaceae | Sutterella | Sutterella wadsworthensis | 2 |
| | | | Neisseriaceae | Eikenella | Eikenella corrodens | 1 |
| | | | | Kingella | Kingella kingae | 3 |
| | | | | | Kingella sp | 1 |
| | | Neisseriales 494.3855 502.3674 526.3673 527.3704 528.3653 544.3774 | | Neisseria | Neisseria cineria | 1 |
| | | | | | Neisseria elongata | 2 |
| | | | | | Neisseria flavescens | 3 |
| | | | | | Neisseria gonorrhoea | 4 |
| | | | | | Neisseria lactamica | 3 |
| | | | | | Neisseria meningitidis | 4 |
| | | | | | Neisseria mucosa | 2 |
| | Epsilon-Proteobacteria 730.5422 731.5452 867.6582 993.8381 | Campylobacterales | Campylobacteraceae 867.6582 993.8381 | Campylobacter | Campylobacter coli | 1 |
| | | | | | Campylobacter fetus | 3 |
| | | | | | Campylobacter jejuni | 3 |
| | | | | | Campylobacter sp | 6 |
| | | | Helicobacteraceae 271.2284 272.2305 299.2595 300.2625 400.2644 543.4623 544.4634 | Helicobacter | Helicobacter pylori | 3 |
| | Gamma-Proteobacteria | Aeromonadales | Aeromonadaceae | Aeromonas | Aeromonas hydrophila | 1 |
| | | Cardiobacteriales 648.4603 649.4623 650.4653 793.4792 794.4802 | Cardiobacteriaceae | Cardiobacterium | Cardiobacterium hominis | 4 |
| | | Enterobacteriales 702.5083 703.5092 993.7282 994.7272 | Enterobacteriaceae | Citrobacter | Citrobacter amalonaticus | 1 |
| | | | | | Citrobacter braakii | 3 |
| | | | | | Citrobacter freundii | 4 |
| | | | | | Citrobacter koseri | 4 |
| | | | | Enterobacter | Enterobacter absuriae | 2 |
| | | | | | Enterobacter aerogenes | 3 |
| | | | | | Enterobacter amnigenus | 1 |
| | | | | | Enterobacter cloacae | 3 |
| | | | | | Enterobacter gergoviae | 1 |
| | | | | Escherichia | Escherichia coli | 7 |
| | | | | Hafnia | Hafnia alvei | 3 |
| | | | | | Hafnia paralvei | 2 |
| | | | | | Hafnia sp | 1 |
| | | | | Klebsiella | Klebsiella oxytoca | 5 |
| | | | | | Klebsiella pneumoniae | 5 |
| | | | | Morganella | Morganella morganii | 7 |
| | | | | Panthoea | Panthoea sp | 1 |
| | | | | Proteus | Proteus mirabilis | 5 |
| | | | | | Proteus vulgaris | 5 |
| | | | | Providencia | Providencia rettgeri | 2 |
| | | | | | Providencia stuartii | 2 |
| | | | | Raoultella | Raoultella ornitholollytica | 1 |
| | | | | | Raoultella planticola | 1 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | | | | *Salmonella* | *Salmonella poona* | 1 |
| | | | | *Serratia* | *Serratia liguifaciens* | 3 |
| | | | | | *Serratia marcescens* | 5 |
| | | | | *Shigella* | *Shigella sonnei* | 1 |
| | | Pasteurellales 690.4983 746.4503 823.5453 898.6921 915.6902 977.7282 | Pasteurellaceae | *Aggregatibacter* | *Aggregatibacter aphrophilus* | 5 |
| | | | | *Haemophilus* | *Haemophilus influenzae* | 5 |
| | | | | | *Haemophilus parahaemolyticus* | 2 |
| | | | | | *Haemophilus parainfluenzae* | 1 |
| | | | | *Pasteurella* | *Pasteurella multocida* | 2 |
| | | Pseudo-monadales | Moraxellaceae | *Acinetobacter* | *Acinetobacter baumanii* | 5 |
| | | | | | *Acinetobacter iwoffii* | 5 |
| | | | | | *Acinetobacter johnsonii* | 2 |
| | | | | | *Acinetobacter junii* | 1 |
| | | | | *Moraxella* | *Moraxella catarrhalls* | 5 |
| | | | | | *Moraxella osloensis* | 2 |
| | | | Pseudo-monadaceae 286.1805 490.3304 514.3294 | *Pseudomonas* | *Pseudomonas aearuginosa* | 7 |
| | | | | | *Pseudomonas luteola* | 1 |
| | | | | | *Pseudomonas monteilii* | 2 |
| | | | | | *Pseudomonas oryzihabitans* | 2 |
| | | | | | *Pseudomonas putida* | 1 |
| | | | | | *Pseudomonas stutzeri* | 5 |
| | | Vibrionales 605.3823 607.3983 608.4013 633.4134 | Vibrionaceae | *Vibrio* | *Vibrio alginolyticus* | 1 |
| | | | | | *Vibrio cholerae* | 1 |
| | | | | | *Vibrio furnissii* | 1 |
| | | Xantho-monadales 377.2105 562.3504 619.4353 620.4384 705.4713 706.4743 929.6852 930.6892 942.6912 943.7012 944.7052 | Xantho-monadaceae | *Stenotrophomonas* | *Stenotrophomonas maltophilia* | 7 |
| Gram positive | Actinobacteria | Actinobacteria | Actinomycetales | Actinomycetaceae 757.5403 879.6112 | *Actinobaculum* | *Actinobaculum schaalii* | 2 |
| | | | | *Actinomyces* | *Actinomyces graevenitzii* | 1 |
| | | | | | *Actinomyces israelii* | 1 |
| | | | | | *Actinomyces odontolyticus* | 2 |
| | | | | | *Actinomyces oris* | 5 |
| | | | | | *Actinomyces* sp | 1 |
| | | | | | *Actinomyces turicensis* | 1 |
| | | | | | *Actinomyces viscosis* | 2 |
| | | | Corynebacteriaceae 493.4624 495.4784 497.4845 521.4934 535.4734 537.4904 538.4934 | *Corynebacterium* | *Corynebacterium afermentans* | 2 |
| | | | | | *Corynebacterium amycolatum* | 3 |
| | | | | | *Corynebacterium diphtheriae* | 2 |
| | | | | | *Corynebacterium imitans* | 3 |
| | | | | | *Corynebacterium minutissimum* | 1 |
| | | | | | *Corynebacterium* sp | 5 |
| | | | | | *Corynebacterium striatum* | 3 |
| | | | Micro-bacteriaceae | *Microbacterium* | *Microbacterium* sp | 1 |
| | | | Myco-bacteriaceae 391.3684 427.0965 724.8873 817.4152 850.5592 | *Mycobacterium* | *Mycobacterium avium* | 2 |
| | | | | | *Mycobacterium fortuitum* | 1 |
| | | | | | *Mycobacterium peregrium* | 1 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | | | 851.5662 | | | |
| | | | 852.5672 | | | |
| | | | Nocardiaceae | Nocardia | Nocardia sp | 1 |
| | | | 321.2915 | Rhodococcus | Rhodococcus egui | 1 |
| | | | 743.7273 | | Rhodococcus sp | 2 |
| | | | 771.7592 | | | |
| | | | 797.7762 | | | |
| | | | 800.7962 | | | |
| | | | 827.8162 | | | |
| | | | 828.8222 | | | |
| | | | 970.7871 | | | |
| | | | Propioni-bacteriaceae | Propioni-bacterium | Propionibacterium acnes | 7 |
| | | | 361.2155 | | | |
| | | | 617.4564 | | | |
| | | | 713.4752 | | | |
| | | | 714.4812 | | | |
| | | | 779.5072 | | | |
| | | | 877.5592 | | | |
| | | | 906.5872 | | | |
| | | Bifido-bacteriales | Bifido-bacteriaceae | Bifido-bacterium | Bifidobacterium adolescentis | 1 |
| | | 789.5293 | | | Bifidobacterium bifidum | 2 |
| | | 792.5502 | | | Bifidobacterium breve | 3 |
| | | 819.5783 | | | Bifidobacterium infantis | 1 |
| | | 830.5622 | | | Bifidobacterium longum | 3 |
| | | 855.5272 | | | Bifidobacterium pseudocatenulatum | 2 |
| | | 884.6092 | | | | |
| | | 885.6142 | | Gardnerella | Gardnerella vaginalis | 2 |
| | | Micro-coccales | Micrococcaceae | Arthrobacter | Arthrobacter creatinolyticus | 1 |
| | | | 914.5711 | | | 1 |
| | | 913.5682 | 915.5671 | | Arthrobacter sp | |
| | | | 913.5682 | Kokuria | Kokuria kristina | 2 |
| | | | | | Kokuria rhizophila | 2 |
| | | | | | Kokuria varians | 1 |
| | | | | Micrococcus | Micrococcus luteus | 5 |
| | | | | | Micrococcus lylae | 2 |
| | | | | Rothia | Rothia aeria | 3 |
| | | | | | Rothia amarne | 1 |
| | | | | | Rothia dentocariosa | 5 |
| | | | | | Rothia mucilaginosa | 5 |
| | | | | | Rothia sp | 1 |
| | | | Micrococcineae | Brevi-bacterium | Brevibacterium paucivorans | 1 |
| | | | | | | 3 |
| | | | | | Brevibacterium sp | |
| | | | | Dermabacter | Dermabacter hominis | 2 |
| | | | | | Dermobacter sp | 1 |
| Firmi-cutes | Bacilli | Bacillales | Bacillaceae | Bacillus | Bacillus cereus | 3 |
| | | | | | Bacillus clausii | 3 |
| | | | | | Bacillus lichenformis | 3 |
| | | | | | Bacillus pumilus | 1 |
| | | | | | Bacillus sonorensis | 1 |
| | | | | | Bacillus sp | 3 |
| | | | | | Bacillus subtilis | 3 |
| | | | Listeriaceae | Listeria | Listeria monocytogenes | 7 |
| | | | 675.9793 | | | |
| | | | 832.5352 | | | |
| | | | Paeni-bacillaceae | Paenibacillus | Paenibacillus sp | 5 |
| | | | | | Paenibacillus unalis | 1 |
| | | | 871.5892 | | | |
| | | | 903.7221 | | | |
| | | | 914.7282 | | | |
| | | | 915.7282 | | | |
| | | | 916.7282 | | | |
| | | | Staphylo-coccaceae | Staphyl-ococcus | Staphylococcus aureus | 3 |
| | | | | | Staphylococcus capitis | 3 |
| | | | 763.5512 | | Staphylococcus caprae | 1 |
| | | | 765.5482 | | Staphylococcus cohnii | 4 |
| | | | | | Staphylococcus epidermis | 3 |
| | | | | | Staphylococcus haemolyticus | 3 |
| | | | | | Staphylococcus hominis | 3 |
| | | | | | Staphylococcus lugdunensis | 3 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | | | | | Staphylococcus pasteuri | 3 |
| | | | | | Staphylococcus pettenkoferi | |
| | | | | | Staphylococcus saprophyticus | |
| | | | | | Staphylococcus warneri | |
| | | | Aerococcaceae 163.0506 | Abiotrophia | Abiotrophia defectiva | 1 |
| | | | | Aerococcus | Aerococcus sp | 1 |
| | | | | | Aerococcus viridans | 2 |
| | | | Carno-bacteriaceae | Granuli-catella | Granulicatella adiacens | 1 |
| | | | Entero-coccaceae | Enterococcus | Enterococcus avium | 3 |
| | | | | | Enterococcus casseliflavus | 2 |
| | | | | | | 1 |
| | | | | | Enterococcus cecorum | 3 |
| | | | | | Enterococcus faecalis | 3 |
| | | | | | Enterococcus faecium | 3 |
| | | | | | Enterococcus gallinarum | 3 |
| | | | | | Enterococcus raffinosus | |
| | | | Lacto-bacillaceae | Lactococcus | Lactococcus lactis | 1 |
| | | | | | Lactococcus spp | 2 |
| | | | Leucono-stocaceae | Leuconostoc | Leuconostoc sp | 1 |
| | | | | Lactobacillus | Lactobacillus gasseri | 2 |
| | | | | | Lactobacillus rhamnosus | 3 |
| | | Lacto-bacillales 898.5391 923.5512 925.5671 926.5701 928.5952 949.5672 950.5692 951.5832 952.5861 953.5981 954.6011 955.5971 956.5971 979.6111 990.6001 | Strepto-coccaceae 897.5351 | Strepto-coccus | Streptococcus agalactiae | 3 |
| | | | | | Streptococcus anginosus | 3 |
| | | | | | Streptococcus bovis | 3 |
| | | | | | Streptococcus canis | 1 |
| | | | | | Streptococcus constellatus | 2 |
| | | | | | | 2 |
| | | | | | Streptococcus cristatus | 3 |
| | | | | | Streptococcus dysagalactiae | 3 |
| | | | | | Streptococcus gallolyticus | 3 |
| | | | | | Streptococcus gordonii | 3 |
| | | | | | Streptococcus intermedius | 3 |
| | | | | | Streptococcus lutetiensis | 3 |
| | | | | | Streptococcus milieri | 3 |
| | | | | | Streptococcus mitis | 3 |
| | | | | | Streptococcus mutans | 1 |
| | | | | | Streptococcus oralis | 2 |
| | | | | | Streptococcus parasanguinus | 3 |
| | | | | | Streptococcus pneumoniae | 3 |
| | | | | | | 1 |
| | | | | | Streptococcus povas | 3 |
| | | | | | Streptococcus pseudoporcinus | |
| | | | | | Streptococcus pyogenes | |
| | | | | | Streptococcus salivarius | |
| | | | | | Streptococcus sanguinis | |
| | | | | | Streptococcus vestibularis | |
| | | | | | Streptococcus viridans | |
| | Clostridia 449.2685 703.4923 704.4953 731.5253 732.5283 925.7262 | Clostridiales | Clostridiaceae 649.4453 731.5253 897.6951 925.7262 969.7481 970.7541 | Clostridium | Clostridium celerecrescens | 1 |
| | | | | | | 4 |
| | | | | | Clostridium difficile | 2 |
| | | | | | Clostridium histolyticum | 3 |
| | | | | | Clostridium innocuum | 2 |
| | | | | | Clostridium paraputrificum | 3 |
| | | | | | | 3 |
| | | | | | Clostridium perfringens | 2 |
| | | | | | Clostridium ramosum | 2 |
| | | | | | Clostridium septicum | 3 |
| | | | | | Clostridium sporogenes | |
| | | | | | Clostridium tertium | |
| | | | | Parvinomas | Parvinomas micra | 1 |
| | | | Peptostrepto-coccaceae 496.4124 497.4214 | Peptoni-philus | Peptoniphilus harei | 5 |

TABLE 14-continued

Taxon-specific biomarkers.
No markers were calculated where the size of sample set was insufficient.

| Phylum | Class | Order | Family | Genus | Species | No. |
|---|---|---|---|---|---|---|
| | Negativicutes 423.3505 425.3644 426.3674 461.3394 560.4194 851.7352 | Seleno-monadales | Acidamino-coccaceae 498.4244 635.3944 645.4133 646.4173 681.3923 627.4403 643.4343 644.4383 730.4652 734.5933 831.5902 977.6971 978.6931 | *Acida-minocoecus* | *Acidaminococcus fermentans* | 2 |
| | | | Veillonellaceae 218.1855 229.1815 358.2145 364.2495 655.4713 | *Dialister* *Veillonella* | *Dialister* sp *Veillonella atypica* *Veillonella dispar* *Veillonella parvula* *Veillonella ratti* | 1 1 1 1 1 |

TABLE 16

Taxon-specific markers as determined on phylum-level.

| Phylogenetic information | Taxonomic level | m/z value | Compound ID |
|---|---|---|---|
| Gram-negatives | Bacteroidetes (Phylum) | 381.2765 | spingolipid |
| | | 653.5113 | Isotope m/z = 653 |
| | | 654.5143 | CerP(d34:1)) |
| | | 623.5024 | isotope m/z = 623 |
| | | 640.4993 | isotope m/z = 635 |
| | | 639.4954 | isotope m/z = 590 |
| | | 393.2764 | Cer(d18:0/h17:0) |
| | | 616.4724 | isotope m/z = 604 |
| | | 624.5054 | isotope m/z = 604 |
| | | 637.5044 | Cer(d34:0(2OH) |
| | | 592.4883 | isotope m/z = 590 |
| | | 604.5083 | PE-DHC |
| | | 605.5113 | PE-DHC |
| | | 606.5033 | PE-DHC |
| | | 590.4923 | |
| | | 591.4963 | |
| | | 705.5562 | |
| | | 691.5395 | |
| | | 677.5238 | |
| | Fusobacteria (Phylum) | 646.4833 | PE plasmalogen |
| | | 227.2015 | PE plasmalogen |
| | | 648.4832 | combinatorial marker |
| | | 856.6782 | with m/z = 227 |
| | | 865.6632 | |
| | | 696.4953 | |
| | | 714.5492 | |
| | | 673.4443 | |
| | | 644.4652 | |
| | | 884.7083 | |
| | | 645.4633 | |
| | | 647.4812 | |
| | Proteobacteria | 768.5182 | |
| | | 782.5342 | |
| | | 783.5293 | |
| Gram-positives | Actinobacteria | — | |
| | Firmicutes | — | |

TABLE 17

Taxon-specific markers as determined on class-level.

| Phylogenetic information | Taxonomic level | m/z value | Compound ID |
|---|---|---|---|
| Gram-negatives *L*Bacteroidetes | Bacteroidetes | 635.5004 | sphingolipid |
| | | 616.5094 | Cer(d36:1(2OH)) |
| | | 628.4913 | |
| | | 636.5044 | |
| | | 627.4883 | PE-Cer(33:1) |
| | | 644.5033 | |
| | | 711.5902 | CerP(d36:1) |
| | | 618.5233 | Cer(d36:0(2OH)) |
| | | 712.5933 | |
| | | 619.5273 | isotope 618 |
| | | 697.5743 | DG(42:5) |
| | | 620.5184 | |
| | | 698.5763 | |
| | | 648.5003 | |

TABLE 17-continued

Taxon-specific markers as determined on class-level.

| Phylogenetic information | Taxonomic level | m/z value | Compound ID |
|---|---|---|---|
| | Flavobacteria | 637.5044 | |
| | | 617.5124 | isotope m/z = 616 |
| | | 333.2084 | |
| | | 390.2324 | |
| | | 566.4794 | |
| | | 567.4834 | |
| | | 568.4864 | |
| | | 556.4034 | |
| | | 600.4664 | |
| | | 565.4654 | |
| | | 553.4674 | |
| | | 392.2484 | |
| | | 651.4953 | |
| | | 618.4773 | |
| | | 619.4813 | |
| | | 324.2545 | |
| | | 620.4883 | |
| | | 393.2504 | |
| | | 891.7411 | |
| | | 554.4714 | |
| | | 552.4643 | |
| | | 553.4674 | |
| | | 651.4953 | |
| | | 601.4723 | |
| Gram-negatives $^L$Fusobacteria | Fusobacteria (class) | | |
| Gram-negatives $^L$Proteobacteria | | | |
| | Alpha-Proteobacteria | | |
| | Beta-Proteobacteria | — | |
| | Epsilon-Proteobacteria | 993.8381 | |
| | | 867.6582 | |
| | | 731.5452 | |
| | | 730.5422 | |
| | Gamma-Proteobacteria | — | |
| Gram-positives $^L$Actinobacteria | Actinobacteria (class) | — | |
| Gram-positives $^L$Firmicutes | Bacilli | — | |
| | Clostridia | | |
| | | 731.5253 | PG plasmalogen |
| | | 732.5283 | Isotope m/z = 731 |
| | | 449.2685 | |
| | | 703.4923 | PG plasmalogen |
| | | 925.7262 | |
| | | 704.4953 | Isotope m/z = 703 |
| | Negativicutes | 560.4194 | |
| | | 426.3674 | Isotope m/z = 425 |
| | | 425.3644 | |
| | | 423.3505 | |
| | | 461.3394 | |
| | | 851.7352 | |

TABLE 18

Taxon-specific markers as determined on order-level.

| Phylogenetic information | Taxonomic level | m/z value | Compound ID |
|---|---|---|---|
| Gram-negatives $^L$Bacteroidetes $^L$Bacteroidetes | Bacteroidales | | |
| Gram-negatives $^L$Bacteroidetes $^L$Flavobacteria | Flavobacteriales | | |
| Gram-negatives $^L$Fusobacteria $^L$Fusobacteria | Fusobacteriales | | |

TABLE 18-continued

Taxon-specific markers as determined on order-level.

| Phylogenetic information | Taxonomic level | m/z value | Compound ID |
|---|---|---|---|
| Gram-negatives | | | |
| ᴸProteobacteria | | | |
| ᴸAlpha-Proteobacteria | | 795.5572 | |
| | Caulobacterales | 797.5723 | |
| | | 769.5502 | |
| | | 770.5562 | |
| | | 957.6261 | |
| | | 771.5582 | |
| | | 818.5673 | |
| | Rhizobiales | | |
| | | 739.5313 | |
| | | 784.5902 | |
| | | 785.5932 | Isotope m/z = 784 |
| | | 439.4155 | |
| | | 440.4195 | Isotope m/z = 439 |
| | | 799.5132 | |
| | Rhodospiralles | 733.5752 | |
| | | 734.5753 | |
| | | 729.5813 | |
| | | 733.6173 | |
| | | 722.5753 | |
| | | 662.5393 | |
| | | 747.6283 | |
| | | 757.6173 | |
| Gram-negatives | Burkholderiales | — | |
| ᴸProteobacteria | Neisseriales | | |
| ᴸBeta-Proteobacteria | | 526.3673 | |
| | | 527.3704 | Isotope m/z = 526 |
| | | 502.3674 | |
| | | 544.3774 | |
| | | 494.3855 | |
| | | 528.3653 | |
| Gram-negatives | Campylobacterales | — | |
| ᴸProteobacteria | | | |
| ᴸEpsilon-Proteobacteria | | | |
| Gram-negatives | | | |
| ᴸProteobacteria | | | |
| ᴸGamma-Proteobacteria | Aeromonadales | | |
| | Cardiobacterales | 648.4603 | |
| | | 649.4623 | Isotope m/z = 648 |
| | | 793.4792 | |
| | | 650.4653 | |
| | | 794.4802 | |
| | | 703.5092 | |
| | Enterobacteriales | 702.5083 | Isotope m/z = 702 |
| | | 993.7282 | |
| | | 994.7272 | |
| | Pasteurellales | 746.4503 | |
| | | 915.6902 | |
| | | 823.5453 | |
| | | 898.6921 | |
| | | 690.4983 | |
| | | 977.7282 | |
| | Pseudomonadales | — | |
| | Vibrionales | 607.3983 | |
| | | 608.4013 | Isotope m/z = 607 |
| | | 633.4134 | |
| | | 605.3823 | |
| | | 562.3504 | |
| | Xanthomonadales | 377.2105 | |
| | | 619.4353 | |
| | | 620.4384 | Isotope m/z = 619 |
| | | 930.6892 | Isotope m/z = 629 |
| | | 929.6852 | |
| | | 944.7052 | Isotope m/z = 643 |
| | | 943.7012 | |
| | | 942.6912 | |
| | | 706.4743 | Isotope m/z = 705 |
| | | 705.4713 | PG(31:1) |
| Gram-positives | Actinomycetales | — | |
| ᴸActinobacteria | Bifidobacteriales | 792.5502 | |
| ᴸActinobacteria | | 819.5783 | |
| | | 884.6092 | |
| | | 885.6142 | |
| | | 789.5293 | |

TABLE 18-continued

Taxon-specific markers as determined on order-level.

| Phylogenetic information | Taxoromic level | m/z value | Compound ID |
|---|---|---|---|
| | | 830.5622 | |
| | | 855.5272 | |
| | Micrococcales | | |
| | | 913.5682 | |
| Gram-positives | Bacillales | | |
| [L]Firmicutes | Lactobacillales | | |
| [L]Bacilli | | | |
| | | 951.5832 | |
| | | 954.6011 | |
| | | 952.5861 | |
| | | 953.5981 | |
| | | 925.5671 | |
| | | 956.5971 | |
| | | 955.5971 | |
| | | 926.5701 | |
| | | 950.5692 | |
| | | 949.5672 | |
| | | 928.5952 | |
| | | 990.6001 | |
| | | 923.5512 | |
| | | 898.5391 | |
| | | 979.6111 | |
| | Clostridiales | | |
| | Selemonadales | | |

TABLE 19

Taxon-specific markers as determined on family-level

| Phylogenetic information | Taxonomic level | m/z value | Compound ID |
|---|---|---|---|
| Gram-negatives | | | |
| [L]Bacteroidetes | | | |
| [L]Bacteroidetes | Bactercidaceae | 820.7522 | |
| [L]Bacteroidales | | | |
| | Porphyromonadaceae | 841.6942 | isotope m/z = 840 |
| | | 840.6842 | |
| | | 948.7562 | isotope m/z = 946 |
| | | 949.7592 | isotope m/z = 946 |
| | | 947.7502 | isotope m/z = 946 |
| | | 946.7472 | SubPG DHC |
| | | 945.7372 | isotope m/z = 944 |
| | | 944.7342 | SubPG DHC |
| | | 933.7362 | isotope m/z = 932 |
| | | 932.7332 | SubPG DHC |
| | | 872.7072 | |
| | | 815.7112 | isotope m/z = 814 |
| | | 814.7063 | |
| | | 858.6972 | |
| | | 934.7422 | |
| | | 962.7691 | isotope m/z = 960 |
| | | 960.7611 | SubPG DHC |
| | | 961.7661 | isotope m/z = 960 |
| | | 828.7232 | |
| | | 829.7262 | isotope m/z = 828 |
| | | 854.7022 | |
| | | 959.7501 | isotope m/z = 958 |
| | | 958.7461 | |
| | | 921.7912 | |
| | | 918.7191 | |
| | | 843.7432 | |
| | | 910.7471 | |
| | | 908.7401 | |
| | | 909.7431 | |
| | Prevotellaceae | | |
| | | 661.5283 | |
| | | 908.7401 | |
| | | 675.5453 | |
| | | 922.7552 | |

TABLE 19-continued

Taxon-specific markers as determined on family-level

| Phylogenetic information | Taxonomic level | m/z value | Compound ID |
|---|---|---|---|
| | | 923.7612 | |
| | | 676.5503 | |
| | | 870.8002 | |
| | Rikenellaceae | | |
| Gram-negatives | | | |
| ᴸBacteroidetes | | | |
| ᴸFlavobacteria | | | |
| ᴸFlavobacteriales | | | |
| | Flavobacteriaceae | | |
| Gram-negatives | | | |
| ᴸFusobacteria | | | |
| ᴸFusobacteria | | | |
| ᴸFusobacteriales | | | |
| | Fusobacteriaceae | | |
| Gram-negatives | | | |
| ᴸProteobacteria | | | |
| ᴸAlpha-Proteobacteria | | | |
| ᴸCaulobacterales | Caulobacteraceae | | |
| Gram-negatives | | | |
| ᴸProteobacteria | | | |
| ᴸAlpha-Proteobacteria | | | |
| ᴸRhizobiales | Rhizobiaceae | | |
| Gram-negatives | | | |
| ᴸProteobacteria | | | |
| ᴸAlpha-Proteobacteria | | | |
| ᴸRhodospiralles | Acetobacteraceae | | |
| Gram-negatives | Alcaligenaceae | — | |
| Proteobacteria | Burkholderiaceae | | |
| ᴸBeta-Proteobacteria | | 589.4013 | |
| ᴸBurkholderiales | | 591.4184 | |
| | | 590.4083 | Isotope m/z = 589 |
| | | 592.4214 | Isotope m/z = 591 |
| | Comamonadaceae | 520.3044 | |
| | Sutterellaceae | — | |
| Gram-negatives | | | |
| ᴸProteobacteria | | | |
| ᴸBeta-Proteobacteria | | | |
| ᴸNeisseriales | | | |
| | Neisseriaceae | | |
| Gram-negatives | Campylobacteraceae | | |
| ᴸProteobacteria | | 993.8381 | |
| ᴸEpsilon- | | 867.6582 | |
| Proteobacteria | Helicobacteriaceae | 299.2595 | C18:0(+O) |
| | | 300.2625 | Isotope m/z = 299 |
| | | 272.2305 | |
| | | 271.2284 | Isotope m/z = 271 |
| ᴸCampylobacterales | | 543.4623 | C16:0(+O) |
| | | 400.2644 | |
| | | 544.4634 | |
| Gram-negatives | | | |
| ᴸProteobacteria | | | |
| ᴸGamma-Proteobacteria | | | |
| ᴸCardiobacterales | Cardiobacteriaceae | | |
| Gram-negatives | | | |
| ᴸProteobacteria | | | |
| ᴸGamma-Proteobacteria | | | |
| ᴸEnterobacterales | Enterobacteriaceae | | |
| Gram-negatives | | | |
| ᴸProteobacteria | | | |
| ᴸGamma-Proteobacteria | | | |
| ᴸPasteurellales | Pasteurellaceae | | |
| Gram-negatives | Moraxellaceae | — | |
| ᴸProteobacteria | Pseudomonadaceae | | |
| ᴸGamma- | | 514.3294 | |
| Proteobacteria | | 490.3304 | |
| ᴸPseudomonadales | | 286.1805 | |
| Gram-negatives | | | |
| ᴸProteobacteria | | | |
| ᴸGamma-Proteobacteria | | | |
| ᴸVibrionales | Vibrionaceae | | |

TABLE 19-continued

Taxon-specific markers as determined on family-level

| Phylogenetic information | Taxonomic level | m/z value | Compound ID |
|---|---|---|---|
| Gram-negatives | | | |
| $^L$Proteobacteria | | | |
| $^L$Gamma-Proteobacteria | | | |
| $^L$Xanthomonadales | Xanthomonadaceae | | |
| Gram-positives | Actinomyceteae | 757.5403 | |
| $^L$Actinobacteria | | | |
| $^L$Actinobacteria | | | Combinatorial |
| $^L$Actinomycetales | | 879.6112 | markers |
| | Corynebacteriaceae | 537.4904 | Mycolic acid C35:0 |
| | | 538.4934 | Isotope m/z = 537 |
| | | 535.4734 | Mycolic acid C35:1 |
| | | 493.4624 | Mycolic acid C32:1 |
| | | 495.4784 | Mycolic acid C32:0 |
| | | 497.4845 | Isotope m/z = 495 |
| | | 521.4934 | Mycolic acid C34:1 |
| | Microbacteriaceae | | |
| | Mycobacteriaceae | 851.5662 | PI(35:0) |
| | | 852.5672 | Isotope m/z = 851 |
| | | 850.5592 | |
| | | 391.3684 | |
| | | 724.8873 | |
| | | 427.0965 | |
| | | 817.4152 | |
| | Nocardiaceae | 798.7762 | Isotope m/z = 797 |
| | | 797.7762 | Mycolic acid C54:3 |
| | | 828.8222 | Isotope m/z = 827 |
| | | 970.7871 | |
| | | 321.2915 | |
| | | 827.8162 | combinatorial |
| | | 800.7962 | Mycolic acid C56:2 |
| | | 743.7273 | Isotope Mycolic acid C54:2 |
| | | 771.7592 | Mycolic acid C50:2 Mycolic acid C52:2 |
| | Propionibacteriaceae | 617.4564 | |
| | | 906.5872 | |
| | | 779.5072 | |
| | | 714.4812 | |
| | | 361.2155 | |
| | | 713.4752 | |
| | | 877.5592 | |
| Gram-positives | Bifidobacteriaceae | | |
| $^L$Actinobacteria | | 792.5502 | |
| $^L$Actinobacteria | | | |
| $^L$Bifidobacteriales | | 819.5783 | |
| Gram-positives | Micrococcaceae | | |
| $^L$Actinobacteria | | 913.5682 | |
| $^L$Actinobacteria | | 914.5711 | Isotope m/z = 913 |
| $^L$Micrococcales | | 915.5671 | |
| | Micrococcineae | | |
| Gram-positives | Bacillaceae | | |
| $^L$Firmicutes | Listeriaceae | | |
| $^L$Bacilli | | 675.9793 | |
| $^L$Bacillales | | 832.5352 | |
| | Paenibacillaceae | 915.7282 | |
| | | 916.7282 | |
| | | 914.7282 | |
| | | 871.5892 | |
| | | 903.7221 | |
| | Staphylococcaceae | | |
| | | 765.5482 | Isotope m/z = 763 |
| | | 763.5512 | PG(35:0) |

TABLE 19-continued

Taxon-specific markers as determined on family-level

| Phylogenetic information | Taxonomic level | m/z value | Compound ID |
|---|---|---|---|
| Gram-positives | Aerococcaceae | | |
| $^L$Firmicutes | | 163.0506 | |
| $^L$Bacilli | Carnobacteriaceae | | |
| $^L$Lactoacillales | Enterococcaceae | — | |
| | Lactobacillaceae | — | |
| | Leuconostocaceae | | |
| | Streptococcaceae | 897.5351 | |
| Gram-positives | Clostridiaceae | | |
| $^L$Firmicutes | | 731.5253 | |
| $^L$Clostridia | | 970.7541 | |
| $^L$Clostridiales | | 649.4453 | |
| | | 897.6951 | |
| | | 969.7481 | |
| | | 925.7262 | |
| | Peptostreptococcaceae | 497.4214 | |
| | | 498.4244 | Isotope m/z = 497 |
| | | 681.3923 | |
| | | 635.3944 | |
| | | 496.4124 | |
| | | 645.4133 | |
| | | 646.4173 | Isotope m/z = 645 |
| Gram-positives | Acidaminococcaceae | | |
| [Firmicutes | | 730.4652 | |
| [Negativicutes | | 627.4403 | |
| [Selemonadales | | 831.5902 | |
| | | 977.6971 | |
| | | 978.6931 | |
| | | 643.4343 | |
| | | 644.4383 | |
| | | 734.5933 | |
| | Veillonellaceae | | |
| | | 229.1815 | |
| | | 218.1855 | |
| | | 364.2495 | |
| | | 655.4713 | |
| | | 358.2145 | |

The invention claimed is:

1. A method of analysis using mass spectrometry and/or ion mobility spectrometry comprising:
    automatically sampling a target comprising or consisting of a tissue sample using a first device to generate smoke, aerosol or vapour from said target;
    adding a matrix to said aerosol, smoke or vapour, wherein the matrix is an organic solvent;
    causing said aerosol, smoke or vapour, or analyte therein, to impact upon a collision surface located within a vacuum chamber of a spectrometer so as to generate a plurality of analyte ions;
    mass analysing and/or ion mobility analysing said analyte ions in order to obtain spectrometric data; and
    analysing said spectrometric data in order to detect necrosis in said target.

2. A method as claimed in claim 1, wherein said step of using said first device to generate aerosol, smoke or vapour from said target further comprises irradiating said target with a laser.

3. A method as claimed in claim 1, wherein said necrosis is selected from the group consisting of coagulative necrosis, liquefactive necrosis, caseous necrosis, fat necrosis, fibrinoid necrosis and gangrenous necrosis.

4. A method as claimed in claim 1, wherein said tissue is adrenal gland tissue, appendix tissue, bladder tissue, bone, bowel tissue, brain tissue, breast tissue, bronchi, ear tissue, oesophagus tissue, eye tissue, endometrioid tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue.

5. A method as claimed in claim 1, wherein said target is affected by or is in the vicinity of cancer.

6. A method as claimed in claim 1, wherein said tissue comprises cancerous tissue.

7. A method as claimed in claim 6, wherein said cancerous tissue is grade I, grade II, grade III or grade IV cancerous tissue; metastatic cancerous tissue; mixed grade cancerous tissue; a sub-grade cancerous tissue; healthy or normal tissue; or cancerous or abnormal tissue.

8. A method as claimed in claim 1, wherein said matrix is selected from the group consisting of: one or more alcohols; isopropanol; acetone; acetonitrile; tetrahydrofuran; ethyl acetate; ethylene glycol; dimethyl sulfoxide; an aldehyde; a ketone; non-polar molecules; hexane; and chloroform.

9. A method according to claim 8, wherein said alcohol is selected from methanol; ethanol; isopropanol; butanol; and propanol.

10. A method according to claim 9, wherein said alcohol is isopropanol.

11. A method according to claim 1, wherein analysing said spectrometric data comprises analysing the phospholipid composition of said target.

12. A method according to claim 11, wherein said phospholipid composition comprises the glycerophospholipid content and/or a variety of lower molecular weight sphingolipid-derived in the mass range of m/z=500-700.

13. A method as claimed in claim 1, wherein analysing said spectrometric data comprises analysing one or more sample spectra so as to classify said aerosol, smoke or vapour sample.

14. A method as claimed in claim 13, wherein analysing said one or more sample spectra so as to classify said aerosol, smoke or vapour sample comprises performing unsupervised analysis of said one or more sample spectra and/or supervised analysis of the one or more sample spectra.

15. A method as claimed in claim 13, wherein analysing said one or more sample spectra so as to classify the aerosol, smoke or vapour sample comprises using one or more of: (i) univariate analysis; (ii) multivariate analysis; (iii) principal component analysis (PCA); (iv) linear discriminant analysis (LDA); (v) maximum margin criteria (MMC); (vi) library-based analysis; (vii) soft independent modelling of class analogy (SIMCA); (viii) factor analysis (FA); (ix) recursive partitioning (decision trees); (x) random forests; (xi) independent component analysis (ICA); (xii) partial least squares discriminant analysis (PLS-DA); (xiii) orthogonal (partial least squares) projections to latent structures (OPLS); (xiv) OPLS discriminant analysis (OPLS-DA); (xv) support vector machines (SVM); (xvi) (artificial) neural networks; (xvii) multilayer perceptron; (xviii) radial basis function (RBF) networks; (xix) Bayesian analysis; (xx) cluster analysis; (xxi) a kernelized method; and (xxii) subspace discriminant analysis; (xxiii) k-nearest neighbours (KNN); (xxiv) quadratic discriminant analysis (QDA); (xxv) probabilistic principal component Analysis (PPCA); (xxvi) non negative matrix factorisation; (xxvii) k-means factorisation; (xxviii) fuzzy c-means factorisation; and (xxix) discriminant analysis (DA).

16. Apparatus comprising:
a device for automatically sampling a target comprising or consisting of a tissue sample, wherein said device comprises a first device for generating smoke, aerosol or vapour from said target;
a device for adding a matrix to said aerosol, smoke or vapour, wherein said matrix is an organic solvent;
a collision surface located within a vacuum chamber of a spectrometer, wherein in use said aerosol, smoke or vapour or analyte therein is caused to impact upon said collision surface so as to generate a plurality of analyte ions;
a mass analyser and/or ion mobility analyser for analysing said analyte ions in order to obtain spectrometric data; and
a processor adapted to analyse said spectrometric data in order to detect necrosis in said target.

17. Apparatus as claimed in claim 16, wherein said first device comprises a laser for irradiating said target.

* * * * *